(12) United States Patent
Bowers et al.

(10) Patent No.: US 9,315,546 B2
(45) Date of Patent: *Apr. 19, 2016

(54) GROWTH HORMONE SECRETATOGUE RECEPTOR ANTAGONISTS AND USES THEREOF

(75) Inventors: Cyril Y. Bowers, New Orleans, LA (US); David H. Coy, New Orleans, LA (US); Simon J. Hocart, New Orleans, LA (US); Gloria S. Tannenbaum, Hampstead (CA)

(73) Assignees: The Administrators of the Tulane Educational Fund, New Orleans, LA (US); McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/704,052

(22) PCT Filed: Jun. 16, 2011

(86) PCT No.: PCT/US2011/040728
§ 371 (c)(1),
(2), (4) Date: Feb. 27, 2013

(87) PCT Pub. No.: WO2011/159917
PCT Pub. Date: Dec. 22, 2011

(65) Prior Publication Data
US 2013/0172242 A1    Jul. 4, 2013

Related U.S. Application Data

(60) Provisional application No. 61/355,446, filed on Jun. 16, 2010.

(51) Int. Cl.
| | | |
|---|---|---|
| A61K 38/08 | (2006.01) | |
| A61K 38/10 | (2006.01) | |
| A61K 38/16 | (2006.01) | |
| A61K 38/22 | (2006.01) | |
| C07K 14/575 | (2006.01) | |
| A61K 38/00 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 38/04 | (2006.01) | |
| C07K 7/08 | (2006.01) | |
| A61K 38/03 | (2006.01) | |
| C07K 14/475 | (2006.01) | |
| A61K 38/25 | (2006.01) | |
| C07K 5/062 | (2006.01) | |
| C07K 14/60 | (2006.01) | |
| C07K 5/08 | (2006.01) | |
| C07K 7/06 | (2006.01) | |
| C07K 14/00 | (2006.01) | |
| C07K 14/72 | (2006.01) | |

(52) U.S. Cl.
CPC . *C07K 7/08* (2013.01); *A61K 38/03* (2013.01); *A61K 38/04* (2013.01); *A61K 38/08* (2013.01);

*A61K 38/10* (2013.01); *A61K 38/16* (2013.01); *A61K 38/25* (2013.01); *C07K 5/06026* (2013.01); *C07K 5/08* (2013.01); *C07K 7/06* (2013.01); *C07K 14/00* (2013.01); *C07K 14/475* (2013.01); *C07K 14/60* (2013.01); *C07K 14/723* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 7,250,399 | B2 * | 7/2007 | Bowers et al. | 514/1.9 |
| 7,385,026 | B1 * | 6/2008 | Kangawa et al. | 530/324 |
| 7,476,653 | B2 | 1/2009 | Hoveyda et al. | |
| 8,883,721 | B2 * | 11/2014 | Bowers et al. | 514/4.8 |
| 2005/0272648 | A1 * | 12/2005 | Dong et al. | 514/12 |
| 2006/0089404 | A1 | 4/2006 | Desai et al. | |
| 2006/0142397 | A1 | 6/2006 | Junien et al. | |
| 2009/0069245 | A1 | 3/2009 | Bowers et al. | |
| 2010/0086955 | A1 | 4/2010 | Harran et al. | |
| 2011/0257086 | A1 | 10/2011 | Cole et al. | |
| 2012/0135918 | A1 * | 5/2012 | Bowers et al. | 514/4.8 |

FOREIGN PATENT DOCUMENTS

| | | |
|---|---|---|
| WO | 0107475 | 2/2001 |
| WO | 2004/009124 A2 | 1/2004 |
| WO | 2005110463 | 11/2005 |

(Continued)

OTHER PUBLICATIONS

Betts et al., "Amino Acid Properties and Consequences of Substitutions" Bioinfomatics for Geneticists, Barnes et al., ed., John Wiley & Sons, pp. 297-327 (2003).*

(Continued)

*Primary Examiner* — James H Alstrum Acevedo
*Assistant Examiner* — Thea D'Ambrosio
(74) *Attorney, Agent, or Firm* — Nixon Peabody LLP

(57) ABSTRACT

The present invention provides novel peptides that can modulate the ghrelin receptor (growth hormone secretagogue receptor, GHS-R1a and sub-types, isoforms and variants thereof). These peptides are useful as antagonists of the ghrelin receptor as well as inverse agonist, partial agonist or a combination of these activities as medicaments for treatment and prevention of a range of medical conditions including, but not limited to, metabolic and/or endocrine disorders, gastrointestinal disorders, cardiovascular disorders, obesity and obesity-associated disorders, diabetes, central nervous system disorders, genetic disorders, and hyperpro-liferative disorders.

17 Claims, 19 Drawing Sheets

(56) References Cited

FOREIGN PATENT DOCUMENTS

| WO | 2007127457 | 11/2007 |
| WO | 2008/148856 | 12/2008 |
| WO | 2010039461 | 4/2010 |
| WO | 2010/132580 | 11/2010 |

OTHER PUBLICATIONS

Brown, S., "β-Amino Acids: Function and Synthesis," Macmillan Group Meeting available online at https://www.princeton.edu/chemistry/macmillan/group-meetings/b-aminoacids-spb.pdf, 5 pages (Nov. 14, 2001).*

Bitar et al., Effects of Substance P/Bombesin antagonists on the release of growth hormone by GHRP and GHRH. Biochem Biophy Res Comm 180(1):156-161, 1991.

Bodart et al., CD36 mediates cardiovascular action of growth hormone-releasing peptides in the heart. Circ Res 2002; 90:844-49.

Bowers et al., Biochemistry of growth hormone-releasing peptides, secretagogues and grehlin, In: Fat Loss, Wasting and Cachexia in Medicine, (Ed) Schuster M and Mantovani G, Springer Verlag, Chapter 5.7, p. 219-234, 2006.

Bowers et al., The role of GHS/Ghrelin in Feeding and Body Composition. Contemporary Endocrinology: Energy Metabolism and Obesity: research and Clinical Applications (Eds) Conn PM and Donohoue P. The Humans Press, 2007. p. 125-154.

Bowers, Growth Hormone Releasing Peptides (GHRPs). In: Handbook of Physiology, Eds. J Kostyo, H Goodman 1999; Oxford University Press, New York, p. 267-297.

Bowers, Octanoyl ghrelin is hypothalamic rooted. Endocrinology 146:2508-9, 2005.

Bowers, Unnatural growth hormone-releasing peptide begets natural ghrelin. J Clin Endocrinol Metab 2001; 86:1464-1469.

Camina JP. Cell biology of the ghrelin receptor. J Neuroendocrinol 2006; 18:65-76.

Gelling et al., Effect of uncontrolled diabetes on plasma ghrelin concentrations and ghrelin-induced feeding. Endocrinology 2004; 145:4575-4582.

Holst et al., Common structural basis for constitutive activity of the ghrelin receptor family. J Biol Chem 2004; 279:53806-53817.

Holst et al., High constitutive signaling of the ghrelin receptor-identification of a potent inverse agonist. Mol. Endocrinol 2003; 17 (11):2201-10.

Holst et al., Identification of an efficacy switch region in the ghrelin receptor responsible for interchange between agonism and inverse agonism. Journal Biol Chem 282:15799, 2007.

Inui et al., Ghrelin, appetite and growth-the emerging role of the stomach as an endocrine organ. FASEB Journal 2004; 18:439-456.

Kojima et al., Ghrelin is a growth-hormone-releasing acylated peptide from stomach. Nature 1999; 402:656-60.

Korbonits et al., Ghrelin-a hormone with multiple functions. Frontiers in Neuroendocrinology 2004; 25:27-68.

Laferrere et al., Growth hormone releasing peptide-2 (GHRP-2), like ghrelin, increases food intake in healthy men. J Clin Endocrinol Metab 2005; 90:611-614.

Laferrere et al., Obese subjects respond to the stimulatory effect of the ghrelin agonist growth hormone releasing peptide-2 on food intake. Obesity 14(6):1056-63, 2006.

Matsumoto et al., Structure-activity relationship of ghrelin: Pharmacological study of ghrelin peptides. Biochemical and Biophysical Research Communications, 287:142-146 (2001).

Sethumadhaven et al., Demonstration and characterization of the specific binding of growth hormone-releasing peptide to rat anterior pituitary and hypothalamic membranes. Biochem Biophy Res Comm 178(1):31-37, 1991.

Tannenbaum et al., Ghrelin and growth hormone neuroendocrine axis. In: Brain Somatic Cross-Talk and the Central Control of Metabolism. Eds. C Kordon et al. 2003; Springer-Verlag, Berlin/Heidelberg p. 65-80.

Tannenbaum et al., Interrelationship between the novel peptide ghrelin and somatostatin/GHRH in regulation of pulsatile growth hormone secretion. Endocrinology 2003; 144:967-974.

Van der Lely et al., Biological, physiological, pathophysiological and pharmacological aspects of ghrelin. Endocrine Reviews 2004; 25:426-457.

Veeraragavan et al., Growth hormone releasing peptide (GHRP) binding to porcine anterior pituitary and hypothalamic membranes. Life Sciences 50:1149-1155, 1992.

Wortley et al., Absence of ghrelin protects against early-onset obesity. J Clin Invest 2005; 115:3573-3578.

Wren et al., Ghrelin enhances appetite and increases food intake in humans. J Clin Endocrinol Metab 2001; 86:5992-5995.

Yang et al., Identification of the acyltransferase that octanoylates ghrelin, an appetite-stimulating peptide hormone.Cell. Feb. 8, 2008;132(3):387-96.

Yang et al., Inhibition of ghrelin O-acyltransferase (GOAT) by octanoylated pentapeptides.Proc Natl Acad Sci U S A. Aug. 5, 2008;105(31):10750-5. Epub Jul. 31, 2008.

Zigman et al., Expression of ghrelin receptor mRNA in the rat and the mouse brain. J Comparative Neurology 2006; 494:528-548.

Zigman et al., Mice lacking ghrelin receptors resist the development of diet induced obesity. J Clin Invest 2005; 115:3564-3572.

Gualillo, O., et al., "Introducing GOAT: a target for obesity and anti-diabetic drugs?" Trends Pharmacol. Sci., Aug. 2008, vol. 29(8):398-401.

Peterson, P.S., et al., "In vitro Characterization of High Basal Signaling from Ghrelin Receptor" Endocrinology, Nov. 2009; vol. 150(11): 4920-4930.

* cited by examiner

*: P< 0.020 or less vs. DMSO 1:2   #: P< 0.030 or less vs. GMAGS # 3

SEQUENCE LISTING

```
<160> NUMBER OF SEQ ID NOS: 386

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<221> NAME/KEY: MOD_RES
<222> LOCATION: (16)..(35)
<223> OTHER INFORMATION: Any amino acid and this region may encompass
      1 to 20 residues
<220> FEATURE:
<223> OTHER INFORMATION: May or may not be C-term NH2 or carboxyl
      protecting group
<220> FEATURE:
<223> OTHER INFORMATION: see specification as filed for detailed
      description of substitutions and preferred embodiments

<400> SEQUENCE: 1

Xaa Xaa Xaa Xaa Xaa Xaa Gly Ser Xaa Phe Leu Ser Pro Glu His Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser(Dap-Oct)
<220> FEATURE:
<223> OTHER INFORMATION: C-term NH2

<400> SEQUENCE: 2

Gly Met Ala Gly Ser Phe Leu Ser Pro Glu His
1               5                   10
```

```
<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser(Dap-Palmityl)
<220> FEATURE:
<223> OTHER INFORMATION: C-term NH2

<400> SEQUENCE: 3

Gly Met Ala Gly Ser Phe Leu Ser Pro Glu His
1               5                   10

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<221> NAME/KEY: MOD_RES
<222> LOCATION: (12)..(35)
<223> OTHER INFORMATION: Any D-, L-, alpha-, or beta- amino acid and
      this region may encompass 0 to 24 residues
<220> FEATURE:
<223> OTHER INFORMATION: May or may not be C-term NH2 or carboxyl
      protecting group
<220> FEATURE:
<223> OTHER INFORMATION: see specification as filed for detailed
      description of substitutions and preferred embodiments

<400> SEQUENCE: 4

Xaa Xaa Xaa Xaa Xaa Xaa Gly Ser Xaa Phe Leu Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(oct)

<400> SEQUENCE: 5

Gly Ser Ser Phe Leu
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Asp Leu Gly Met Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala-psi[CH2NH]

<400> SEQUENCE: 7

Leu Asp Leu Gly Met Ala
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala-psi[CH2NH]

<400> SEQUENCE: 8

Leu Asp Leu Ala Met Ala
1               5

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<221> NAME/KEY: MOD_RES
<222> LOCATION: (16)..(35)
<223> OTHER INFORMATION: Any amino acid and this region may encompass
      1 to 20 residues
<220> FEATURE:
<223> OTHER INFORMATION: May or may not be C-term NH2 or carboxyl
      protecting group
<220> FEATURE:
```

<223> OTHER INFORMATION: see specification as filed for detailed
      description of substitutions and preferred embodiments

<400> SEQUENCE: 9

Xaa Xaa Xaa Xaa Xaa Xaa Gly Ser Xaa Phe Leu Ser Pro Glu His Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Arg Val Gln
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Arg Val Gln Gln
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Arg Val Gln Gln Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Arg Val Gln Gln Arg Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 14

Gln Arg Val Gln Gln Arg Lys Glu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Arg Val Gln Gln Arg Lys Glu Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Arg Val Gln Gln Arg Lys Glu Ser Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Val Gln Gln Arg Lys Glu Ser Lys Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Arg Val Gln Gln Arg Lys Glu Ser Lys Lys Pro
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Arg Val Gln Gln Arg Lys Glu Ser Lys Lys Pro Pro
1               5                   10

<210> SEQ ID NO 20
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Gln Arg Val Gln Gln Arg Lys Glu Ser Lys Lys Pro Pro Ala
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Arg Val Gln Gln Arg Lys Glu Ser Lys Lys Pro Pro Ala Lys
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Arg Val Gln Gln Arg Lys Glu Ser Lys Lys Pro Pro Ala Lys Leu
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Arg Val Gln Gln Arg Lys Glu Ser Lys Lys Pro Pro Ala Lys Leu
1               5                   10                  15

Gln

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Arg Val Gln Gln Arg Lys Glu Ser Lys Lys Pro Pro Ala Lys Leu
1               5                   10                  15

Gln Pro

<210> SEQ ID NO 25
<211> LENGTH: 19
<212> TYPE: PRT
<213> ORGANISM: Homo sapiens

<400> SEQUENCE: 25

Gln Arg Val Gln Gln Arg Lys Glu Ser Lys Lys Pro Pro Ala Lys Leu
```

```
                    1               5              10              15

Gln Pro Arg

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Arg Val Gln Gln Arg Lys Glu Ser Lys Lys Pro Pro Ala Lys Leu
1               5                   10                  15

Gln Pro Arg Trp
            20

<210> SEQ ID NO 27
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Ser(oct)

<400> SEQUENCE: 27

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 28
<211> LENGTH: 28
<212> TYPE: PRT
<213> ORGANISM: Rattus sp.
<220> FEATURE:
<221> NAME/KEY: MOD_RES
<222> LOCATION: (3)..(3)
<223> OTHER INFORMATION: Ser(oct)

<400> SEQUENCE: 28

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Mus sp.
<220> FEATURE:
<221> NAME/KEY: MOD_RES
<222> LOCATION: (3)..(3)
<223> OTHER INFORMATION: Ser(oct)

<400> SEQUENCE: 29

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 30
<211> LENGTH: 28
<212> TYPE: PRT
```

```
<213> ORGANISM: Sus sp.
<220> FEATURE:
<221> NAME/KEY: MOD_RES
<222> LOCATION: (3)..(3)
<223> OTHER INFORMATION: Ser(oct)

<400> SEQUENCE: 30

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 31
<211> LENGTH: 28
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Ser(oct)

<400> SEQUENCE: 31

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg Thr
            20                  25

<210> SEQ ID NO 32
<211> LENGTH: 28
<212> TYPE: PRT
<213> ORGANISM: Canis sp.
<220> FEATURE:
<221> NAME/KEY: MOD_RES
<222> LOCATION: (3)..(3)
<223> OTHER INFORMATION: Ser(oct)

<400> SEQUENCE: 32

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 33
<211> LENGTH: 23
<212> TYPE: PRT
<213> ORGANISM: Homo sapiens

<400> SEQUENCE: 33

Ser Pro Glu His Gln Arg Val Gln Gln Arg Lys Glu Ser Lys Lys Pro
1               5                   10                  15

Pro Ala Lys Leu Gln Pro Arg
            20

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
```

```
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 34

Xaa Xaa Xaa Xaa Xaa Xaa Gly Ser Xaa Phe Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 35

Xaa Xaa Xaa Xaa Xaa Xaa Gly Ser Xaa Phe Leu Ser
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 36

Xaa Xaa Xaa Xaa Xaa Xaa Gly Ser Xaa Phe Leu Ser Pro
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 37

Xaa Xaa Xaa Xaa Xaa Xaa Gly Ser Xaa Phe Leu Ser Pro Glu
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 38

Xaa Xaa Xaa Xaa Xaa Xaa Gly Ser Xaa Phe Leu Ser Pro Glu His
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 39

Xaa Xaa Xaa Xaa Xaa Xaa Gly Ser Xaa Phe Leu Ser Pro Glu His Gln
1               5                   10                  15

<210> SEQ ID NO 40
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 40

Xaa Xaa Xaa Xaa Xaa Xaa Gly Ser Xaa Phe Leu Ser Pro Glu His Gln
1               5                   10                  15

Arg

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 41

Xaa Xaa Xaa Xaa Xaa Xaa Gly Ser Xaa Phe Leu Ser Pro Glu His Gln
1               5                   10                  15

Arg Val

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 42
```

```
Xaa Xaa Xaa Xaa Xaa Xaa Gly Ser Xaa Phe Leu Ser Pro Glu His Gln
1               5                   10                  15

Arg Val Gln

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 43

Xaa Xaa Xaa Xaa Xaa Xaa Gly Ser Xaa Phe Leu Ser Pro Glu His Gln
1               5                   10                  15

Arg Val Gln Gln
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 44

Xaa Xaa Xaa Xaa Xaa Xaa Gly Ser Xaa Phe Leu Ser Pro Glu His Gln
1               5                   10                  15

Arg Val Gln Gln Arg
            20

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
```

```
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 45

Xaa Xaa Xaa Xaa Xaa Xaa Gly Ser Xaa Phe Leu Ser Pro Glu His Gln
1               5                   10                  15

Arg Val Gln Gln Arg Lys
            20

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 46

Xaa Xaa Xaa Xaa Xaa Xaa Gly Ser Xaa Phe Leu Ser Pro Glu His Gln
1               5                   10                  15

Arg Val Gln Gln Arg Lys Glu
            20

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 47

Xaa Xaa Xaa Xaa Xaa Xaa Gly Ser Xaa Phe Leu Ser Pro Glu His Gln
1               5                   10                  15
```

Arg Val Gln Gln Arg Lys Glu Ser
            20

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 48

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys
            20                  25

<210> SEQ ID NO 49
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 49

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys
            20                  25

<210> SEQ ID NO 50
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:

```
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 50

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 51

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro
            20                  25

<210> SEQ ID NO 52
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 52

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala
            20                  25
```

```
<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 53

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala Lys
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 54

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala Lys Leu
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
``` on the side chain OH, diaminopropionic acid conjugated with a
-C(O)C1-C20 alkyl group, L-Trp, or D-Trp
<220> FEATURE:
<223> OTHER INFORMATION: May or may not be C-term NH2 or carboxyl
     protecting group

<400> SEQUENCE: 55

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala Lys Leu Gln
            20                  25                  30

<210> SEQ ID NO 56
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 56

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala Lys Leu Gln
            20                  25                  30

Pro

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 57

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala Lys Leu Gln
            20                  25                  30

Pro Arg

```
<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<223> OTHER INFORMATION: May or may not be C-term NH2 or carboxyl
      protecting group

<400> SEQUENCE: 58

Xaa Xaa Xaa Xaa Xaa Xaa Gly Ser Xaa Phe Leu Ser Pro Glu His Gln
1               5                   10                  15

Arg Val Gln Gln Arg Lys Glu Ser Lys Lys Pro Pro Ala Lys Leu Gln
            20                  25                  30

Pro Arg Trp
        35

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 59

Gly Met Ala Gly Ser Ser Phe Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 60

Gly Met Ala Gly Ser Ser Phe Leu Ser
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(6)
<223> OTHER INFORMATION: Ser(Oct)

<400> SEQUENCE: 61

Gly Met Ala Gly Ser Ser Phe Leu Ser Pro
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 62

Gly Met Ala Gly Ser Ser Phe Leu Ser Pro Glu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 63

Gly Met Ala Gly Ser Ser Phe Leu Ser Pro Glu His
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 64

Gly Met Ala Gly Ser Ser Phe Leu Ser Pro Glu His Gln
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 65
```

```
Gly Met Ala Gly Ser Ser Phe Leu Ser Pro Glu His Gln Arg
1               5                   10
```

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 66

```
Gly Met Ala Gly Ser Ser Phe Leu Ser Pro Glu His Gln Arg Val
1               5                   10                  15
```

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 67

```
Gly Met Ala Gly Ser Ser Phe Leu Ser Pro Glu His Gln Arg Val Gln
1               5                   10                  15
```

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 68

```
Gly Met Ala Gly Ser Ser Phe Leu Ser Pro Glu His Gln Arg Val Gln
1               5                   10                  15

Gln
```

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 69

```
Gly Met Ala Gly Ser Ser Phe Leu Ser Pro Glu His Gln Arg Val Gln
1               5                   10                  15

Gln Arg
```

```
<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 70

Gly Met Ala Gly Ser Ser Phe Leu Ser Pro Glu His Gln Arg Val Gln
1               5                   10                  15

Gln Arg Lys

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 71

Gly Met Ala Gly Ser Ser Phe Leu Ser Pro Glu His Gln Arg Val Gln
1               5                   10                  15

Gln Arg Lys Glu
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 72

Gly Met Ala Gly Ser Ser Phe Leu Ser Pro Glu His Gln Arg Val Gln
1               5                   10                  15

Gln Arg Lys Glu Ser
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 73

Gly Met Ala Gly Ser Ser Phe Leu Ser Pro Glu His Gln Arg Val Gln
1               5                   10                  15
```

```
Gln Arg Lys Glu Ser Lys
            20

<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 74

Gly Met Ala Gly Ser Ser Phe Leu Ser Pro Glu His Gln Arg Val Gln
1               5                   10                  15

Gln Arg Lys Glu Ser Lys Lys
            20

<210> SEQ ID NO 75
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 75

Gly Met Ala Gly Ser Ser Phe Leu Ser Pro Glu His Gln Arg Val Gln
1               5                   10                  15

Gln Arg Lys Glu Ser Lys Lys Pro
            20

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 76

Gly Met Ala Gly Ser Ser Phe Leu Ser Pro Glu His Gln Arg Val Gln
1               5                   10                  15

Gln Arg Lys Glu Ser Lys Lys Pro Pro
            20                  25

<210> SEQ ID NO 77
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
```

```
<400> SEQUENCE: 77

Gly Met Ala Gly Ser Ser Phe Leu Ser Pro Glu His Gln Arg Val Gln
1               5                   10                  15

Gln Arg Lys Glu Ser Lys Lys Pro Pro Ala
            20                  25

<210> SEQ ID NO 78
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 78

Gly Met Ala Gly Ser Ser Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 79

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 80
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 80

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
                    polypeptide
<220> FEATURE:
<221> NAME/KEY: MOD_RES
<222> LOCATION: (6)..(6)
<223> OTHER INFORMATION: Ser(Oct)

<400> SEQUENCE: 81

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 82
<211> LENGTH: 31
<212> TYPE: PRT
<213> ORGANISM: Artificial Sequence
<220> FEATURE:
<223> OTHER INFORMATION: Description of Artificial Sequence: Synthetic
                        polypeptide
<220> FEATURE:
<221> NAME/KEY: MOD_RES
<222> LOCATION: (6)..(6)
<223> OTHER INFORMATION: Ser(Oct)

<400> SEQUENCE: 82

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
                        polypeptide
<220> FEATURE:
<221> NAME/KEY: MOD_RES
<222> LOCATION: (6)..(6)
<223> OTHER INFORMATION: Ser(Oct)

<400> SEQUENCE: 83

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
                        peptide
<220> FEATURE:
<221> NAME/KEY: MOD_RES
<222> LOCATION: (6)..(6)
<223> OTHER INFORMATION: Dap(Oct)

<400> SEQUENCE: 84

Gly Met Ala Gly Ser Xaa Phe Leu
1               5

<210> SEQ ID NO 85
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 85

Gly Met Ala Gly Ser Xaa Phe Leu Ser
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 86

Gly Met Ala Gly Ser Xaa Phe Leu Ser Pro
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 87

Gly Met Ala Gly Ser Xaa Phe Leu Ser Pro Glu
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 88

Gly Met Ala Gly Ser Xaa Phe Leu Ser Pro Glu His
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
```

```
<400> SEQUENCE: 89

Gly Met Ala Gly Ser Xaa Phe Leu Ser Pro Glu His Gln
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 90

Gly Met Ala Gly Ser Xaa Phe Leu Ser Pro Glu His Gln Arg
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 91

Gly Met Ala Gly Ser Xaa Phe Leu Ser Pro Glu His Gln Arg Val
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 92

Gly Met Ala Gly Ser Xaa Phe Leu Ser Pro Glu His Gln Arg Val Gln
1               5                   10                  15

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 93

Gly Met Ala Gly Ser Xaa Phe Leu Ser Pro Glu His Gln Arg Val Gln
1               5                   10                  15

Gln
```

```
<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 94

Gly Met Ala Gly Ser Xaa Phe Leu Ser Pro Glu His Gln Arg Val Gln
1               5                   10                  15

Gln Arg

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 95

Gly Met Ala Gly Ser Xaa Phe Leu Ser Pro Glu His Gln Arg Val Gln
1               5                   10                  15

Gln Arg Lys

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 96

Gly Met Ala Gly Ser Xaa Phe Leu Ser Pro Glu His Gln Arg Val Gln
1               5                   10                  15

Gln Arg Lys Glu
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 97

Gly Met Ala Gly Ser Xaa Phe Leu Ser Pro Glu His Gln Arg Val Gln
1               5                   10                  15
```

Gln Arg Lys Glu Ser
            20

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 98

Gly Met Ala Gly Ser Xaa Phe Leu Ser Pro Glu His Gln Arg Val Gln
1               5                   10                  15

Gln Arg Lys Glu Ser Lys
            20

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 99

Gly Met Ala Gly Ser Xaa Phe Leu Ser Pro Glu His Gln Arg Val Gln
1               5                   10                  15

Gln Arg Lys Glu Ser Lys Lys
            20

<210> SEQ ID NO 100
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 100

Gly Met Ala Gly Ser Xaa Phe Leu Ser Pro Glu His Gln Arg Val Gln
1               5                   10                  15

Gln Arg Lys Glu Ser Lys Lys Pro
            20

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 101

Gly Met Ala Gly Ser Xaa Phe Leu Ser Pro Glu His Gln Arg Val Gln
1               5                   10                  15

Gln Arg Lys Glu Ser Lys Lys Pro Pro
            20                  25

<210> SEQ ID NO 102
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 102

Gly Met Ala Gly Ser Xaa Phe Leu Ser Pro Glu His Gln Arg Val Gln
1               5                   10                  15

Gln Arg Lys Glu Ser Lys Lys Pro Pro Ala
            20                  25

<210> SEQ ID NO 103
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 103

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 104
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 104

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 105
<211> LENGTH: 29
<212> TYPE: PRT
<213> ORGANISM: Artificial Sequence
<220> FEATURE:
<223> OTHER INFORMATION: Description of Artificial Sequence: Synthetic

```
    peptide
<220> FEATURE:
<221> NAME/KEY: MOD_RES
<222> LOCATION: (6)..(6)
<223> OTHER INFORMATION: Dap(Oct)

<400> SEQUENCE: 105

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 106
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)

<400> SEQUENCE: 106

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 107
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)

<400> SEQUENCE: 107

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)

<400> SEQUENCE: 108

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 109
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 109

Ala Met Ala Gly Ser Ser Phe Leu
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 110

Ala Met Ala Gly Ser Ser Phe Leu Ser
1               5

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 111

Ala Met Ala Gly Ser Ser Phe Leu Ser Pro
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 112

Ala Met Ala Gly Ser Ser Phe Leu Ser Pro Glu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (6)..(6)
<223> OTHER INFORMATION: Ser(Oct)

<400> SEQUENCE: 113

Ala Met Ala Gly Ser Ser Phe Leu Ser Pro Glu His
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 114

Ala Met Ala Gly Ser Ser Phe Leu Ser Pro Glu His Gln
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 115

Ala Met Ala Gly Ser Ser Phe Leu Ser Pro Glu His Gln Arg
1               5                   10

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 116

Ala Met Ala Gly Ser Ser Phe Leu Ser Pro Glu His Gln Arg Val
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 117

Ala Met Ala Gly Ser Ser Phe Leu Ser Pro Glu His Gln Arg Val Gln
```

1               5                   10                  15

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 118

Ala Met Ala Gly Ser Ser Phe Leu Ser Pro Glu His Gln Arg Val Gln
1               5                   10                  15

Gln

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 119

Ala Met Ala Gly Ser Ser Phe Leu Ser Pro Glu His Gln Arg Val Gln
1               5                   10                  15

Gln Arg

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 120

Ala Met Ala Gly Ser Ser Phe Leu Ser Pro Glu His Gln Arg Val Gln
1               5                   10                  15

Gln Arg Lys

<210> SEQ ID NO 121
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 121

Ala Met Ala Gly Ser Ser Phe Leu Ser Pro Glu His Gln Arg Val Gln
1               5                   10                  15

Gln Arg Lys Glu
            20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 122

Ala Met Ala Gly Ser Ser Phe Leu Ser Pro Glu His Gln Arg Val Gln
1               5                   10                  15

Gln Arg Lys Glu Ser
            20

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 123

Ala Met Ala Gly Ser Ser Phe Leu Ser Pro Glu His Gln Arg Val Gln
1               5                   10                  15

Gln Arg Lys Glu Ser Lys
            20

<210> SEQ ID NO 124
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 124

Ala Met Ala Gly Ser Ser Phe Leu Ser Pro Glu His Gln Arg Val Gln
1               5                   10                  15

Gln Arg Lys Glu Ser Lys Lys
            20

<210> SEQ ID NO 125
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

```
<400> SEQUENCE: 125

Ala Met Ala Gly Ser Ser Phe Leu Ser Pro Glu His Gln Arg Val Gln
1               5                   10                  15

Gln Arg Lys Glu Ser Lys Lys Pro
            20

<210> SEQ ID NO 126
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 126

Ala Met Ala Gly Ser Ser Phe Leu Ser Pro Glu His Gln Arg Val Gln
1               5                   10                  15

Gln Arg Lys Glu Ser Lys Lys Pro Pro
            20                  25

<210> SEQ ID NO 127
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 127

Ala Met Ala Gly Ser Ser Phe Leu Ser Pro Glu His Gln Arg Val Gln
1               5                   10                  15

Gln Arg Lys Glu Ser Lys Lys Pro Pro Ala
            20                  25

<210> SEQ ID NO 128
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 128

Ala Met Ala Gly Ser Ser Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (6)..(6)
<223> OTHER INFORMATION: Ser(Oct)

<400> SEQUENCE: 129

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 130
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)

<400> SEQUENCE: 130

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)

<400> SEQUENCE: 131

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 132
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)

<400> SEQUENCE: 132

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 133
```

-continued

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)

<400> SEQUENCE: 133

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 134

Ala Met Ala Gly Ser Xaa Phe Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 135

Ala Met Ala Gly Ser Xaa Phe Leu Ser
1               5

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 136

Ala Met Ala Gly Ser Xaa Phe Leu Ser Pro
1               5                   10

<210> SEQ ID NO 137
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 137

Ala Met Ala Gly Ser Xaa Phe Leu Ser Pro Glu
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 138

Ala Met Ala Gly Ser Xaa Phe Leu Ser Pro Glu His
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 139

Ala Met Ala Gly Ser Xaa Phe Leu Ser Pro Glu His Gln
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 140

Ala Met Ala Gly Ser Xaa Phe Leu Ser Pro Glu His Gln Arg
1               5                   10

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
```

```
<400> SEQUENCE: 141

Ala Met Ala Gly Ser Xaa Phe Leu Ser Pro Glu His Gln Arg Val
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 142

Ala Met Ala Gly Ser Xaa Phe Leu Ser Pro Glu His Gln Arg Val Gln
1               5                   10                  15

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 143

Ala Met Ala Gly Ser Xaa Phe Leu Ser Pro Glu His Gln Arg Val Gln
1               5                   10                  15

Gln

<210> SEQ ID NO 144
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 144

Ala Met Ala Gly Ser Xaa Phe Leu Ser Pro Glu His Gln Arg Val Gln
1               5                   10                  15

Gln Arg

<210> SEQ ID NO 145
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 145

Ala Met Ala Gly Ser Xaa Phe Leu Ser Pro Glu His Gln Arg Val Gln
```

```
1               5                   10                  15

Gln Arg Lys

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 146

Ala Met Ala Gly Ser Xaa Phe Leu Ser Pro Glu His Gln Arg Val Gln
1               5                   10                  15

Gln Arg Lys Glu
            20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 147

Ala Met Ala Gly Ser Xaa Phe Leu Ser Pro Glu His Gln Arg Val Gln
1               5                   10                  15

Gln Arg Lys Glu Ser
            20

<210> SEQ ID NO 148
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 148

Ala Met Ala Gly Ser Xaa Phe Leu Ser Pro Glu His Gln Arg Val Gln
1               5                   10                  15

Gln Arg Lys Glu Ser Lys
            20

<210> SEQ ID NO 149
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
```

```
<400> SEQUENCE: 149

Ala Met Ala Gly Ser Xaa Phe Leu Ser Pro Glu His Gln Arg Val Gln
1               5                   10                  15

Gln Arg Lys Glu Ser Lys Lys
            20

<210> SEQ ID NO 150
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 150

Ala Met Ala Gly Ser Xaa Phe Leu Ser Pro Glu His Gln Arg Val Gln
1               5                   10                  15

Gln Arg Lys Glu Ser Lys Lys Pro
            20

<210> SEQ ID NO 151
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 151

Ala Met Ala Gly Ser Xaa Phe Leu Ser Pro Glu His Gln Arg Val Gln
1               5                   10                  15

Gln Arg Lys Glu Ser Lys Lys Pro Pro
            20                  25

<210> SEQ ID NO 152
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 152

Ala Met Ala Gly Ser Xaa Phe Leu Ser Pro Glu His Gln Arg Val Gln
1               5                   10                  15

Gln Arg Lys Glu Ser Lys Lys Pro Pro Ala
            20                  25

<210> SEQ ID NO 153
<211> LENGTH: 27
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (6)..(6)
<223> OTHER INFORMATION: Dap(Oct)

<400> SEQUENCE: 153

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 154
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 154

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 155
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 155

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 156
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)

<400> SEQUENCE: 156

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 157
```

```
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)

<400> SEQUENCE: 157

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)

<400> SEQUENCE: 158

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 159

Gly Met Ala Gly Ser Ser Phe Leu
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 160

Gly Met Ala Gly Ser Ser Phe Leu Ser
1               5
```

```
<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 161

Gly Met Ala Gly Ser Ser Phe Leu Ser Pro
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 162

Gly Met Ala Gly Ser Ser Phe Leu Ser Pro Glu
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 163

Gly Met Ala Gly Ser Ser Phe Leu Ser Pro Glu His
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 164

Gly Met Ala Gly Ser Ser Phe Leu Ser Pro Glu His Gln
```

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 165

Gly Met Ala Gly Ser Ser Phe Leu Ser Pro Glu His Gln Arg
1               5                   10

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 166

Gly Met Ala Gly Ser Ser Phe Leu Ser Pro Glu His Gln Arg Val
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 167

Gly Met Ala Gly Ser Ser Phe Leu Ser Pro Glu His Gln Arg Val Gln
1               5                   10                  15

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 168

```
Gly Met Ala Gly Ser Ser Phe Leu Ser Pro Glu His Gln Arg Val Gln
1               5                   10                  15

Gln

<210> SEQ ID NO 169
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 169

Gly Met Ala Gly Ser Ser Phe Leu Ser Pro Glu His Gln Arg Val Gln
1               5                   10                  15

Gln Arg

<210> SEQ ID NO 170
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 170

Gly Met Ala Gly Ser Ser Phe Leu Ser Pro Glu His Gln Arg Val Gln
1               5                   10                  15

Gln Arg Lys

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 171

Gly Met Ala Gly Ser Ser Phe Leu Ser Pro Glu His Gln Arg Val Gln
1               5                   10                  15

Gln Arg Lys Glu
            20

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 172

Gly Met Ala Gly Ser Ser Phe Leu Ser Pro Glu His Gln Arg Val Gln
1               5                   10                  15

Gln Arg Lys Glu Ser
            20

<210> SEQ ID NO 173
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 173

Gly Met Ala Gly Ser Ser Phe Leu Ser Pro Glu His Gln Arg Val Gln
1               5                   10                  15

Gln Arg Lys Glu Ser Lys
            20

<210> SEQ ID NO 174
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 174

Gly Met Ala Gly Ser Ser Phe Leu Ser Pro Glu His Gln Arg Val Gln
1               5                   10                  15

Gln Arg Lys Glu Ser Lys Lys
            20

<210> SEQ ID NO 175
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 175
```

```
Gly Met Ala Gly Ser Ser Phe Leu Ser Pro Glu His Gln Arg Val Gln
1               5                   10                  15

Gln Arg Lys Glu Ser Lys Lys Pro
            20
```

<210> SEQ ID NO 176
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 176

```
Gly Met Ala Gly Ser Ser Phe Leu Ser Pro Glu His Gln Arg Val Gln
1               5                   10                  15

Gln Arg Lys Glu Ser Lys Lys Pro Pro
            20                  25
```

<210> SEQ ID NO 177
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 177

```
Gly Met Ala Gly Ser Ser Phe Leu Ser Pro Glu His Gln Arg Val Gln
1               5                   10                  15

Gln Arg Lys Glu Ser Lys Lys Pro Pro Ala
            20                  25
```

<210> SEQ ID NO 178
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 178

```
Gly Met Ala Gly Ser Ser Phe Leu Ser Pro Glu His Gln Arg Val Gln
1               5                   10                  15

Gln Arg Lys Glu Ser Lys Lys Pro Pro Ala Lys
            20                  25
```

<210> SEQ ID NO 179
<211> LENGTH: 28
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 179

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 180
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 180

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 181
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 181

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 182
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2
```

<400> SEQUENCE: 182

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 183

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 184

Gly Met Ala Gly Ser Xaa Phe Leu
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 185

Gly Met Ala Gly Ser Xaa Phe Leu Ser
1               5

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 186

Gly Met Ala Gly Ser Xaa Phe Leu Ser Pro
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 187

Gly Met Ala Gly Ser Xaa Phe Leu Ser Pro Glu
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 188

Gly Met Ala Gly Ser Xaa Phe Leu Ser Pro Glu His
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 189

Gly Met Ala Gly Ser Xaa Phe Leu Ser Pro Glu His Gln
1               5                   10

<210> SEQ ID NO 190
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 190

Gly Met Ala Gly Ser Xaa Phe Leu Ser Pro Glu His Gln Arg
1               5                   10

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 191

Gly Met Ala Gly Ser Xaa Phe Leu Ser Pro Glu His Gln Arg Val
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 192

Gly Met Ala Gly Ser Xaa Phe Leu Ser Pro Glu His Gln Arg Val Gln
1               5                   10                  15

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 193

Gly Met Ala Gly Ser Xaa Phe Leu Ser Pro Glu His Gln Arg Val Gln
1               5                   10                  15

Gln

<210> SEQ ID NO 194
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 194

Gly Met Ala Gly Ser Xaa Phe Leu Ser Pro Glu His Gln Arg Val Gln
1               5                   10                  15

Gln Arg

<210> SEQ ID NO 195
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 195

Gly Met Ala Gly Ser Xaa Phe Leu Ser Pro Glu His Gln Arg Val Gln
1               5                   10                  15

Gln Arg Lys

<210> SEQ ID NO 196
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 196

Gly Met Ala Gly Ser Xaa Phe Leu Ser Pro Glu His Gln Arg Val Gln
1               5                   10                  15

Gln Arg Lys Glu
            20

<210> SEQ ID NO 197
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2
```

<400> SEQUENCE: 197

Gly Met Ala Gly Ser Xaa Phe Leu Ser Pro Glu His Gln Arg Val Gln
1               5                   10                  15

Gln Arg Lys Glu Ser
            20

<210> SEQ ID NO 198
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 198

Gly Met Ala Gly Ser Xaa Phe Leu Ser Pro Glu His Gln Arg Val Gln
1               5                   10                  15

Gln Arg Lys Glu Ser Lys
            20

<210> SEQ ID NO 199
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 199

Gly Met Ala Gly Ser Xaa Phe Leu Ser Pro Glu His Gln Arg Val Gln
1               5                   10                  15

Gln Arg Lys Glu Ser Lys Lys
            20

<210> SEQ ID NO 200
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 200

Gly Met Ala Gly Ser Xaa Phe Leu Ser Pro Glu His Gln Arg Val Gln
1               5                   10                  15

Gln Arg Lys Glu Ser Lys Lys Pro
            20

<210> SEQ ID NO 201

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 201

Gly Met Ala Gly Ser Xaa Phe Leu Ser Pro Glu His Gln Arg Val Gln
1               5                   10                  15

Gln Arg Lys Glu Ser Lys Lys Pro Pro
            20                  25

<210> SEQ ID NO 202
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 202

Gly Met Ala Gly Ser Xaa Phe Leu Ser Pro Glu His Gln Arg Val Gln
1               5                   10                  15

Gln Arg Lys Glu Ser Lys Lys Pro Pro Ala
            20                  25

<210> SEQ ID NO 203
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 203

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 204
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
```

```
<220> FEATURE:
<223> OTHER INFORMATION: C-term NH2

<400> SEQUENCE: 204

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 205
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 205

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 206
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 206

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 207
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 207

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30
```

```
<210> SEQ ID NO 208
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 208

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 209

Ala Met Ala Gly Ser Ser Phe Leu
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 210

Ala Met Ala Gly Ser Ser Phe Leu Ser
1               5

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2
```

```
<400> SEQUENCE: 211

Ala Met Ala Gly Ser Ser Phe Leu Ser Pro
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 212

Ala Met Ala Gly Ser Ser Phe Leu Ser Pro Glu
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 213

Ala Met Ala Gly Ser Ser Phe Leu Ser Pro Glu His
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 214

Ala Met Ala Gly Ser Ser Phe Leu Ser Pro Glu His Gln
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2
```

<400> SEQUENCE: 215

Ala Met Ala Gly Ser Ser Phe Leu Ser Pro Glu His Gln Arg
1               5                   10

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 216

Ala Met Ala Gly Ser Ser Phe Leu Ser Pro Glu His Gln Arg Val
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 217

Ala Met Ala Gly Ser Ser Phe Leu Ser Pro Glu His Gln Arg Val Gln
1               5                   10                  15

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 218

Ala Met Ala Gly Ser Ser Phe Leu Ser Pro Glu His Gln Arg Val Gln
1               5                   10                  15

Gln

<210> SEQ ID NO 219
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)

```
<223> OTHER INFORMATION: Ser(Oct)
<220> FEATURE:
<223> OTHER INFORMATION: C-term NH2

<400> SEQUENCE: 219

Ala Met Ala Gly Ser Ser Phe Leu Ser Pro Glu His Gln Arg Val Gln
1               5                   10                  15

Gln Arg

<210> SEQ ID NO 220
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 220

Ala Met Ala Gly Ser Ser Phe Leu Ser Pro Glu His Gln Arg Val Gln
1               5                   10                  15

Gln Arg Lys

<210> SEQ ID NO 221
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 221

Ala Met Ala Gly Ser Ser Phe Leu Ser Pro Glu His Gln Arg Val Gln
1               5                   10                  15

Gln Arg Lys Glu
            20

<210> SEQ ID NO 222
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 222

Ala Met Ala Gly Ser Ser Phe Leu Ser Pro Glu His Gln Arg Val Gln
1               5                   10                  15

Gln Arg Lys Glu Ser
            20
```

```
<210> SEQ ID NO 223
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 223

Ala Met Ala Gly Ser Ser Phe Leu Ser Pro Glu His Gln Arg Val Gln
1               5                   10                  15

Gln Arg Lys Glu Ser Lys
            20

<210> SEQ ID NO 224
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 224

Ala Met Ala Gly Ser Ser Phe Leu Ser Pro Glu His Gln Arg Val Gln
1               5                   10                  15

Gln Arg Lys Glu Ser Lys Lys
            20

<210> SEQ ID NO 225
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 225

Ala Met Ala Gly Ser Ser Phe Leu Ser Pro Glu His Gln Arg Val Gln
1               5                   10                  15

Gln Arg Lys Glu Ser Lys Lys Pro
            20

<210> SEQ ID NO 226
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)..(6)
<223> OTHER INFORMATION: Ser(Oct)
<220> FEATURE:
<223> OTHER INFORMATION: C-term NH2

<400> SEQUENCE: 226

Ala Met Ala Gly Ser Ser Phe Leu Ser Pro Glu His Gln Arg Val Gln
1               5                   10                  15

Gln Arg Lys Glu Ser Lys Lys Pro Pro
            20                  25

<210> SEQ ID NO 227
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 227

Ala Met Ala Gly Ser Ser Phe Leu Ser Pro Glu His Gln Arg Val Gln
1               5                   10                  15

Gln Arg Lys Glu Ser Lys Lys Pro Pro Ala
            20                  25

<210> SEQ ID NO 228
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 228

Ala Met Ala Gly Ser Ser Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 229
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 229

Ala Met Ala Gly Ser Ser Phe Leu Ser Pro Glu His Gln Arg Val Gln
1               5                   10                  15
```

Gln Arg Lys Glu Ser Lys Lys Pro Pro Ala Lys Leu
            20                  25

<210> SEQ ID NO 230
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 230

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 231
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 231

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 232

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<221> NAME/KEY: MOD_RES
<222> LOCATION: (6)..(6)
<223> OTHER INFORMATION: Ser(Oct)
<220> FEATURE:
<223> OTHER INFORMATION: C-term NH2

<400> SEQUENCE: 233

Ala Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 234

Ala Met Ala Gly Ser Xaa Phe Leu
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 235

Ala Met Ala Gly Ser Xaa Phe Leu Ser
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 236

Ala Met Ala Gly Ser Xaa Phe Leu Ser Pro
1               5                   10

<210> SEQ ID NO 237
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 237

Ala Met Ala Gly Ser Xaa Phe Leu Ser Pro Glu
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 238

Ala Met Ala Gly Ser Xaa Phe Leu Ser Pro Glu His
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 239

Ala Met Ala Gly Ser Xaa Phe Leu Ser Pro Glu His Gln
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 240

Ala Met Ala Gly Ser Xaa Phe Leu Ser Pro Glu His Gln Arg
1               5                   10

<210> SEQ ID NO 241
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 241

Ala Met Ala Gly Ser Xaa Phe Leu Ser Pro Glu His Gln Arg Val
1               5                  10                  15

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 242

Ala Met Ala Gly Ser Xaa Phe Leu Ser Pro Glu His Gln Arg Val Gln
1               5                  10                  15

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 243

Ala Met Ala Gly Ser Xaa Phe Leu Ser Pro Glu His Gln Arg Val Gln
1               5                  10                  15

Gln

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 244

Ala Met Ala Gly Ser Xaa Phe Leu Ser Pro Glu His Gln Arg Val Gln
1               5                  10                  15
```

```
<210> SEQ ID NO 245
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 245

Ala Met Ala Gly Ser Xaa Phe Leu Ser Pro Glu His Gln Arg Val Gln
1               5                  10                  15

Gln Arg Lys

<210> SEQ ID NO 246
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 246

Ala Met Ala Gly Ser Xaa Phe Leu Ser Pro Glu His Gln Arg Val Gln
1               5                  10                  15

Gln Arg Lys Glu
            20

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 247

Ala Met Ala Gly Ser Xaa Phe Leu Ser Pro Glu His Gln Arg Val Gln
1               5                  10                  15

Gln Arg Lys Glu Ser
            20

<210> SEQ ID NO 248
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

Gln Arg

```
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 248

Ala Met Ala Gly Ser Xaa Phe Leu Ser Pro Glu His Gln Arg Val Gln
1               5                   10                  15

Gln Arg Lys Glu Ser Lys
            20

<210> SEQ ID NO 249
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 249

Ala Met Ala Gly Ser Xaa Phe Leu Ser Pro Glu His Gln Arg Val Gln
1               5                   10                  15

Gln Arg Lys Glu Ser Lys Lys
            20

<210> SEQ ID NO 250
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 250

Ala Met Ala Gly Ser Xaa Phe Leu Ser Pro Glu His Gln Arg Val Gln
1               5                   10                  15

Gln Arg Lys Glu Ser Lys Lys Pro
            20

<210> SEQ ID NO 251
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 251

Ala Met Ala Gly Ser Xaa Phe Leu Ser Pro Glu His Gln Arg Val Gln
```

```
1               5                   10                  15

Gln Arg Lys Glu Ser Lys Lys Pro Pro
            20                  25

<210> SEQ ID NO 252
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 252

Ala Met Ala Gly Ser Xaa Phe Leu Ser Pro Glu His Gln Arg Val Gln
1               5                   10                  15

Gln Arg Lys Glu Ser Lys Lys Pro Pro Ala
            20                  25

<210> SEQ ID NO 253
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 253

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 254
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 254

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 255
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 255

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 256
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 256

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 257
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2

<400> SEQUENCE: 257

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-term NH2
```

```
<400> SEQUENCE: 258

Ala Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Met Ala Gly Ser Tyr Phe Leu
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Met Ala Gly Ser Tyr Phe Leu Ser
1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Met Ala Gly Ser Tyr Phe Leu Ser Pro
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Met Ala Gly Ser Tyr Phe Leu Ser Pro Glu
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Met Ala Gly Ser Tyr Phe Leu Ser Pro Glu His
1               5                   10
```

```
<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Met Ala Gly Ser Tyr Phe Leu Ser Pro Glu His Gln
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Met Ala Gly Ser Tyr Phe Leu Ser Pro Glu His Gln Arg
1               5                   10

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Met Ala Gly Ser Tyr Phe Leu Ser Pro Glu His Gln Arg Val
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Met Ala Gly Ser Tyr Phe Leu Ser Pro Glu His Gln Arg Val Gln
1               5                   10                  15

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Met Ala Gly Ser Tyr Phe Leu Ser Pro Glu His Gln Arg Val Gln
1               5                   10                  15

Gln

<210> SEQ ID NO 269
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 269

Gly Met Ala Gly Ser Tyr Phe Leu Ser Pro Glu His Gln Arg Val Gln
1               5                   10                  15

Gln Arg

<210> SEQ ID NO 270
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Met Ala Gly Ser Tyr Phe Leu Ser Pro Glu His Gln Arg Val Gln
1               5                   10                  15

Gln Arg Lys

<210> SEQ ID NO 271
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Met Ala Gly Ser Tyr Phe Leu Ser Pro Glu His Gln Arg Val Gln
1               5                   10                  15

Gln Arg Lys Glu
            20

<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Met Ala Gly Ser Tyr Phe Leu Ser Pro Glu His Gln Arg Val Gln
1               5                   10                  15

Gln Arg Lys Glu Ser
            20

<210> SEQ ID NO 273
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Met Ala Gly Ser Tyr Phe Leu Ser Pro Glu His Gln Arg Val Gln
1               5                   10                  15

Gln Arg Lys Glu Ser Lys
            20

<210> SEQ ID NO 274
<211> LENGTH: 23
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 274

Gly Met Ala Gly Ser Tyr Phe Leu Ser Pro Glu His Gln Arg Val Gln
1               5                   10                  15

Gln Arg Lys Glu Ser Lys Lys
            20

<210> SEQ ID NO 275
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gly Met Ala Gly Ser Tyr Phe Leu Ser Pro Glu His Gln Arg Val Gln
1               5                   10                  15

Gln Arg Lys Glu Ser Lys Lys Pro
            20

<210> SEQ ID NO 276
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Met Ala Gly Ser Tyr Phe Leu Ser Pro Glu His Gln Arg Val Gln
1               5                   10                  15

Gln Arg Lys Glu Ser Lys Lys Pro Pro
            20                  25

<210> SEQ ID NO 277
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gly Met Ala Gly Ser Tyr Phe Leu Ser Pro Glu His Gln Arg Val Gln
1               5                   10                  15

Gln Arg Lys Glu Ser Lys Lys Pro Pro Ala
            20                  25

<210> SEQ ID NO 278
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys
```

20                  25

<210> SEQ ID NO 279
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu
                20                  25

<210> SEQ ID NO 280
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln
                20                  25

<210> SEQ ID NO 281
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro
                20                  25                  30

<210> SEQ ID NO 282
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg
                20                  25                  30

<210> SEQ ID NO 283
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 283

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Met Ala Gly Ser Tyr Phe Leu
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Met Ala Gly Ser Tyr Phe Leu Ser
1               5

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Met Ala Gly Ser Tyr Phe Leu Ser Pro
1               5                   10

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Met Ala Gly Ser Tyr Phe Leu Ser Pro Glu
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ala Met Ala Gly Ser Tyr Phe Leu Ser Pro Glu His
1               5                   10
```

```
<210> SEQ ID NO 289
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Met Ala Gly Ser Tyr Phe Leu Ser Pro Glu His Gln
1               5                   10

<210> SEQ ID NO 290
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Met Ala Gly Ser Tyr Phe Leu Ser Pro Glu His Gln Arg
1               5                   10

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Met Ala Gly Ser Tyr Phe Leu Ser Pro Glu His Gln Arg Val
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Met Ala Gly Ser Tyr Phe Leu Ser Pro Glu His Gln Arg Val Gln
1               5                   10                  15

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Met Ala Gly Ser Tyr Phe Leu Ser Pro Glu His Gln Arg Val Gln
1               5                   10                  15

Gln

<210> SEQ ID NO 294
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 294

Ala Met Ala Gly Ser Tyr Phe Leu Ser Pro Glu His Gln Arg Val Gln
1               5                   10                  15

Gln Arg

<210> SEQ ID NO 295
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ala Met Ala Gly Ser Tyr Phe Leu Ser Pro Glu His Gln Arg Val Gln
1               5                   10                  15

Gln Arg Lys

<210> SEQ ID NO 296
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ala Met Ala Gly Ser Tyr Phe Leu Ser Pro Glu His Gln Arg Val Gln
1               5                   10                  15

Gln Arg Lys Glu
            20

<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ala Met Ala Gly Ser Tyr Phe Leu Ser Pro Glu His Gln Arg Val Gln
1               5                   10                  15

Gln Arg Lys Glu Ser
            20

<210> SEQ ID NO 298
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ala Met Ala Gly Ser Tyr Phe Leu Ser Pro Glu His Gln Arg Val Gln
1               5                   10                  15

Gln Arg Lys Glu Ser Lys
            20

<210> SEQ ID NO 299
<211> LENGTH: 23
<212> TYPE: PRT

<213> ORGANISM: Artificial Sequence
<220> FEATURE:
<223> OTHER INFORMATION: Description of Artificial Sequence: Synthetic peptide

<400> SEQUENCE: 299

Ala Met Ala Gly Ser Tyr Phe Leu Ser Pro Glu His Gln Arg Val Gln
1               5                   10                  15

Gln Arg Lys Glu Ser Lys Lys
            20

<210> SEQ ID NO 300
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Ala Met Ala Gly Ser Tyr Phe Leu Ser Pro Glu His Gln Arg Val Gln
1               5                   10                  15

Gln Arg Lys Glu Ser Lys Lys Pro
            20

<210> SEQ ID NO 301
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 301

Ala Met Ala Gly Ser Tyr Phe Leu Ser Pro Glu His Gln Arg Val Gln
1               5                   10                  15

Gln Arg Lys Glu Ser Lys Lys Pro Pro
            20                  25

<210> SEQ ID NO 302
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Ala Met Ala Gly Ser Tyr Phe Leu Ser Pro Glu His Gln Arg Val Gln
1               5                   10                  15

Gln Arg Lys Glu Ser Lys Lys Pro Pro Ala
            20                  25

<210> SEQ ID NO 303
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 303

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys 20                  25

<210> SEQ ID NO 304
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu
                20                  25

<210> SEQ ID NO 305
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln
                20                  25

<210> SEQ ID NO 306
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro
                20                  25                  30

<210> SEQ ID NO 307
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg
                20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 308

Ala Met Ala Gly Ser Tyr Phe Leu Ser Pro Glu His Gln Arg Val Gln
1               5                   10                  15

Gln Arg Lys Glu Ser Lys Lys Pro Ala Lys Leu Gln Pro Arg Trp
            20                  25                  30

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 309

Gly Met Ala Gly Ser Tyr Phe Leu
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 310

Gly Met Ala Gly Ser Tyr Phe Leu Ser
1               5

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 311

Gly Met Ala Gly Ser Tyr Phe Leu Ser Pro
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 312

Gly Met Ala Gly Ser Tyr Phe Leu Ser Pro Glu
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<223> OTHER INFORMATION: C-term NH2

<400> SEQUENCE: 313

Gly Met Ala Gly Ser Tyr Phe Leu Ser Pro Glu His
1               5                   10

<210> SEQ ID NO 314
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 314

Gly Met Ala Gly Ser Tyr Phe Leu Ser Pro Glu His Gln
1               5                   10

<210> SEQ ID NO 315
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 315

Gly Met Ala Gly Ser Tyr Phe Leu Ser Pro Glu His Gln Arg
1               5                   10

<210> SEQ ID NO 316
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 316

Gly Met Ala Gly Ser Tyr Phe Leu Ser Pro Glu His Gln Arg Val
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 317

Gly Met Ala Gly Ser Tyr Phe Leu Ser Pro Glu His Gln Arg Val Gln
1               5                   10                  15

<210> SEQ ID NO 318
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: C-term NH2

<400> SEQUENCE: 318

Gly Met Ala Gly Ser Tyr Phe Leu Ser Pro Glu His Gln Arg Val Gln
1               5                   10                  15

Gln

<210> SEQ ID NO 319
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 319

Gly Met Ala Gly Ser Tyr Phe Leu Ser Pro Glu His Gln Arg Val Gln
1               5                   10                  15

Gln Arg

<210> SEQ ID NO 320
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 320

Gly Met Ala Gly Ser Tyr Phe Leu Ser Pro Glu His Gln Arg Val Gln
1               5                   10                  15

Gln Arg Lys

<210> SEQ ID NO 321
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 321

Gly Met Ala Gly Ser Tyr Phe Leu Ser Pro Glu His Gln Arg Val Gln
1               5                   10                  15

Gln Arg Lys Glu
            20

<210> SEQ ID NO 322
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 322
```

Gly Met Ala Gly Ser Tyr Phe Leu Ser Pro Glu His Gln Arg Val Gln
1               5                   10                  15

Gln Arg Lys Glu Ser
            20

<210> SEQ ID NO 323
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 323

Gly Met Ala Gly Ser Tyr Phe Leu Ser Pro Glu His Gln Arg Val Gln
1               5                   10                  15

Gln Arg Lys Glu Ser Lys
            20

<210> SEQ ID NO 324
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 324

Gly Met Ala Gly Ser Tyr Phe Leu Ser Pro Glu His Gln Arg Val Gln
1               5                   10                  15

Gln Arg Lys Glu Ser Lys Lys
            20

<210> SEQ ID NO 325
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 325

Gly Met Ala Gly Ser Tyr Phe Leu Ser Pro Glu His Gln Arg Val Gln
1               5                   10                  15

Gln Arg Lys Glu Ser Lys Lys Pro
            20

<210> SEQ ID NO 326
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 326

Gly Met Ala Gly Ser Tyr Phe Leu Ser Pro Glu His Gln Arg Val Gln
1               5                   10                  15

```
Gln Arg Lys Glu Ser Lys Pro Pro
            20                  25

<210> SEQ ID NO 327
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 327

Gly Met Ala Gly Ser Tyr Phe Leu Ser Pro Glu His Gln Arg Val Gln
1               5                   10                  15

Gln Arg Lys Glu Ser Lys Pro Pro Ala
            20                  25

<210> SEQ ID NO 328
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 328

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 329
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 329

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 330
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 330

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln
            20                  25
```

```
<210> SEQ ID NO 331
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 331

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 332
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 332

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 333
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 333

Gly Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 334

Ala Met Ala Gly Ser Tyr Phe Leu
1               5

<210> SEQ ID NO 335
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 335

Ala Met Ala Gly Ser Tyr Phe Leu Ser
1               5

<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 336

Ala Met Ala Gly Ser Tyr Phe Leu Ser Pro
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 337

Ala Met Ala Gly Ser Tyr Phe Leu Ser Pro Glu
1               5                   10

<210> SEQ ID NO 338
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 338

Ala Met Ala Gly Ser Tyr Phe Leu Ser Pro Glu His
1               5                   10

<210> SEQ ID NO 339
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 339

Ala Met Ala Gly Ser Tyr Phe Leu Ser Pro Glu His Gln
1               5                   10

<210> SEQ ID NO 340
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 340

Ala Met Ala Gly Ser Tyr Phe Leu Ser Pro Glu His Gln Arg
1               5                   10

<210> SEQ ID NO 341
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 341

Ala Met Ala Gly Ser Tyr Phe Leu Ser Pro Glu His Gln Arg Val
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 342

Ala Met Ala Gly Ser Tyr Phe Leu Ser Pro Glu His Gln Arg Val Gln
1               5                   10                  15

<210> SEQ ID NO 343
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 343

Ala Met Ala Gly Ser Tyr Phe Leu Ser Pro Glu His Gln Arg Val Gln
1               5                   10                  15

Gln

<210> SEQ ID NO 344
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 344

Ala Met Ala Gly Ser Tyr Phe Leu Ser Pro Glu His Gln Arg Val Gln
1               5                   10                  15

Gln Arg
```

```
<210> SEQ ID NO 345
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 345

Ala Met Ala Gly Ser Tyr Phe Leu Ser Pro Glu His Gln Arg Val Gln
1               5                   10                  15

Gln Arg Lys

<210> SEQ ID NO 346
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 346

Ala Met Ala Gly Ser Tyr Phe Leu Ser Pro Glu His Gln Arg Val Gln
1               5                   10                  15

Gln Arg Lys Glu
            20

<210> SEQ ID NO 347
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 347

Ala Met Ala Gly Ser Tyr Phe Leu Ser Pro Glu His Gln Arg Val Gln
1               5                   10                  15

Gln Arg Lys Glu Ser
            20

<210> SEQ ID NO 348
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 348

Ala Met Ala Gly Ser Tyr Phe Leu Ser Pro Glu His Gln Arg Val Gln
1               5                   10                  15

Gln Arg Lys Glu Ser Lys
            20

<210> SEQ ID NO 349
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 349

Ala Met Ala Gly Ser Tyr Phe Leu Ser Pro Glu His Gln Arg Val Gln
1               5                   10                  15

Gln Arg Lys Glu Ser Lys Lys
            20

<210> SEQ ID NO 350
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 350

Ala Met Ala Gly Ser Tyr Phe Leu Ser Pro Glu His Gln Arg Val Gln
1               5                   10                  15

Gln Arg Lys Glu Ser Lys Lys Pro
            20

<210> SEQ ID NO 351
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 351

Ala Met Ala Gly Ser Tyr Phe Leu Ser Pro Glu His Gln Arg Val Gln
1               5                   10                  15

Gln Arg Lys Glu Ser Lys Lys Pro Pro
            20                  25

<210> SEQ ID NO 352
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 352

Ala Met Ala Gly Ser Tyr Phe Leu Ser Pro Glu His Gln Arg Val Gln
1               5                   10                  15

Gln Arg Lys Glu Ser Lys Lys Pro Pro Ala
            20                  25

<210> SEQ ID NO 353
<211> LENGTH: 27
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: C-term NH2

<400> SEQUENCE: 353

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys
            20                  25

<210> SEQ ID NO 354
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 354

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu
            20                  25

<210> SEQ ID NO 355
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 355

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln
            20                  25

<210> SEQ ID NO 356
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 356

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro
            20                  25                  30

<210> SEQ ID NO 357
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: C-term NH2

<400> SEQUENCE: 357

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 358
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 358

Ala Met Ala Gly Ser Tyr Phe Leu Ser Pro Glu His Gln Arg Val Gln
1               5                   10                  15

Gln Arg Lys Glu Ser Lys Lys Pro Pro Ala Lys Leu Gln Pro Arg Trp
            20                  25                  30

<210> SEQ ID NO 359
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)

<400> SEQUENCE: 359

Gly Met Ala Gly Ser Xaa Phe Leu Ser Pro Glu His
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(palmityl)

<400> SEQUENCE: 360

Gly Met Ala Gly Ser Xaa Phe Leu Ser Pro Glu His
1               5                   10

<210> SEQ ID NO 361
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Des-Octanoyl)

<400> SEQUENCE: 361

```
Gly Met Ala Gly Ser Ser Phe Leu
1               5

<210> SEQ ID NO 362
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Dap(Octanoyl)

<400> SEQUENCE: 362

Gly Met Ala Gly Ser Xaa Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Octanoyl)

<400> SEQUENCE: 363

Gly Met Ala Gly Ser Xaa Phe Leu
1               5

<210> SEQ ID NO 364
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Des-Octanoyl)

<400> SEQUENCE: 364

Gly Met Ala Gly Ser Ser Phe
1               5

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser(Des-Octanoyl)

<400> SEQUENCE: 365

Gly Met Ala Gly Ser Ser Phe Leu Ser Pro Glu His Gln Arg Val Gln
1               5                   10                  15
```

Gln Arg Lys Glu Ser
            20

<210> SEQ ID NO 366
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser(Des-Octanoyl)

<400> SEQUENCE: 366

Gly Met Ala Gly Ser Ser Phe Leu Ser Pro Glu His Gln Arg Val Gln
1               5                   10                  15

Gln Arg Lys Glu Ser Lys Lys Pro Pro Ala Lys Leu Gln Pro Arg Tyr
            20                  25                  30

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any D-, L-, alpha-, beta-, or gamma- amino acid
      and this region may encompass 0 to 6 residues
<220> FEATURE:
<221> NAME/KEY: MOD_RES
<222> LOCATION: (9)..(9)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp and not D-Tyr or L-Tyr
<220> FEATURE:
<223> OTHER INFORMATION: May or may not be C-term NH2 or carboxyl
      protecting group

<400> SEQUENCE: 367

Xaa Xaa Xaa Xaa Xaa Xaa Gly Ser Xaa Phe Leu
1               5                   10

<210> SEQ ID NO 368
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Oct)

<400> SEQUENCE: 368

Gly Ser Xaa Phe Leu
1               5

<210> SEQ ID NO 369
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (3)..(3)
<223> OTHER INFORMATION: Ser(Des-Octanoyl)
<220> FEATURE:
<223> OTHER INFORMATION: C-term NH2

<400> SEQUENCE: 369

Gly Ser Ser Phe Leu
1               5

<210> SEQ ID NO 370
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Octanoyl)
<220> FEATURE:
<223> OTHER INFORMATION: C-term NH2

<400> SEQUENCE: 370

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 371
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Octanoyl)
<220> FEATURE:
<223> OTHER INFORMATION: C-term NH2

<400> SEQUENCE: 371

Gly Ser Xaa Phe Leu
1               5

<210> SEQ ID NO 372
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Des-Octanoyl)
<220> FEATURE:
<223> OTHER INFORMATION: C-term NH2

<400> SEQUENCE: 372

Gly Ser Ser Phe
1

<210> SEQ ID NO 373
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Des-Octanoyl)
<220> FEATURE:
<223> OTHER INFORMATION: C-term NH2

<400> SEQUENCE: 373

Gly Ser Ser Phe Leu Ser Pro Glu His Gln Arg Val Gln Gln Arg Lys
1               5                  10                  15

Glu Ser

<210> SEQ ID NO 374
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Des-Octanoyl)
<220> FEATURE:
<223> OTHER INFORMATION: C-term NH2

<400> SEQUENCE: 374

Gly Ser Ser Phe Leu Ser Pro Glu His Gln Arg Val Gln Gln Arg Lys
1               5                  10                  15

Glu Ser Lys Lys Pro Pro Ala Lys Leu Gln Pro Arg Tyr
            20                  25

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Inip
<220> FEATURE:
<223> OTHER INFORMATION: C-term NH2

<400> SEQUENCE: 375

Gly Met Ala Xaa Trp Trp Phe
1               5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Inip

<400> SEQUENCE: 376

Gly Met Ala Xaa Trp Trp Phe
1               5
```

```
<210> SEQ ID NO 377
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: alpha-Aib
<220> FEATURE:
<221> NAME/KEY: MOD_RES
<222> LOCATION: (5)..(5)
<223> OTHER INFORMATION: Ser(Bzl)
<220> FEATURE:
<223> OTHER INFORMATION: C-term may be 4-phenylpiperazin-1-yl,
      3a-benzyl-4,5,6,7-tetrahydro-2-methyl-2H-pyrazolo[4,3-c]pyridin-
      3(3aH)-on-5-yl or 1-(methylsulfonyl)spiro[indoline-3,4'-
      piperdine]-1'-yl

<400> SEQUENCE: 377

Gly Met Ala Xaa Ser
1               5

<210> SEQ ID NO 378
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala-psi[CH2NH]
<220> FEATURE:
<221> NAME/KEY: MOD_RES
<222> LOCATION: (4)..(4)
<223> OTHER INFORMATION: alpha-Aib
<220> FEATURE:
<221> NAME/KEY: MOD_RES
<222> LOCATION: (5)..(5)
<223> OTHER INFORMATION: Ser(Bzl)
<220> FEATURE:
<223> OTHER INFORMATION: C-term may be 4-phenylpiperazin-1-yl,
      3a-benzyl-4,5,6,7-tetrahydro-2-methyl-2H-pyrazolo[4,3-c]pyridin-
      3(3aH)-on-5-yl or 1-(methylsulfonyl)spiro[indoline-3,4'-
      piperdine]-1'-yl

<400> SEQUENCE: 378

Gly Met Ala Xaa Ser
1               5

<210> SEQ ID NO 379
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala[C(O)N(Me)]
<220> FEATURE:
<221> NAME/KEY: MOD_RES
<222> LOCATION: (4)..(4)
<223> OTHER INFORMATION: alpha-Aib
<220> FEATURE:
<221> NAME/KEY: MOD_RES
<222> LOCATION: (5)..(5)
<223> OTHER INFORMATION: Ser(Bzl)
<220> FEATURE:
<223> OTHER INFORMATION: C-term may be 4-phenylpiperazin-1-yl,
```

```
      3a-benzyl-4,5,6,7-tetrahydro-2-methyl-2H-pyrazolo[4,3-c]pyridin-
      3(3aH)-on-5-yl or 1-(methylsulfonyl)spiro[indoline-3,4'-
      piperdine]-1'-yl

<400> SEQUENCE: 379

Gly Met Ala Xaa Ser
1               5

<210> SEQ ID NO 380
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser conjugated with a -C(O)C1-C20 alkyl group
      on the side chain OH, diaminopropionic acid conjugated with a
      -C(O)C1-C20 alkyl group, L-Trp, or D-Trp
<220> FEATURE:
<221> NAME/KEY: MOD_RES
<222> LOCATION: (13)..(32)
<223> OTHER INFORMATION: Any amino acid and this region may encompass
      1 to 20 residues
<220> FEATURE:
<223> OTHER INFORMATION: May or may not be C-term NH2 or carboxyl
      protecting group
<220> FEATURE:
<223> OTHER INFORMATION: see specification as filed for detailed
      description of substitutions and preferred embodiments

<400> SEQUENCE: 380

Gly Met Ala Gly Ser Xaa Phe Leu Ser Pro Glu His Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala[C(O)N(Me)]

<400> SEQUENCE: 381

Leu Asp Leu Gly Met Ala
1               5

<210> SEQ ID NO 382
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala[C(O)N(Me)]

<400> SEQUENCE: 382

Leu Asp Leu Ala Met Ala
1               5
```

```
<210> SEQ ID NO 383
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser(OctDap)
<220> FEATURE:
<223> OTHER INFORMATION: C-term NH2

<400> SEQUENCE: 383

Gly Met Ala Gly Ser Phe Leu Ser Pro Glu His
1               5                   10

<210> SEQ ID NO 384
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Ser(OctDap)
<220> FEATURE:
<223> OTHER INFORMATION: C-term NH2

<400> SEQUENCE: 384

Gly Met Ala Gly Ser Phe Leu Ser Pro Glu His Gln Arg Val Gln Gln
1               5                   10                  15

Arg Lys Glu Ser Lys Lys Pro Pro Ala Lys Leu Gln Pro Arg
            20                  25                  30

<210> SEQ ID NO 385
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Gly Met Ala Gly Ser Trp Phe Leu Ser Pro Glu His Gln Arg Val Gln
1               5                   10                  15

Gln Arg Lys Glu Ser Lys Lys Pro Pro Ala Lys Leu Gln Pro Arg
            20                  25                  30

<210> SEQ ID NO 386
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Ser Pro Glu His
```

GROWTH HORMONE SECRETATOGUE RECEPTOR ANTAGONISTS AND USES THEREOF

RELATED APPLICATIONS

This application is a 35 U.S.C. §371 National Phase Entry Application of International Application No. PCT/US2011/040728 filed Jun. 16, 2011, which designates the U.S., and which claims benefit under 35 U.S.C. 119(e) of U.S. Provisional Patent Application Ser. No. 61/355,466 filed Jun. 16, 2010, the content of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy was created on Dec. 1, 2015 is named 2015-12-01_Sequence_Listing_732224-068312-US.txt and is 151 KB in size.

FIELD OF THE INVENTION

This invention relates to novel peptides that disrupt the activity of ghrelin, growth hormone releasing peptide and the growth hormone secretatogue receptor when introduced to animals, preferably humans, and methods of use thereof.

BACKGROUND OF THE INVENTION

The elevation of growth hormone (GH) levels in animals, e.g., mammals including humans, upon administration of GH-releasing compounds can lead to enhanced body weight. Ghrelin, identified as an endogenous ligand for the GH secretatogue receptor (GHS-R) is a powerful stimulator of pulsatile GH secretion and exhibits intricate interactions with the primary hypothalamic GH regulators (1-3). Ghrelin as well as growth hormone releasing peptides (GHRPs) and growth hormone secretatogues (GHSs) also function as potent orexigenic peptides (4-7). Initial peptide antagonists that inhibited the binding activity of GHSs in hypothalamic tissue in vitro were reported in 1991-92 (8-10). This included the Substance P analog, [$Arg^1$ $DPhe^5$ $DTrp^{7,9}$ $Leu^{11}$-]Substance P, that subsequently was demonstrated by Holst et al (vide infra) to have both inverse agonist and ghrelin-R antagonist activity. Orexigneic compounds stimulate appetite.

Ghrelin is a 28 amino acid peptide, which has a unique structure among peptide hormones as it is acylated at Ser3 usually with an n-octanoyl moiety (Bednarek et al., 2000; Kojima et al., 1999). This post-translational modification is essential for the activity of the hormone—as mediated through the seven transmembrane G (7TMG) protein coupled ghrelin receptor—both in vitro and in vivo (Kojima et al., 1999; Nakazato et al., 2001; Tschop et al., 2000).

Plasma levels of ghrelin rise precipitously in the blood before meals, when the stomach is empty, and fall after or during food consumption. Since intracadiac venous (i.v.) or intracerebroventricular (i.c.v) administration of ghrelin increases food intake, it appears that the physiological role of ghrelin is a link or messenger between the stomach and the hypothalamus and the pituitary. One hypothesis that when an organism is getting ready for a meal, the CNS sends signals to the GI tract telling that a meal is about to be consumed in order to obtain information back about the status of the digestive process, state of distension etc. from the various chemical and mechanical sensors in the gut. Here, ghrelin could be an important hormonal messenger, which is sent back to the central nervous system (CNS) as a signal telling that there is no food in the stomach and that the gastrointestinal (GI) tract is ready for a new meal. In such a paradigm it is clear that a blocker of the ghrelin receptor would be a very efficient anti-obesity agent, as it would block the meal initiating, appetite signal from the GI tract.

The ghrelin receptor, GHS-R 1a, belongs to a relatively small family of 7 transmembrane G-protein coupled receptors (11). A number of findings demonstrate how the ghrelin receptor may uniquely play a role in mediating the action on GH release and food intake. This includes ghrelin receptor genetics, mutations, structure, intracellular signaling, high constitutive activity, enhancement of the number of hypothalamic ghrelin receptors during starvation, etc. A spectrum of growth and metabolic changes occur in mice as a result of knockout of the ghrelin molecule as well as the ghrelin receptor. Adiposity in mice followed overexpression of the ghrelin receptor in hypothalamic growth hormone releasing hormone (GHRH) arcuate neurons. Over time, select biological effects of ghrelin/GHSs, especially non-endocrine effects, have been revealed which presumably occur via subtypes receptors of ghrelin or perhaps ghrelin receptors with select mutations. Evidence indicates binding and activation of the multifunctional CD36 receptor by GHSs. Another noteworthy finding of the ghrelin receptor was that under pathophysiological conditions the density of this receptor was reported to be five times greater in atherosclerotic coronary arteries (12).

Holst and Schwartz characterized the high constitutive activity of this receptor. Also, they demonstrated inhibition of the constitutive activity of the [$DArg^1$, $DPhe^5$, $DTrp^{7,9}$ $Leu^{11}$]-substance P analog which has been previously characterized both in vitro and in vivo as a weak competitive receptor antagonist to acute and chronic actions of GHRP-2 and ghrelin. These investigators demonstrated in vitro that this analog has 2 types of ghrelin receptor inhibiting activities. At a low dose (5 nM, $IC_{50}$), this Sub P analog is a potent inverse receptor agonist since it decreases elevated intracellular IP3 levels in the absence of ghrelin but also it is a weak ghrelin GHRP-6 competitive receptor antagonist since high dosages (630 nM, $IC_{50}$) inhibit receptor binding of both peptides (13,14). Petersen, Holst, Schwartz et. al. reported that continuous i.c.v 7 day infusion of a very low dose of the Sub P ghrelin receptor inverse agonist inhibited body weight gain of male rats (15). This was a dose that would be too low to function as a competitive ghrelin receptor antagonist and thus it was considered to be due to the inverse agonist activity of the Sub P analog. In vitro evidence supports GHS-R antagonists with only inverse agonist or only ghrelin/GHS-R activity or a combination of the two (16).

Another possible novel functional role of the high constitutive activity of the ghrelin receptor in the CNS was proposed by Zigman et el on the distribution and functional implication of the ghrelin receptor in the brain of the rat and mouse (17). They proposed that the high constitutive activity of the ghrelin receptor plays a key functional role at CNS sites at which the receptor is expressed within the blood brain barrier and thus does not have immediate access to circulating ghrelin. This in contrast to the ghrelin receptor located in the arcuate nucleus and dorsal vagal complex role. Thus it is possible that select GHSs, because of their different chemistry, may have ready access to brain sites inaccessible to ghrelin. If this occurs, GHSs' actions at these sites may alter the CNS ghrelin constitutive activity via receptor number and/or activity.

Although regulation of food intake by numerous hormones reveals its complexity, the inhibition of ghrelin induced food intake implies a fundamental biological functional aspect of the ghrelin system. For example, in the absence of the ghrelin receptor, transgenic female and male mice fed a high fat diet eat less food, less of the consumed calories are stored, fat is more of the energy substrate, and body weight and body fat are less in these mice than control mice (17, 18). When the ghrelin receptor was absent and mice were fed a normal diet, body weight and body fat were decreased in female but not in male mice. In the absence of the ghrelin peptide, transgenic male mice (female mice not studied) had less rapid body weight gain on a high fat diet (10). This was associated with increased energy expenditure and increased locomotive activity as well as decreased adiposity. Both of these studies indicate the ghrelin system is involved in body weight control especially when consuming a high caloric type of obese inducing diet. In the absence of the ghrelin receptor (GHS-R 1a), ghrelin no longer increased food intake. Thus, the singularity of this receptor for mediating ghrelin induced food intake is indicated. Also, hyperphagia is an established risk factor in diabetes mellitus in humans and evidence indicates that sub-threshold doses of ghrelin increases food intake in streptozotocin treated rats (20). Experimental studies in rats revealed interrelationships of ghrelin, somatostatin and GHRH on function of the GH axis (21,22).

Thus, compounds which effectively inhibit the ghrelin receptor are needed to disrupt the activity of ghrelin at the level of the CNS. Such compounds would be useful in the treatment of metabolic diseases and disorders such as obesity, diabetes mellitus, and inhibition of growth hormone secreted from tumors such as pituitary, prostate, osteoblast, pancreatic and hepatoma. Relevant basic and clinical ghrelin and GHS data have been presented by Bowers et al (23,24).

SUMMARY OF THE INVENTION

The inventors have surprisingly discovered that adding a GlyMetAla tripeptide at the N terminus of GHRPs/ghrelin peptide agonists and also nonpeptide receptor agonists converts them into ghrelin receptor antagonists. Accordingly, in one aspect the invention provides a ghrelin receptor antagonist, wherein the antagonist comprises a ghrelin/GHRPS agonist wherein is linked at its N-terminus by a GlyMetAla tripeptide. The linkage between the tripeptide and the agonist can be a regular amide linkage or a modified amide (i.e., modified peptide) linkage. Furthermore, the tripeptide can comprise one or more of D-, L-, α-, and/or β-amino acids. Additionally, the tripeptide can also comprise one or more modified amide linkages within the tripeptide.

Accordingly, in one aspect, the invention provides compounds of formula $X^1$—Y, wherein Y is an GHRPs/ghrelin peptide or nonpeptide agonist; $X^1$ is $A^1$-$A^2$-$A^3$-$A^4$-$A^5$-$A^6$-; each of $A^1$, $A^2$, $A^3$, $A^4$, $A^5$, and $A^6$ is the same or different and is absent (i.e., need not be present), a D amino acid, L amino acid, α-amino acid, β-amino acid, γ-amino acid, or an amino protecting group, an amino acid, or an amino protecting group, provided that at least one of $A^1$, $A^2$, $A^3$, $A^4$, $A^5$, and $A^6$ is present; and wherein, $X^1$ is linked to the N-terrminus of the GHRPs/ghrelin peptide or nonpeptide agonist. In some embodiments, Y is an GHS antagonist.

In some embodiments, a peptide antagonist of ghrelin receptor is of formula (I'):

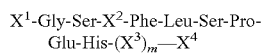

(Formula I') (SEQ ID NO: 1), wherein:
$X^1$ is $A^1$-$A^2$-$A^3$-$A^4$-$A^5$-$A^6$-;
$X^2$ is a serine conjugated with a —C(O)$C_1$-$C_{20}$ alkyl group on the side chain OH of said serine or a diaminopropionic acid conjugated with a —C(O)$C_1$-$C_{20}$ alkyl group on one of the amino groups of the diaminopropionic acid or amino acid Trp which can be of D or L conformation;
each $X^3$ is independently an amino acid for each occurrence;
$X^4$ is absent, $NH_2$, or a carboxyl protecting group;
each of $A^1$, $A^2$, $A^3$, $A^4$, $A^5$, and $A^6$ is the same or different and is absent (i.e., need not be present), a D amino acid, L amino acid, α-amino acid, β-amino acid, γ-amino acid, or an amino protecting group, provided that at least one of $A^1$, $A^2$, $A^3$, $A^4$, $A^5$, and $A^6$ is present;
m is an integer from 1 to 20; and
derivatives, analogs, and pharmaceutically acceptable salts thereof. Preferably pharmaceutically acceptable salts thereof.

In another aspect, the invention provides a method of modulating a ghrelin receptor, the method comprising contacting a ghrelin receptor with a ghrelin receptor antagonist described herein.

In yet another aspect, the invention provides a method for treatment, prevention, or management of obesity or obesity related disease or disorder, diabetes mellitus, metabolic syndrome, or cancer in a subject in need thereof, the method comprising the step of administering an effective amount of a ghrelin receptor antagonist described herein to the subject.

Figure 6:
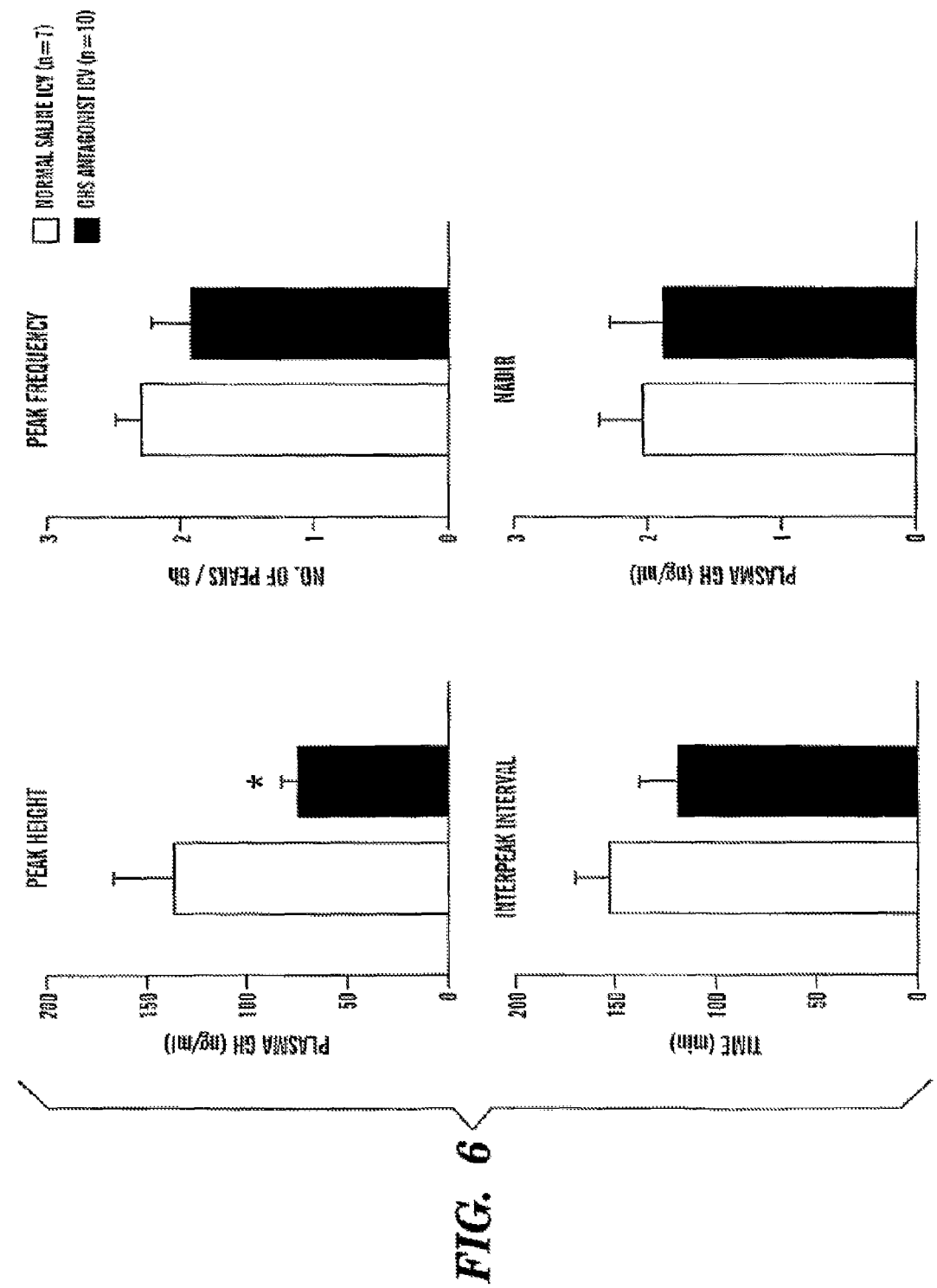

FIG. 6 shows a cluster analysis of the effects of centrally-administered GHS-A (5 μg) or normal saline on spontaneous GH pulse parameters. Cluster analysis revealed a significant suppression of GH peak height, but no significant effect of GHS-A on any other parameters of GH pulsatility, including GH peak frequency, interpeak interval and nadir, compared with normal saline icv-treated controls. Values are the mean±SE. *, P<0.03 vs. normal saline i.c.v.-treated controls.

Figure 7A:
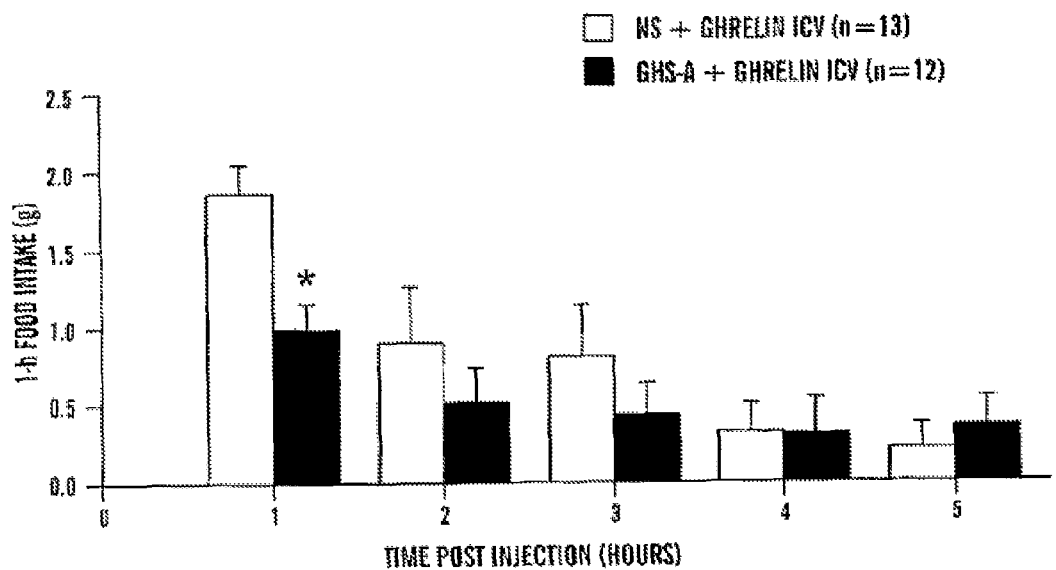
Figure 7B:
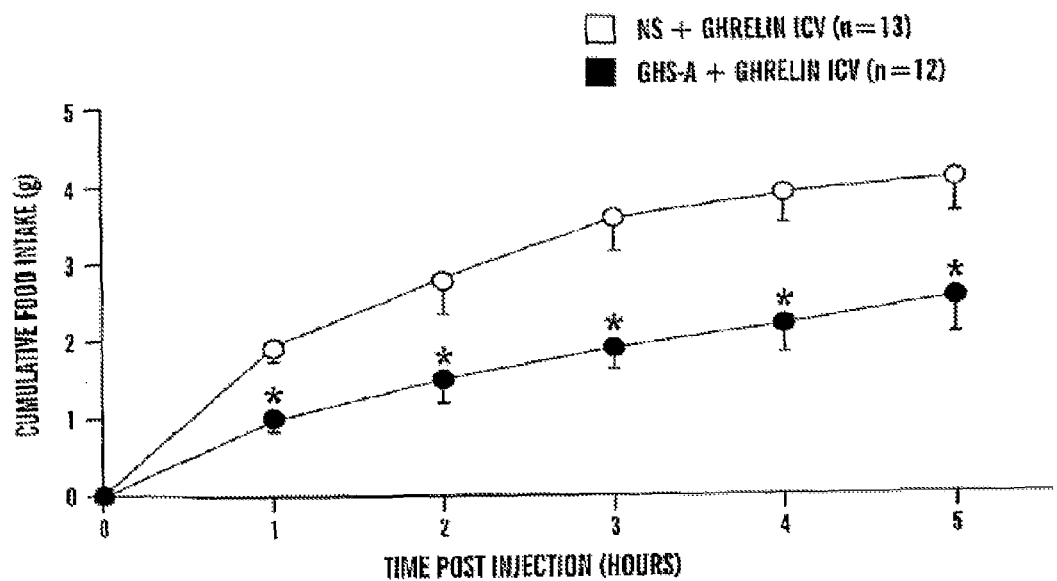

FIGS. 7A and 7B show a feeding response to icy-administered ghrelin (500 ng) in animals pretreated icy with either GHS-A (5 μg) or normal saline (FIG. 7A). GHS-A significantly inhibited ghrelin's stimulatory effects on food intake in the first hour after injections, compared with normal saline i.c.v.-pretreated controls (FIG. 7B). Cumulative food intake was significantly suppressed for up to 5 h after GHS-A injection. Values are the mean±SE. *, P<0.02 or less compared with normal saline icv-pretreated controls.

Figure 8A:
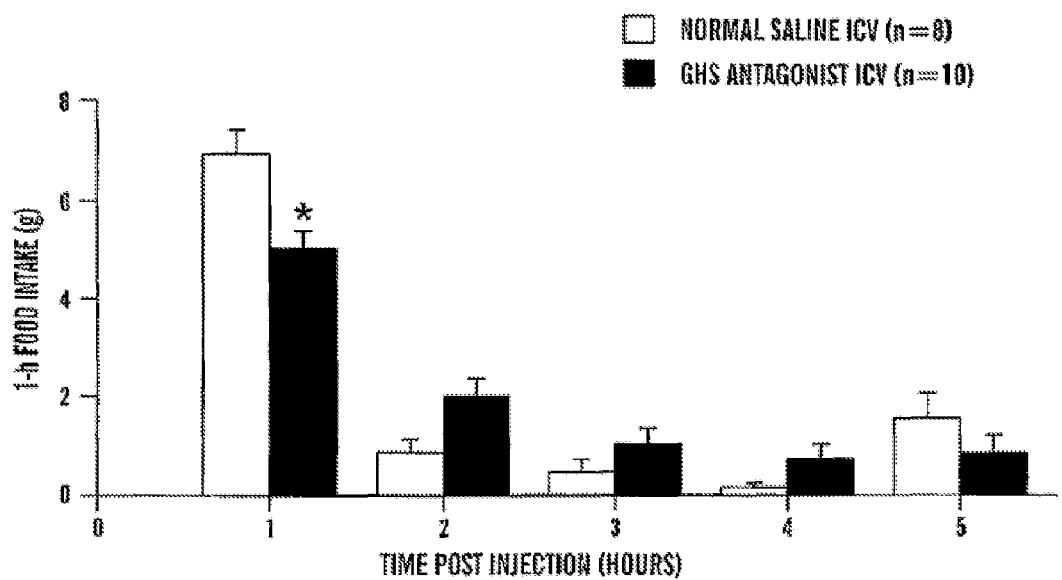
Figure 8B:
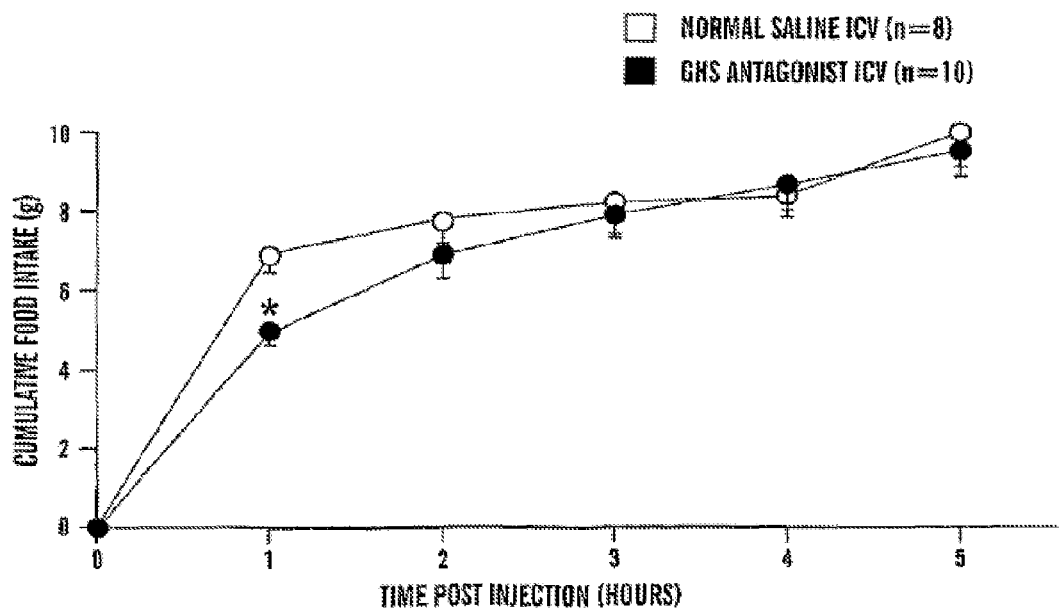

FIGS. 8A and 8B show the effects of icv-administered GHS-A (5 μg) or normal saline on spontaneous food intake in overnight-fasted animals (FIG. 8A). GHS-A significantly inhibited spontaneous food intake in the first hour after injection, compared with normal saline icy-treated controls (FIG. 8B). Cumulative food intake was not inhibited by GHS-A beyond the first hour after injection. Values are the mean± SE. *, P<0.004 compared with normal saline icy-treated controls.

Figure 9:
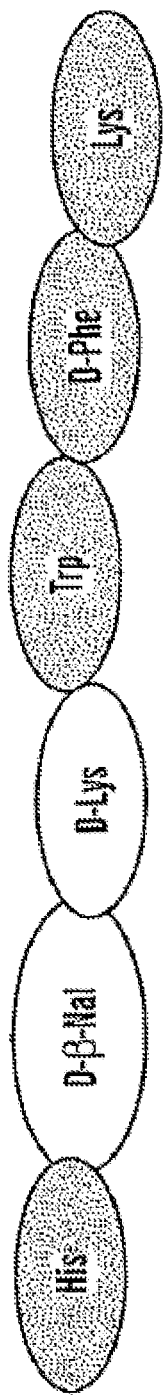

FIG. 9 shows a diagram of one ghrelin receptor antagonist HisDβNalDLysTrpDPheLysNH$_2$.

Figure 10:
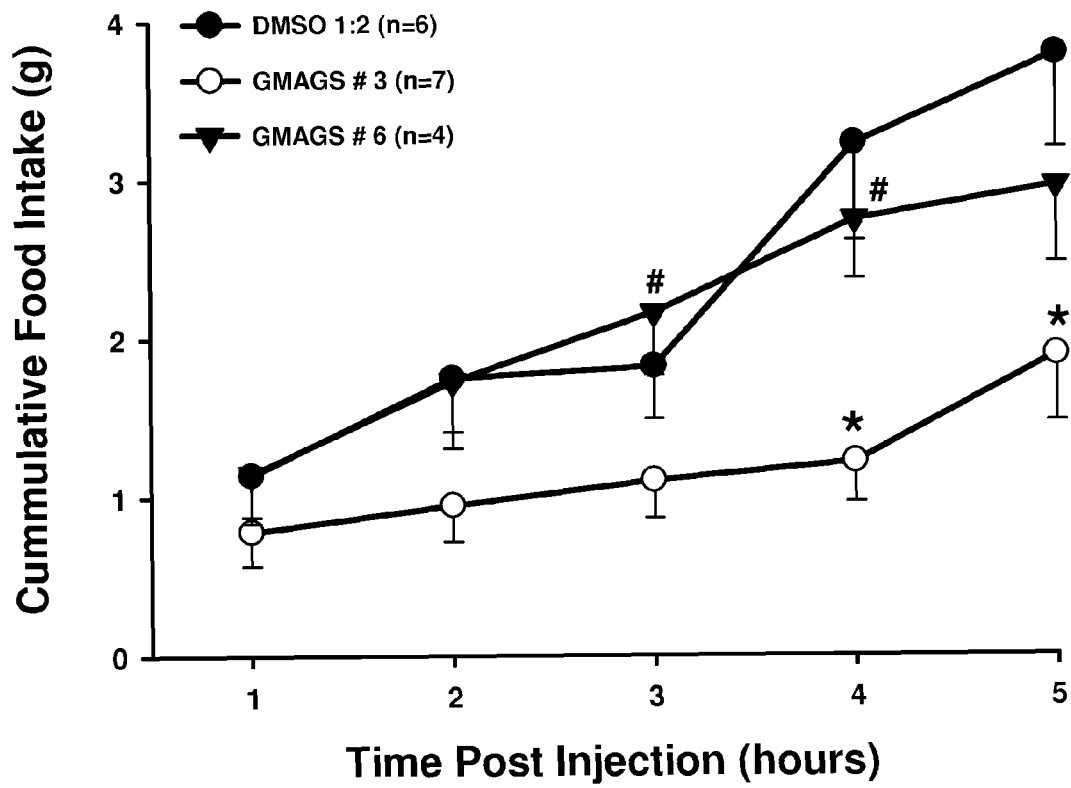

FIG. 10 shows GMAGS(Dap-Oct)FLSPEH-NH$_2$ (peptide #3) (SEQ ID NO: 2), but not GMAGS(Dap-Palmityl)FL-SPEH-NH$_2$ (peptide #6) (SEQ ID NO: 3) inhibited food intake. FIG. 10 discloses "GMAGS #3" and "GMAGS #6" as residues 1-5 of SEQ ID NOS 2 and 3, respectively.

Figure 11:
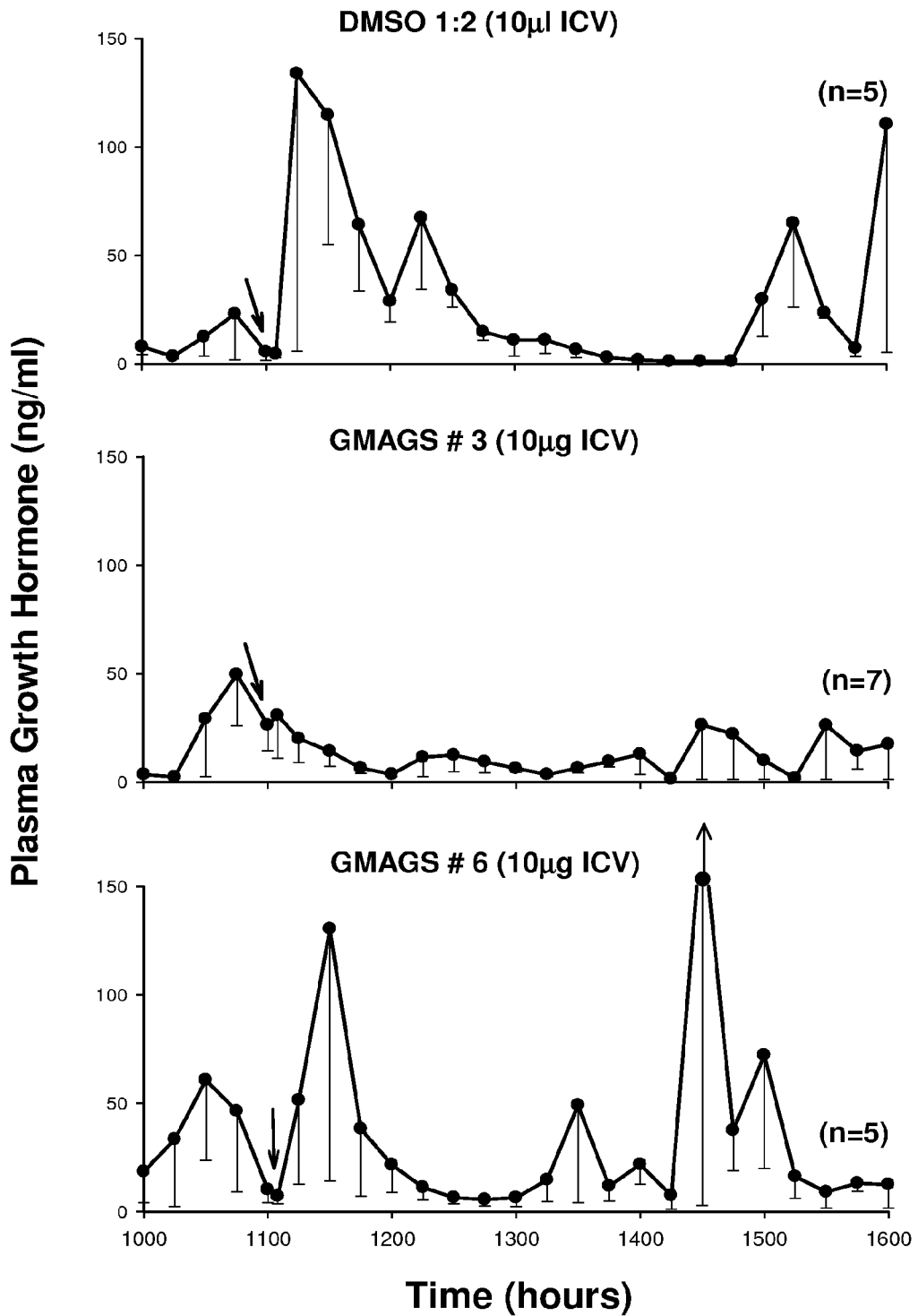

FIG. 11 shows GMAGS(Dap-Oct)FLSPEH-NH$_2$ (peptide #3) (SEQ ID NO: 2), but not GMAGS(Dap-Palmityl)FL-SPEH-NH$_2$ (peptide #6) (SEQ ID NO: 3) inhibited growth hormone secretion. FIG. 11 discloses "GMAGS #3" and "GMAGS #6" as residues 1-5 of SEQ ID NOS 2 and 3, respectively.

Figure 12:
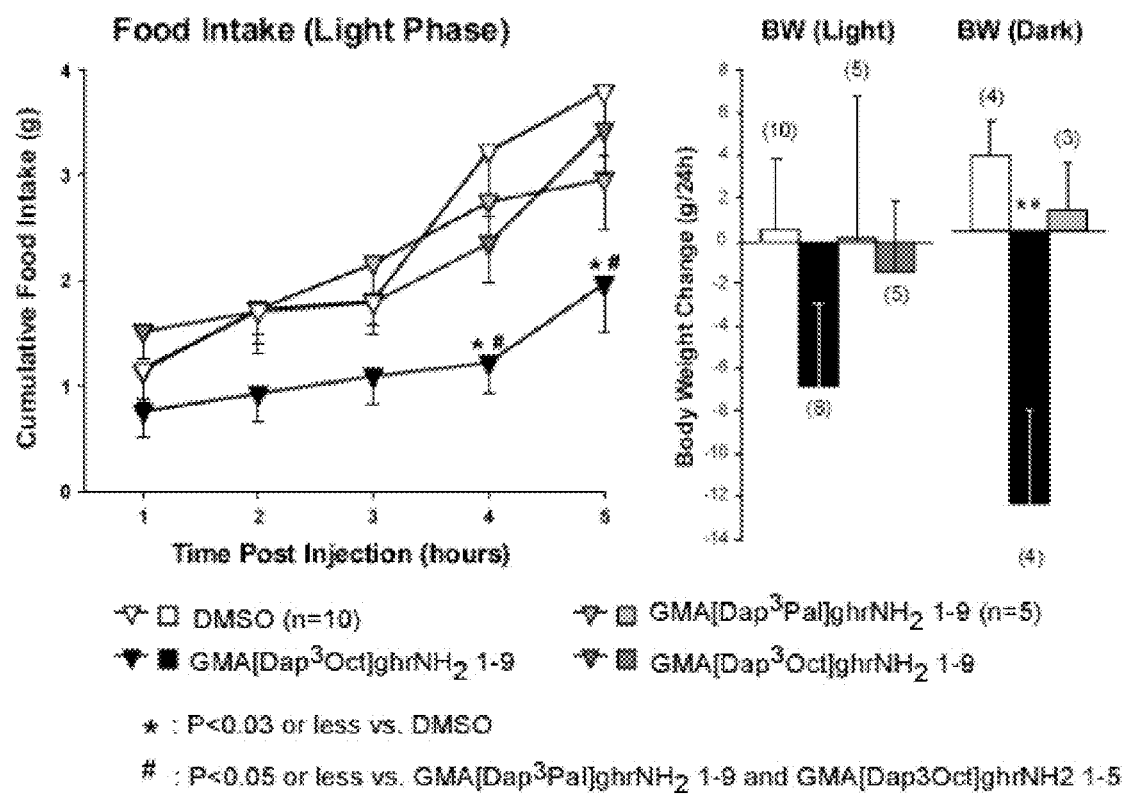

FIG. 12 shows that GMA{Dap$^3$Oct}ghrelinNH$_2$ 1-9 inhibits food intake and body weight gain.

Figure 13:
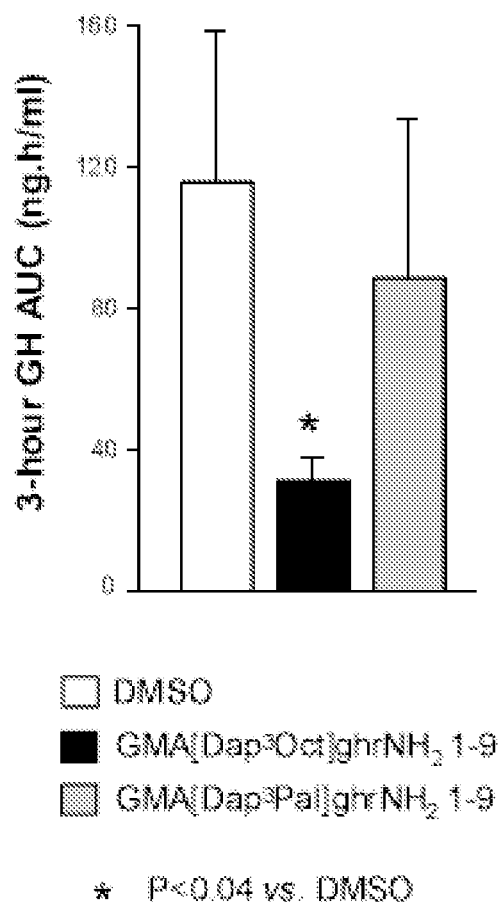

FIG. 13 shows that GMA duodecapeptide ghrelin analog has inhibitory activity on spontaneous pulsatil GH secrtion. Central administration of GMA{Dap$^3$Oct]ghrelinNH$_2$ 1-9 caused a 3-to-4-fold decrease in mean plasma GH levels compared with controls.

Figure 14:
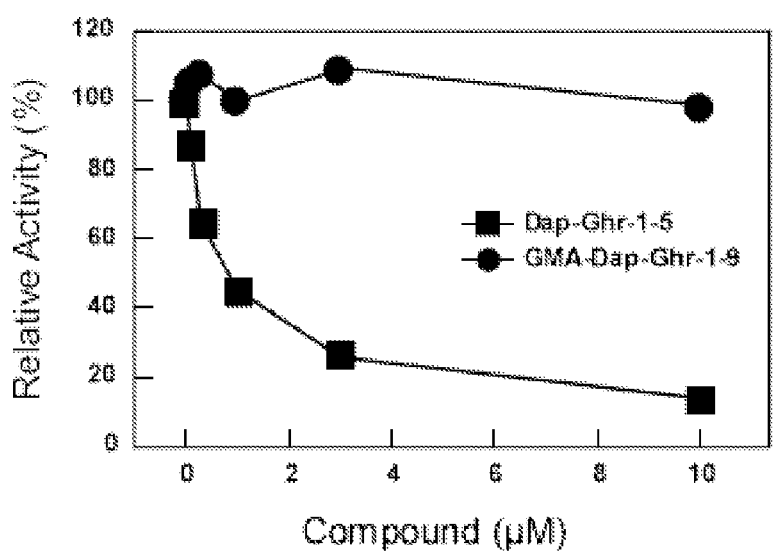

FIG. 14 shows that the GMA dudecapeptide ghrelin analog was ineffective in inhibiting the Acyl Transferase activity of GOAT in vitro. Moreover, the six ghrelin analogs did not inhibit the acyl (octanoyl) trasferase activity of ERAT (data not shown).

Figure 15:
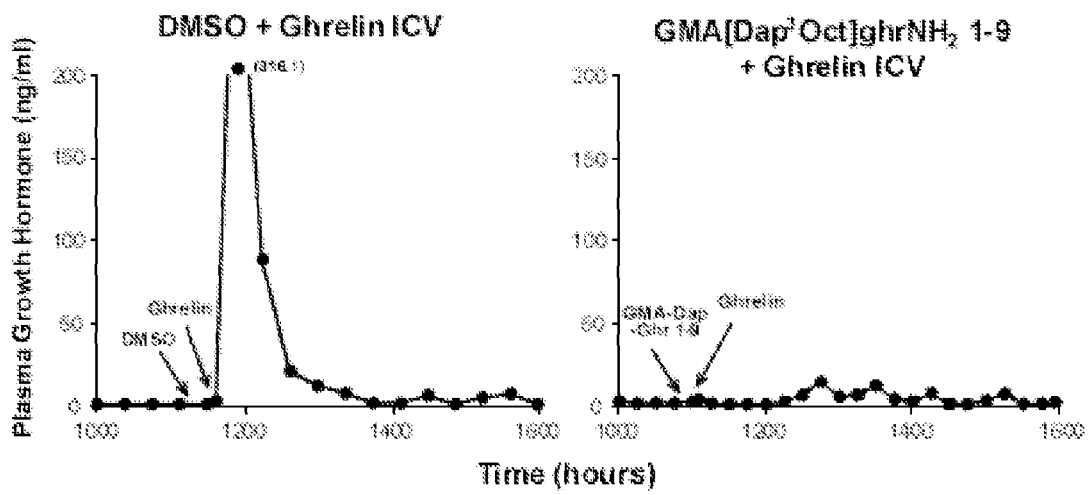

FIG. 15 shows that pretreatment with GMA[Dap$^3$Oct]ghrelionNH$_2$ 1-9 blocked the stimulatory action of ghrelin on GH release. This indicates that GMA[Dap$^3$Oct]ghrelionNH$_2$ 1-9 may be acting via a direct inhibition of the hypothalamic ghrelin receptor.

Figure 16:
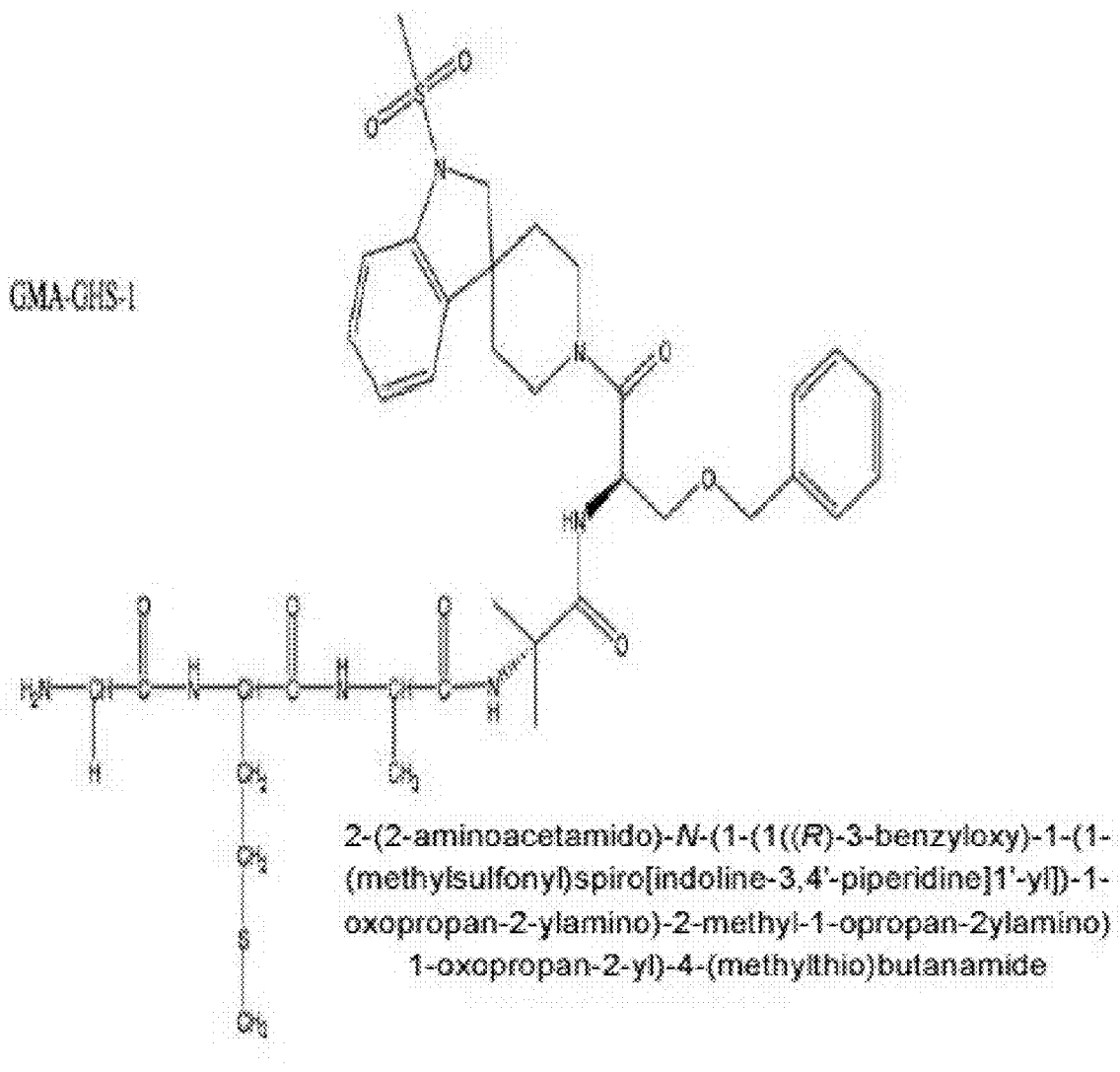

FIG. 16 shows the structure of 2-(2-aminoacetamido)-N-(1-(1-((R)-1-((R)-3-benzyloxy)-1-(1-(methylsulfonyl)spiro[indoline-3,4'-piperdin]-1'-yl)-1-oxopropan-2-ylamino)-2-methyl-1-oxopropan-2-ylamino)-1-oxopropan-2-yl)-4-(methylthio)butanamide (GMA-GHS-1GMA-GHS-1).

Figure 17:
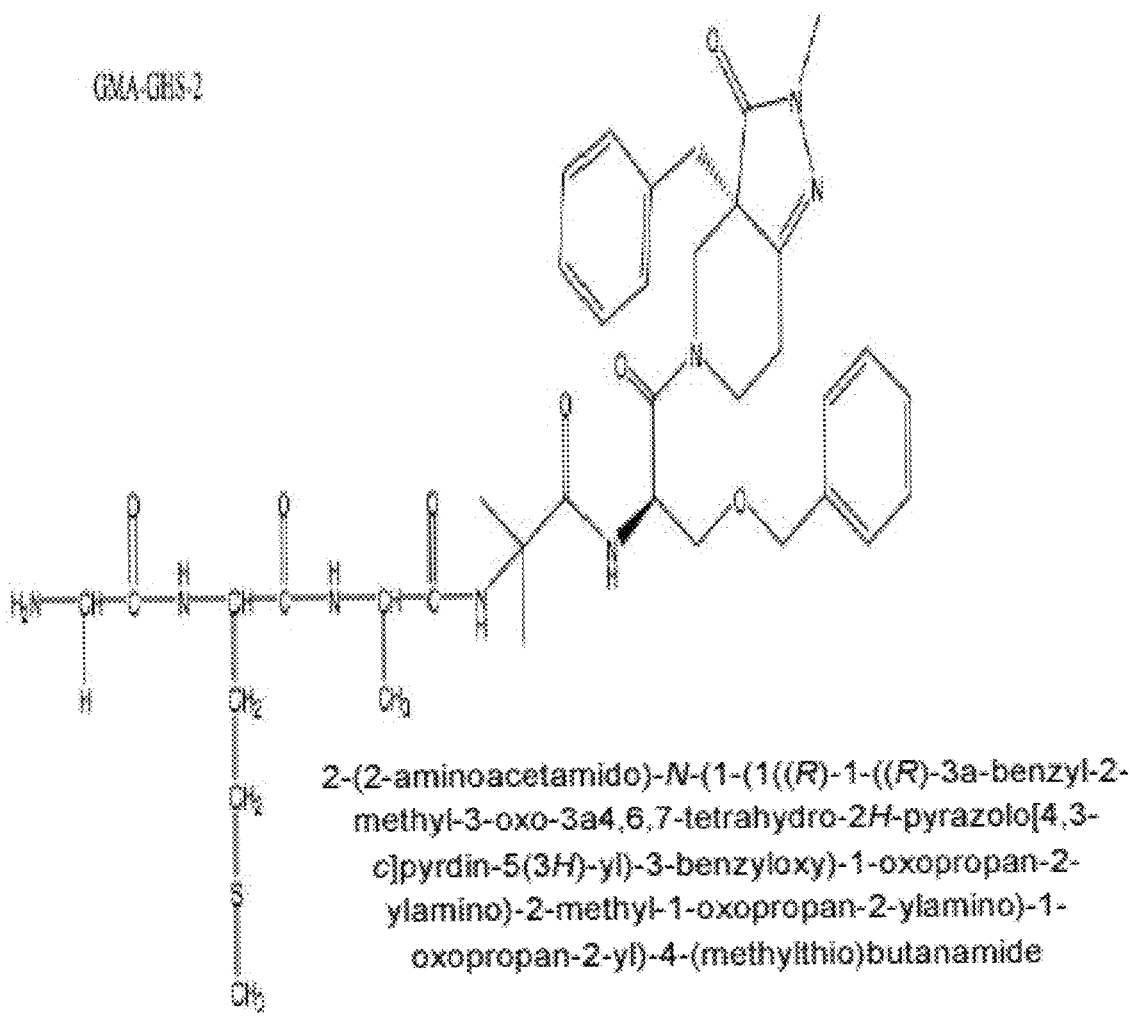

FIG. 17 shows the structure of 2-(2-aminoacetamido)-N-(1-(1-((R)-1-((R)-3a-benzyl-2-methyl-3-oxo-3a,4,6,7,-tetrahydro-2H-pyrazolo[4,3-c]pyridine-5 (3H)-yl)-3-(benzyloxy)-1-oxopropan-2-ylamino)-2-methyl-1-oxopropan-2-ylamino)-1-oxopropan-2-yl)-4-(methylthio)butanamide (GMA-GHS-2).

Figure 18:
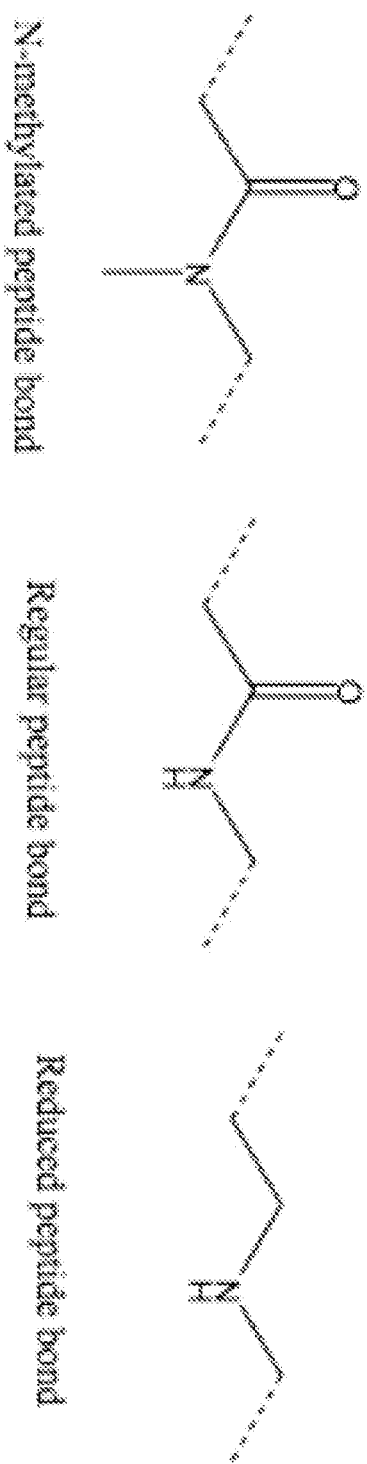

FIG. 18 is a schematic representation of exemplary modified and unmodified peptide-linkages.

DETAILED DESCRIPTION OF THE INVENTION

The inventors have surprisingly discovered that adding a GlyMetAla tripeptide at the N terminus of GHRPs/ghrelin peptide agonists and also nonpeptide receptor agonists converts them into ghrelin receptor antagonists. Accordingly, the invention provides a new class of peptides that provide in vitro and in vivo inhibition of activation of the ghrelin receptor, GHS-R 1a. Accordingly, in one aspect, the invention provides compounds of formula $X^1$—Y, wherein Y is an GHRPs/ghrelin peptide or nonpeptide agonist; $X^1$ is $A^1$-$A^2$-$A^3$-$A^4$-$A^5$-$A^6$-; each of $A^1$, $A^2$, $A^3$, $A^4$, $A^5$, and $A^6$ is the same or different and is absent (i.e., need not be present), a D amino acid, L amino acid, α-amino acid, β-amino acid, γ-amino acid, or an amino protecting group, provided that at least one of $A^1$, $A^2$, $A^3$, $A^4$, $A^5$, and $A^6$ is present; and wherein, $X^1$ is linked to the N-terrminus of the GHRPs/ghrelin peptide or nonpeptide agonist.

In some embodiments, the linkage between $X^1$ and the GHRPs/ghrelin peptide or nonpeptide agonist is a modified peptide or a non-amide linkage. In some embodiments, the linkage between $X^1$ and the GHRPs/ghrelin peptide or nonpeptide agonist is a non-amide linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. In some embodiments, the amine in the amide linkagae between $X^1$ and GHRPs/ghrelin peptide or nonpeptide agonist is alkylated, e.g., methylated.

Accordingly, in one aspect, the invention provides novel peptides that are antagonists of ghrelin receptor. In some embodiments, the peptide is of formula (I):

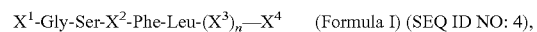

wherein:
$X^1$ is $A^1$-$A^2$-$A^3$-$A^4$-$A^5$-$A^6$-;
$X^2$ is a serine conjugated with a —C(O)C$_1$-C$_{20}$ alkyl group on the side chain OH of said serine or a diaminopropionic acid conjugated with a —C(O)C$_1$-C$_{20}$ alkyl group on one of the amino groups of the diaminopropionic acid or amino acid Trp which can be of D or L conformation;
each $X^3$ is independently a D amino acid, L amino acid, α-amino acid, or β-amino acid for each occurrence;
$X^4$ is absent, NH$_2$, or a carboxyl protecting group;
each of $A^1$, $A^2$, $A^3$, $A^4$, $A^5$, and $A^6$ is the same or different and is absent (i.e., need not be present), a D amino acid, L amino acid, α-amino acid, β-amino acid, γ-amino acid, or an amino protecting group, provided that at least one of $A^1$, $A^2$, $A^3$, $A^4$, $A^5$, and $A^6$ is present;
n is an integer from 0 to 24; and
derivatives, analogs, and pharmaceutically acceptable salts thereof.

In some embodiments, n is an integer from 5 to 24.

In some embodiments, a peptide of formula (I) is a peptide of formula (I'). The term "alkyl" refers to saturated non-aromatic hydrocarbon chains that may be a straight chain or branched chain, containing the indicated number of carbon atoms (these include without limitation propyl, allyl, or propargyl), which chain can be optionally inserted with one or more of heteroatoms (e.g. N, O, and S), aryls, heteroaryls, cyclyls, and heterocyclyls. For example, $C_1$-$C_6$ indicates that the group may have from 1 to 6 (inclusive) carbon atoms in it. In some embodiments, the alkyl is a $C_1$-$C_{16}$ alkyl, e.g., methyl, ethyl, butyl, pentyl, hexyl, heptyl, octyl, nonyl, decyl, undecyl, dodecyl, tridecyl, myristyl, pentadecyl, palmityl, margaryl, stearyl and nonadecyl. In some embodiments, the alkyl is a $C_6$-$C_{16}$ alkyl. The alkyl can be optionally substituted with 1 or more (e.g., 1, 2, 3, 4, 5 or more) substitutents.

The —C(O)$C_1$-$C_{20}$ alkyl group can be acyl portion (e.g. —C(O)-alkyl group) of a fatty acid. Exemplary fatty acids include, but are not limited to, Arachidic acid, Arachidonic acid, Capric acid, Caproic acid, Caprylic acid, Dihomo-γ-linolenic acid, Eicosapentaenoic acid, Eicosenoic acid, Eixosapentaen acid, Elaidic acid, Enanthic acid, Lauric acid, Linoelaidic acid, Linoleic acid, Margaric acid, Myristic acid, Myristoleic acid, Nonadecylic acid, Oleic acid, Palmitic acid, Palmitoleic acid, Pelargonic acid, Pentadecylic acid, Sapienic acid, Stearic acid, Stearidonic acid, Tridecylic acid, Undecylic acid, Vaccenic acid, Vaccenic acid, α-Linolenic acid, and γ-Linolenic acid.

In some embodiments, $X^2$ is a serine conjugated with an octanoyl group on the side chain OH of the serine.

In some embodiments, $X^2$ is a diaminopropanic acid conjugated with a —C(O)$C_1$-$C_{20}$ alkyl group on one of the two amino groups of the diaminopropanic acid. The —C(O)$C_1$-$C_{20}$ alkyl group can can be linked to the amino group at the 2 position or the 3 position of the diaminopropionic acid. In some embodiments, the —C(O)$C_1$-$C_{20}$ alkyl group is linked to the amino group on the 2 position of the diaminopropionic acid. In some other embodiments, the —C(O)$C_1$-$C_{20}$ alkyl group is linked to the amino group on the 3 position of the diaminopropionic acid. Additionally, diaminopropionic acid can have either the D or the L configuration.

In some embodiments, $X^2$ is an octanyolated diaminopropionic acid. In some embodiments, $X^2$ is not a palmitolyted diaminopropionic acid, i.e., a diaminopropionic acid conjugated with —C(O)$C_{17}$ alkyl on one of the amino groups of the diaminopropionic acid.

As used herein, the alkyl can also comprise one ore more double bonds or triple bonds. Accordingly, in some embodiments, the alkyl group comprises at least one (e.g., 1, 2, 3, 4, 5 or more) double bond. In some embodiments, the alkyl group comprises at least one (e.g., 1, 2, 3, 4, 5 or more) triple bond. In some embodiments, the alkyl group comprises at least one (e.g., 1, 2, 3, 4, 5 or more) double bond and at least one (e.g., 1, 2, 3, 4, 5 or more) triple bond.

In some embodiments, the peptide is of formula (II):

$$X^1\text{-}A^{21}\text{-}A^{22}\text{-}A^{23}\text{-}A^{24}\text{-}A^{25}\text{-}A^{26}\text{-}A^{27}\text{-}X^4 \qquad \text{(Formula II)},$$

wherein:
$X^1$ and $X^4$ are as defined above for formula (I);
each of $A^{21}$ and $A^{22}$ is independently a D amino acid, L amino acid, α-amino acid, β-amino acid, or γ-amino acid;
each of $A^{23}, A^{24}, A^{25}, A^{26}$, and $A^{27}$ is independently absent (i.e., need not be present), a D amino acid, L amino acid, α-amino acid, β-amino acid, or γ-amino acid; and derivatives, analogs, and pharmaceutically acceptable salts thereof.

In some embodiments, the peptide is of formula (III):

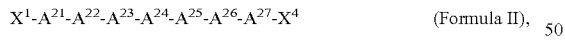

wherein:
$X^1$ and $X^4$ are as defined above for formula (I);
each of $A^{31}, A^{32}, A^{33}$, and $A^{34}$ is independently absent (i.e., need not be present), a D amino acid, L amino acid, α-amino acid, β-amino acid, or γ-amino acid; and derivatives, analogs, and pharmaceutically acceptable salts thereof.

In some embodiments, the peptide is of formula (IV):

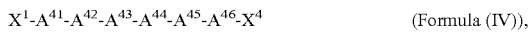

wherein:
$X^1$ and $X^4$ are as defined above for formula (I);
each of $A^{31}, A^{32}, A^{33}$, and $A^{34}$ is independently absent (i.e., need not be present), a D amino acid, L amino acid, α-amino acid, β-amino acid, or γ-amino acid; and derivatives, analogs, and pharmaceutically acceptable salts thereof.

In some embodiments, the ghrelin receptor antagonist is of formula (V)

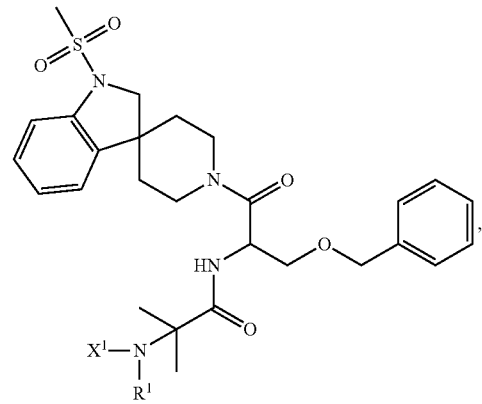

wherein:
$X^1$ is as defined above for formula (I);
$R^1$ is H or an $C_1$-$C_6$ alkyl; and derivatives, analogs, and pharmaceutically acceptable salts thereof.

In some embodiments, the antagonist of formula (V) has the stereochemistry as shown in formula (V'):

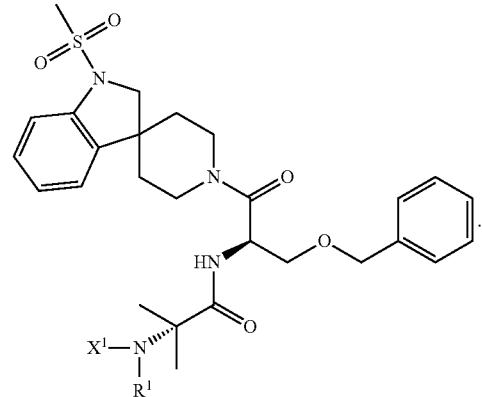

In some embodiments, $R^1$ is H or methyl.

In some embodiments, the linkage between $X^1$ and rest of the peptide of formula (V) is —C(O)NH— (regular amide bond), —C(O)N(CH$_3$)— (methylated amide bond), or —CH$_2$NH— (reduced amide bond).

In some embodiments, a ghrelin receptor antagonist of formula (V) is 2-(2-amino acetamido)-N-(1-(1-((R)-1-((R)-3-benzyloxy)-1-(1-(methylsulfonyl)spiro[indoline-3,4'-piperdin]-1'-yl)-1-oxopropan-2-ylamino)-2-methyl-1-oxopropan-2-yl)-4-(methylthio) butanamide (GMA-GHS-1, shown in FIG. 16)

In some embodiments, the ghrelin receptor antagonist is of formula (VI)

Formula (VI')

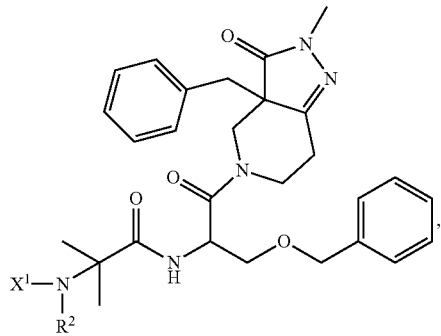

wherein:

X¹ is as defined above for formula (I);

R² is H or a $C_1$-$C_6$ alkyl group; and derivatives, analogs, and pharmaceutically acceptable salts thereof.

In some embodiments, an antagonist of formula (VI) has the stereochemistry as shown in formula (VI'):

Formula (VI')

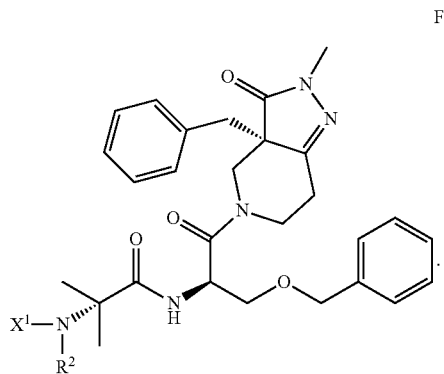

In some embodiments, R² is H or methyl.

In some embodiments, the linkage between X¹ and rest of the peptide of formula (VI) is —C(O)NH— (regular amide bond), —C(O)N(CH₃)— (methylated amide bond), or —CH₂NH— (reduced amide bond).

In some embodiments, a ghrelin receptor antagonist of formula (VI) is 2-(2-aminoacetamido)-N-(1-(1-((R)-1-((R)-3a-benzyl-2-methyl-3-oxo-3a,46,7,-tetrahydro-2H-pyrazolo[4,3-c]pyridine-5(3H)-yl)-3-(benzyloxy)-1-oxopropan-2-ylamino)-2-methyl-1-oxopropan-2-ylamino)-1-oxopropan-2-yl)-4-(methylthio)butanamide (GMA-GHS-2, shown in FIG. 17)

In some embodiments, Y is:

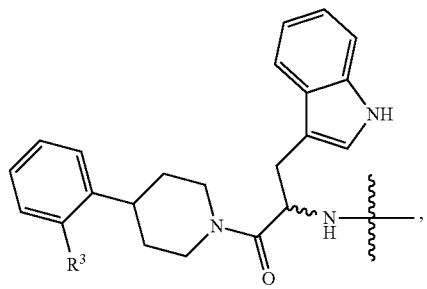

wherein: R³ is H, alkyl, O-alkyl, $NO_2$, CN, $SO_2H$, $NH_2$, OH, halogen, $CF_3$, cyclyl, heterocyclyl, aryl, or heteroaryl, each of which can be optionally substituted. A skilled artisan is well aware that the above structure is a D- or L-Tryptophan amino acid that is conjugated on the carboxyl group with an optionally substituted 4-phenylpiperidin-1-yl and is conjugated on the N-terminus amino group with X¹.

In some embodiments, Y a D- or L-Tryptophan amino acid that is conjugated on the carboxyl group with an optionally substituted 4-phenylpiperidin-1-yl.

In some embodiments, a D- or L-Tryptophan amino acid that is conjugated on the carboxyl group with an optionally substituted 4-phenylpiperazin-1-yl.

In some embodiments, R¹ is H or $OCH_3$.

In some embodiments, Y is:

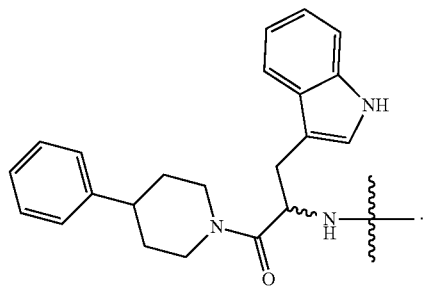 [SMILES: *NC(Cc1c[nH]c2ccccc12)C(=O)N1CCC(c2ccccc2)CC1]

In some embodiments, Y is:

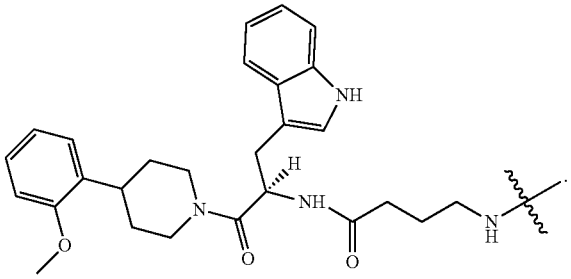 [SMILES: *NCCCC(=O)N[C@H](Cc1c[nH]c2ccccc12)C(=O)N1CCC(c2ccccc2OC)CC1]

A skilled artisan is well aware that this structure is a γAbu-DTrp dipeptide conjugated with 4-(2-methoxyphenyl)piperidin-1-yl at the C-terminus carboxyl group.

In some embodiments, Y is:

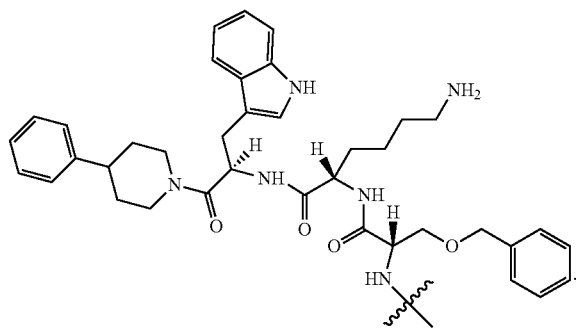 [SMILES: *N[C@@H](COCc1ccccc1)C(=O)N[C@@H](CCCCN)C(=O)N[C@H](Cc1c[nH]c2ccccc12)C(=O)N1CCC(c2ccccc2)CC1]

A skilled artisan is well aware that this structure is a Ser-Lys-DTrp tripeptide conjugated with a 4-phenylpiperidin-1-yl at the C-terminus carboxyl group and alkylated with a benzyl group at the Serine side-chain hydroxyl group.

In some embodiments, Y is:

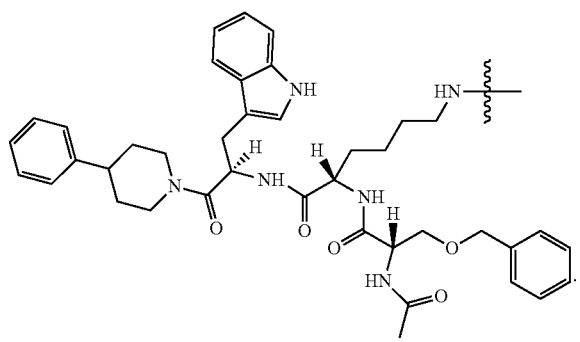 [SMILES: *NCCCC[C@H](NC(=O)[C@H](COCc1ccccc1)NC(C)=O)C(=O)N[C@H](Cc1c[nH]c2ccccc12)C(=O)N1CCC(c2ccccc2)CC1]

A skilled artisan is well aware that this structure is a Ser-Lys-DTrp tripeptide conjugated with a 4-phenylpiperidin-1-yl at the C-terminus carboxyl group, acylated with an acetyl at the N-terminus amino group and alkylated with a benzyl group at the Serine side-chain hydroxyl group. Linkage to $X^1$ is through the lysine side-chain amino group.

In some embodiments, Y is:

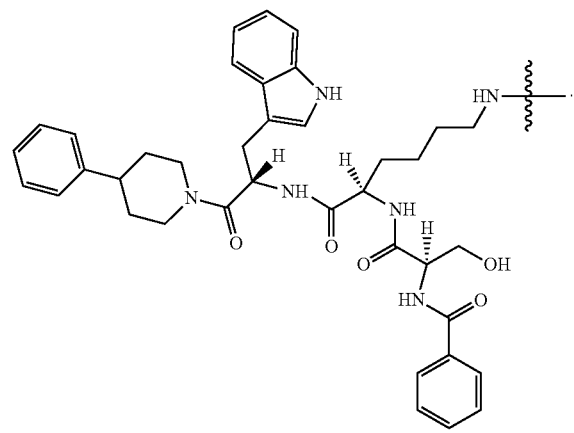 [SMILES: *NCCCC[C@@H](NC(=O)[C@@H](CO)NC(=O)c1ccccc1)C(=O)N[C@@H](Cc1c[nH]c2ccccc12)C(=O)N1CCC(c2ccccc2)CC1]

A skilled artisan is well aware that this structure is a DSer-DLys-Trp tripeptide conjugated with a 4-phenylpiperidin-1-yl at the C-terminus carboxyl group and acylated with a benzoyl group at the N-terminus amino group. Linkage to $X^1$ is through the Lysine side-chain amino acid.

In some embodiments, Y is:

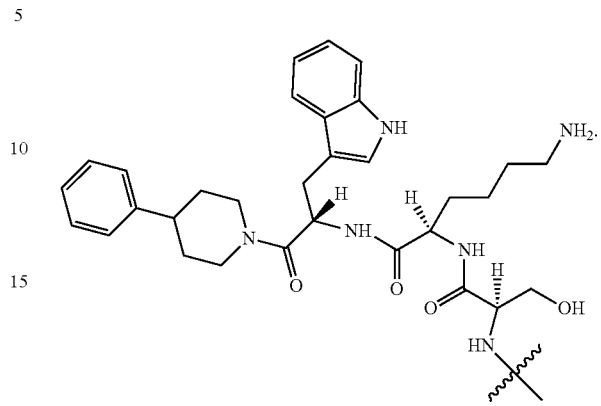

A skilled artisan is well aware that this structure is a DSer-DLys-Trp tripeptide conjugated with a 4-phenylpiperidin-1-yl at the C-terminus carboxyl group. Linkage to $X^1$ is through the N-terminus amino group.

In some embodiments, Y is:

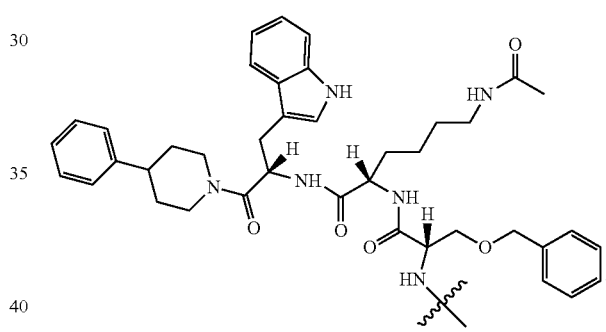

A skilled artisan is well aware that this structure is a Ser-Lys-Trp tripeptide conjugated with a 4-phenylpiperidin-1-yl at the C-terminus carboxyl group, acylated with an acetyl group at the Lysine side-chain amino group, and alkylated with a benzyl group at the Serine side-chain hydroxyl group. Linkage to $X^1$ is through the N-terminus amino group.

In some embodiments, Y is:

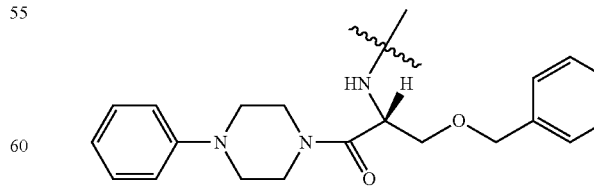

A skilled artisan is well aware that this structure is a D-serine amino acid conjugated with a 4-phenylpiperazin-1-yl at the C-terminus carboxyl group and is alkylated with a benzyl group at the Serine side-chain hydroxyl group.

In some embodiments, Y is:

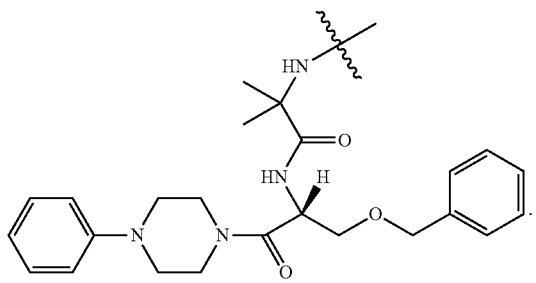 [SMILES: *NC(C)(C)C(=O)N[C@H](COCc1ccccc1)C(=O)N1CCN(c2ccccc2)CC1]

A skilled artisan is well aware that this structure is a αAib-DSer peptide conjugated with a 4-phenylpiperazin-1-yl at the C-terminus carboxyl group and alkylated with a benzyl group at the Serine side-chain hydroxyl group.

In some embodiments, Y is:

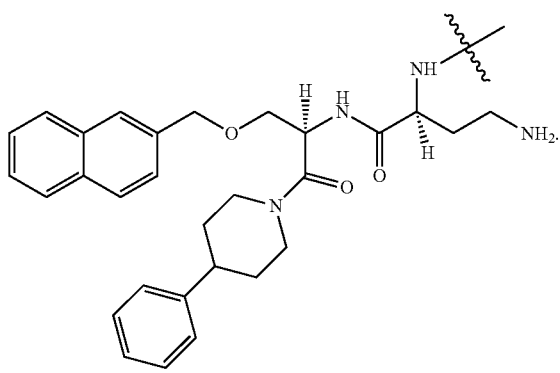 [SMILES: *N[C@@H](CCN)C(=O)N[C@H](COCc1ccc2ccccc2c1)C(=O)N1CCC(c2ccccc2)CC1]

A skilled artisan is well aware that this structure is a αγABu-DSer dipeptide conjugated with the amino a 4-phenylpiperidin-1-yl at the C-terminus carboxyl group and is alkylated with a naphthalene-2-yl group at the side-chain hydroxyl group of serine. Linkage to $X^1$ is through the α-amino group of αγAbu.

In some embodiments, Y is:

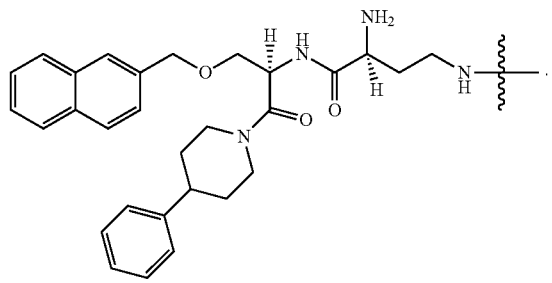 [SMILES: *NCC[C@H](N)C(=O)N[C@H](COCc1ccc2ccccc2c1)C(=O)N1CCC(c2ccccc2)CC1]

A skilled artisan is well aware that this structure is a αγABu-DSer dipeptide conjugated with the amino a 4-phenylpiperidin-1-yl at the C-terminus carboxyl group and is alkylated with a naphthalene-2-yl group at the side-chain hydroxyl group of serine. Linkage to $X^1$ is through the γ-amino group of αγAbu.

In some embodiments, an antagonist of the invention is a derivative of an antagonist of formula (I)-(VI).

In some embodiments, an antagonist of the invention an analog of an antagonist of formula (I)-(VI).

In some embodiments, an antagonist of the invention is a pharmaceutically acceptable salt of an antagonist of formula (I)-(VI).

Without wishing to be bound by theory, addition of at least one of $A^1$, $A^2$, $A^3$, $A^4$, $A^5$, or $A^6$ on the N-terminus of the peptides of formula (I) blocks the N-terminal glycine of the ghrelin pentapetide (GSS(oct)FL) (SEQ ID NO: 5) which is necessary for ghrelin activity.

In some embodiments; each of $A^1$, $A^2$, $A^3$, $A^4$, $A^5$, $A^6$, $A^{21}$, $A^{22}$, $A^{23}$, $A^{24}$, $A^{25}$, $A^{26}$, $A^{27}$, $A^{31}$, $A^{32}$, $A^{33}$, $A^{34}$, $A^{41}$, $A^{42}$, $A^{43}$, $A^{44}$, $A^{45}$, $A^{46}$, and $X^3$ is independently selected from the group consisting of alanine; argnine; asparagine; aspartic acid; cysteine; glutamic acid; glutamine; glycine; histidine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4,-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; gamma-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (<Glu); α-aminoisobutyric acid (αAib); γ-aminobutyric acid (γAbu); α-aminobutyric acid (αAbu); αγ-aminobutyric acid (αγAbu); β-pyridylalanine (Pal); Isopropyl-α-$N^\epsilon$lysine (ILys); Naphthyalanine (Nal); α-naphthyalanine (α-Nal); β-naphthyalanine (β-Nal); Acetyl-β-naphthyalanine (Ac-β-naphthyalanine); α,β-naphthyalanine; $N^\epsilon$-picoloyl-lysine (PicLys); 4-halo-Phenyl; 4-pyrolidylalanine; isonipecotic carboxylic acid (inip); beta-amino acids; and isomers, analogs and derivatives thereof. One of skill in the art would know that this definition includes, D- and L-amino acids, alpha- and beta-amino acids, chemically modified amino acids, naturally occurring non-proteogenic amino acids, rare amino acids, and chemically synthesized compounds that have properties known in the art to be characteristic of an amino acid. The members can be the same or different. Additionally, each embodiment can include any combinations of the groups.

Furthermore, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways.

Without limitations, each of $A^1$, $A^2$, $A^3$, $A^4$, $A^5$, $A^6$, $A^{21}$, $A^{22}$, $A^{23}$, $A^{24}$, $A^{25}$, $A^{26}$, $A^{27}$, $A^{31}$, $A^{32}$, $A^{33}$, $A^{34}$, $A^{41}$, $A^{42}$, $A^{43}$, $A^{44}$, $A^{45}$, $A^{46}$, and $X^3$ can be independently a D- or L-amino acid. Accordingly, in some embodiments, a peptide of formula (I)-(VI) comprises at least one (e.g., 1, 2, 3, 4, 5, 6, 7, 8, 9, 10 or more) D-amino acid. In some embodiments, at least one (e.g., 1, 2, 3, 4, 5, 6, or 7) of $A^1, A^2, A^3, A^4, A^5, A^6$, and $X^3$ is a D-amino acid or derivative thereof. The D-amino acid can be present at any position in the peptide of formula (I)-(VI), for example reading from the N-terminal at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34. When more than one D-amino acids are present, they can be positioned next to or not next to each other. When three or more D-amino acids are present some of the D-amino acids can be present next to another D-amino acid while some of the D-amino acids are not next to another D-amino acid.

In some embodiments, a peptide of formula (I)-(VI) comprises at least one of (e.g., 1, 2, 3, 4, 5, 6, 7, 8, 9, 10, 11, 12, 13, 14, 15, or more) chemically modified amino acid. For example, at least one of $A^1, A^2, A^3, A^4, A^5, A^6, A^{21}, A^{22}, A^{23}, A^{24}, A^{25}, A^{26}, A^{27}, A^{31}, A^{32}, A^{33}, A^{34}, A^{41}, A^{42}, A^{43}, A^{44}, A^{45}, A^{46}$, and/or $X^3$ is a chemically modified amino acid. Such a chemically modified amino acid can be present at any position in the peptide of formula (I)-(VI), for example reading from the N-terminal at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34. When more than one chemically modified amino acids are present, they can be positioned next to or not next to each other. When three or more chemically modified amino acids are present some of the chemically modified amino acids can be present next to each other while some of the chemically modified amino are not next to another chemically modified amino acid. As used herein, the term "chemically modified amino acid" refers to an amino acid that has been treated with one or more reagents.

In some embodiments, the peptide of formula (I)-(VI) comprises at least one (e.g., 1, 2, 3, 4, 5, 6, 7, 8, 9, 10 or more) beta-amino acid. In some embodiments, at least one (e.g., 1, 2, 3, 4, 5, 6, or 7) of $A^1, A^2, A^3$, and $X^3$ is a beta-amino acid. The beta-amino acid can be present at any position in the peptide of formula (I)-(VI), for example reading from the N-terminal at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34. When more than one beta-amino acids are present, they can be positioned next to or not next to each other. When three or more beta-amino acids are present some of the beta-amino acids can be present next to another beta-amino acid while some of the beta-amino are not next to another beta-amino acid.

Exemplary beta-amino acids include, but are not limited to, L-β-Homoproline hydrochloride; (±)-3-(Boc-amino)-4-(4-biphenylyl)butyric acid; (±)-3-(Fmoc-amino)-2-phenylpropionic acid; (1S,3R)-(+)-3-(Boc-amino)cyclopentanecarboxylic acid; (2R,3R)-3-(Boc-amino)-2-hydroxy-4-phenylbutyric acid; (2S,3R)-3-(Boc-amino)-2-hydroxy-4-phenylbutyric acid; (R)-2-[(Boc-amino)methyl]-3-phenylpropionic acid; (R)-3-(Boc-amino)-2-methylpropionic acid; (R)-3-(Boc-amino)-2-phenylpropionic acid; (R)-3-(Boc-amino)-4-(2-naphthyl)butyric acid; (R)-3-(Boc-amino)-5-phenylpentanoic acid; (R)-3-(Fmoc-amino)-4-(2-naphthyl)butyric acid; (R)-(−)-Pyrrolidine-3-carboxylic acid; (R)-Boc-3,4-dimethoxy-β-Phe-OH; (R)-Boc-3-(3-pyridyl)-β-Ala-OH; (R)-Boc-3-(trifluoromethyl)-β-Phe-OH; (R)-Boc-3-cyano-β-Phe-OH; (R)-Boc-3-methoxy-β-Phe-OH; (R)-Boc-3-methyl-β-Phe-OH; (R)-Boc-4-(4-pyridyl)-β-Homoala-OH; (R)-Boc-4-(trifluoromethyl)-β-Homophe-OH; (R)-Boc-4-(trifluoromethyl)-β-Phe-OH; (R)-Boc-4-bromo-β-Phe-OH; (R)-Boc-4-chloro-β-Homophe-OH; (R)-Boc-4-chloro-β-Phe-OH; (R)-Boc-4-cyano-β-Homophe-OH; (R)-Boc-4-cyano-β-Phe-OH; (R)-Boc-4-fluoro-β-Phe-OH; (R)-Boc-4-methoxy-β-Phe-OH; (R)-Boc-4-methyl-β-Phe-OH; (R)-Boc-β-Tyr-OH; (R)-Fmoc-4-(3-pyridyl)-β-Homoala-OH; (R)-Fmoc-4-fluoro-β-Homophe-OH; (S)-(+)-Pyrrolidine-3-carboxylic acid; (S)-3-(Boc-amino)-2-methylpropionic acid; (S)-3-(Boc-amino)-4-(2-naphthyl)butyric acid; (S)-3-(Boc-amino)-5-phenylpentanoic acid; (S)-3-(Fmoc-amino)-2-methylpropionic acid; (S)-3-(Fmoc-amino)-4-(2-naphthyl)butyric acid; (S)-3-(Fmoc-amino)-5-hexenoic acid; (S)-3-(Fmoc-amino)-5-phenyl-pentanoic acid; (S)-3-(Fmoc-amino)-6-phenyl-5-hexenoic acid; (S)-Boc-2-(trifluoromethyl)-β-Homophe-OH; (S)-Boc-2-(trifluoromethyl)-β-Homophe-OH; (S)-Boc-2-(trifluoromethyl)-β-Phe-OH; (S)-Boc-2-cyano-β-Homophe-OH; (S)-Boc-2-methyl-β-Phe-OH; (S)-Boc-3,4-dimethoxy-β-Phe-OH; (S)-Boc-3-(trifluoromethyl)-β-Homophe-OH; (S)-Boc-3-(trifluoromethyl)-β-Phe-OH; (S)-Boc-3-methoxy-β-Phe-OH; (S)-Boc-3-methyl-β-Phe-OH; (5)-Boc-4-(4-pyridyl)-β-Homoala-OH; (S)-Boc-4-(trifluoromethyl)-β-Phe-OH; (S)-Boc-4-bromo-β-Phe-OH; (S)-Boc-4-chloro-β-Homophe-OH; (S)-Boc-4-chloro-β-Phe-OH; (S)-Boc-4-cyano-β-Homophe-OH; (S)-Boc-4-cyano-β-Phe-OH; (S)-Boc-4-fluoro-β-Phe-OH; (S)-Boc-4-iodo-β-Homophe-OH; (S)-Boc-4-methyl-β-Homophe-OH; (S)-Boc-4-methyl-β-Phe-OH; (S)-Boc-β-Tyr-OH; (S)-Boc-γ,γ-diphenyl-β-Homoala-OH; (S)-Fmoc-2-methyl-β-Homophe-OH; (S)-Fmoc-3,4-difluoro-β-Homophe-OH; (S)-Fmoc-3-(trifluoromethyl)-β-Homophe-OH; (S)-Fmoc-3-cyano-β-Homophe-OH; (S)-Fmoc-3-methyl-β-Homophe-OH; (S)-Fmoc-γ,γ-diphenyl-β-Homoala-OH; 2-(Boc-aminomethyl) phenylacetic acid; 3-Amino-3-(3-bromophenyl)propionic acid; 3-Amino-4,4,4-trifluorobutyric acid; 3-Aminobutanoic acid; DL-3-Aminoisobutyric acid; DL-β-Aminoisobutyric acid puriss; DL-β-Homoleucine; DL-β-Homomethionine; DL-β-Homophenylalanine; DL-β-Leucine; DL-β-Phenylalanine; L-β-Homoalanine hydrochloride; L-β-Homoglutamic acid hydrochloride; L-β-Homoglutamine hydrochloride; L-β-Homohydroxyproline hydrochloride; L-β-Homoisoleucine hydrochloride; L-β-Homoleucine hydrochloride; L-β-Homolysine dihydrochloride; L-β-Homomethionine hydrochloride; L-β-Homophenylalanine allyl ester hydrochloride; L-β-Homophenylalanine hydrochloride; L-β-Homoserine; L-β-Homothreonine; L-β-Homotryptophan hydrochloride; L-β-Homotyrosine hydrochloride; L-β-Leucine hydrochloride; Boc-D-β-Leu-OH; Boc-D-β-Phe-OH; Boc-β³-Homopro-OH; Boc-β-Glu(OBzl)-OH; Boc-β-Homoarg(Tos)-OH; Boc-β-Homoglu(OBzl)-OH; Boc-β-Homohyp(Bzl)-OH (dicyclohexylammonium) salt technical; Boc-β-Homolys(Z)—OH; Boc-β-Homoser(Bzl)-OH; Boc-β-Homothr(Bzl)-OH; Boc-β-Homotyr(Bzl)-OH; Boc-β-Ala-OH; Boc-β-Gln-OH; Boc-β-Homoala-OAll; Boc-β-Homoala-OH; Boc-β-Homogln-OH; Boc-β-Homoile-OH; Boc-β-Homoleu-OH; Boc-β-Homomet-OH; Boc-β-Homophe-OH; Boc-β-Homotrp-OH; Boc-β-Homotrp-OMe; Boc-β-Leu-OH; Boc-β-Lys(Z)—OH (dicyclohexylammonium) salt; Boc-β-Phe-OH; Ethyl 3-(benzylamino)propionate; Fmoc-D-β-Homophe-OH; Fmoc-L-β³-homoproline; Fmoc-β-D-Phe-OH; Fmoc-β-Gln(Trt)-OH; Fmoc-β-Glu(OtBu)-OH; Fmoc-β-Homoarg(Pmc)-OH; Fmoc-β-Homogln(Trt)-OH; Fmoc-β-Homoglu(OtBu)-OH; Fmoc-β-Homohyp(tBu)-OH; Fmoc-β-Homolys(Boc)-OH; Fmoc-β-Homoser(tBu)-OH; Fmoc-β-Homothr(tBu)-OH; Fmoc-β-Homotyr(tBu)-OH; Fmoc-β-Ala-OH; Fmoc-β-Gln-OH; Fmoc-β-Homoala-OH; Fmoc-β-Homogln-OH; Fmoc-β-Homoile-OH; Fmoc-β-Homoleu-OH; Fmoc-β-Homomet-OH; Fmoc-β-Homophe-OH; Fmoc-β-Homotrp-OH; Fmoc- β-Leu-OH; Fmoc-β-Phe-OH; N-Acetyl-DL-β-phenylalanine; Z-D-β-Dab(Boc)-OH; Z-D-β-Dab(Fmoc)-OH purum; Z-DL-β-Homoalanine; Z-β-D-Homoala-OH; Z-β-Glu(OtBu)-OH technical; Z-β-Homotrp(Boc)-OH; Z-β-Ala-OH purum; Z-β-Ala-ONp purum; Z-β-Dab(Boc)-OH; Z-β-Dab(Fmoc)-OH; Z-β-Homoala-OH; β-Alanine; β-Alanine BioXtra; β-Alanine ethyl ester hydrochloride; β-Alanine methyl ester hydrochloride; β-Glutamic acid hydrochloride; cis-2-Amino-3-cyclopentene-1-carboxylic acid hydrochloride; cis-3-(Boc-amino)cyclohexanecarboxylic acid; and cis-3-(Fmoc-amino)cyclohexanecarboxylic acid.

In some embodiments, the peptide of formula (I)-(VI) comprises at least one (e.g., 1, 2, 3, 4, 5, 6, 7, 8, 9, or 10 or more) modified peptide linkage, e.g., a peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. The peptide replacement linkage can be present at any position in the peptide of formula (I)-(VI), for example reading from the N-terminal at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33. When more than peptide replacement linkages are present, they can be positioned next to (e.g., on both sides of a given amino acid) or not next to each other (e.g., only one side of a given amino acid is linked via a peptide replacement linkage to the next amino acid).

In some embodiments, the N-terminus amino group of a peptide of formula (I)-(VI) is conjugated with nitrogen- or amino-protecting group. As used herein, a "nitroger protecting group" or an "amino protecting group" refers to moieties that block or mask the $NH_2$ group. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Further amino protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991, content of which is herein incorporated by reference in its entirety.

In some embodiments, the N-terminus amino acid of the peptide of formula (I)-(VI) is acetylated or alkylated, e.g., with acetyl, ethanoyl, propionyl, t-butanoyl, methyl, ethyl, propyl, butyl, pentyl, or hexanyl.

In some embodiments, a peptide of formula (I)-(VI) is conjugated with polyethylene glycol (PEG). Without wishing to be bound by theory, such conjugation can increase the in vivo half life of the peptide. As used herein, "PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof. Methods of conjugating PEGs to peptides are well known in the art. A peptide of the invention can comprise a PEG at the N-terminus, C-terminus, or at an internal amino acid. The PEG can be linked to the N-terminus amino group, C-terminus carboxyl group, or to an amino, hydroxyl or thiol group on the side chain of an amino acid.

In some embodiments, an antagonist of formula (I)-(VI) inhibits the activity of ghrelin receptor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% (i.e. complete inhibition) relative to a reference level.

In some embodiments, an antagonist of formula (I)-(VI) inhibits the an activity of ghrelin o-acyltransferase (GOAT) by at less than 95%, less than 90%, less than 80%, less than 70%, less than 60%, less than 50%, less than 40%, less than 30%, less than 20%, less than 15%, less than 10%, or less than 5% relative to a reference level.

In some embodiments, an antagonist of formula (I)-(VI) does not inhibits the activity of ghrelin o-acyltransferase (GOAT).

$X^1$

Without limitations, $X^1$ can be a single amino acid ($A^1$), a dipeptide ($A^1$-$A^2$), a tripeptide ($A^1$-$A^2$-$A^3$), a pentapeptide ($A^1$-$A^2$-$A^3$-$A^4$-$A^5$), or a hexapeptide ($A^1$-$A^2$-$A^3$-$A^4$-$A^5$-$A^6$). Furthermore, $X^1$ can comprise one or more D amino acids, one or more beta amino acids (e.g., 1, 2, 3, 4, 5, or 6), and/or one or more (e.g., 1, 2, 3, 4, or 5) modified peptide linkages. In some embodiments, the linkage between $X^1$ and the rest of the peptide is a modified peptide or a non-amide linkage. In some embodiments, the linkage between $X^1$ and the rest of the peptide is a non-amide linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. In some embodiments, the amine in the amide linkage between $X^1$ and rest of the peptide is alkylated, e.g., methylated.

In some embodiments, the amide linkage between $A^1$ and rest of the $X^1$ peptide is replaced by a modified amide or peptide linkage. In some embodiments, the amide linkage between $A^1$ and $A^2$, and/or $A^1$ and $A^3$ (e.g., when $A^2$ is absent) is replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group.

In some embodiments, the amide linkage between $A^2$ and $A^3$ is replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group.

In some embodiments, each of $A^1$, $A^2$, $A^3$, $A^4$, $A^5$, and $A^6$ is selected independently from the group consisting of L- or D-alanine; argnine; asparagine; aspartic acid; cysteine; glutamic acid; glutamine; glycine; histidine; isoleucine; leucine; lysine; methionine; phenylalanine; proline; serine; threonine; tryptophan; tyrosine; valine; and homocysteine.

In some embodiments, $A^1$ is D- or L-Gly, D- or L-Ala, D- or L-Leu.

In some embodiments, $A^2$ is D- or L-Met, D- or L-Asp.

In some embodiments, $A^3$ is D- or L-Ala or D- or L-Leu.

In some embodiments, $A^4$ is absent, D- or L-Gly or D- or L-Ala.

In some embodiments, $A^5$ is absent or D- or L-Met

In some embodiments, $A^6$ is absent or D- or L-Ala.

In some embodiments, $A^1$ is D- or L-Gly, D- or L-Ala, D- or L-Leu; $A^2$ is D- or L-Met, D- or L-Asp; $A^3$ is D- or L-Ala or D- or L-Leu; and $A^4$, $A^5$ and $A^6$ are absent.

In some embodiments, $X^1$ is tripeptide. In some embodiments, the second amino acid of the $X^1$ tripeptide is a D amino acid, beta-amino acid, and/or a chemically modified amino acid.

Exemplary tripeptides for $X^1$ include, but are not limited to Gly-Met-Ala-, Ala-Met-Ala-, Gly-DMet-Ala-, Ala-DMet-Ala-, Gly-Met-Alaψ[CH$_2$NH]—, Ala-Met-Alaψ[CH$_2$NH]—, Gly-DMet-Alaψ[CH$_2$NH]—, Ala-DMet-Alaψ[CH$_2$NH]—, Gly-Met-Ala[C(O)N(CH$_3$)]—, Ala-Met-Ala[C(O)N(CH$_3$)]—, Gly-DMet-Ala[C(O)N(CH$_3$)]—, or Ala-DMet-Ala[C(O)N(CH$_3$)]—

In some embodiments, $X^1$ is a GlyMetAla tripeptide.

In some embodiments, $X^1$ is hexapeptide. In some embodiments, the fifth amino acid of the $X^1$ hexapeptide is a D amino acid, beta-amino acid, and/or a chemically modified amino acid.

Exemplary hexapetides for $X^1$ include, but are not limited to, Leu-Asp-Leu-Gly-Met-Ala-(SEQ ID NO: 6), Leu-Asp-Leu-Gly-Met-Ala-(SEQ ID NO: 6), Leu-Asp-Leu-Gly-DMet-Ala-, Leu-Asp-Leu-Ala-DMet-Ala-, Leu-Asp-Leu-Gly-Met-Alaψ[CH$_2$NH]— (SEQ ID NO: 7), Leu-Asp-Leu-Ala-Met-Alaψ[CH$_2$NH]— (SEQ ID NO: 8), Leu-Asp-Leu-Gly-DMet-Alaψ[CH$_2$NH]—, and Leu-Asp-Leu-Ala-DMet-Alaψ[CH$_2$NH]—.

$X^4$

The C-terminus of the peptide of formula (I)-(VI) can be unmodified or modified by conjugating a carboxyl protecting group or an amide group. Accordingly, in some embodiments, $X^4$ is absent, NH$_2$, NH-alkyl, N(alkyl)$_2$, optionally substituted heterocyclyl comprising at least one nitrogen, optionally substituted heteroaryl comprising at least one nitrogen atom. Exemplary carboxyl protecting groups include, but are not limited to, esters such as methyl, ethyl, t-butyl, methoxymethyl, 2,2,2-trichloroethyl and 2-haloethyl; benzyl esters such as triphenylmethyl, diphenylmethyl, p-bromobenzyl, o-nitrobenzyl and the like; silyl esters such as trimethylsilyl, triethylsilyl, t-butyldimethylsilyl and the like; amides; and hydrazides. Other carboxylic acid protecting groups can include optionally protected alpha-amino acids which are linked with the amino moiety of the alpha-amino acids.

In some embodiments, a peptide of formula (I)-(VI) is conjugated at the C-terminus with an optionally substituted 4-phenylpiperazine, e.g. 4-phenylpiperazin-1-yl and 4-(2-methylphenyl)piperazin-1-yl.

In some embodiments, a peptide of formula (I)-(VI) is conjugated at the C-terminus with 3a-benzyl-4,5,6,7-tetrahydro-2-methyl-2H-pyrazolo[4,3-c]pyridin-3 (3 aH)-on-5-yl group.

In some embodiments, a peptide of formula (I)-(VI) is conjugated at the C terminus with 1-(methylsulfonyl)spiro[indoline-3,4'-piperdin]-1'-yl.

Peptides of Formula (I)

In some embodiments, the peptide of formula (I) is 8-20, 8-15, or 8-12 amino acids longs.

In some embodiments, the peptide of formula (I) is 10-20, 10-15, or 10-12 amino acids long.

In some embodiments, the peptide of formula (I) is of formula (I'): $X^1$-GS-$X^2$-FLSPEH-$(X^3)_m$—$X^4$(SEQ ID NO: 9), wherein m is an integer from 1 to 20.

$(X^3)_m$ can range from a single amino acid to a peptide comprising upto and including 20 amino acids. When $(X^3)_m$ is comprises more than one amino acid, each amino acid can be selected independently. Accordingly, in some embodiments, $(X^3)_m$ is Q, QR, QRV, QRVQ (SEQ ID NO: 10), QRVQQ (SEQ ID NO: 11), QRVQQR (SEQ ID NO: 12), QRVQQRK (SEQ ID NO: 13), QRVQQRKE (SEQ ID NO: 14), QRVQQRKES (SEQ ID NO: 15), QRVQQRKESK (SEQ ID NO: 16), QRVQQRKESKK (SEQ ID NO: 17), QRVQQRKESKKP (SEQ ID NO: 18), QRVQQRKESKKPP (SEQ ID NO: 19), QRVQQRKESKKPPA (SEQ ID NO: 20), QRVQQRKESKKPPAK (SEQ ID NO: 21), QRVQQRKESKKPPAKL (SEQ ID NO: 22), QRVQQRKESKKPPAKLQ (SEQ ID NO: 23), QRVQQRKESKKPPAKLQP (SEQ ID NO: 24), QRVQQRKESKKPPAKLQPR (SEQ ID NO: 25), or QRVQQRKESKKPPAKLQPRW (SEQ ID NO: 26).

In some embodiments, $(X^3)_n$ comprises the amino acid sequence selected from amino acid 6 to amino acid p, wherein p is 6-28, of the sequence selected from the group consisting of GSS(Oct)FLSPEHQRVQQRKESKKPPAKLQPR (human ghrelin) (SEQ ID NO: 27), GSS(Oct)FLSPEHQKAQQRKESKKPPAKLQPR (rat ghrelin) (SEQ ID NO: 28) GSS(Oct)FLSPEHQKAQQRKESKKPPAKLQPR (mouse ghrelin) (SEQ ID NO: 29), GSS(Oct)FLSPEHQKVQQRKESKKPAAKLKPR (porcine ghrelin) (SEQ ID NO: 30), GSS(Oct)FLSPEHQKLQRKEAKKPSGRLKPRT (bovine ghrelin) (SEQ ID NO: 31), and GSS(Oct)FLSPEHQKLQQRKESKKPPAKLQPR (canine ghrelin) (SEQ ID NO: 32). To clarify, $(X^3)_n$ can consist of the amino acid sequence represented by amino acids 6, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 6-26, 6-27, and 6-28 of the human, rat, mouse, porcine, bovine, or canine ghrelin amino acid sequence. For example, $(X^3)_n$, consisting of amino acids 6-28 of human ghrelin sequence, would have the sequence SPEHQRVQQRKESKKPPAKLQPR (SEQ ID NO: 33).

In some embodiments, $(X^3)_m$ comprises the amino acid sequence selected from amino acid 10 to amino acid p, wherein p is 10-28, of the sequence selected from the group consisting of the human, rat, mouse, porcine, bovine, and canine ghrelin amino acid sequences. To clarify, $(X^3)_m$ can consist of the amino acid sequence represented by amino acids 10, 10-11, 10-12, 10-13, 10-14, 10-15, 10-16, 10-17, 10-18, 10-19, 10-20, 10-21, 10-22, 10-23, 10-24, 10-25, 10-26, 10-27, and 10-28 of the human, rat, mouse, porcine, bovine, or canine ghrelin amino acid sequence. For example, $(X^3)_m$, consisting of amino acids 10-28 of human ghrelin sequence, would have the sequence QRVQQRKESKKPPAKLQPR (SEQ ID NO: 25).

In some embodiments, the peptide of formula (I) is selected from the group consisting of $X^1$-GS-$X^2$-FL-$X^4$ (SEQ ID NO: 34), $X^1$-GS-$X^2$-FL-S—$X^4$(SEQ ID NO: 35), $X^1$-GS-$X^2$-FL-SP-$X^4$ (SEQ ID NO: 36), $X^1$-GS-$X^2$-FL-SPE-$X^4$ (SEQ ID NO: 37), $X^1$-GS-$X^2$-FL-SPEH-$X^4$(SEQ ID NO: 38), $X^1$-GS-$X^2$-FL-SPEHQ-$X^4$(SEQ ID NO: 39), $X^1$-GS-$X^2$-FL-SPEHQR-$X^4$(SEQ ID NO: 40), $X^1$-GS-$X^2$-FL-SPEHQRV-$X^4$ (SEQ ID NO: 41), $X^1$-GS-$X^2$-FL-SPEHQRVQ-$X^4$(SEQ ID NO: 42), $X^1$-GS-$X^2$-FL-SPEHQRVQQ-$X^4$(SEQ ID NO: 43), $X^1$-GS-$X^2$-FL-SPEHQRVQQR-$X^4$ (SEQ ID NO: 44), $X^1$-GS-$X^2$-FL-SPEHQRVQQRK-$X^4$(SEQ ID NO: 45), $X^1$-GS-$X^2$-FL-SPEHQRVQQRKE-$X^4$(SEQ ID NO: 46), $X^1$-GS-$X^2$-FL-SPEHQRVQQRKES-$X^4$(SEQ ID NO: 47), $X^1$-GS-$X^2$-FL-SPEHQRVQQRKESK-$X^4$(SEQ ID NO: 48), $X^1$-GS-$X^2$-FL-SPEHQRVQQRKESKK-$X^4$(SEQ ID NO: 49), $X^1$-GS-$X^2$-FL-SPEHQRVQQRKESKKP-$X^4$ (SEQ ID NO: 50), $X^1$-GS-$X^2$-FL-SPEHQRVQQRKESKKPP-$X^4$ (SEQ ID NO: 51), X$^1$-GS-X$^2$-FL-SPE-HQRVQQRKESKKPPA-X$^4$(SEQ ID NO: 52), X$^1$-GS-X$^2$-FL-SPEHQRVQQRKESKKPPAK-X$^4$(SEQ ID NO: 53), X$^1$-GS-X$^2$-FL-SPEHQRVQQRKESKKPPAKL-X$^4$(SEQ ID NO: 54), X$^1$-GS-X$^2$-FL-SPEHQRVQQRKESKKPPAKLQ-X$^4$(SEQ ID NO: 55), X$^1$-GS-X$^2$-FL-SPEHQRVQQRKESKKPPAKLQP-X$^4$(SEQ ID NO: 56), X$^1$-GS-X$^2$-FL-SPEHQRVQQRKESKKPPAKLQPR-X$^4$ (SEQ ID NO: 57), and X$^1$-GS-X$^2$-FL-SPEHQRVQQRKESKKPPAKLQPRW-X$^4$(SEQ ID NO: 58).

Exemplary peptides of formula (I) or formula (I') include, but are not limited to, GMAGSS(Oct)FL (SEQ ID NO: 59); GMAGSS(Oct)FLS (SEQ ID NO: 60); GMAGSS(Oct)FLSP (SEQ ID NO: 61); GMAGSS(Oct)FLSPE (SEQ ID NO: 62); GMAGSS(Oct)FLSPEH (SEQ ID NO: 63); GMAGSS(Oct)FLSPEHQ (SEQ ID NO: 64); GMAGSS(Oct)FLSPEHQR (SEQ ID NO: 65); GMAGSS(Oct)FLSPEHQRV (SEQ ID NO: 66); GMAGSS(Oct)FLSPEHQRVQ (SEQ ID NO: 67); GMAGSS(Oct)FLSPEHQRVQQ (SEQ ID NO: 68); GMAGSS(Oct)FLSPEHQRVQQR (SEQ ID NO: 69); GMAGSS(Oct)FLSPEHQRVQQRK (SEQ ID NO: 70); GMAGSS(Oct)FLSPEHQRVQQRKE (SEQ ID NO: 71); GMAGSS(Oct)FLSPEHQRVQQRKES (SEQ ID NO: 72); GMAGSS(Oct)FLSPEHQRVQQRKESK (SEQ ID NO: 73); GMAGSS(Oct)FLSPEHQRVQQRKESKK (SEQ ID NO: 74); GMAGSS(Oct)FLSPEHQRVQQRKESKKP (SEQ ID NO: 75); GMAGSS(Oct)FLSPEHQRVQQRKESKKPP (SEQ ID NO: 76); GMAGSS(Oct)FLSPEHQRVQQRKESKKPPA (SEQ ID NO: 77); GMAGSS(Oct)FLSPEHQRVQQRKESKKPPAK (SEQ ID NO: 78); GMAGSS(Oct)FLSPEHQRVQQRKESKKPPAKL (SEQ ID NO: 79); GMAGSS(Oct)FLSPEHQRVQQRKESKKPPAKLQ (SEQ ID NO: 80); GMAGSS(Oct)FLSPEHQRVQQRKESKKPPAKLQP (SEQ ID NO: 81); GMAGSS(Oct)FLSPEHQRVQQRKESKKPPAKLQPR (SEQ ID NO: 82); GMAGSS(Oct)FLSPEHQRVQQRKESKKPPAKLQPRW (SEQ ID NO: 83); GMAGSDap(Oct)FL (SEQ ID NO: 84); GMAGSDap(Oct)FLS (SEQ ID NO: 85); GMAGSDap(Oct)FLSP (SEQ ID NO: 86); GMAGSDap(Oct)FLSPE (SEQ ID NO: 87); GMAGSDap(Oct)FLSPEH (SEQ ID NO: 88); GMAGSDap(Oct)FLSPEHQ (SEQ ID NO: 89); GMAGSDap(Oct)FLSPEHQR (SEQ ID NO: 90); GMAGSDap(Oct)FLSPEHQRV (SEQ ID NO: 91); GMAGSDap(Oct)FLSPEHQRVQ (SEQ ID NO: 92); GMAGSDap(Oct)FLSPEHQRVQQ (SEQ ID NO: 93); GMAGSDap(Oct)FLSPEHQRVQQR (SEQ ID NO: 94); GMAGSDap(Oct)FLSPEHQRVQQRK (SEQ ID NO: 95); GMAGSDap(Oct)FLSPEHQRVQQRKE (SEQ ID NO: 96); GMAGSDap(Oct)FLSPEHQRVQQRKES (SEQ ID NO: 97); GMAGSDap(Oct)FLSPEHQRVQQRKESK (SEQ ID NO: 98); GMAGSDap(Oct)FLSPEHQRVQQRKESKK (SEQ ID NO: 99); GMAGSDap(Oct)FLSPEHQRVQQRKESKKP (SEQ ID NO: 100); GMAGSDap(Oct)FLSPEHQRVQQRKESKKPP (SEQ ID NO: 101); GMAGSDap(Oct)FLSPEHQRVQQRKESKKPPA (SEQ ID NO: 102); GMAGSDap(Oct)FLSPEHQRVQQRKESKKPPAK (SEQ ID NO: 103); GMAGSDap(Oct)FLSPEHQRVQQRKESKKPPAKL (SEQ ID NO: 104); GMAGSDap(Oct)FLSPEHQRVQQRKESKKPPAKLQ (SEQ ID NO: 105); GMAGSDap(Oct)FLSPEHQRVQQRKESKKPPAKLQP (SEQ ID NO: 106); GMAGSDap(Oct)FLSPEHQRVQQRKESKKPPAKLQPR (SEQ ID NO: 107); GMAGSDap(Oct)FLSPEHQRVQQRKESKKPPAKLQPRW (SEQ ID NO: 108); AMAGSS(Oct)FL (SEQ ID NO: 109); AMAGSS(Oct)FLS (SEQ ID NO: 110); AMAGSS(Oct)FLSP (SEQ ID NO: 111); AMAGSS(Oct)FLSPE (SEQ ID NO: 112); AMAGSS(Oct)FLSPEH (SEQ ID NO: 113); AMAGSS(Oct)FLSPEHQ (SEQ ID NO: 114); AMAGSS(Oct)FLSPEHQR (SEQ ID NO: 115); AMAGSS(Oct)FLSPEHQRV (SEQ ID NO: 116); AMAGSS(Oct)FLSPEHQRVQ (SEQ ID NO: 117); AMAGSS(Oct)FLSPEHQRVQQ (SEQ ID NO: 118); AMAGSS(Oct)FLSPEHQRVQQR (SEQ ID NO: 119); AMAGSS(Oct)FLSPEHQRVQQRK (SEQ ID NO: 120); AMAGSS(Oct)FLSPEHQRVQQRKE (SEQ ID NO: 121); AMAGSS(Oct)FLSPEHQRVQQRKES (SEQ ID NO: 122); AMAGSS(Oct)FLSPEHQRVQQRKESK (SEQ ID NO: 123); AMAGSS(Oct)FLSPEHQRVQQRKESKK (SEQ ID NO: 124); AMAGSS(Oct)FLSPEHQRVQQRKESKKP (SEQ ID NO: 125); AMAGSS(Oct)FLSPEHQRVQQRKESKKPP (SEQ ID NO: 126); AMAGSS(Oct)FLSPEHQRVQQRKESKKPPA (SEQ ID NO: 127); AMAGSS(Oct)FLSPEHQRVQQRKESKKPPAK (SEQ ID NO: 128); AMAGSS(Oct)FLSPEHQRVQQRKESKKPPAKL (SEQ ID NO: 129); AMAGSS(Oct)FLSPEHQRVQQRKESKKPPAKLQ (SEQ ID NO: 130); AMAGSS(Oct)FLSPEHQRVQQRKESKKPPAKLQP (SEQ ID NO: 131); AMAGSS(Oct)FLSPEHQRVQQRKESKKPPAKLQPR (SEQ ID NO: 132); AMAGSS(Oct)FLSPEHQRVQQRKESKKPPAKLQPRW (SEQ ID NO: 133); AMAGSDap(Oct)FL (SEQ ID NO: 134); AMAGSDap(Oct)FLS (SEQ ID NO: 135); AMAGSDap(Oct)FLSP (SEQ ID NO: 136); AMAGSDap(Oct)FLSPE (SEQ ID NO: 137); AMAGSDap(Oct)FLSPEH (SEQ ID NO: 138); AMAGSDap(Oct)FLSPEHQ (SEQ ID NO: 139); AMAGSDap(Oct)FLSPEHQR (SEQ ID NO: 140); AMAGSDap(Oct)FLSPEHQRV (SEQ ID NO: 141); AMAGSDap(Oct)FLSPEHQRVQ (SEQ ID NO: 142); AMAGSDap(Oct)FLSPEHQRVQQ (SEQ ID NO: 143); AMAGSDap(Oct)FLSPEHQRVQQR (SEQ ID NO: 144); AMAGSDap(Oct)FLSPEHQRVQQRK (SEQ ID NO: 145); AMAGSDap(Oct)FLSPEHQRVQQRKE (SEQ ID NO: 146); AMAGSDap(Oct)FLSPEHQRVQQRKES (SEQ ID NO: 147); AMAGSDap(Oct)FLSPEHQRVQQRKESK (SEQ ID NO: 148); AMAGSDap(Oct)FLSPEHQRVQQRKESKK (SEQ ID NO: 149); AMAGSDap(Oct)FLSPEHQRVQQRKESKKP (SEQ ID NO: 150); AMAGSDap(Oct)FLSPEHQRVQQRKESKKPP (SEQ ID NO: 151); AMAGSDap(Oct)FLSPEHQRVQQRKESKKPPA (SEQ ID NO: 152); AMAGSDap(Oct)FLSPEHQRVQQRKESKKPPAK (SEQ ID NO: 153); AMAGSDap(Oct)FLSPEHQRVQQRKESKKPPAKL (SEQ ID NO: 154); AMAGSDap(Oct)FLSPEHQRVQQRKESKKPPAKLQ (SEQ ID NO: 155); AMAGSDap(Oct)FLSPEHQRVQQRKESKKPPAKLQP (SEQ ID NO: 156); AMAGSDap(Oct)FLSPEHQRVQQRKESKKPPAKLQPR (SEQ ID NO: 157); AMAGSDap(Oct)FLSPEHQRVQQRKESKKPPAKLQPRW (SEQ ID NO: 158); GMAGSS(Oct)FL-NH$_2$ (SEQ ID NO: 159); GMAGSS(Oct)FLS-NH$_2$ (SEQ ID NO: 160); GMAGSS(Oct)FLSP-NH$_2$ (SEQ ID NO: 161); GMAGSS(Oct)FLSPE-NH$_2$ (SEQ ID NO: 162); GMAGSS(Oct)FLSPEH-NH$_2$ (SEQ ID NO: 163); GMAGSS(Oct)FLSPEHQ-NH$_2$ (SEQ ID NO: 164); GMAGSS(Oct)FLSPEHQR-NH$_2$ (SEQ ID NO: 165); GMAGSS(Oct)FLSPEHQRV-NH$_2$ (SEQ ID NO: 166); GMAGSS(Oct)FLSPEHQRVQ-NH$_2$ (SEQ ID NO: 167); GMAGSS(Oct)FLSPEHQRVQQ-NH$_2$ (SEQ ID NO: 168); GMAGSS(Oct)FLSPEHQRVQQR-NH$_2$ (SEQ ID NO: 169); GMAGSS(Oct)FLSPEHQRVQQRK-NH$_2$ (SEQ ID NO: 170); GMAGSS(Oct)FLSPEHQRVQQRKE-NH$_2$ (SEQ ID NO: 171); GMAGSS(Oct)FLSPEHQRVQQRKES-NH$_2$ (SEQ ID NO: 172); GMAGSS(Oct)FLSPEHQRVQQRKESK-NH$_2$ (SEQ ID NO: 173); GMAGSS(Oct)FLSPEHQRVQQRKESKK-NH$_2$ (SEQ ID NO: 174); GMAGSS(Oct)FLSPEHQRVQQRKESKKP-NH$_2$ (SEQ ID NO: 175); GMAGSS(Oct)FLSPEHQRVQQRKESKKPP-NH$_2$ (SEQ ID NO: 176); GMAGSS(Oct)FLSPEHQRVQQRKESKKPPA-NH$_2$ (SEQ ID NO: 177); GMAGSS(Oct)FLSPEHQRVQQRKESKKPPAK-NH$_2$ (SEQ ID NO: 178); GMAGSS(Oct)FLSPEHQRVQQRKESKKPPAKL-NH$_2$ (SEQ ID NO: 179); GMAGSS(Oct)FLSPEHQRVQQRKESKKPPAKLQ-NH$_2$ (SEQ ID NO: 180); GMAGSS(Oct)FLSPEHQRVQQRKESKKPPAKLQP-NH$_2$ (SEQ ID NO: 181); GMAGSS(Oct)FLSPEHQRVQQRKESKKPPAKLQPR-NH$_2$ (SEQ ID NO: 182); GMAGSS(Oct)FLSPEHQRVQQRKESKKPPAKLQPRW-NH$_2$ (SEQ ID NO: 183); GMAGSDap(Oct)FL-NH$_2$ (SEQ ID NO: 184); GMAGSDap(Oct)FLS-NH$_2$ (SEQ ID NO: 185); GMAGSDap(Oct)FLSP-NH$_2$ (SEQ ID NO: 186); GMAGSDap(Oct)FLSPE-NH$_2$ (SEQ ID NO: 187); GMAGSDap(Oct)FLSPEH-NH$_2$ (SEQ ID NO: 188); GMAGSDap(Oct)FLSPEHQ-NH$_2$ (SEQ ID NO: 189); GMAGSDap(Oct)FLSPEHQR-NH$_2$(SEQ ID NO: 190); GMAGSDap(Oct)FLSPEHQRV-NH$_2$ (SEQ ID NO: 191); GMAGSDap(Oct)FLSPEHQRVQ-NH$_2$ (SEQ ID NO: 192); GMAGSDap(Oct)FLSPEHQRVQQ-NH$_2$ (SEQ ID NO: 193); GMAGSDap(Oct)FLSPEHQRVQQR-NH$_2$ (SEQ ID NO: 194); GMAGSDap(Oct)FLSPEHQRVQQRK-NH$_2$ (SEQ ID NO: 195); GMAGSDap(Oct)FLSPEHQRVQQRKE-NH$_2$ (SEQ ID NO: 196); GMAGSDap(Oct)FLSPEHQRVQQRKES-NH$_2$ (SEQ ID NO: 197); GMAGSDap(Oct)FLSPEHQRVQQRKESK-NH$_2$ (SEQ ID NO: 198); GMAGSDap(Oct)FLSPEHQRVQQRKESKK-NH$_2$ (SEQ ID NO: 199); GMAGSDap(Oct)FLSPEHQRVQQRKESKKP-NH$_2$ (SEQ ID NO: 200); GMAGSDap(Oct)FLSPEHQRVQQRKESKKPP-NH$_2$ (SEQ ID NO: 201); GMAGSDap(Oct)FLSPEHQRVQQRKESKKPPA-NH$_2$ (SEQ ID NO: 202); GMAGSDap(Oct)FLSPEHQRVQQRKESKKPPAK-NH$_2$ (SEQ ID NO: 203); GMAGSDap(Oct)FLSPEHQRVQQRKESKKPPAKL-NH$_2$ (SEQ ID NO: 204); GMAGSDap(Oct)FLSPEHQRVQQRKESKKPPAKLQ-NH$_2$ (SEQ ID NO: 205); GMAGSDap(Oct)FLSPEHQRVQQRKESKKPPAKLQP-NH$_2$ (SEQ ID NO: 206); GMAGSDap(Oct)FLSPEHQRVQQRKESKKPPAKLQPR-NH$_2$ (SEQ ID NO: 207); GMAGSDap(Oct)FLSPEHQRVQQRKESKKPPAKLQPRW-NH$_2$ (SEQ ID NO: 208); AMAGSS(Oct)FL-NH$_2$ (SEQ ID NO: 209); AMAGSS(Oct)FLS-NH$_2$ (SEQ ID NO: 210); AMAGSS(Oct)FLSP-NH$_2$(SEQ ID NO: 211); AMAGSS(Oct)FLSPE-NH$_2$ (SEQ ID NO: 212); AMAGSS(Oct)FLSPEH-NH$_2$ (SEQ ID NO: 213); AMAGSS(Oct)FLSPEHQ-NH$_2$ (SEQ ID NO: 214); AMAGSS(Oct)FLSPEHQR-NH$_2$ (SEQ ID NO: 215); AMAGSS(Oct)FLSPEHQRV-NH$_2$ (SEQ ID NO: 216); AMAGSS(Oct)FLSPEHQRVQ-NH$_2$ (SEQ ID NO: 217); AMAGSS(Oct)FLSPEHQRVQQ-NH$_2$ (SEQ ID NO: 218); AMAGSS(Oct)FLSPEHQRVQQR-NH$_2$ (SEQ ID NO: 219); AMAGSS(Oct)FLSPEHQRVQQRK-NH$_2$ (SEQ ID NO: 220); AMAGSS(Oct)FLSPEHQRVQQRKE-NH$_2$ (SEQ ID NO: 221); AMAGSS(Oct)FLSPEHQRVQQRKES-NH$_2$ (SEQ ID NO: 222); AMAGSS(Oct)FLSPEHQRVQQRKESK-NH$_2$ (SEQ ID NO: 223); AMAGSS(Oct)FLSPEHQRVQQRKESKK-NH$_2$ (SEQ ID NO: 224); AMAGSS(Oct)FLSPEHQRVQQRKESKKP-NH$_2$ (SEQ ID NO: 225); AMAGSS(Oct)FLSPEHQRVQQRKESKKPP-NH$_2$ (SEQ ID NO: 226); AMAGSS(Oct)FLSPEHQRVQQRKESKKPPA-NH$_2$ (SEQ ID NO: 227); AMAGSS(Oct)FLSPEHQRVQQRKESKKPPAK-NH$_2$ (SEQ ID NO: 228); AMAGSS(Oct)FLSPEHQRVQQRKESKKPPAKL-NH$_2$ (SEQ ID NO: 229); AMAGSS(Oct)FLSPEHQRVQQRKESKKPPAKLQ-NH$_2$ (SEQ ID NO: 230); AMAGSS(Oct)FLSPEHQRVQQRKESKKPPAKLQP-NH$_2$ (SEQ ID NO: 231); AMAGSS(Oct)FLSPEHQRVQQRKESKKPPAKLQPR-NH$_2$ (SEQ ID NO: 232); AMAGSS(Oct)FLSPEHQRVQQRKESKKPPAKLQPRW-NH$_2$ (SEQ ID NO: 233); AMAGSDap(Oct)FL-NH$_2$ (SEQ ID NO: 234); AMAGSDap(Oct)FLS-NH$_2$ (SEQ ID NO: 235); AMAGSDap(Oct)FLSP-NH$_2$ (SEQ ID NO: 236); AMAGSDap(Oct)FLSPE-NH$_2$ (SEQ ID NO: 237); AMAGSDap(Oct)FLSPEH-NH$_2$ (SEQ ID NO: 238); AMAGSDap(Oct)FLSPEHQ-NH$_2$ (SEQ ID NO: 239); AMAGSDap(Oct)FLSPEHQR-NH$_2$(SEQ ID NO: 240); AMAGSDap(Oct)FLSPEHQRV-NH$_2$ (SEQ ID NO: 241); AMAGSDap(Oct)FLSPEHQRVQ-NH$_2$ (SEQ ID NO: 242); AMAGSDap(Oct)FLSPEHQRVQQ-NH$_2$ (SEQ ID NO: 243); AMAGSDap(Oct)FLSPEHQRVQQR-NH$_2$ (SEQ ID NO: 244); AMAGSDap(Oct)FLSPEHQRVQQRK-NH$_2$ (SEQ ID NO: 245); AMAGSDap(Oct)FLSPEHQRVQQRKE-NH$_2$ (SEQ ID NO: 246); AMAGSDap(Oct)FLSPEHQRVQQRKES-NH$_2$ (SEQ ID NO: 247); AMAGSDap(Oct)FLSPEHQRVQQRKESK-NH$_2$ (SEQ ID NO: 248); AMAGSDap(Oct)FLSPEHQRVQQRKESKK-NH$_2$ (SEQ ID NO: 249); AMAGSDap(Oct)FLSPEHQRVQQRKESKKP-NH$_2$ (SEQ ID NO: 250); AMAGSDap(Oct)FLSPEHQRVQQRKESKKPP-NH$_2$ (SEQ ID NO: 251); AMAGSDap(Oct)FLSPEHQRVQQRKESKKPPA-NH$_2$ (SEQ ID NO: 252); AMAGSDap(Oct)FLSPEHQRVQQRKESKKPPAK-NH$_2$ (SEQ ID NO: 253); AMAGSDap(Oct)FLSPEHQRVQQRKESKKPPAKL-NH$_2$ (SEQ ID NO: 254); AMAGSDap(Oct)FLSPEHQRVQQRKESKKPPAKLQ-NH$_2$ (SEQ ID NO: 255); AMAGSDap(Oct)FLSPEHQRVQQRKESKKPPAKLQP-NH$_2$ (SEQ ID NO: 256); AMAGSDap(Oct)FLSPEHQRVQQRKESKKPPAKLQPR-NH$_2$ (SEQ ID NO: 257); AMAGSDap(Oct)FLSPEHQRVQQRKESKKPPAKLQPRW-NH$_2$ (SEQ ID NO: 258); GMAGSYFL (SEQ ID NO: 259); GMAGSYFLS (SEQ ID NO: 260); GMAGSYFLSP (SEQ ID NO: 261); GMAGSYFLSPE (SEQ ID NO: 262); GMAGSYFLSPEH (SEQ ID NO: 263); GMAGSYFLSPEHQ (SEQ ID NO: 264); GMAGSYFLSPEHQR (SEQ ID NO: 265); GMAGSYFLSPEHQRV (SEQ ID NO: 266); GMAGSYFLSPEHQRVQ (SEQ ID NO: 267); GMAGSYFLSPEHQRVQQ (SEQ ID NO: 268); GMAGSYFLSPEHQRVQQR (SEQ ID NO: 269); GMAGSYFLSPEHQRVQQRK (SEQ ID NO: 270); GMAGSYFLSPEHQRVQQRKE (SEQ ID NO: 271); GMAGSYFLSPEHQRVQQRKES (SEQ ID NO: 272); GMAGSYFLSPEHQRVQQRKESK (SEQ ID NO: 273); GMAGSYFLSPEHQRVQQRKESKK (SEQ ID NO: 274); GMAGSYFLSPEHQRVQQRKESKKP (SEQ ID NO: 275); GMAGSYFLSPEHQRVQQRKESKKPP (SEQ ID NO: 276); GMAGSYFLSPEHQRVQQRKESKKPPA (SEQ ID NO: 277); GMAGSYFLSPEHQRVQQRKESKKPPAK (SEQ ID NO: 278); GMAGSYFLSPEHQRVQQRKESKKPPAKL (SEQ ID NO: 279); GMAGSYFLSPEHQRVQQRKESKKPPAKLQ (SEQ ID NO: 280); GMAGSYFLSPEHQRVQQRKESKKPPAKLQP (SEQ ID NO: 281); GMAGSYFLSPEHQRVQQRKESKKPPAKLQPR (SEQ ID NO: 282); GMAGSYFLSPEHQRVQQRKESKKPPAKLQPRW (SEQ ID NO: 283); AMAGSYFL (SEQ ID NO: 284); AMAGSYFLS (SEQ ID NO: 285); AMAGSYFLSP (SEQ ID NO: 286); AMAGSYFLSPE (SEQ ID NO: 287); AMAGSYFLSPEH (SEQ ID NO: 288); AMAGSYFLSPEHQ (SEQ ID NO: 289); AMAGSYFLSPEHQR (SEQ ID NO: 290); AMAGSYFLSPEHQRV (SEQ ID NO: 291); AMAGSYFLSPEHQRVQ (SEQ ID NO: 292); AMAGSYFLSPEHQRVQQ (SEQ ID NO: 293); AMAGSYFLSPEHQRVQQR (SEQ ID NO: 294); AMAGSYFLSPEHQRVQQRK (SEQ ID NO: 295); AMAGSYFLSPEHQRVQQRKE (SEQ ID NO: 296);

AMAGSYFLSPEHQRVQQRKES (SEQ ID NO: 297); AMAGSYFLSPEHQRVQQRKESK (SEQ ID NO: 298); AMAGSYFLSPEHQRVQQRKESKK (SEQ ID NO: 299); AMAGSYFLSPEHQRVQQRKESKKP (SEQ ID NO: 300); AMAGSYFLSPEHQRVQQRKESKKPP (SEQ ID NO: 301); AMAGSYFLSPEHQRVQQRKESKKPPA (SEQ ID NO: 302); AMAGSYFLSPEHQRVQQRKESKKPPAK (SEQ ID NO: 303); AMAGSYFLSPEHQRVQQRKESKKPPAKL (SEQ ID NO: 304); AMAGSYFLSPEHQRVQQRKESKKPPAKLQ (SEQ ID NO: 305); AMAGSYFLSPEHQRVQQRKESKKPPAKLQP (SEQ ID NO: 306); AMAGSYFLSPEHQRVQQRKESKKPPAKLQPR (SEQ ID NO: 307); AMAGSYFLSPEHQRVQQRKESKKPPAKLQPRW (SEQ ID NO: 308); GMAGSYFL-NH$_2$ (SEQ ID NO: 309); GMAGSYFLS-NH$_2$ (SEQ ID NO: 310); GMAGSYFLSP-NH$_2$ (SEQ ID NO: 311); GMAGSYFLSPE-NH$_2$ (SEQ ID NO: 312); GMAGSYFLSPEH-NH$_2$ (SEQ ID NO: 313); GMAGSYFLSPEHQ-NH$_2$ (SEQ ID NO: 314); GMAGSYFLSPEHQR-NH$_2$ (SEQ ID NO: 315); GMAGSYFLSPEHQRV-NH$_2$ (SEQ ID NO: 316); GMAGSYFLSPEHQRVQ-NH$_2$ (SEQ ID NO: 317); GMAGSYFLSPEHQRVQQ-NH2 (SEQ ID NO: 318); GMAGSYFLSPEHQRVQQR-NH$_2$ (SEQ ID NO: 319); GMAGSYFLSPEHQRVQQRK-NH$_2$ (SEQ ID NO: 320); GMAGSYFLSPEHQRVQQRKE-NH$_2$ (SEQ ID NO: 321); GMAGSYFLSPEHQRVQQRKES-NH$_2$ (SEQ ID NO: 322); GMAGSYFLSPEHQRVQQRKESK-NH$_2$ (SEQ ID NO: 323); GMAGSYFLSPEHQRVQQRKESKK-NH$_2$ (SEQ ID NO: 324); GMAGSYFLSPEHQRVQQRKESKKP-NH$_2$ (SEQ ID NO: 325); GMAGSYFLSPEHQRVQQRKESKKPP-NH$_2$ (SEQ ID NO: 326); GMAGSYFLSPEHQRVQQRKESKKPPA-NH$_2$ (SEQ ID NO: 327); GMAGSYFLSPEHQRVQQRKESKKPPAK-NH$_2$ (SEQ ID NO: 328); GMAGSYFLSPEHQRVQQRKESKKPPAKL-NH$_2$ (SEQ ID NO: 329); GMAGSYFLSPEHQRVQQRKESKKPPAKLQ-NH$_2$ (SEQ ID NO: 330); GMAGSYFLSPEHQRVQQRKESKKPPAKLQP-NH$_2$ (SEQ ID NO: 331); GMAGSYFLSPEHQRVQQRKESKKPPAKLQPR-NH$_2$ (SEQ ID NO: 332); GMAGSYFLSPEHQRVQQRKESKKPPAKLQPRW-NH$_2$ (SEQ ID NO: 333); AMAGSYFL-NH$_2$ (SEQ ID NO: 334); AMAGSYFLS-NH$_2$ (SEQ ID NO: 335); AMAGSYFLSP-NH$_2$(SEQ ID NO: 336); AMAGSYFLSPE-NH$_2$ (SEQ ID NO: 337); AMAGSYFLSPEH-NH$_2$ (SEQ ID NO: 338); AMAGSYFLSPEHQ-NH$_2$ (SEQ ID NO: 339); AMAGSYFLSPEHQR-NH$_2$ (SEQ ID NO: 340); AMAGSYFLSPEHQRV-NH$_2$ (SEQ ID NO: 341); AMAGSYFLSPEHQRVQ-NH$_2$ (SEQ ID NO: 342); AMAGSYFLSPEHQRVQQ-NH$_2$ (SEQ ID NO: 343); AMAGSYFLSPEHQRVQQR-NH$_2$ (SEQ ID NO: 344); AMAGSYFLSPEHQRVQQRK-NH$_2$ (SEQ ID NO: 345); AMAGSYFLSPEHQRVQQRKE-NH$_2$ (SEQ ID NO: 346); AMAGSYFLSPEHQRVQQRKES-NH$_2$ (SEQ ID NO: 347); AMAGSYFLSPEHQRVQQRKESK-NH$_2$ (SEQ ID NO: 348); AMAGSYFLSPEHQRVQQRKESKK-NH$_2$ (SEQ ID NO: 349); AMAGSYFLSPEHQRVQQRKESKKP-NH$_2$ (SEQ ID NO: 350); AMAGSYFLSPEHQRVQQRKESKKPP-NH$_2$ (SEQ ID NO: 351); AMAGSYFLSPEHQRVQQRKESKKPPA-NH$_2$ (SEQ ID NO: 352); AMAGSYFLSPEHQRVQQRKESKKPPAK-NH$_2$ (SEQ ID NO: 353); AMAGSYFLSPEHQRVQQRKESKKPPAKL-NH$_2$ (SEQ ID NO: 354); AMAGSYFLSPEHQRVQQRKESKKPPAKLQ-NH$_2$ (SEQ ID NO: 355); AMAGSYFLSPEHQRVQQRKESKKPPAKLQP-NH$_2$ (SEQ ID NO: 356); AMAGSYFLSPEHQRVQQRKESKKPPAKLQPR-NH$_2$ (SEQ ID NO: 357); AMAGSYFLSPEHQRVQQRKESKKPPAKLQPRW-NH$_2$ (SEQ ID NO: 358); Gly-Met-Ala-Gly-Ser-Dap(Oct)-Phe-Leu-Ser-Pro-Glu-His (SEQ ID NO: 359); Gly-Met-Ala-Gly-Ser-Dap(palmityl)-Phe-Leu-Ser-Pro-Glu-His (SEQ ID NO: 360); Gly-Met-Ala-Gly-Ser-Ser(Des-Octanoyl)-Phe-Leu (SEQ ID NO: 361); Gly-Met-Ala-Gly-Ser-Dap(Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO: 362); Gly-Met-Ala-Gly-Ser-Dap(Octanoyl)-Phe-Leu (SEQ ID NO: 363); Gly-Met-Ala-Gly-Ser-Ser(Des-Octanoyl)-Phe (SEQ ID NO: 364); Gly-Met-Ala-Gly-Ser-Ser(Des-Octanoyl)-Phe-Leu-Ser-Pro-Glu-His-Gln-Arg-Val-Gln-Gln-Arg-Lys-Glu-Ser (SEQ ID NO: 365); and Gly-Met-Ala-Gly-Ser-Ser(Des-Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-Tyr (SEQ ID NO: 366).

In some embodiments, a peptide of formula (I) is not $X^1$-GS-$X^2$-FL-$(X^4)$q (SEQ ID NO: 367), $X^1$-GS-$X^2$-FL-S—$X^4$(SEQ ID NO: 35), $X^1$-GS-$X^2$-FL-SP—$X^4$ (SEQ ID NO: 36), $X^1$-GS-$X^2$-FL-SPE-$X^4$ (SEQ ID NO: 37), $X^1$-GS-$X^2$-FL-SPEH-$X^4$(SEQ ID NO: 38), wherein q is an integer froml to 4 and $X^2$ is as defined above but not D- or L-Tyr. In some embodiments, a peptide of formula (I) is not GMAGSS(Oct)FL (SEQ ID NO: 59); GMAGSS(Oct)FLS (SEQ ID NO: 60); GMAGSS(Oct)FLSP (SEQ ID NO: 61); GMAGSS(Oct)FLSPE (SEQ ID NO: 62); GMAGSS(Oct)FLSPEH (SEQ ID NO: 63); GMAGSDap(Oct)FL (SEQ ID NO: 84); GMAGSDap(Oct)FLS (SEQ ID NO: 85); GMAGSDap(Oct)FLSP (SEQ ID NO: 86); GMAGSDap(Oct)FLSPE (SEQ ID NO: 87); GMAGSDap(Oct)FLSPEH (SEQ ID NO: 88); AMAGSS(Oct)FL (SEQ ID NO: 109); AMAGSS(Oct)FLS (SEQ ID NO: 110); AMAGSS(Oct)FLSP (SEQ ID NO: 111); AMAGSS(Oct)FLSPE (SEQ ID NO: 112); AMAGSS(Oct)FLSPEH (SEQ ID NO: 113); AMAGSDap(Oct)FL (SEQ ID NO: 134); AMAGSDap(Oct)FLS (SEQ ID NO: 135); AMAGSDap(Oct)FLSP (SEQ ID NO: 136); AMAGSDap(Oct)FLSPE (SEQ ID NO: 137); AMAGSDap(Oct)FLSPEH (SEQ ID NO: 138); GMAGSS(Oct)FL-NH$_2$ (SEQ ID NO: 159); GMAGSS(Oct)FLS-NH$_2$ (SEQ ID NO: 160); GMAGSS(Oct)FLSP-NH$_2$ (SEQ ID NO: 161); GMAGSS(Oct)FLSPE-NH$_2$ (SEQ ID NO: 162); GMAGSS(Oct)FLSPEH-NH$_2$ (SEQ ID NO: 163); GMAGSDap(Oct)FL-NH$_2$ (SEQ ID NO: 184); GMAGSDap(Oct)FLS-NH$_2$ (SEQ ID NO: 185); GMAGSDap(Oct)FLSP-NH$_2$ (SEQ ID NO: 186); GMAGSDap(Oct)FLSPE-NH$_2$ (SEQ ID NO: 187); GMAGSDap(Oct)FLSPEH-NH$_2$ (SEQ ID NO: 188); AMAGSS(Oct)FL-NH$_2$ (SEQ ID NO: 209); AMAGSS(Oct)FLS-NH$_2$ (SEQ ID NO: 210); AMAGSS(Oct)FLSP-NH$_2$ (SEQ ID NO: 211); AMAGSS(Oct)FLSPE-NH$_2$ (SEQ ID NO: 212); AMAGSS(Oct)FLSPEH-NH$_2$ (SEQ ID NO: 213); AMAGSDap(Oct)FL-NH$_2$ (SEQ ID NO: 234); AMAGSDap(Oct)FLS-NH$_2$ (SEQ ID NO: 235); AMAGSDap(Oct)FLSP-NH$_2$ (SEQ ID NO: 236); AMAGSDap(Oct)FLSPE-NH$_2$ (SEQ ID NO: 237); AMAGSDap(Oct)FLSPEH-NH$_2$ (SEQ ID NO: 238); Gly-Met-Ala-Gly-Ser-Dap(Oct)-Phe-Leu-Ser-Pro-Glu-His (SEQ ID NO: 359); Gly-Met-Ala-Gly-Ser-Dap (palmityl)-Phe-Leu-Ser-Pro-Glu-His (SEQ ID NO: 360); Gly-Met-Ala-Gly-Ser-Ser(Des-Octanoyl)-Phe-Leu (SEQ ID NO: 361); Gly-Met-Ala-Gly-Ser-Dap(Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO: 362); Gly-Met-Ala-Gly-Ser-Dap(Octanoyl)-Phe-Leu (SEQ ID NO: 363); Gly-Met-Ala-Gly-Ser-Ser(Des-Octanoyl)-Phe (SEQ ID NO: 364); Gly-Met-Ala-Gly-Ser-Ser(Des-Octanoyl)-Phe-Leu-Ser-Pro-Glu-His-Gln-Arg-Val-Gln-Gln-Arg-Lys-Glu-Ser (SEQ ID NO: 365); Gly-Met-Ala-Gly-Ser-Ser(Des-Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-Tyr (SEQ ID NO: 366); Gly-Ser-Ser(Oct)-Phe- Leu (SEQ ID NO: 5); Gly-Ser-Dap(Oct)-Phe-Leu (SEQ ID NO: 368); Gly-Met-Ala-Gly-Ser-Dap(Oct)-Phe-Leu-Ser-Pro-Glu-His-NH$_2$ (SEQ ID NO: 188); Gly-Met-Ala-Gly-Ser-Dap(palmityl)-Phe-Leu-Ser-Pro-Glu-His-NH$_2$(SEQ ID NO: 3); Gly-Ser-Ser(Des-Octanoyl)-Phe-Leu-NH$_2$(SEQ ID NO: 369); Gly-Ser-Dap(Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$(SEQ ID NO: 370); Gly-Ser-Dap(Octanoyl)-Phe-Leu-NH$_2$(SEQ ID NO: 371); Gly-Ser-Ser(Des-Octanoyl)-Phe-NH$_2$(SEQ ID NO: 372); Gly-Ser-Ser(Des-Octanoyl)-Phe-Leu-Ser-Pro-Glu-His-Gln-Arg-Val-Gln-Gln-Arg-Lys-Glu-Ser-NH$_2$(SEQ ID NO: 373); and Gly-Ser-Ser(Des-Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-Tyr-NH$_2$ (SEQ ID NO: 374).

Peptides of Formula (II)

In some embodiments, $A^{11}$ is His; Tyr; desamino Tyr; D- or L-Ala; β-Ala; D- or L-cyclohexylAla (Cyclohexylalanine); D-Arg, Ava (aminovaleric acid); Gly; <Glu (pyroglutaminic acid); αAib (alpha-aminoisobutyric acid); γAbu (gamma-aminobutyric acid); αAbu (alpha-aminobutyric acid); α,γAbu (alpha, gamma-aminobutyric acid); D-Val; D-phe; D-Thr; D-Pal (pyridylalanine); D-Lys; Acetyl-D-Lys; D-Leu; D-Phe; D- or L-Trp; D- or L α-naphthyalanine; D- or L-β-naphthyalanine; D- or L-Ser; D- or L-Ser which is acylated at the side-chain hydroxyl group (Ser(acyl)); or Acetyl-D-β-naphthyalanine There can be a normal or reduced psi peptide (CH$_2$NH) at position 1. Alternatively, $A^{21}$ may be amino acids with methylation of the terminal nitrogen of the alpha carbon atom of the $A^{21}$ residue. In some embodiments, when $A^{21}$ is an acylated serine, the side-chain is acylated with benzyl (Ser(Bzl)) or naphthalenyl (Ser(Nap), e.g., naphthalene-2-yl.

In some embodiments, $A^{22}$ is D-α,β-naphthyalanine; D- or L-α-naphthyalanine; D-opr L-β-naphthyalanine; D- or L-Trp; D- or L-Phe; Ala; His; D- or L-Lys; D- or L-Lys which is acylated at the side-chain amino group (Lys(acyl)); D-Pro; D-Orn; Ser; D- or L-Ser which is acylated at the side-chain hydroxyl group; D-Pal; D- or L-Leu; Phe; PicLys (N$^\epsilon$-picoloyl-lysine); D-Cyclohexylalanine; D-4-halo-Phe; D-4-pyrolidylalanine; or an amino acid with methylation of the terminal nitrogen of the α carbon atom of the $A^{22}$ residue. In one embodiment, $A^{22}$ could have extended aromatic chains, such as, for example, D-4-halo-Phe, D-4-pyrolidylalanine, or homologues or analogues thereof. In some embodiments, when $A^{22}$ is an acylated serine, the side-chain is acylated with benzyl or naphthalenyl, e.g., naphthalene-2-yl. In some embodiments, when $A^{22}$ is an acylated lysine, the side-chain is acylated with an acetyl group (Lys(Ac)).

In some embodiments, $A^{23}$ is absent; D- or L-Lys; lysine derivatives; Arg; arginine derivatives, Orn; L- or D-Phe; D- or L-Trp; Leu; L- or D-Pro, Ala; D-Ile; D- or L-Val; Ser; Pal; D- or L-cyclohexylAla; cyclopentylAla; βNal; αNal; or α,γAbu.

In some embodiments, $A^{24}$ is absent; D- or L-Trp; D- or L-Phe; D- or L-Ile; D- or L-Val; D- or L-Arg; Ala; Ser; Tyr; Met; Pro; Thr; ILys; or CyclohexylAla.

In some embodiments, $A^{25}$ is absent; D- or L-Trp; L- or D-Phe; Ala; Lys; Arg; Orn; Thr; Leu; or DCyclohexylAla.

In some embodiments, $A^{26}$ is absent; Lys; Gln; Arg; Orn; D- or L-Phe, Pro(cyclic Arg-Pro); Nle (norleucine); or α,γ Abu amide.

In some embodiments, $A^{27}$ is absent or Gly.

In some embodiments, $A^{23}$, $A^{24}$, $A^{25}$, $A^{26}$, and $A^{27}$ are absent.

In some embodiments, $A^{24}$, $A^{25}$, $A^{26}$, and $A^{27}$ are absent.

In some embodiments, $A^{25}$, $A^{26}$, and $A^{27}$ are absent.

In some embodiments, $A^{26}$, and $A^{27}$ are absent.

In some embodiments, $A^{21}$ is His, Tyr, desamino Tyr, D- or L-Ala, β-Ala, CyclohexylAla (Cyclohexylalanine), D-Arg, Ava (aminovaleric acid), Gly, <Glu (pyroglutaminic acid), αAib (alpha-aminoisobutyric acid), γAbu (gamma-aminobutyric acid), αAbu (alpha-aminobutyric acid), α,γ-Abu (alpha, gamma-aminobutyric acid), D-Val, D-phe, D-Thr, D-Pal (pyridylalanine), D-Lys, Acetyl-D-Lys, D-Leu, D-Trp, D-β-naphthyalanine, Acetyl-D-β-naphthyalanine, or an amino acid with methylation of the terminal nitrogen of the alpha carbon; $A^{22}$ is D-α,β-naphthyalanine, D-α-naphthyalanine, D-β-naphthyalanine, D- or L-Trp, D- or L-Phe, Ala, His, D-Lys, D-Pro, PicLys (N$^\epsilon$-picoloyl-lysine), D-Cyclohexylalanine, D-4-halo-Phe, D-4-pyrolidylalanine, or an amino acid with methylation of the terminal nitrogen of the α carbon atom; $A^{23}$ is absent, D- or L-Lys, lysine derivatives, Arg, arginine derivatives, Orn, Phe, Trp, Leu, L- or D-Pro, Ala, D-Ile, D-Val, Ser, Pal, or α,γ Abu; $A^{24}$ is absent, D- or L-Trp, D- or L-Phe, D or L-Ile, D- or L-Val, D- or L-Arg, Ala, Ser, Tyr, Met, Pro, Thr, ILys, or CyclohexylAla; $A^{25}$ is absent, D- or L-Trp, L- or D-Phe, Ala, Lys, Arg, Orn, Thr, Leu, or DCyclohexylAla; $A^{26}$ is absent, Lys, Gln, Arg, Orn, D- or L-Phe, Pro(cyclic Arg-Pro), Nle (norleucine), or α,γ Abu amide; and $A^{27}$ is absent or Gly.

In some embodiments, $A^{21}$ is D-Trp, D-βNal, D-αNal, D-Phe or D-cyclohexylAla; $A^{22}$ is D-Lys, D-Orn, Ser, D-Pal, D-Leu, or Phe; $A^{23}$ is D or L-Pro; $A^{24}$ is D-Phe, D-Ile, or D-Arg; and $A^{25}$, $A^{26}$ and $A^{27}$ are absent.

In some embodiments, $A^{21}$ is D-Ala, αAib, D-Trp, or DβNal; $A^{22}$ is DTrp or Leu; $A^{23}$ is Phe, D-cyclohexylAla, Lys, Pro, Trp, Leu, Val, Ile, Pro, or Phe; and $A^{24}$, $A^{25}$, $A^{26}$ and $A^{27}$ are absent.

In some embodiments, $A^{21}$ is D-Trp, D-βNal, D-αNal, D-Phe, D-cyclohexylAla; $A^{22}$ is D- or L-Trp, D- or L-βNal, D- or L-αNal, D- or L-Leu, or D-Lys; $A^{23}$ is D-Trp, D-βNal, D-αNal, D-Phe, D-cyclohexylAla; and $A^{24}$, $A^{25}$, $A^{26}$ and $A^{27}$ are absent.

In some embodiments, $A^{21}$ is D-βNal or DThr; $A^{22}$ is DTrp or D-αNal; $A^{23}$ is absent or DTrp; $A^{24}$ is absent or D-Pro; $A^{25}$ is absent or Arg; and $A^{26}$ and $A^{27}$ are absent.

Exemplary amino acid sequences of $A^{21}$-$A^{22}$-$A^{23}$-$A^{24}$-$A^{25}$-$A^{26}$-$A^{27}$ include, but are not limited to, <GluHisTrpDSerDArg, AlaHisDTrpDLysTrpDPheLys, Alaψ[CH$_2$NH] DβNalAlaTrpDPheLys, Alaψ[CH$_2$NH] HisDTrpAlaTrpDPheLys, ArgDTrpLeuTyrTrpPro(cyclic ArgPro), AvaTrpDTrpDTrpOrn, CyclohexylAlaDαNalDTrpPheArg, DAlaAlaDAIaDTrpPheLys, DAlaDcyclohexylAlaAlaAlaPheDPheNle, DAlaDcyclohexylAlaAlaPheDPhe, DAlaDTrpPhe; DAlaDβNalAlaAlaDAlaLys, DAlaDβNalAlaThrDThrLys, DAlaDβNalAlaTrpDPheLys, DAlaDβ-NalDAlaDTrpPheLys, DAlaDβNalDProPheArg, DcyclohexylAlaAlaPheDTrpLys, DcyclohexylAlaAlaTrpDPhe, DesaminoTyrDTrpDLysTrpDPhe, DesaminoTyrDTrpSerTrpDPhe, DesaminoTyrDTrpSerTrpDPheLys, DHISDTrpDProDArg, DHisDTrpDProDIle, DLeuDαNalDTrpPheArg, DLysDβNalAlaTrpDPheLys, DLysTyrDTrpAlaTrpDPhe, DLysTyrDTrpDTrpPhe, DLysTyrDTrpDTrpPheLys, DPalPheDTrpPheMet, DPheAlaPheDPal, DPheAlaPheDPheLys, DPheDPheDTrpMetDLys, DPheTrpDPhePheMet, DThrDαNalDTrpDProArg, DTrpAlaTrpDPhe, DTrpDPro, DTrpDProDIle, DTrpDProDIleArg, DTrpDProDVal, DTrpDProDValArg, DTrpDTrpLys, DTrpDTrpLys; DTrpDαNalDTrpPheArg, DTrpPheDTrp; DValDαNalDTrpPheArg, DαNalDTrpPheArg, DβNalAlaTrpDPheAla, DβNalAlaTrpDPheLeu, DβNalAlaTrpDPheLysGlnGly, DβNalDLysTrpDPheLys, DβNalDTrp, DβNalDTrpProDArg, DβNalPicLysILysDPhe, GlyψDβNalAlaTipDPheLys, GlyψDβNalDLysTrpDPheLys, HisDTrpDArgTrp- DPhe, HisDTrpDLysTrpDPheLys, HisDTrpDTrpLys, HisDTrpDTrpPheMet, HisDTrpPheTrpDPheLys, HisDβ-NalDLysTrpDPheLys, HisTrpDAlaDTrpPheLys, TyrDTrp-DLysTrpDPhe, TyrDTrpDTrpPhePhe, TyrDTrpLysTrpD-Phe, αAbuDTrpDTrpOrn, αAibDTrpCyclohexylDAla, αAibDTrpDAlacyclohexylAla, αAibDTrpDcyclohexylAla, αAibDTrpDPro, αAibDTrpDProDIle, αAibDTrpDProDIle-Arg, αAibDTrpDProDVal, αAibDTrpDProDValArg, αγAbuTrpDTrpDTrpOrn, βAlaPalDTrpDTrpOrn, AlaTrp-DAlaDTrpPhe, βAlaTrpDTrpDTrpLys, βAlaTrpDTrpDTr-pOrn, γAbuTrpDTrpDTrpOrn, Ser(Bzl)LysDTrp, αAib-DTrp, γAbuDTrp, αAibDSer(Bzl), αγAbuDSer(Nap), DSerDLysTrp, Ser(Bzl)Lys(Ac)DTrp.

In some embodiments, amino acid sequence of $A^{21}$-$A^{22}$-$A^{23}$-$A^{24}$-$A^{25}$-$A^{26}$-$A^{27}$ is not DTrpAlaTrpDPhe, DHisDTrp-DProDIle, DHisDTrpDProDArg, DβNalDTrpDProDArg, DAlaDTrpPhe, AibDTrpCyclohexylDAla, DTrpDTrpLys, DThrDαNalDTrpDProArg, DTrpDTrp, DβNalDTrp, DTRp-DαNalDTrpDProArg, or DTrpPheDTrp.

Other exemplary amino acid sequences of $A^{21}$-$A^{22}$-$A^{23}$-$A^{24}$-$A^{25}$-$A^{26}$-$A^{27}$ include those described as compounds of formula (I) in Int. Pat. Pub. No. WO2007/127457, content of which is incorporated herein by reference in its entirety.

In some embodiments, a peptide of formula (II) is selected from the group consisting of: $X^1$-<GluHisTrpDSerDArg-$X^4$, $X^1$-AlaHisDTrpDLysTrpDPheLys-$X^4$, $X^1$-Alaψ[CH$_2$NH]DβNalAlaTrpDPheLys-$X^4$, $X^1$-Alaψ[CH$_2$NH]HisDTrpAla-TrpDPheLys-$X^4$, $X^1$-ArgDTrpLeuTyrTrpPro(cyclic Arg-Pro)-$X^4$, $X^1$-AvaTrpDTrpDTrpOrn-$X^4$, $X^1$-CyclohexylAlaDαNalDTrpPheArg-$X^4$, $X^1$-DAlaAla-DAlaDTrpPheLys-$X^4$, $X^1$-DAlaDcyclohexylAlaAlaAl-aPheDPheNle-$X^4$, $X^1$-DAlaDcyclohexylAlaAlaPheDPhe-$X^4$, $X^1$-DAlaDTrpPhe; DAlaDβNalAlaAlaDAlaLys-$X^4$, $X^1$-DAlaDβNalAlaThrDThrLys-$X^4$, $X^1$-DAlaDβNalAlaTr-pDPheLys-$X^4$, $X^1$-DAlaDβNalDAlaDTrpPheLys-$X^4$, $X^1$-DAlaDβNalDProPheArg-$X^4$, $X^1$-DcyclohexylAlaAl-aPheDTrpLys-$X^4$, $X^1$-DcyclohexylAlaAlaTrpDPhe-$X^4$, $X^1$-DesaminoTyrDTrpDLysTrpDPhe-$X^4$, $X^1$-Desamino-TyrDTrpSerTrpDPhe-$X^4$, $X^1$-DesaminoTyrDTrpSerTrpD-PheLys-$X^4$, $X^1$-DHISDTrpDProDArg-$X^4$, $X^1$-DHisDTrpD-ProDIle-$X^4$, $X^1$-DLeuDαNalDTrpPheArg-$X^4$, $X^1$-DLysDβNalAlaTrpDPheLys-$X^4$, $X^1$-DLysTyrDTrpAla-TrpDPhe-$X^4$, $X^1$-DLysTyrDTrpDTrpPhe-$X^4$, $X^1$-DLy-sTyrDTrpDTrpPheLys-$X^4$, $X^1$-DPalPheDTrpPheMet-$X^4$, $X^1$-DPheAlaPheDPal-$X^4$, $X^1$-DPheAlaPheDPheLys-$X^4$, $X^1$-DPheDPheDTrpMetDLys-$X^4$, $X^1$-DPheTrpDPheP-heMet-$X^4$, $X^1$-DThrDαNalDTrpDProArg-$X^4$, $X^1$-DTrpAla-TrpDPhe-$X^4$, $X^1$-DTrpDPro-$X^4$, $X^1$-DTrpDProDIle-$X^4$, $X^1$-DTrpDProDIleArg-$X^4$, $X^1$-DTrpDProDVal-$X^4$, $X^1$-DTr-pDProDValArg-$X^4$, $X^1$-DTrpDTrpLys-$X^4$, $X^1$-DTrpDTr-pLys; DTrpDαNalDTrpPheArg-$X^4$, $X^1$-DTrpPheDTrp; DValDαNalDTrpPheArg-$X^4$, $X^1$-DαNalDTrpPheArg-$X^4$, $X^1$-DβNalAlaTrpDPheAla-$X^4$, $X^1$-DβNalAlaTrpDPheLeu-$X^4$, $X^1$-DβNalAlaTrpDPheLysGlnGly-$X^4$, $X^1$-Dβ-NalDLysTrpDPheLys-$X^4$, $X^1$-DβNalDTrp-$X^4$, $X^1$-Dβ-NalDTrpDProDArg-$X^4$, $X^1$-DβNalPicLysILysDPhe-$X^4$, $X^1$-GlyψDβNalAlaTipDPheLys-$X^4$, $X^1$-GlyψDβ-NalDLysTrpDPheLys-$X^4$, $X^1$-HisDTrpDArgTrpDPhe-$X^4$, $X^1$-HisDTrpDLysTrpDPheLys-$X^4$, $X^1$-HisDTrpDTrpLys-$X^4$, $X^1$-HisDTrpDTrpPheMet-$X^4$, $X^1$-HisDTrpPheTrpD-PheLys-$X^4$, $X^1$-HisDβNalDLysTrpDPheLys-$X^4$, $X^1$-HisTrp-DAlaDTrpPheLys-$X^4$, $X^1$-TyrDTrpDLysTrpDPhe-$X^4$, $X^1$-TyrDTrpDTrpPhePhe-$X^4$, $X^1$-TyrDTrpLysTrpDPhe-$X^4$, $X^1$-αAbuDTrpDTrpOrn-$X^4$, $X^1$-αAibDTrpCyclohexy-lDAla; αAibDTrpDAlacyclohexylAla-$X^4$, $X^1$-αAibDTrpD-cyclohexylAla-$X^4$, $X^1$-αAibDTrpDPro-$X^4$, $X^1$-αAibDTrp-DProDIle-$X^4$, $X^1$-αAibDTrpDProDIleArg-$X^4$, $X^1$-αAibDTrpDProDVal-$X^4$, $X^1$-αAibDTrpDProDValArg-$X^4$, $X^1$-αγAbuTrpDTrpDTrpOrn-$X^4$, $X^1$-βAlaPalDTrpDTr-pOrn-$X^4$, $X^1$-AlaTrpDAlaDTrpPhe-$X^4$, $X^1$-βAlaTrpDTrp-DTrpLys-$X^4$, $X^1$-βAlaTrpDTrpDTrpOrn-$X^4$, $X^1$-γAbuTrpDTrpDTrpOrn-$X^4$, $X^1$-Ser(Bzl)LysDTrp-$X^4$, $X^1$-αAibDTrp-$X^4$, $X^1$-γAbuDTrp-$X^4$, $X^1$-αAibDSer(Bzl)-$X^4$, $X^1$-αγAbuDSer(Nap)-$X^4$, $X^1$-DSerDLysTrp-$X^4$, $X^1$-Ser(Bzl)Lys(Ac)DTrp-$X^4$ Exemplary peptide of formula (II) include, but are not limited to, Gly-Met-Ala-Tyr-DTrp-DLys-Trp-DPhe-NH$_2$; Gly-Met-Ala-Tyr-DTrp-Lys-Trp-DPhe-NH$_2$; Gly-Met-Ala-His-DTrp-DLys-Trp-DPhe-NH$_2$; Gly-Met-Ala-His-DTrp-DLys-Phe-DTrp-NH$_2$; Gly-Met-Ala-His-DTrp-DArg-Trp-DPhe-NH$_2$; Gly-Met-Ala-His-DTrp-DLys-Trp-DPhe-Lys-NH$_2$; Gly-Met-Ala-DesaminoTyr-DTrp-Ala-Trp-DPhe-NH$_2$; Gly-Met-Ala-DesaminoTyr-DTrp-DLys-Trp-DPhe-NH$_2$; Gly-Met-Ala-DeaminoTyr-DTrp-Ser-Trp-DPhe-Lys-NH$_2$; Gly-Met-Ala-DesaminoTyr-DTrp-Ser-Trp-DPhe-NH$_2$; Gly-Met-Ala-His-DTrp-DTrp-Phe-Met-NH$_2$; Gly-Met-Ala-Tyr-DTrp-DTrp-Phe-Phe-NH$_2$; Gly-Met-Ala-Glyψ[CH$_2$NH]-DβNal-Ala-Trp-DPhe-Lys-NH$_2$; Gly-Met-Ala-Glyψ[CH$_2$NH]-DβNal-DLys-Trp-DPhe-Lys-NH$_2$; Gly-Met-Ala-DAla-DβNal-DLys-DTrp-Phe-Lys-NH$_2$; Gly-Met-Ala-His-DβNal-DLys-Trp-DPhe-Lys-NH$_2$; Gly-Met-Ala-Ala-His-DTrp-DLys-Trp-DPhe-Lys-NH$_2$; Gly-Met-Ala-Alaψ[CH$_2$NH]-DβNal-Ala-Trp-DPhe-Lys-NH$_2$; Gly-Met-Ala-Alaψ[CH$_2$NH]-Ala-DβNal-Ala-Trp-DPhe-Lys-NH$_2$; Gly-Met-Ala-DβNal-Ala-Trp-DPhe-Ala-NH$_2$; Gly-Met-Ala-DAla-DcyclohexylAla-Ala-Phe-DPhe-Nle-NH$_2$; Gly-Met-Ala-DcyclohexylAla-Ala-Phe-DTrp-Lys-NH$_2$; Gly-Met-Ala-DAla-DβNal-Ala-Thr-DThr-Lys-NH$_2$; Gly-Met-Ala-DcyclohexylAla-Ala-Trp-DPhe-NH$_2$; Gly-Met-Ala-DAla-DβNal-Ala-Ala-DAla-Lys-NH$_2$; Gly-Met-Ala-DβNal-Ala-Trp-DPhe-Leu-NH$_2$; Gly-Met-Ala-His-DTrp-Phe-Trp-DPhe-Lys-NH$_2$; Gly-Met-Ala-DAla-DβNal-DAla-DTrp-Phe-Lys-NH$_2$; Gly-Met-Ala-βAla-Trp-DAla-DTrp-Phe-NH$_2$; Gly-Met-Ala-His-Trp-DAla-DTrp-Phe-LysNH$_2$; Gly-Met-Ala-DLys-DβNal-Ala-Trp-DPhe-Lys-NH$_2$; Gly-Met-Ala-DAla-DβNal-DLys-DTrp-Phe-Lys-NH$_2$; Gly-Met-Ala-Tyr-DAla-Phe-Aib-NH$_2$; Gly-Met-Ala-Tyr-DAla-Sar-NMePhe-NH$_2$; Gly-Met-Ala-αγAbu-DTrp-DTrp-Ser-NH$_2$; Gly-Met-Ala-αγAbu-DTrp-DTrp-Lys-NH$_2$; Gly-Met-Ala-αγAbu-DTrp-DTrp-Orn-NH$_2$; Gly-Met-Ala-αAbu-DTrp-DTrp-Orn-NH$_2$; Gly-Met-Ala-DThr-DαNal-DTrp-DPro-Arg-NH$_2$; Gly-Met-Ala-DAla-Ala-DAla-DTrp-Phe-NH$_2$; Gly-Met-Ala-Alaψ[CH$_2$NH]His-DTrp-Ala-Trp-DPhe-Lys-NH$_2$; Gly-Met-Ala-Lys-DHis-DTrp-Phe-NH$_2$; Gly-Met-Ala-γAbu-DTrp-DTrp-Orn-NH$_2$; Gly-Met-Ala-inip-Trp-Trp-Phe-NH$_2$ (SEQ ID NO: 375); Gly-Met-Ala-DTrp-Phe-DTrp-Leu-NH$_2$; Gly-Met-Ala-DTrp-Phe-DTrp-Lys-NH$_2$; Gly-Met-Ala-DTrp-DTrp-Lys-NH$_2$; Gly-Met-Ala-DLys-Tyr-DTrp-DTrp-Phe-Lys-NH$_2$; Gly-Met-Ala-DβNal-Leu-Pro-NH$_2$; Gly-Met-Ala-βAla-Trp-DTrp-DTrp-Orn-NH$_2$; Gly-Met-Ala-DVal-DαNal-DTrp-Phe-Arg-NH$_2$; Gly-Met-Ala-DLeu-DαNal-DTrp-Phe-Arg-NH$_2$; Gly-Met-Ala-CyclohexylAla-DαNal-DTrp-Phe-Arg-NH$_2$; Gly-Met-Ala-DTrp-DαNal-DTrp-Phe-Arg-NH$_2$; Gly-Met-Ala-DAla-DβNal-DPro-Phe-Arg-NH$_2$; Gly-Met-Ala-DαNal-DTrp-Phe-Arg-NH$_2$; Gly-Met-Ala-DαNal-DTrp-Phe-Arg-NH$_2$; Gly-Met-Ala-His-DTrp-DTrp-Lys-NH$_2$; Gly-Met-Ala-Dβ-Nal-DTrp-NH$_2$; Gly-Met-Ala-αAib-DTrp-DcyclohexylAla-NH$_2$; Gly-Met-Ala-αAib-DTrp-DAla-cyclohexylAla-NH$_2$; Gly-Met-Ala-DAla-cyclohexylAla-Ala-Ala-Phe-DPhe-Nle-NH$_2$; Gly-Met-Ala-DPhe-Ala-DPhe-Ala-Phe-DPal-NH$_2$; Gly-Met-Ala-DPhe-Ala-Phe-DPhe-Lys-NH$_2$; Gly-Met-Ala-DLys-Tyr-DTrp-DTrp-Phe-NH$_2$; Gly-Met-Ala-DLys-Tyr-DTrp-DTrp-Phe-NH$_2$; Gly-Met-Ala-Arg-DTrp-Leu-Tyr-Trp-Pro (cyclicArg-Pro); Gly-Met-Ala-DβNal-PicLys-ILys-DPhe-NH₂; Gly-Met-Ala-DPal-Phe-DTrp-Phe-Met-NH₂; Gly-Met-Ala-DPhe-Trp-DPhe-Phe-Phe-Met-NH₂; Gly-Met-Ala-DPal-Trp-DPhe-Phe-Met-NH₂; Gly-Met-Ala-βAla-Pal-DTrp-DTrp-Orn-NH₂; Gly-Met-Ala-αγAbu-Trp-DTrp-DTrp-Orn-NH₂; Gly-Met-Ala-βAla-Trp-DTrp-DTrp-Lys-NH₂; Gly-Met-Ala-γAbu-Trp-DTrp-DTrp-Orn-NH₂; Gly-Met-Ala-Ava-Trp-DTrp-DTrp-Orn-NH₂; Gly-Met-Ala-DLys-Tyr-DTrp-Ala-Trp-DPhe-NH₂; Gly-Met-Ala-His-DTrp-DArg-Trp-DPhe-NH₂; Gly-Met-Ala-<Glu-His-Trp-DSer-DArg-NH₂; Gly-Met-Ala-DPhe-DPhe-DTrp-Met-DLys-NH₂; Gly-Met-Ala-DHis-DTrp-DPro-DIleNH₂; Gly-Met-Ala-DHis-DTrp-DPro-DArgNH₂; Gly-Met-Ala-DβNal-DTrp-DPro-DArgNH₂; Gly-Met-Ala-Tyr-DTrp-DLys-Trp-DPhe; Gly-Met-Ala-Tyr-DTrp-Lys-Trp-DPhe; Gly-Met-Ala-His-DTrp-DLys-Trp-DPhe; Gly-Met-Ala-His-DTrp-DLys-Phe-DTrp; Gly-Met-Ala-His-DTrp-DArg-Trp-DPhe; Gly-Met-Ala-His-DTrp-DLys-Trp-DPhe-Lys; Gly-Met-Ala-DesaminoTyr-DTrp-Ala-Trp-DPhe; Gly-Met-Ala-DesaminoTyr-DTrp-DLys-Trp-DPhe; Gly-Met-Ala-DeaminoTyr-DTrp-Ser-Trp-DPhe-Lys; Gly-Met-Ala-DesaminoTyr-DTrp-Ser-Trp-DPhe; Gly-Met-Ala-His-DTrp-DTrp-Phe-Met; Gly-Met-Ala-Tyr-DTrp-DTrp-Phe-Phe; Gly-Met-Ala-Glyψ[CH₂NH]-DβNal-Ala-Trp-DPhe-Lys; Gly-Met-Ala-Glyψ[CH2NH]-DβNal-DLys-Trp-DPhe-Lys; Gly-Met-Ala-DAla-DβNal-DLys-DTrp-Phe-Lys; Gly-Met-Ala-His-DβNal-DLys-Trp-DPhe-Lys; Gly-Met-Ala-Ala-His-DTrp-DLys-Trp-DPhe-Lys; Gly-Met-Ala-Alaψ[CH₂NH]-DβNal-Ala-Trp-DPhe-Lys; Gly-Met-Ala-DβNal-Ala-Trp-DPhe-Ala; Gly-Met-Ala-DAla-DcyclohexylAla-Ala-Phe-DPhe-Nle; Gly-Met-Ala-DcyclohexylAla-Ala-Phe-DTrp-Lys; Gly-Met-Ala-DAla-DβNal-Ala-Thr-DThr-Lys; Gly-Met-Ala-DcyclohexylAla-Ala-Trp-DPhe; Gly-Met-Ala-DAla-DβNal-Ala-Ala-DAla-Lys; Gly-Met-Ala-DβNal-Ala-Trp-DPhe-Leu; Gly-Met-Ala-His-DTrp-Phe-Trp-DPhe-Lys; Gly-Met-Ala-DAla-DβNal-DAla-DTrp-Phe-Lys; Gly-Met-Ala-βAla-Trp-DAla-DTrp-Phe; Gly-Met-Ala-His-Trp-DAla-DTrp-Phe-LysNH₂; Gly-Met-Ala-DLys-DβNal-Ala-Trp-DPhe-Lys; Gly-Met-Ala-DAla-DβNal-DLys-DTrp-Phe-Lys; Gly-Met-Ala-Tyr-DAla-Phe-Aib; Gly-Met-Ala-Tyr-DAla-Sar-NMePhe; Gly-Met-Ala-αγAbu-DTrp-DTrp-Ser; Gly-Met-Ala-αγAbu-DTrp-DTrp-Lys; Gly-Met-Ala-αγAbu-DTrp-DTrp-Orn; Gly-Met-Ala-αAbu-DTrp-DTrp-Orn; Gly-Met-Ala-DThr-DαNal-DTrp-DPro-Arg; Gly-Met-Ala-DAla-Ala-DAla-DTrp-Phe-Lys; Gly-Met-Ala-Alaψ[CH₂NH]His-DTrp-Ala-Trp-DPhe-Lys; Gly-Met-Ala-Lys-DHis-DTrp-Phe; Gly-Met-Ala-γAbu-DTrp-DTrp-Orn; Gly-Met-Ala-inip-Trp-Trp-Phe (SEQ ID NO: 376); Gly-Met-Ala-DTrp-Phe-DTrp-Leu; Gly-Met-Ala-DTrp-Phe-DTrp-Lys; Gly-Met-Ala-DTrp-DTrp-Lys; Gly-Met-Ala-DLys-Tyr-DTrp-DTrp-Phe-Lys; Gly-Met-Ala-Dβ-Nal-Leu-Pro; Gly-Met-Ala-βAla-Trp-DTrp-DTrp-Orn; Gly-Met-Ala-DVal-DαNal-DTrp-Phe-Arg; Gly-Met-Ala-DLeu-DαNal-DTrp-Phe-Arg; Gly-Met-Ala-CyclohexylAla-DαNal-DTrp-Phe-Arg; Gly-Met-Ala-DTrp-DαNal-DTrp-Phe-Arg; Gly-Met-Ala-DAla-DβNal-DPro-Phe-Arg; Gly-Met-Ala-DαNal-DTrp-Phe-Arg; Gly-Met-Ala-DαNal-DTrp-Phe-Arg; Gly-Met-Ala-His-DTrp-DTrp-Lys; Gly-Met-Ala-DβNal-DTrp; Gly-Met-Ala-αAib-DTrp-DcyclohexylAla; Gly-Met-Ala-αAib-DTrp-DAla-cyclohexylAla; Gly-Met-Ala-DAla-DcyclohexylAla-Ala-Ala-Phe-DPhe-Nle; Gly-Met-Ala-DPhe-Ala-Phe-DPal; Gly-Met-Ala-DPhe-Ala-Phe-DPhe-Lys; Gly-Met-Ala-DLys-Tyr-DTrp-DTrp-Phe; Gly-Met-Ala-DLys-Tyr-DTrp-DTrp-Phe; Gly-Met-Ala-Arg-DTrp-Leu-Tyr-Trp-Pro(cyclicArg-Pro); Gly-Met-Ala-DβNal-PicLys-ILys-DPhe; Gly-Met-Ala-DPal-Phe-DTrp-Phe-Met; Gly-Met-Ala-DPhe-Trp-DPhe-Phe-Met; Gly-Met-Ala-DPal-Trp-DPhe-Phe-Met; Gly-Met-Ala-βAla-Pal-DTrp-DTrp-Orn; Gly-Met-Ala-αγAbu-Trp-DTrp-DTrp-Orn; Gly-Met-Ala-βAla-Trp-DTrp-DTrp-Lys; Gly-Met-Ala-γAbu-Trp-DTrp-DTrp-Orn; Gly-Met-Ala-Ava-Trp-DTrp-DTrp-Orn; Gly-Met-Ala-DLys-Tyr-DTrp-Ala-Trp-DPhe; Gly-Met-Ala-His-DTrp-DArg-Trp-DPhe; Gly-Met-Ala-<Glu-His-Trp-DSer-DArg; Gly-Met-Ala-DPhe-DPhe-DTrp-Met-DLys; Gly-Met-Ala-DHis-DTrp-DPro-DIle; Gly-Met-Ala-DHis-DTrp-DPro-DArg; Gly-Met-Ala-DβNal-DTrp-DPro-DArg; Gly-Met-Ala-DbetaNalAlaTrpDPheLysGlnGly; Gly-Met-Ala-alphaAibDTrpDPro; Gly-Met-Ala-alphaAibDTrpDProDIle; Gly-Met-Ala-alphaAibDTrpDProDVal; Gly-Met-Ala-alphaAibDTrpDProDIleArg; Gly-Met-Ala-alphaAibDTrpDProDValArg; Gly-Met-Ala-DAlaDBNalDLysTrpDPheLys; Gly-Met-Ala-HisDBNalDLysTrpDPheLys; Gly-Met-Ala-DBNalAlaTrpDPheLysGlnGlyNH2; Gly-Met-Ala-alphaAibDTrpDProNH2; Gly-Met-Ala-alphaAibDTrpDProDIleNH2; Gly-Met-Ala-alphaAibDTrpDProDValNH2; Gly-Met-Ala-alphaAibDTrpDProDIleArgNH2; Gly-Met-Ala-alphaAibDTrpDProDValArgNH2; Gly-Met-Ala-DAlaDBNalDLysTrpDPheLysNH2; Gly-Met-Ala-HisDBNalDLysTrpDPheLysNH2; Gly-Met-Ala-DBNalAlaTrpDPheLysGlnGlyNH2; Gly-Met-Ala-DBNalDLysTrpDPheLysNH2; Gly-Met-Ala-DAlaDBNalDLysTrpDPheLysNH2; Gly-Met-Ala-DTrpDProDIleNH2; Gly-Met-Ala-alphaAibDTrpDProDIleArgNH2; Gly-Met-Ala-DTrpDProDIleArgNH2; Gly-Met-Ala-DTrpDProDValNH2; Gly-Met-Ala-DTrpDProDValArgNH2; Gly-Met-Ala-alphaAibDTrpDProDValArgNH2; Gly-Met-Ala-HisDBNalDLysTrpDPheLysNH2; Gly-Met-Ala-alphaAibDTrpDProNH2; Gly-Met-Ala-DTrpDProNH2; Ala-Met-Ala-DBNalAlaTrpDPheLysGlnGlyNH2; Ala-Met-Ala-alphaAibDTrpDProNH2; Ala-Met-Ala-alphaAibDTrpDProDIleNH2; Ala-Met-Ala-alphaAibDTrpDProDValNH2; Ala-Met-Ala-alphaAibDTrpDProDIleArgNH2; Ala-Met-Ala-alphaAibDTrpDProDValArgNH2; Ala-Met-Ala-DAlaDBNalDLysTrpDPheLysNH2; Ala-Met-Ala-HisDBNalDLysTrpDPheLysNH2; Ala-Met-Ala-DBNa1AlaTrpDPheLysGlnGlyNH2; Ala-Met-Ala-DBNalDLysTrpDPheLysNH2; Ala-Met-Ala-DAlaDBNa1DLysTrpDPheLysNH2; Ala-Met-Ala-DTrpDProDIleNH2; Ala-Met-Ala-alphaAibDTrpDProDIleArgNH2; Ala-Met-Ala-DTrpDProDIleArgNH2; Ala-Met-Ala-DTrpDProDValNH2; Ala-Met-Ala-DTrpDProDValArgNH2; Ala-Met-Ala-alphaAibDTrpDProDValArgNH2; Ala-Met-Ala-HisDBNalDLysTrpDPheLysNH2; Ala-Met-Ala-alphaAibDTrpDProNH2; Ala-Met-Ala-DTrpDProNH2; Gly-Met-Ala-DAlaDβNalAlaTrpDPheLys; Ala-Met-Ala-DAlaDβNalAlaTrpDPheLys; Ala-Met-Ala-DAlaDβNalDLysTrpDPheLys; Gly-Met-Ala-DAlaDβNalDLysTrpDPheLys; GlyMetAlaSer(Bzl)LysDTrp; GlyMetAlaαAibDTrp; GlyMetAlaγAbuDTrp; GlyMetAlaαAibDSer(Bzl); GlyMetAlaαγAbuDSer(Nap); GlyMetAlaDSerDLysTrp; GlyMetAlaSer(Bzl)Lys(Ac)DTrp; GlyMetAlaαAibSer(Bzl)-X⁴ (SEQ ID NO: 377), wherein X⁴ is optionally substituted 4-phenylpiperazin-1-yl, 3a-benzyl-4,5,6,7-tetrahydro-2-methyl-2H-pyrazolo[4,3-c]pyridin-3(3 aH)-on-5-yl or 1-(methylsulfonyl)spiro[indoline-3,4'-piperdine]-1'-yl; GlyMetAlaψ[CH₂NH]αAibSer(Bzl)-X⁴ (SEQ ID NO: 378), wherein X⁴ is optionally substituted 4-phenylpiperazin-1-yl, 3a-benzyl-4,5,6,7-tetrahydro-2-methyl-2H-pyrazolo[4,3-c]pyridin-3(3 aH)-on-5-yl or 1-(methylsulfonyl)spiro[indoline-3,4'-piperdine]-1'-yl; GlyMetAlaψ[CH$_2$NH]αAibSer(Bzl)-X$^4$ (SEQ ID NO: 379), wherein X$^4$ is optionally substituted 4-phenylpiperazin-1-yl, 3a-benzyl-4,5,6,7-tetrahydro-2-methyl-2H-pyrazolo[4,3-c] pyridin-3(3 aH)-on-5-yl or 1-(methylsulfonyl)spiro[indoline-3,4'-piperdine]-1'-yl; and any combinations thereof Peptides of Formula (III)

In some embodiments, A$^{31}$ is DαNal, DβNal, AcDβNal, AcDαNal, Tyr, AcDTyr, Lys, D Phe, His, αAbu α,γAbu, γAbu, DcyclohexylAla, or isonipecotic carboxylic acid (inip).

In some embodiments, A$^{32}$ is D or L Trp, Ala, His, Phe, or Leu.

In some embodiments, A$^{33}$ is D or L Trp, Ala, Cyclohexy-lAla, Phe, Pro, Lys, or Sarcosine (N-methylglycine) (Sar).

In some embodiments, A$^{34}$ is D or L Arg, Phe, Cyclohexy-lAla, Lys, Ser, or NMePhe (methylated phenylalanine amino nitrogen), DPal, Aib, or Orn.

In some embodiments, A$^{31}$ is D-α-Nal, D-β-Nal, Acetyl-D-β-Nal, Acetyl-D-α-Nal, Tyr, Acetyl-D-Tyr, Lys, D-Phe, His, α-Abu, α,γ-Abu, γ-Abu, DcyclohexylAla, or isonipecotic carboxylic acid (inip); A$^{32}$ is D- or L-Trp, Ala, His, Phe, or Leu; A$^{33}$ is D- or L-Trp, Ala, CyclohexylAla, Phe, Pro, Lys, or Sarcosine; and A$^{34}$ is D- or L-Arg, Phe, CyclohexylAla, Lys, Ser, or NMePhe (methylated phenylalanine amino nitrogen), D-Pal, Aib, or Orn.

Exemplary aminoacids sequences for A$^{31}$-A$^{32}$-A$^{33}$-A$^{34}$ include, but are not limited to, αγAbuDTrpDTrpLys; αγAbuDTrpDTrpOrn; αγAbuDTrpDTrpSer; TyrDAlaPheAib; TyrDAlaSarNMePhe; LysDHisDTrpPhe; γAbuDTrpDTrpOrn; inipTrpTrpPhe; TrpPheDTrpLeu; DTrpPheDTrpLys; and DβNalLeuPro.

Additional amino acid sequences of A$^{21}$-A$^{22}$-A$^{23}$-A$^{24}$-A$^{25}$-A$^{26}$-A$^{27}$ include those described as compounds of formula (II) in Int. Pat. Pub. No. WO2007/127457, content of which is incorporated herein by reference in its entirety.

In some embodiments, a peptide of formula (III) is selected from the group consisting of X$^1$-αγAbuDTrpDTrpLys-X$^4$; X$^1$-αγAbuDTrpDTrpOrn-X$^4$; X$^1$-αγAbuDTrpDTrpSer-X$^4$; X$^1$-TyrDAlaPheAib-X$^4$; X$^1$-TyrDAlaSarNMePhe-X$^4$; X$^1$-LysDHisDTrpPhe-X$^4$; X$^1$-γAbuDTrpDTrpOrn-X$^4$; X$^1$-inipTrpTrpPhe-X$^4$; X$^1$-TrpPheDTrpLeu-X$^4$; X$^1$-DTrpPheDTrpLys-X$^4$; X$^1$- and DβNalLeuPro-X$^4$.

Exemplary peptides of formula (III) include, but are not limited to, GlyMetAlaαγAbuDTrpDTrpLys; GlyMetAlaαγAbuDTrpDTrpOrn; GlyMetAlaαγAbuDTrpDTrpSer; GlyMetAlaTyrDAlaPheAib; GlyMetAlaTyrDAlaSarNMePhe; GlyMetAlaLysDHisDTrpPhe; GlyMetAlaγAbuDTrpDTrpOrn; GlyMetAlainipTrpTrpPhe (SEQ ID NO: 376); GlyMetAlaTrpPheDTrpLeu; GlyMetAlaDTrpPheDTrpLys; and GlyMetAlaDβNalLeuPro.

Peptides of Formula (IV)

In some embodiments, A$^{41}$ is His, Gly, αAib (alpha-aminoisobutyric acid), γAbu (gamma-aminobutyric acid), or α,γ-Abu (alpha, gamma-aminobutyric acid). There can be a normal or reduced psi peptide (CH$_2$NH) at carboxyl position of A$^{41}$. Alternatively, A$^{41}$ may be an amino acid with methylation of the terminal nitrogen of the alpha carbon atom of the A$^{41}$ residue.

In some embodiments, A$^{42}$ is D-α-naphthyalanine, D-β-naphthyalanine D-α,β-naphthyalanine, D-Trp, D-Phe, or D-Cyclohexylalanine or an amino acid with methylation of the terminal nitrogen of the α carbon atom of the A$^{42}$ residue. In one embodiment, A$^{42}$ could have extended aromatic chains, such as, for example, D-4-halo-Phe, D-4-pyrolidyla-lanine, or homologues or analogues thereof In some embodiments, A$^{43}$ is D- or L-Lys, Arg, Orn, or α,γ-Abu.

In some embodiments, A$^{44}$ is D- or L-Trp, Phe, or Cyclohexylalanine

In some embodiments, A$^{45}$ is D-Phe or D-Cyclohexylalanine

In some embodiments, A$^{46}$ is Lys, Arg, Orn, or α,γ-Abu.

In some embodiments, A$^{41}$ is His, Gly, αAib, γAbu, α,γAbu, or an amino acid with methylation of the terminal nitrogen of the alpha carbon; A$^{42}$ is D-α-naphthyalanin, D-β-naphthyalanine D-α,β-naphthyalanine, D-Trp, D-Phe, D-4-halo-Phe, D-4-pyrolidylalanine or D-Cyclohexylalanine or an amino acid with methylation of the terminal nitrogen of the α carbon; A$^{43}$ is D- or L-Lys, Arg, Orn, or α,γ-Abu; A$^{44}$ is D- or L-Trp, Phe, or Cyclohexylalanine; A$^{45}$ is D-Phe or D-Cyclohexylalanine; and $^{46}$ is Lys, Arg, Orn, or α,γ-Abu.

Exemplary aminoacids sequences for A$^{41}$-A$^{42}$-A$^{43}$-A$^{44}$-A$^{45}$-A$^{46}$ include described as compounds of formula (I') in Int. Pat. Pub. No. WO2007/127457, content of which is incorporated herein by reference in its entirety.

In some embodiments, the peptide is not Gly-Met-Ala-Gly-Ser-Dap(Oct)-Phe-Leu-Ser-Pro-Glu-His-NH$_2$ (SEQ ID NO: 2) or Gly-Met-Ala-Gly-Ser-Dap(palmityl)-Phe-Leu-Ser-Pro-Glu-His-NH$_2$ (SEQ ID NO: 3).

The abbreviations for the residues of amino acids used herein are in agreement with the standard nomenclature, and are as follows: L Gly—Glycine, L Tyr—Tyrosine, L Ile—Isoleucine, L Glu—Glutamic Acid, L Thr—Threonine, L Phe—Phenylalanine, L Ala—Alanine, L Lys—Lysine, L Asp—Aspartic Acid, L Cys—Cysteine, L Arg—Arginine, L Gln—Glutamine, L Pro—Proline, L Leu—Leucine, L Met—Methionine, L Ser—Serine, L Asn—Asparagine, L His—Histidine, L Trp—Tryptophan, L Val—Valine, L Orn—Ornithine, Desamino Tyr-Desamino Tyrosine, Desamino His-Desamino Histidine, Desamino alpha Aib-Desamino alpha aminoisobutyric acid, Desamino alpha Abu-Desamino alpha aminobutyric acid, Desamino alpha, gamma Abu-Desamino alpha, gamma aminobutyric acid. Dap(Oct) is an α,β-diaminopropionic acid conjugated with an octanoyl group at the amino group. The octanoyl group can be linked to the amino group at the 2 position or the 3 position. In some embodiments, the octanoyl group is is linked to the amino group on the 2 position of the diaminopropionic acid.

Moreover, all of the three letter-abbreviations of the amino acids preceded by a "D" indicate the dextro-isomer of the amino acid residue, and glycine is considered to be included in the term naturally occurring L-amino acids. Other abbreviations used herein include: Aib—aminoisobutyric acid, inip—isonipecotyl, Abu—aminobutyric acid, alpha Nal—alpha-naphthyl alanine, beta Nal—beta-naphthyl alanine, D alpha Nal—alpha-naphthyl-D-alanine, D beta Nal—beta-naphthyl-D-alanine, Pal 3-pyridyl alanine, CHx—cyclohexyl, CHxAla—L-cyclohexylalanine, Ava—Aminovaleric acid, IMA—N alpha-imidazole acetic acid, imc-imidazole carboxylic acid, beta Ala-beta-Alanine, ILys—Lysine (iPr) which isopropylαN$^ε$lysine, αγAbu—alpha gamma diaminobutyric acid, Nle—norleucine, inip—isonipecotoc carboxylic acid, NMePhe—methylated phenylalanine amino nitrogen, Sar—sarcosine (N-methylglycine), <Glu—pyroglutamic acid, AcDβNal—acetylated D beta-naphthyl alanine, and AcDαNal—acetylated D alpha-naphthyl alanine, N Ac-Dbeta Nal—acetyl N-DβNaphthylalanine, Ser(Bzl)—serine benzylated at the side chain hydroxyl, Ser(Nap)—serine conjugated with naphthalanine at the side chain hydroxyl, and Lys(Ac)—lysine acetylated at the side chain amino group.

Synthesis of Peptides

The peptides of the invention can be synthesized according to the usual methods of solution and solid phase peptide chemistry, or by classical methods known in the art. Purification of peptides is well known in the art and can be, for example, HPLC. Methods describing useful peptide synthesis and purification methods can be found, for example, in U.S. Patent Application No. 20060084607.

Peptides described herein can be synthetically constructed by suitable known peptide polymerization techniques, such as exclusively solid phase techniques, partial solid-phase techniques, fragment condensation or classical solution couplings. For example, the peptides of the invention can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis exemplified in U.S. Pat. No. 3,972,859. Other available syntheses are exemplified in U.S., Pat. No. 3,842,067, U.S. Pat. No. 3,872,925, issued Jan. 28, 1975, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego. #9830). Contents of all of the foregoing disclosures are incorporated herein by reference.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor. Modificaitons of peptides to produce peptide mimetics are described, for example, in U.S. Pat. No. 5,643,873 and U.S. Pat. No. 5,654,276, content of both of which is incorporated herein by reference.

Peptide Mimetics

Methods of designing peptide mimetics and screening of functional peptide mimetics are well known to those skilled in the art. One basic method of designing a molecule which mimics a known protein or peptide is first to identify the active region(s) of the known protein (for example, in the case of an antibody-antigen interaction, one identifies which region(s) of the antibody that permit binding to the antigen), and then searches for a mimetic which emulates the active region. If the active region of a known protein is relatively small, it is anticipated that a mimetic will be smaller (e.g. in molecular weight) than the protein, and correspondingly easier and cheaper to synthesize. Such a mimetic could be used as a convenient substitute for the protein, as an agent for interacting with the target molecule.

For example, Reineke et al. (1999, Nature Biotechnology, 17; 271-275, contents of which is herein incorporated by reference) designed a mimic molecule which mimics a binding site of the interleukin-10 protein using a large library of short synthetic peptides, each of which corresponded to a short section of interleukin 10. The binding of each of these peptides to the target (in this case an antibody against interleukin-10) was then tested individually by an assay technique, to identify potentially relevant peptides. Phage display libraries of peptides and alanine scanning method can be used.

Other methods for designing peptide mimetics to a particular peptide or protein include those described in European Patent EP1206494, the SuperMimic program by Andrean Goede et. al. 2006 BMC Bioinformatics, 7:11; and MIMETIC program by W. Campbell et. al., 2002, Microbiology and Immunology 46:211-215. The SuperMimic program is designed to identify compounds that mimic parts of a protein, or positions in proteins that are suitable for inserting mimetics. The application provides libraries that contain peptidomimetic building blocks on the one hand and protein structures on the other. The search for promising peptidomimetic linkers for a given peptide is based on the superposition of the peptide with several conformers of the mimetic. New synthetic elements or proteins can be imported and used for searching. The MIMETIC computer program, which generates a series of peptides for interaction with a target peptide sequence is taught by W. Campbell et. al., 2002. In depth discussion of the topic is reviewed in "Peptide Mimetic Design with the Aid of Computational Chemistry" by James R. Damewood Jr. in Reviews in Computational Chemistry Reviews in Computational Chemistry, January 2007, Volume 9 Book Series: Reviews in Computational Chemistry, Editor(s): Kenny B. Lipkowitz, Donald B. BoydPrint ISBN: 9780471186397 ISBN: 9780470125861 Published by John Wiley & Sons, Inc.; and in T. Tselios, et. al., Amino Acids, 14: 333-341, 1998. Content of all of the references described in this paragraph is herein incorporated by reference.

Methods for preparing libraries containing diverse populations of peptides, peptoids and peptidomimetics are well known in the art and various libraries are commercially available (see, for example, Ecker and Crooke, Biotechnology 13:351-360 (1995), and Blondelle et al., Trends Anal. Chem. 14:83-92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803-861, and Gordon et al., J. Med. Chem. 37:1385-1401 (1994), each of which is incorporated herein by reference). One skilled in the art understands that a peptide can be produced in vitro directly or can be expressed from a nucleic acid, which can be produced in vitro. Methods of synthetic peptide and nucleic acid chemistry are well known in the art. Content of all of the references described in this paragraph is herein incorporated by reference.

A library of peptide molecules also can be produced, for example, by constructing a cDNA expression library from mRNA collected from a tissue of interest. Methods for producing such libraries are well known in the art (see, for example, Sambrook et. al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA.

Methods of the Invention

The antagonists of the invention can be administered to a subject, e.g. a human, to disrupt the activity of ghrelin at the level of the CNS. Thus, the present invention provides novel peptides and methods for their use in disrupting ghrelin. Accordingly, methods for the treatment of various diseases and disorders such as obesity, overeating, diabetes, unregulated cellular proliferation, and cancer using the novel peptides of the present invention are encompassed. Accordingly, uses of the antagonists of the invention for the modulation, specifically inhibition of grhelin receptor are also provided. Thus, in one aspect the invention provides a method for modulating the activity of ghrelin receptor, the method comprising contacting a ghrelin receptor with an antagonist of the invention.

Additionally, the invention provides uses of these compounds for the treatment of diseases wherein inhibition of ghrelin receptor is advantageous. Such diseases include but are not limited to obesity, diabetes mellitus, metabolic syndrome or certain types of cancer as described in this specification. Accordingly, in another aspect, the invention provides a method for treatment, prevention, or management of obesity or obesity related disease or disorder, diabetes mellitus, metabolic syndrome, unregulated cellular proliferation, cancer, or hormonally functional endocrine or non-endocrine tumor in a subject in need thereof, the method comprising the step of administering an effective amount of an antagonist described herein to the subject.

By "treating," "treatment," "prevention," or "amelioration" of a disease or disorder is meant delaying or preventing the onset of such a disease or disorder, reversing, alleviating, ameliorating, inhibiting, slowing down or stopping the progression, aggravation, deterioration or severity of a condition associated with such a disease or disorder. Treatment of a disease or disorder can be determined by standard medical methods. In one embodiment, the symptoms of a disease or disorder are alleviated by at least 5%, at least 10%, at least 20%, at least 30%, at least 40%, or at least 50%.

In some embodiments, the antagonists described herein are administered to a subject in need of such treatment for any of the disease or disorders or associated disorders discussed and described herein, e. g. obesity, overeating, diabetes mellitus, metabolic syndrome, hypertension, elevated plasma insulin concentrations, insulin resistance, dyslipidemias, and hyperlipidemia, unregulated cellular proliferation, and cancer such as hormonally functional endocrine or non-endocrine tumors, breast and prostate cancer, ectopic neuroendocrine tumors, carcinoid and pancreatic tumors, and prostate cancer, osteoblast cancer, pancreatic cancer, adenocarcinomas and hepatoma.

In some embodiments, the subject who is in need of treatment is one who has been clinically diagnosed with a disease, disorders or associated disorders described herein by methods well known to one skilled in the art, e. g. a physician. In some embodiments, a subject who is in need of treatment is one who is at risk of developing the disease, disorders or associated disorders described herein. For example, a subject who has had a sudden gain of weight in a short period of time, e. g. gaining 5 kilograms, 10 kilograms, 20 kilograms, 30 kilograms, 40 kilograms, or 50 kilogram within a period of 1 month, 2 months, 3 months, or four months. Without wishing to be bound by theory, such a subject is at high risk for developing diabetes mellitus, metabolic syndrome, hypertension, elevated plasma insulin concentrations, insulin resistance, dyslipidemias, and hyperlipidemia and other obesity related disorders.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

In some embodiments of the methods described herein, the method further comprising selecting a subject identified as being in need of treatment by a ghrelin antagonist. A subject suffering from a disease or disorder can be selected based on the symptoms presented by the subject. Some exemplary symptoms are described herein.

In some embodiments, the subject is a mammal. In some embodiments, the subject is an animal, e. g. a cat, a dog, a horse. In one preferred embodiment, the subject is a human.

In some embodiments, the subject is obese or overweight. Typically, an overweigh subject is considered to have a body mass index (BMI) of over 25 but under 30 and an obese subject is considered to have a BMI of over 30.

The peptides of the invention can be used alone or in combination with other art known treatments of the diseases and disorders associated with obesity, overeating, diabetes, unregulated cellular proliferation, metabolic syndrome, and cancer. For example, a peptiode of the invention can be used for the treatment of obesity alone or in combination with other obesity treatments.

In some embodiments, use of the peptide for the treatment of obesity is combined with a surgical or mechanical procedure used to treat obesity. Such procedures include but are not limited to gastric bypass surgery and gastric banding.

The invention also comprises methods for regulating food intake in a human subject; for improving a compliance of a human subject to caloric restriction; and for reducing a desire of a human subject to consume an over-abundance of calories and/or fats. This method comprises the administration of a peptide described herein to a subject. In some embodiments, the food intake is reduced by at least 5%, at least 10%, at least 20%, at least 30%, at least 40%, at least 50%, at least 60%, at least 70%, at least 80%, at least 90%, at least 95% or more relative to subject that is not undergoing treatment. The amount of food intake can be based on the number of calories or on the weight of food.

The invention further provides a method for preventing or reducing weight gain in a human subject, by administration of peptides described herein that have a pharmacological half-life that allows an efficient treatment regime thereof.

Also encompassed are methods for reducing a desire of a human subject to consume calories following gastric banding or gastric bypass surgery, by administration of a peptide described herein.

Exemplary obesity related diseases and/or disorders include, but are not limited to: overeating; bulimia; hypertension; diabetes, elevated plasma insulin concentrations; insulin resistance; dyslipidemias; hyperlipidemia; endometrial, breast, prostate and colon cancer; osteoarthritis; obstructive sleep apnea; cholelithiasis; gallstones; abnormal heart rhythms; heart arrythymias; myocardial infarction; congestive heart failure; coronary heart disease; sudden death; stroke; polycystic ovarian disease; craniopharyngioma; the Prader-Willi Syndrome; Frohlich's syndrome; GH-deficient subjects; normal variant short stature; Turner's syndrome; and other pathological conditions showing reduced metabolic activity or a decrease in resting energy expenditure as a percentage of total fat-free mass, e.g, children with acute lymphoblastic leukemia.

The present invention also encompasses the treatment of obesity and obesity related diseases and disorders by administering a combination of a peptide described herein and an anti-obesity agent, which may be administered separately or concurrently.

Anti-obesity agents to be used in combination with the peptides described herein are known to those of skill in the art and may include, but are not limited to, a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, leptin, a leptin derivative, an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a GHS (growth hormone secretagogue receptor) agonist, a 5HT2C (serotonin receptor 2C) agonist, a Mc4r (melanocortin 4 receptor) agonist, a monoamine reuptake inhibitor, an UCP-1 (uncoupling protein-1), 2, or 3 activator, a β3 (beta adrenergic receptor 3) agonist, a thyroid hormone β agonist, a PDE (phosphodiesterase) inhibitor, a FAS (fatty acid synthase) inhibitor, a DGAT1 (diacylglycerol acyltransferase) inhibitor, a DGAT2 inhibitor, an ACC2 (acetyl-CoA carboxylase-2) inhibitor, a glucocorticoid antagonist, an acyl-estrogen, a lipase inhibitor, a fatty acid transporter inhibitor, a dicarboxylate transporter inhibitor, a glucose transporter inhibitor, a serotonin reuptake inhibitors, metformin, and topiramate.

The anti-obesity compound to be used in combination with the peptides of the present invention may act via a mechanism other than ghrelin, thus providing for additive anti-obesity effects.

In some embodiments, a method for treating diabetes is encompassed. Diabetes may include both insulin-dependent diabetes mellitus (i.e., IDDM, also known as type I diabetes) and non-insulin-dependent diabetes mellitus (i.e., NIDDM, also known as Type II diabetes). In this method, individuals with or at risk for developing diabetes are administered the peptide of the present invention alone or in combination with other diabetes treatments known to those of skill in the art.

In some embodiments, the peptides of the present invention are used to treat or prevent hormonally functional endocrine or non-endocrine tumors.

In some embodiments, the invention provides a method to decrease/regulate gastrointestinal motility/acidity in a mammal, said method comprising use of a peptide described herein.

In some embodiments, the peptides of the invention can be used for the treatment, prevention or management of psychobehavior related to under and over nutrition such as hunger, satiety and anxiety.

In yet some other embodiments, peptides of the invention can be used for for augmenting the actions of desacyl ghrelin by decreasing the action of acyl ghrelin and its receptor.

In some embodiments, the peptides described herein are administered to a subject for the treatment of pituitary tumor, e.g. to inhibit pituitary tumor producing growth hormone.

The present invention also provides methods for treating hormonally functional endocrine or non-endocrine tumors, such as, pituitary tumors, including ACTH-secreting pituitary tumors, in a mammal. The inventive methods involve administering to the mammal having or at risk for developing a pituitary tumor a therapeutically effective amount of the peptide described herein. In one embodiment, the peptide is administered in combination with other compounds useful in the treatment of pituitary tumor such as, for example, PPARγ ligands. Such PPARγ ligands include thiazolidinediones (TZDs), such as troglitazone, pioglitazone, and rosiglitazone.

In some embodiments, a peptide described herein is administered in conjunction with methods for the treatment of tumors that produce prolactin. Prolactin ("PRL") is a 23-kDa neuroendocrine hormone which is structurally related to growth hormone. Prolactin secretion has been associated with several types of cancer including, but not limited to breast and prostrate. Thus, the present invention relates to methods and compositions for inhibiting the cell proliferation-promoting effects of prolactin on its receptor. Conditions which may benefit from the administration of a peptide of the invention include both benign and malignant proliferation of cells which express a prolactin receptor. Such conditions include but are not limited to proliferative diseases of the breast, including benign conditions such as breast adenomas and fibrocystic disease, and malignant conditions such as breast cancer, including ductal, scirrhous, medullary, colloid and lobular carcinomas (local or metastatic); and proliferative diseases of the prostate, including benign prostatic hypertrophy and prostate cancer (local or metastatic).

Also encompassed are methods for the treatment of metabolic syndrome. Metabolic syndrome is obesity related and thus administration of the peptides of the present invention are useful in its treatment.

Furthermore, methods for the diagnosis of obesity and obesity related diseases and disorders, including diabetes are encompassed. In this embodiment, a peptide of the present invention is administered to subject and subject's response is closely analyzed. A decrease in desire for food immediately following administration of the peptide or a decrease in weight gain or a reduction in weight indicates a propensity to or a current affliction with obesity or an obesity related disease or disorder.

In some embodiments, the peptides described herein can be utilized as a diagnostic agent to assess the role of ghrelin, other ghrelin-like molecules, and ghrelin receptor agonists or its receptor in the regulation of GH secretion, food intake, and gastrointestinal motility. The peptides can also be used to rule out endogenous pathophysiological activities of ghrelin, assess the role of ghrelin in various physiological and metabolic processes, assess the effects of exogenous ghrelin, GHSs as well as other agents that possibly act via release of endogenous ghrelin or via ghrelin mimics, and determine biological actions of acylated ghrelin over that of desacylated ghrelin.

In some embodiments, the peptide of the present invention is administered prior to taking a meal, for example, 4 hours, 3 hours, 2 hours, 1 hour, or 0.5 hours prior to expected meal time. Preferably, the peptide is administered 0.5 hours prior to feeding. Alternatively, the peptide may be administered continuously, for example, systemically, as a single administration every 6, 5, 4, 3, 2, or 1 month, preferably every 3 months. Here, the peptide of the present invention may normalize an otherwise dysfunctional endocrine system. The peptide may be active in the individual for several months.

In another aspect, the invention provides a method for inhibiting and/or disrupting the GHS-R signaling pathway in a subject in need thereof, the method comprising administering an effective amount of a peptide described herein along with a ghrelin O-acyltransferase (GOAT) inhibitor and/or a ghrelin receptor antagonist and/or inverse agonist. Without wishing to be bound by theory, inhibition and/or disruption of the GHS-R signaling pathway in a subject can be used for treatment of ghrelin related disease and disorder diseases and disorders such as obesity, overeating, diabetes, unregulated cellular proliferation, and cancer.

Exemplary GOAT inhibitors and ghrelin receptor antagonists and/or inverse agonists are described, for example, in Int. Pat. App. No. PCT/US2007/010389, filed Apr. 30, 2007 and No. PCT/US2010/034570, filed May 12, 2010, content of both of which is herein incorporated by reference in its entirety.

Pharmaceutical Compositions

For administration to a subject, the peptides described herein can be provided in pharmaceutically acceptable compositions. These pharmaceutically acceptable compositions comprise a therapeutically-effective amount of one or more of the peptides described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, peptides and pharmaceutical compositions comprising peptides can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Peptides and pharmaceutical compositions comprising peptides can also be administered in the form of a depot injection or implant preparation, which may be formulated in such a manner as to permit a sustained release of the active ingredient. The formulation can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

Peptides or pharmaceutical compositions comprising the peptides can also be administered in the form of liposome delivery systems, such as small unilamellar vesicles, large unilamellar vesicles and multilamellar vesicles. Liposomes can be formed from a variety of phospholipids, such as cholesterol, stearylamine, phosphatidylethanolamines, or phosphatidylcholines. Liposomal preparations of diabetes-modulating agents may also be used in the methods of the invention.

Peptides or pharmaceutical compositions comprising the peptides can also be delivered by the use of monoclonal antibodies as individual carriers to which the compound molecules are coupled.

Peptides or pharmaceutical compositions comprising the peptides can also be prepared with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, Peptides or pharmaceutical compositions comprising the peptides can be prepared with biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

This invention also encompasses pharmaceutical compositions comprising any solid or liquid physical form of one or more of the peptides of the invention. For example, the peptide can be in a crystalline form, in amorphous form, and have any particle size. The peptide particles may be micronized, or may be agglomerated, particulate granules, powders, oils, oily suspensions or any other form of solid or liquid physical form.

In some embodiments, the peptides of the present invention can be used in the form of a pharmaceutically acceptable salt. Suitable acids which are capable of forming salts with the peptides include inorganic acids such as hydrochloric acid, hydrobromic acid, perchloric acid, nitric acid, thiocyanic acid, sulfuric acid, phosphoric acid, and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, trifluoroacetic acid, methansulfonic acid, benzenesulfonic acid, p-toulenesulfonic acid, and the like. Suitable bases capable of forming salts with the peptides include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine, pyridine, picoline, dicyclohexylamine, N,N'-dibezylethylenediamine, and the like) and optionally substituted ethanol-amines (e.g., ethanolamine, diethanolamine, trierhanolamine and the like).

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As indicated above, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In some embodiments, the peptides are prepared with carriers that will protect the peptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) comprised of neutral lipids, anionic lipids, cationic lipids, or mixtures thereof can also be used as pharmaceutically acceptable carriers. These can be prepared according to methods known to those skilled in the art, for example, as described in U.S. Pat. No. 4,522,811.

It is especially advantageous to formulate oral and intravenous compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration. A pharmaceutical composition typically contains an amount of at least 0.001 weight % of active ingredient, i.e., a peptide of this invention, per weight of total pharmaceutical composition. A weight % is a ratio by weight of active ingredient to total composition. Thus, for example, 0.1 weight % is 0.1 grams of peptide inhibitor per 100 grams of total composition.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic, or oily solutions and the like as detailed above.

For intravenous administration, Glucuronic acid, L-lactic acid, acetic acid, citric acid or any pharmaceutically acceptable acid/conjugate base with reasonable buffering capacity in the pH range acceptable for intravenous administration can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12.

Subcutaneous formulations can be prepared according to procedures well known in the art at a pH in the range between about 5 and about 12, which include suitable buffers and isotonicity agents. They can be formulated to deliver a daily dose of the active agent in one or more daily subcutaneous administrations. The choice of appropriate buffer and pH of a formulation, depending on solubility of one or more peptides to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12.

One can formulate the peptides into slow-release formulations as well as into formulations that can be administered using devices similar to those used to deliver insulin, such as insulin pumps and such, or in aerosol formation used in inhalators. Accordingly, the peptides of the invention may be admixed with biologically compatible polymers or matrices which control the release rate of the antagonists into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral.

Controlled release permits dosages to be administered over time, with controlled release kinetics. In some instances, delivery of the therapeutic agent is continuous to the site where treatment is needed, for example, over several weeks. Controlled release over time, for example, over several days or weeks, or longer, permits continuous delivery of the therapeutic agent to obtain optimal treatment. The controlled delivery vehicle is advantageous because it protects the therapeutic agent from degradation in vivo in body fluids and tissue, for example, by proteases.

Controlled release from the pharmaceutical formulation may be designed to occur over time, for example, for greater than about 12 or 24 hours. The time of release may be selected, for example, to occur over a time period of about 12 hours to 24 hours; about 12 hours to 42 hours; or, e.g., about 12 to 72 hours. In another embodiment, release may occur for example on the order of about 2 to 90 days, for example, about 3 to 60 days. In one embodiment, the therapeutic agent is delivered locally over a time period of about 7-21 days, or about 3 to 10 days. In other instances, the therapeutic agent is administered over 1,2,3 or more weeks in a controlled dosage. The controlled release time may be selected based on the condition treated.

The phrase "therapeutically-effective amount" as used herein means that amount of a peptide, or composition comprising a peptide of the present invention which is effective for producing some desired therapeutic effect in at least a sub-population of cells in an animal at a reasonable benefit/risk ratio applicable to any medical treatment. For example, an amount of a peptide administered to a subject that is sufficient to produce a statistically significant, measurable change in at least one symptom of a disease. Generally, dosage levels of between 0.0001 to 100 mg/kg of body weight daily are administered to subject in need thereof.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The terms "administration of" and or "administering" a peptide should be understood to mean providing a peptide of the invention to a subject in need of treatment. As such, the term "administer" refers to the placement of a composition into a subject by a method or route which results in at least partial localization of the composition at a desired site such that ghrelin receptor is antagonized. Peptides described herein can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

The peptides described herein can be administered to a subject in combination with another pharmaceutically active agent or treatment modality for a particular indication. Exemplary pharmaceutically active compound include, but are not limited to, those found in *Harrison's Principles of Internal Medicine*, $13^{th}$ Edition, Eds. T. R. Harrison et al. McGraw-Hill N.Y., NY; Physicians Desk Reference, $50^{th}$ Edition, 1997, Oradell N.J., Medical Economics Co.; Pharmacological Basis of Therapeutics, $8^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, the pharmaceutically active agent is selected from the group consisting of anti-obesity agent, an anti-diabetes agent, an anti-cancer agent, anti-inflammatory agent, antibiotic agent, and combinations thereof.

Exemplary anti-diabetes agents include, but are not limited to, sulfonylureas like glimepiride, glyburide (also known in the art as glibenclamide), glipizide, gliclazide; biguanides such as metformin; insulin (including inhaled formulations such as Exubera), and insulin analogs such as insulin lispro (Humalog), insulin glargine (Lantus), insulin detemir, and insulin glulisine; peroxisome proliferator-activated receptor-γ(PPAR-γ) agonists such as the thiazolidinediones including troglitazone (Rezulin), pioglitazone (Actos), rosiglitazone (Avandia), and isaglitzone (also known as netoglitazone); dual-acting PPAR agonists such as BMS-298585 and tesaglitazar; insulin secretagogues including metglitinides such as repaglinide and nateglinide; analogs of glucagon-like peptide-1 (GLP-1) such as exenatide (AC-2993) and liraglutide (insulinotropin); inhibitors of dipeptidyl peptidase IV like LAF-237; pancreatic lipase inhibitors such as orlistat; a-glucosidase inhibitors such as acarbose, miglitol, and voglibose; and combinations thereof, particularly metformin and glyburide (Glucovance), metformin and rosiglitazone (Avandamet), and metformin and glipizide (Metaglip).

In some embodiments, the pharmaceutically active agent is an antibiotic agent. The term "antibiotic" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim, sulfamethoxazole, and the like.

The peptide and the pharmaceutically active agent can be administrated to the subject in the same pharmaceutical composition or in different pharmaceutical compositions (at the same time or at different times). When administrated at different times, peptide and the pharmaceutically active agent can be administered within 5 minutes, 10 minutes, 20 minutes, 60 minutes, 2 hours, 3 hours, 4, hours, 8 hours, 12 hours, 24 hours of administration of the other When administered in different pharmaceutical compositions, routes of administration can be different. For example, a peptide is administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and pharmaceutically active agent is administration by same or a different route, e.g. a route commonly used in the art for administration of said pharmaceutically active agent. In embodiments where the peptide and pharmaceutically active agent are administrated separately, one would generally ensure that a significant period of time did not expire between the time of each delivery, such that the peptide and pharmaceutically active agent would still be able to exert an advantageously combined effect.

The amount of peptide which can be combined with a carrier material to produce a single dosage form will generally be that amount of the peptide which produces a therapeutic effect. Generally out of one hundred percent, this amount will range from about 0.001% to 99% of compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio D50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that a peptide is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis actually true. The decision is often made using the p-value.

The term "ghrelin receptor" as used herein includes growth hormone secretagogue receptor, GHS-R1a and subtypes, isoforms and variants thereof.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

There are two forms of Diabetes mellitus: (1) insulin dependent or Type 1 Diabetes (a.k.a., Juvenile Diabetes, Brittle Diabetes, Insulin Dependent Diabetes Mellitus (IDDM)) and (2) non-insulin-dependent or Type II Diabetes (a.k.a., NIDDM). Type 1 Diabetes develops most often in young people but can appear in adults. Type 2 Diabetes develops most often in middle aged and older adults, but can appear in young people. Diabetes is a disease derived from multiple causative factors and characterized by elevated levels of plasma glucose (hyperglycemia) in the fasting state or after administration of glucose during an oral glucose tolerance test. A decrease in β-cell mass occurs in both Type 1 and Type 2 Diabetes.

The terms "diabetes" and "diabetes mellitus" are used interchangeably herein. The World Health Organization defines the diagnostic value of fasting plasma glucose concentration to 7.0 mmol/l (126 mg/dl) and above for Diabetes Mellitus (whole blood 6.1 mmol/1 or 110 mg/dl), or 2-hour glucose level ≥11.1 mmol/L (≥200 mg/dL). Other values suggestive of or indicating high risk for Diabetes Mellitus include elevated arterial pressure ≥140/90 mm Hg; elevated plasma triglycerides (≥1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio >0.90; females: waist to hip ratio >0.85) and/or body mass index exceeding 30 kg/m$^2$; microalbuminuria, where the urinary albumin excretion rate 20 μg/min or albumin:creatinine ratio ≥30 mg/g).

A "pre-diabetic condition" refers to a metabolic state that is intermediate between normal glucose homeostasis, metabolism, and states seen in Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL)(whole blood 6.1 mmol/L; 110 mg/dL). Metabolic Syndrome according to National Cholesterol Education Program (NCEP) criteria are defined as having at least three of the following: blood pressure ≥130/85 mm Hg; fasting plasma glucose ≥6.1 mmol/L; waist circumference >102 cm (men) or >88 cm (women); triglycerides ≥1.7 mmol/L; and HDL cholesterol <1.0 mmol/L (men) or 1.3 mmol/L (women).

"Impaired glucose tolerance" (IGT) is defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75 g oral glucose tolerance test. These glucose levels are above normal but below the level that is diagnostic for Diabetes. Subjects with impaired glucose tolerance or impaired fasting glucose have a significant risk of developing Diabetes and thus are an important target group for primary prevention.

"Normal glucose levels" is used interchangeably with the term "normoglycemic" and refers to a fasting venous plasma glucose concentration of less than 6.1 mmol/L (110 mg/dL). Although this amount is arbitrary, such values have been observed in subjects with proven normal glucose tolerance, although some may have IGT as measured by oral glucose tolerance test (OGTT). A baseline value, index value, or reference value in the context of the present invention and defined herein can comprise, for example, "normal glucose levels."

In general, treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbAlc; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Type 1 Diabetes is an autoimmune disease that results in destruction of insulin-producing beta cells of the pancreas. Lack of insulin causes an increase of fasting blood glucose (around 70-120 mg/dL in nondiabetic people) that begins to appear in the urine above the renal threshold (about 190-200 mg/dl in most people). Type 1 Diabetes can be diagnosed using a variety of diagnostic tests that include, but are not limited to, the following: (1) glycated hemoglobin (A1C) test, (2) random blood glucose test and/or (3) fasting blood glucose test.

The Glycated hemoglobin (A1C) test is a blood test that reflects the average blood glucose level of a subject over the preceding two to three months. The test measures the percentage of blood glucose attached to hemoglobin, which correlates with blood glucose levels (e.g., the higher the blood glucose levels, the more hemoglobin is glycosylated). An A1C level of 6.5 percent or higher on two separate tests is indicative of Diabetes. A result between 6 and 6.5 percent is considered prediabetic, which indicates a high risk of developing Diabetes.

The Random Blood Glucose Test comprises obtaining a blood sample at a random time point from a subject suspected of having Diabetes. Blood glucose values can be expressed in milligrams per deciliter (mg/dL) or millimoles per liter (mmol/L). A random blood glucose level of 200 mg/dL (11.1 mmol/L) or higher indicates the subject likely has Diabetes, especially when coupled with any of the signs and symptoms of Diabetes, such as frequent urination and extreme thirst.

For the fasting blood glucose test, a blood sample is obtained after an overnight fast. A fasting blood glucose level less than 100 mg/dL (5.6 mmol/L) is considered normal. A fasting blood glucose level from 100 to 125 mg/dL (5.6 to 6.9 mmol/L) is considered prediabetic, while a level of 126 mg/dL (7 mmol/L) or higher on two separate tests is indicative of Diabetes.

Type 1 Diabetes can also be distinguished from type 2 Diabetes using a C-peptide assay, which is a measure of endogenous insulin production. The presence of anti-islet antibodies (to Glutamic Acid Decarboxylase, Insulinoma Associated Peptide-2 or insulin), or lack of insulin resistance, determined by a glucose tolerance test, is also indicative of type 1, as many type 2 diabetics continue to produce insulin internally, and all have some degree of insulin resistance.

Testing for GAD 65 antibodies has been proposed as an improved test for differentiating between type 1 and type 2 Diabetes as it appears that the immune system is involved in Type 1 Diabetes etiology.

The non-obese diabetic (NOD) mouse provides an animal model for the spontaneous development of Type 1 Diabetes. NOD mice develop insulitis as a result of leukocyte infiltration into the pancreatic islet, which in turn leads to the destruction of pancreatic islets and a Type 1 diabetic phenotype (Makino S, et al., (1980) *Jikken Dobutsu* 29 (1): 1-13; Kikutani H, and Makino S (1992) *Adv. Immunol.* 51: 285-322).

The methods described herein are also useful for treating Type 1 Diabetes in a subject.

In the context of type 1 Diabetes, "treating" or "treatment" refers to partial or total inhibition, delay or prevention of the progression of type 1 Diabetes, pre-diabetic conditions, and complications associated with type 1 Diabetes or pre-diabetic conditions; inhibition, delay or prevention of the recurrence of type 2 Diabetes, pre-diabetic conditions, or complications associated with type 1 Diabetes or pre-diabetic conditions; or the prevention of the onset or development of type 1 Diabetes, pre-diabetic conditions, or complications associated with type 1 Diabetes or pre-diabetic conditions (chemoprevention) in a subject.

In the context of Type 1 Diabetes, "therapeutically effective amount" refers to an amount of peptide administered to a subject that is sufficient to produce a statistically significant, measurable change in at least one symptom of Type 1 Diabetes, such as glycosylated hemoglobin level, fasting blood glucose level, hypoinsulinemia, etc. Efficacy of treatment with a peptide can be assessed by measuring changes in blood glucose and/or insulin levels or as described below.

The efficacy of a given treatment for Type 1 Diabetes can be determined by the skilled clinician. However, a treatment is considered "effective treatment," as the term is used herein, if any one or all of the signs or symptoms of Type 1 Diabetes, for example, hyperglycemia are altered in a beneficial manner, other clinically accepted symptoms or markers of disease are improved, or even ameliorated, e.g., by at least 10% following treatment with a peptide as described herein. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the loss of beta cells; or (2) relieving the disease, e.g., causing regression of symptoms, increasing pancreatic beta cell mass; and (3) preventing or reducing the likelihood of the development of a complication of Type 1 Diabetes, e.g., diabetic retinopathy.

As used herein, the term "delaying the onset of Type 1 Diabetes" in a subject refers to a delay of onset of at least one symptom of Type 1 Diabetes (e.g., hyperglycemia and/or hypoinsulinemia) of at least one week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

Type 2 Diabetes results from a combination of insulin resistance and impaired insulin secretion but ultimately many people with Type 2 Diabetes show markedly reduced pancreatic f3-cell mass and function which, in turn, causes Type 2 diabetic persons to have a "relative" deficiency of insulin because pancreatic β-cells are producing some insulin, but the insulin is either too little or isn't working properly to adequately allow glucose into cells to produce energy. Recent autopsy studies have shown clear evidence of ongoing β-cell death (apoptosis) in people with Type 2 Diabetes. Therefore, therapeutic approaches to provide more β-cells could provide a significant treatment for reversing or curing Type 2 Diabetes.

Uncontrolled Type 2 Diabetes leads to excess glucose in the blood, resulting in hyperglycemia, or high blood sugar. A person with Type 2 Diabetes experiences fatigue, increased thirst, frequent urination, dry, itchy skin, blurred vision, slow healing cuts or sores, more infections than usual, numbness and tingling in feet. Without treatment, a person with Type 2 Diabetes will become dehydrated and develop a dangerously low blood volume. If Type 2 Diabetes remains uncontrolled for a long period of time, more serious symptoms may result, including severe hyperglycemia (blood sugar over 600 mg) lethargy, confusion, shock, and ultimately "hyperosmolar hyperglycemic non-ketotic coma." Persistent or uncontrolled hyperglycemia is associated with increased and premature morbidity and mortality. As such, therapeutic control of glucose homeostasis, lipid metabolism, obesity, and hypertension are critically important in the clinical management and treatment of Diabetes mellitus.

The methods of the invention are useful for treating type 2 Diabetes Mellitus or a pre-diabetic condition in a subject or preventing type 2 Diabetes or pre-diabetic conditions in a subject. Skilled artisan is well aware that type 2 Diabetes Mellitus is also known as non-insulin dependent Diabetes mellitus.

"Complications related to type 2 Diabetes" or "complications related to a pre-diabetic condition" can include, without limitation, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof.

In the context of type 2 Diabetes, "treating" or "treatment" refers to partial or total inhibition, delay or prevention of the progression of type 2 Diabetes, pre-diabetic conditions, and complications associated with type 2 Diabetes or pre-diabetic conditions; inhibition, delay or prevention of the recurrence of type 2 Diabetes, pre-diabetic conditions, or complications associated with type 2 Diabetes or pre-diabetic conditions; or the prevention of the onset or development of type 2 Diabetes, pre-diabetic conditions, or complications associated with type 2 Diabetes or pre-diabetic conditions (chemoprevention) in a subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$. Typically, an overweigh individual is considered to have a body mass index (BMI) of over 25 but under 30 and an obese individual is considered to have a BMI of over 30.

Obesity related diseases and disorders include, but are not limited to diabetes mellitus, metabolic syndrome, hypertension, elevated plasma insulin concentrations, insulin resistance, dyslipidemias, and hyperlipidemia.

"Treatment" (of obesity and obesity-related disorders) refers to the administration of a peptide described herein to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. Another outcome of treatment may be to maintain weight loss. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects. The ghrelin receptor antagonists described herein are effective in treating obesity and obesity related diseases and disorders including diabetes and various types of cancer.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

The term "inverse agonist" as used herein refers to an agent which binds to the same ghrelin receptor binding-site as an agonist for that receptor but exerts the opposite pharmacological effect, decrease intracellular IP3 levels.

The term "antagonist" is used in the broadest sense, and includes any molecule that partially or fully blocks, inhibits, or neutralizes a biological activity of ghrelin receptor.

As used herein, the term "metabolic syndrome" refer to a group of metabolic risk factors in one person. They include: abdominal obesity (excessive fat tissue in and around the abdomen), atherogenic dyslipidemia (blood fat disorders—high triglycerides, low HDL cholesterol and high LDL cholesterol—that foster plaque buildups in artery walls), elevated blood pressure, insulin resistance or glucose intolerance (the body can't properly use insulin or blood sugar), rrothrombotic state (e. g., high fibrinogen or plasminogen activator inhibitor-1 in the blood), and proinflammatory state (e.g., elevated C-reactive protein in the blood). There are currently no well-accepted criteria for diagnosing the metabolic syndrome. The criteria proposed by the National Cholesterol Education Program (NCEP) Adult Treatment Panel III (ATP III), with minor modifications, are currently recommended and widely used.

To the extent not already indicated, it will be understood by those of ordinary skill in the art that any one of the various embodiments herein described and illustrated may be further modified to incorporate features shown in any of the other embodiments disclosed herein.

The invention may be described as in any of the following paragraphs.

1. A peptide of formula (I'):

$$X^1\text{-Gly-Ser-}X^2\text{-Phe-Leu-Ser-Pro-Glu-His-}(X^3)_m\text{—}X^4 \quad \text{(I') (SEQ ID NO: 1),}$$

wherein:

$X^1$ is $A^1\text{-}A^2\text{-}A^3\text{-}A^4\text{-}A^5\text{-}A^6\text{-}$;

$X^2$ is a serine conjugated with a —$C(O)C_1\text{-}C_{20}$ alkyl group on the side chain OH of said serine, a diaminopropionic acid conjugated with a —$C(O)C_1\text{-}C_{20}$ alkyl group on one of the amino groups of the diaminopropionic acid, or D- or L-tryptophan;

each $X^3$ is independently an amino acid;

$X^4$ is absent, $NH_2$, or a carboxyl protecting group;

each of $A^1$, $A^2$, $A^3$, $A^4$, $A^5$, and $A^6$ is independently absent (i.e., need not be present), a D amino acid, L amino acid, α-amino acid, β-amino acid, γ-amino acid, γ-amino acid, or an amino protecting group, provided that at least one of $A^1$, $A^2$, $A^3$, $A^4$, $A^5$, and $A^6$ is present;

m is an integer from 1 to 20; and pharmaceutically acceptable salts thereof.

2. The peptide of paragraph 1, wherein $X^2$ is a serine conjugated with an octanoyl group on the side chain OH of the serine, a diaminopropionic acid conjugated with an octanoyl group on one of the amino groups of the diaminopropionic acid, or L-tryptophan.

3. The peptide of any of paragraphs 1-2, wherein the peptide is of formula (I'): GMA-GS-$X^2$-FLSPEH-$(X^3)_m$—$X^4$ (SEQ ID NO: 380).

4. The peptide of any of paragraphs 1-3, wherein $(X^3)_m$ is Q, QR, QRV, QRVQ (SEQ ID NO: 10), QRVQQ (SEQ ID NO: 11), QRVQQR (SEQ ID NO: 12), QRVQQRK (SEQ ID NO: 13), QRVQQRKE (SEQ ID NO: 14), QRVQQRKES (SEQ ID NO: 15), QRVQQRKESK (SEQ ID NO: 16), QRVQQRKESKK (SEQ ID NO: 17), QRVQQRKESKKP (SEQ ID NO: 18), QRVQQRKESKKPP (SEQ ID NO: 19), QRVQQRKESKKPPA (SEQ ID NO: 20), QRVQQRKESKKPPAK (SEQ ID NO: 21), QRVQQRKESKKPPAKL (SEQ ID NO: 22), QRVQQRKESKKPPAKLQ (SEQ ID NO: 23), QRVQQRKESKKPPAKLQP (SEQ ID NO: 24), QRVQQRKESKKPPAKLQPR (SEQ ID NO: 25), or QRVQQRKESKKPPAKLQPRW (SEQ ID NO: 26).

5. The peptide of any of paragraphs 1-4, wherein the peptide is selected from the group consisting of $X^1$-GS-$X^2$-FL-SPEHQ-$X^4$ (SEQ ID NO: 39), $X^1$-GS-$X^2$-FL-SPEHQR-$X^4$ (SEQ ID NO: 40), $X^1$-GS-$X^2$-FL-SPEHQRV-$X^4$ (SEQ ID NO: 41), $X^1$-GS-$X^2$-FL-SPEHQRVQ-$X^4$ (SEQ ID NO: 42), $X^1$-GS-$X^2$-FL-SPEHQRVQQ-$X^4$ (SEQ ID NO: 43), $X^1$-GS-$X^2$-FL-SPEHQRVQQR-$X^4$ (SEQ ID NO: 44), $X^1$-GS-$X^2$-FL-SPEHQRVQQRK-$X^4$ (SEQ ID NO: 45), $X^1$-GS-$X^2$-FL-SPEHQRVQQRKE-$X^4$ (SEQ ID NO: 46), $X^1$-GS-$X^2$-FL-SPEHQRVQQRKES-$X^4$ (SEQ ID NO: 47), $X^1$-GS-$X^2$-FL-SPEHQRVQQRKESK-$X^4$ (SEQ ID NO: 48), $X^1$-GS-$X^2$-FL-SPEHQRVQQRKESKK-$X^4$ (SEQ ID NO: 49), $X^1$-GS-$X^2$-FL-SPEHQRVQQRKESKKP-$X^4$ (SEQ ID NO: 50), $X^1$-GS-$X^2$-FL-SPEHQRVQQRKESKKPP-$X^4$ (SEQ ID NO: 51), $X^1$-GS-$X^2$-FL-SPEHQRVQQRKESKKPPA-$X^4$ (SEQ ID NO: 52), $X^1$-GS-$X^2$-FL-SPEHQRVQQRKESKKPPAK-$X^4$ (SEQ ID NO: 53), $X^1$-GS-$X^2$-FL-SPEHQRVQQRKESKKPPAKL-$X^4$ (SEQ ID NO: 54), $X^1$-GS-$X^2$-FL-SPEHQRVQQRKESKKPPAKLQ-$X^4$ (SEQ ID NO: 55), $X^1$-GS-$X^2$-FL-SPEHQRVQQRKESKKPPAKLQP-$X^4$ (SEQ ID NO: 56), $X^1$-GS-$X^2$-FL-SPEHQRVQQRKESKKPPAKLQPR-$X^4$ (SEQ ID NO: 57), and $X^1$-GS-$X^2$-FL-SPEHQRVQQRKESKKPPAKLQPRW-$X^4$ (SEQ ID NO: 58).

6. A peptide of formula (II):

$$X^1\text{-}A^{21}\text{-}A^{22}\text{-}A^{23}\text{-}A^{24}\text{-}A^{25}\text{-}A^{26}\text{-}X^4 \quad \text{(Formula II),}$$

wherein:

$X^1$ is $A^1\text{-}A^2\text{-}A^3\text{-}A^4\text{-}A^5\text{-}A^6\text{-}$;

$X^4$ is absent, $NH_2$, or a carboxyl protecting group;

each of $A^1$, $A^2$, $A^3$, $A^4$, $A^5$, and $A^6$ is independently absent (i.e., need not be present), a D amino acid, L amino acid, α-amino acid, β-amino acid, γ-amino acid, γ-amino acid, or an amino protecting group, provided that at least one of $A^1$, $A^2$, $A^3$, $A^4$, $A^5$, and $A^6$ is present;

$A^{21}$ is His, Tyr, desamino Tyr, D- or L-Ala, β-Ala, D- or L-cyclohexylAla (Cyclohexylalanine), D-Arg, Ava (aminovaleric acid), Gly, <Glu (pyroglutaminic acid), αAib (alpha-aminoisobutyric acid), γAbu (gamma-aminobutyric acid), αAbu (alpha-aminobutyric acid), α,γAbu (alpha, gamma-aminobutyric acid), D-Val, D-phe, D-Thr, D-Pal (pyridylalanine), D-Lys, Acetyl-D-Lys, D-Leu, D-Phe, D- or L-Trp, D- or L α-naphthyalanine, D- or L-β-naphthyalanine, D- or L-Ser, D- or L-Ser which is acylated at the side-chain hydroxyl group (Ser (acyl)), Acetyl-D-β-naphthyalanine, D-4-halo-Phe, D-4-pyrolidylalanine, an amino acid which is methylated at the amino group of the alpha carbon atom, or an amino acid with an extended aromatic chain;

$A^{22}$ is D-α,β-naphthyalanine, D- or L-α-naphthyalanine, D- or L-β-naphthyalanine, D- or L-Trp, D- or L-Phe, Ala, His, D- or L-Lys, D- or L-Lys which is acylated at the side-chain amino group (Lys(acyl)), D-Pro, D-Orn, Ser, D- or L-Ser which is acylated at the side-chain hydroxyl group, D-Pal, D- or L-Leu, Phe, PicLys (N$^ε$-picoloyl-lysine), D-Cyclohexylalanine, D-4-halo-Phe, D-4-pyrolidylalanine, an amino acid with methylation of the terminal nitrogen of the α carbon atom, or an amino acid with an extended aromatic chain;

A²³ is absent, D- or L-Lys, lysine derivatives, Arg, arginine derivatives, Orn, L- or D-Phe, D- or L-Trp, Leu, L- or D-Pro, Ala, D-Ile, D- or L-Val, Ser, Pal, D- or L-cyclohexylAla, cyclopentylAla, βNal, αNal, or α,γ Abu;

A²⁴ is absent, D- or L-Trp, D- or L-Phe, D- or L-Ile, D- or L-Val, D- or L-Arg, Ala, Ser, Tyr, Met, Pro, Thr, ILys, or CyclohexylAla;

A²⁵ is absent, D- or L-Trp, L- or D-Phe, Ala, Lys, Arg, Orn, Thr, Leu, or DCyclohexylAla;

A²⁶ is absent, Lys, Gln, Arg, Orn, D- or L-Phe, Pro(cyclic Arg-Pro), Nle (norleucine), or α,γ Abu amide;

A²⁷ is absent or Gly; and pharmaceutically acceptable salts thereof.

7. The peptide of paragraph 6, wherein the peptide is selected from the group consisting of X¹⁻<GluHisTrpDSerDArg-X⁴, X¹-AlaHisDTrpDLysTrpDPheLys-X⁴, X¹-Alaψ[CH₂NH]DβNalAlaTrpDPheLys-X⁴, X¹-Alaψ[CH₂NH]HisDTrpAlaTrpDPheLys-X⁴, X¹-ArgDTrpLeuTyrTrpPro(cyclic ArgPro)-X⁴, X¹-AvaTrpDTrpDTrpOrn-X⁴, X¹-CyclohexylAlaDαNalDTrpPheArg-X⁴, X¹-DAlaAla-DAIaDTrpPheLys-X⁴, X¹-DAlaDcyclohexylAlaAlaAlaPheDPheNle-X⁴, X¹-DAlaDcyclohexylAlaAlaPheD-Phe-X⁴, X¹-DAlaDTrpPhe; DAlaDβNalAlaAlaDAlaLys-X⁴, X¹-DAlaDβNalAlaThrDThrLys-X⁴, X¹-DAlaDβNalAlaTrpDPheLys-X⁴, X¹-DAlaDβNalDAlaDTrpPheLys-X⁴, X¹-DAlaDβNalDProPheArg-X⁴, X¹-DcyclohexylAlaAlaPheDTrpLys-X⁴, X¹-DcyclohexylAlaAlaTrpDPhe-X⁴, X¹-DesaminoTyrDTrpDLysTrpD-Phe-X⁴, X¹-DesaminoTyrDTrpSerTrpDPhe-X⁴, X¹-DesaminoTyrDTrpSerTrpDPheLys-X⁴, X¹-DHISDTrpDProDArg-X⁴, X¹-DHisDTrpDProDIle-X⁴, X¹-DLeuDαNalDTrpPheArg-X⁴, X¹-DLysDβNalAlaTrpDPheLys-X⁴, X¹-DLysTyrDTrpAlaTrpDPhe-X⁴, X¹-DLysTyrDTrpDTrpPhe-X⁴, X¹-DLysTyrDTrpDTrpPheLys-X⁴, X¹-DPalPheDTrpPheMet-X⁴, X¹-DPheAlaPheDPal-X⁴, X¹-DPheAlaPheDPheLys-X⁴, X¹-DPheDPheDTrpMetDLys-X⁴, X¹-DPheTrpDPhePheMet-X⁴, X¹-DThrDαNalDTrpDProArg-X⁴, X¹-DTrpAlaTrpD-Phe-X⁴, X¹-DTrpDPro-X⁴, X¹-DTrpDProDIle-X⁴, X¹-DTrpDProDIleArg-X⁴, X¹-DTrpDProDVal-X⁴, X¹-DTrpDProDValArg-X⁴, X¹-DTrpDTrpLys-X⁴, X¹-DTrpDTrpLys; DTrpDαNalDTrpPheArg-X⁴, X¹-DTrpPheDTrp; DValDαNalDTrpPheArg-X⁴, X¹-DαNalDTrpPheArg-X⁴, X¹-DβNalAlaTrpDPheAla-X⁴, X¹-DβNalAlaTrpDPheLeu-X⁴, X¹-DβNalAlaTrpDPheLysGlnGly-X⁴, X¹-DβNalDLysTrpDPheLys-X⁴, X¹-DβNalDTrp-X⁴, X¹-DβNalDTrpDProDArg-X⁴, X¹-DβNalPicLysILysDPhe-X⁴, X¹-GlyψDβNalAlaTipDPheLys-X⁴, X¹-GlyψDβ-NalDLysTrpDPheLys-X⁴, X¹-HisDTrpDArgTrpDPhe-X⁴, X¹-HisDTrpDLysTrpDPheLys-X⁴, X¹-HisDTrpDTrpLys-X⁴, X¹-HisDTrpDTrpPheMet-X⁴, X¹-HisDTrpPheTrpDPheLys-X⁴, X¹-HisDβNalDLysTrpDPheLys-X⁴, X¹-HisTrpDAlaDTrpDPheLys-X⁴, X¹-TyrDTrpDLysTrpDPhe-X⁴, X¹-TyrDTrpDTrpPhePhe-X⁴, X¹-TyrDTrpLysTrpDPhe-X⁴, X¹-αAbuDTrpDTrpOrn-X⁴, X¹-αAibDTrpCyclohexylDAla; αAibDTrpDAlacyclohexylAla-X⁴, X¹-αAibDTrpDcyclohexylAla-X⁴, X¹-αAibDTrpDPro-X⁴, X¹-αAibDTrpDProDIle-X⁴, X¹-αAibDTrpDProDIleArg-X⁴, X¹-αAibDTrpDProD-Val-X⁴, X¹-αAibDTrpDProDValArg-X⁴, X¹-αγAbuTrpDTrpDTrpOrn-X⁴, X¹-βAlaPalDTrpDTrpOrn-X⁴, X¹-AlaTrpDAlaDTrpDPhe-X⁴, X¹-βAlaTrpDTrpDTrpLys-X⁴, X¹-βAlaTrpDTrpDTrpOrn-X⁴, X¹-γAbuTrpDTrpDTrpOrn-X⁴, X¹-Ser(Bzl)LysDTrp-X⁴, X¹-αAibDTrp-X⁴, X¹-γAbuDTrp-X⁴, X¹-αAibDSer(Bzl)-X⁴, X¹-αγAbuDSer(Nap)-X⁴, X¹-DSerDLysTrp-X⁴, X¹-Ser(Bzl)Lys(Ac)DTrp-X⁴.

8. A peptide of formula (III):

X¹-A³¹-A³²-A³³-A³⁴-X⁴ (Formula III), wherein:

X¹ is A¹-A²-A³-A⁴-A⁵-A⁶-;

X⁴ is absent, NH₂, or a carboxyl protecting group;

each of A¹, A², A³, A⁴, A⁵, and A⁶ is independently absent (i.e., need not be present), a D amino acid, L amino acid, α-amino acid, β-amino acid, γ-amino acid, γ-amino acid, or an amino protecting group, provided that at least one of A¹, A², A³, A⁴, A⁵, and A⁶ is present;

A³¹ is DαNal, DβNal, AcDβNal, AcDαNal, Tyr, AcDTyr, Lys, D Phe, His, αAbu α,γAbu, γAbu, DcyclohexylAla, or isonipecotic carboxylic acid (inip);

A³² is D- or L-Trp, Ala, His, Phe, or Leu;

A³³ is D or L Trp, Ala, CyclohexylAla, Phe, Pro, Lys, or Sarcosine (N-methylglycine) (Sar);

A³⁴ is D or L Arg, Phe, CyclohexylAla, Lys, Ser, or NMe-Phe (methylated phenylalanine amino nitrogen), DPal, Aib, or Orn; and derivatives, analogs, and pharmaceutically acceptable salts thereof.

9. The peptide of paragraph 8, wherein the peptide is selected from the group consisting of X¹-αγAbuDTrpDTrpLys-X⁴; X¹-αγAbuDTrpDTrpOrn-X⁴; X¹-αγAbuDTrpDTrpSer-X⁴; X¹-TyrDAlaPheAib-X⁴; X¹-TyrDAlaSarNMePhe-X⁴; X¹-LysDHisDTrpDPhe-X⁴; X¹-γAbuDTrpDTrpOrn-X⁴; X¹-inipTrpTrpPhe-X⁴; X¹-TrpPheDTrpLeu-X⁴; X¹-DTrpPheDTrpLys-X⁴; X¹- and DβNalLeuPro-X⁴.

10. A peptide of formula (IV):)

X¹-A⁴¹-A⁴²-A⁴³-A⁴⁴-A⁴⁵-A⁴⁶-X⁴ (Formula (IV), wherein:

X¹ is A¹-A²-A³-A⁴-A⁵-A⁶-;

X⁴ is absent, NH₂, or a carboxyl protecting group;

each of A¹, A², A³, A⁴, A⁵, and A⁶ is independently absent (i.e., need not be present), a D amino acid, L amino acid, α-amino acid, β-amino acid, γ-amino acid, γ-amino acid, or an amino protecting group, provided that at least one of A¹, A², A³, A⁴, A⁵, and A⁶ is present;

A⁴¹ is His, Gly, αAib (alpha-aminoisobutyric acid), γAbu (gamma-aminobutyric acid), α,γ-Abu (alpha, gamma-aminobutyric acid), or an amino acid with methylation of the terminal nitrogen of the alpha carbon atom;

A⁴² is D-α-naphthyalanine, D-β-naphthyalanine D-α,β-naphthyalanine, D-Trp, D-Phe, or D-Cyclohexylalanine, an amino acid with methylation of the terminal nitrogen of the α carbon atom, or an amino acid with an extended aromatic chain;

A⁴³ is D- or L-Lys, Arg, Orn, or α,γ-Abu;

A⁴⁴ is D- or L-Trp, Phe, or Cyclohexylalanine;

A⁴⁵ is D-Phe or D-Cyclohexylalanine;

A⁴⁶ is Lys, Arg, Orn, or α,γ-Abu; and pharmaceutically acceptable salts thereof.

11. A peptide of formula (V):

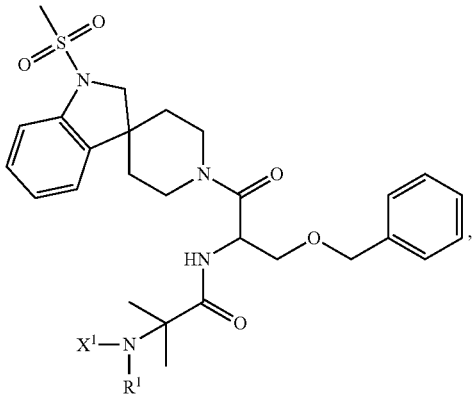

Formula (V)

wherein:
X¹ is A¹-A²-A³-A⁴-A⁵-A⁶-;
each of A¹, A², A³, A⁴, A⁵, and A⁶ is independently absent (i.e., need not be present), a D amino acid, L amino acid, α-amino acid, β-amino acid, γ-amino acid, γ-amino acid, or an amino protecting group, provided that at least one of A¹, A², A³, A⁴, A⁵, and A⁶ is present;
R¹ is H or $C_1$-$C_6$ alkyl; and
pharmaceutically acceptable salts thereof.

12. A peptide of formula (VI):

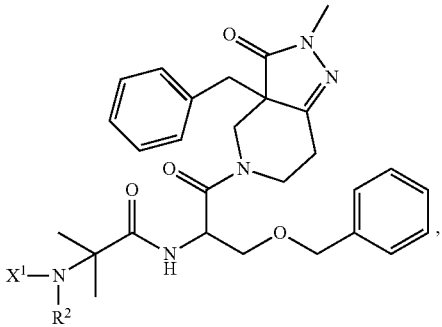

Formula (VI)

wherein:
X¹ is A¹-A²-A³-A⁴-A⁵-A⁶-;
each of A¹, A², A³, A⁴, A⁵, and A⁶ is independently absent (i.e., need not be present), a D amino acid, L amino acid, α-amino acid, β-amino acid, γ-amino acid, γ-amino acid, or an amino protecting group, provided that at least one of A¹, A², A³, A⁴, A⁵, and A⁶ is present;
R² is H or $C_1$-$C_6$ alkyl group; and
pharmaceutically acceptable salts thereof.

13. The peptide of any of paragraphs 1-12, wherein X¹ is Gly-Met-Ala-, Ala-Met-Ala-, Gly-DMet-Ala-, Ala-DMet-Ala-, Gly-Met-Alaψ[CH₂NH]—, Ala-Met-Alaψ[CH₂NH]—, Gly-DMet-Alaψ[CH₂NH]—, Ala-DMet-Alaψ[CH₂NH]—, Gly-Met-Ala[C(O)N(Me)]-, Ala-Met-Ala[C(O)N(Me)]-, Gly-DMet-Ala[C(O)N(Me)]-, Ala-DMet-Ala[C(O)N(Me)]-, Leu-Asp-Leu-Gly-Met-Ala-(SEQ ID NO: 6), Leu-Asp-Leu-Gly-Met-Ala-(SEQ ID NO: 6), Leu-Asp-Leu-Gly-DMet-Ala-, Leu-Asp-Leu-Ala-DMet-Ala-, Leu-Asp-Leu-Gly-Met-Alaψ[CH₂NH]-(SEQ ID NO: 7), Leu-Asp-Leu-Ala-Met-Alaψ[CH₂NH]-(SEQ ID NO: 8), Leu-Asp-Leu-Gly-DMet-Alaψ[CH₂NH]—, Leu-Asp-Leu-Ala-DMet-Alaψ[CH₂NH]—, Leu-Asp-Leu-Gly-Met-Ala[C(O)N(Me)]-(SEQ ID NO: 381), Leu-Asp-Leu-Ala-Met-Ala[C(O)N(Me)]-(SEQ ID NO: 382), Leu-Asp-Leu-Gly-DMet-Ala[C(O)N(Me)]-, or Leu-Asp-Leu-Ala-DMet-Ala[C(O)N(Me)]-.

14. The peptide of any of paragraphs 1-13, wherein X⁴ is absent, NH₂, optionally substituted 4-phenylpiperazine, optionally substituted 4-phenylpiperidine, or 1-(methylsulfonyl)spiro[indoline-3,4'-piperdine].

15. The peptide of any of paragraphs 1-14, wherein the peptide comprises at least one D amino acid.

16. The peptide of any of paragraphs 1-15, wherein the peptide comprises at least one beta amino acid.

17. The peptide of any of paragraphs 1-16, wherein the peptide comprises at least one peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group.

18. A peptide selected from the group consisting of GMAGSS(Oct)FL (SEQ ID NO: 59); GMAGSS(Oct)FLS (SEQ ID NO: 60); GMAGSS(Oct)FLSP (SEQ ID NO: 61); GMAGSS(Oct)FLSPE (SEQ ID NO: 62); GMAGSS(Oct)FLSPEH (SEQ ID NO: 63); GMAGSS(Oct)FLSPEHQ (SEQ ID NO: 64); GMAGSS(Oct)FLSPEHQR (SEQ ID NO: 65); GMAGSS(Oct)FLSPEHQRV (SEQ ID NO: 66); GMAGSS(Oct)FLSPEHQRVQ (SEQ ID NO: 67); GMAGSS(Oct)FLSPEHQRVQQ (SEQ ID NO: 68); GMAGSS(Oct)FLSPEHQRVQQR (SEQ ID NO: 69); GMAGSS(Oct)FLSPEHQRVQQRK (SEQ ID NO: 70); GMAGSS(Oct)FLSPEHQRVQQRKE (SEQ ID NO: 71); GMAGSS(Oct)FLSPEHQRVQQRKES (SEQ ID NO: 72); GMAGSS(Oct)FLSPEHQRVQQRKESK (SEQ ID NO: 73); GMAGSS(Oct)FLSPEHQRVQQRKESKK (SEQ ID NO: 74); GMAGSS(Oct)FLSPEHQRVQQRKESKKP (SEQ ID NO: 75); GMAGSS(Oct)FLSPEHQRVQQRKESKKPP (SEQ ID NO: 76); GMAGSS(Oct)FLSPEHQRVQQRKESKKPPA (SEQ ID NO: 77); GMAGSS(Oct)FLSPEHQRVQQRKESKKPPAK (SEQ ID NO: 78); GMAGSS(Oct)FLSPEHQRVQQRKESKKPPAKL (SEQ ID NO: 79); GMAGSS(Oct)FLSPEHQRVQQRKESKKPPAKLQ (SEQ ID NO: 80); GMAGSS(Oct)FLSPEHQRVQQRKESKKPPAKLQP (SEQ ID NO: 81); GMAGSS(Oct)FLSPEHQRVQQRKESKKPPAKLQPR (SEQ ID NO: 82); GMAGSS(Oct)FLSPEHQRVQQRKESKKPPAKLQPRW (SEQ ID NO: 83); GMAGSDap(Oct)FL (SEQ ID NO: 84); GMAGSDap(Oct)FLS (SEQ ID NO: 85); GMAGSDap(Oct)FLSP (SEQ ID NO: 86); GMAGSDap(Oct)FLSPE (SEQ ID NO: 87); GMAGSDap(Oct)FLSPEH (SEQ ID NO: 88); GMAGSDap(Oct)FLSPEHQ (SEQ ID NO: 89); GMAGSDap(Oct)FLSPEHQR (SEQ ID NO: 90); GMAGSDap(Oct)FLSPEHQRV (SEQ ID NO: 91); GMAGSDap(Oct)FLSPEHQRVQ (SEQ ID NO: 92); GMAGSDap(Oct)FLSPEHQRVQQ (SEQ ID NO: 93); GMAGSDap(Oct)FLSPEHQRVQQR (SEQ ID NO: 94); GMAGSDap(Oct)FLSPEHQRVQQRK (SEQ ID NO: 95); GMAGSDap(Oct)FLSPEHQRVQQRKE (SEQ ID NO: 96); GMAGSDap(Oct)FLSPEHQRVQQRKES (SEQ ID NO: 97); GMAGSDap(Oct)FLSPEHQRVQQRKESK (SEQ ID NO: 98); GMAGSDap(Oct)FLSPEHQRVQQRKESKK (SEQ ID NO: 99); GMAGSDap(Oct)FLSPEHQRVQQRKESKKP (SEQ ID NO: 100); GMAGSDap(Oct)FLSPEHQRVQQRKESKKPP (SEQ ID NO: 101); GMAGSDap(Oct)FLSPEHQRVQQRKESKKPPA (SEQ ID NO: 102); GMAGSDap(Oct)FLSPEHQRVQQRKESKKPPAK (SEQ ID NO: 103); GMAGSDap(Oct)FLSPEHQRVQQRKESKKPPAKL (SEQ ID NO: 104); GMAGSDap(Oct)FLSPEHQRVQQRKESKKPPAKLQ (SEQ ID NO: 105); GMAGSDap(Oct)FLSPEHQRVQQRKESKKPPAKLQP (SEQ ID NO: 106); GMAGSDap(Oct)FLSPEHQRVQQRKESKKPPAKLQPR (SEQ ID NO: 107); GMAGSDap(Oct)FLSPEHQRVQQRKESKKPPAKLQPRW (SEQ ID NO: 108); AMAGSS(Oct)FL (SEQ ID NO: 109); AMAGSS(Oct)FLS (SEQ ID NO: 110); AMAGSS(Oct)FLSP (SEQ ID NO: 111); AMAGSS(Oct)FLSPE (SEQ ID NO: 112); AMAGSS(Oct)FLSPEH (SEQ ID NO: 113); AMAGSS(Oct)FLSPEHQ (SEQ ID NO: 114); AMAGSS(Oct)FLSPEHQR (SEQ ID NO: 115); AMAGSS(Oct)FLSPEHQRV (SEQ ID NO: 116); AMAGSS(Oct)FLSPEHQRVQ (SEQ ID NO: 117); AMAGSS(Oct)FLSPEHQRVQQ (SEQ ID NO: 118); AMAGSS(Oct)FLSPEHQRVQQR (SEQ ID NO: 119); AMAGSS(Oct)FLSPEHQRVQQRK (SEQ ID NO: 120); AMAGSS(Oct)FLSPEHQRVQQRKE (SEQ ID NO: 121); AMAGSS(Oct)FLSPEHQRVQQRKES (SEQ ID NO: 122); AMAGSS(Oct)FLSPEHQRVQQRKESK (SEQ ID NO: 123); AMAGSS(Oct)FLSPEHQRVQQRKESKK (SEQ ID NO: 124); AMAGSS(Oct)FLSPEHQRVQQRKESKKP (SEQ ID NO: 125); AMAGSS(Oct)FLSPEHQRVQQRKESKKPP (SEQ ID NO: 126); AMAGSS(Oct)FLSPEHQRVQQRKESKKPPA (SEQ ID NO: 127); AMAGSS(Oct)FLSPEHQRVQQRKESKKPPAK (SEQ ID NO: 128); AMAGSS(Oct)FLSPEHQRVQQRKESKKPPAKL (SEQ ID NO: 129); AMAGSS(Oct)FLSPEHQRVQQRKESKKPPAKLQ (SEQ ID NO: 130); AMAGSS(Oct)FLSPEHQRVQQRKESKKPPAKLQP (SEQ ID NO: 131); AMAGSS(Oct)FLSPEHQRVQQRKESKKPPAKLQPR (SEQ ID NO: 132); AMAGSS(Oct)FLSPEHQRVQQRKESKKPPAKLQPRW (SEQ ID NO: 133); AMAGSDap(Oct)FL (SEQ ID NO: 134); AMAGSDap(Oct)FLS (SEQ ID NO: 135); AMAGSDap(Oct)FLSP (SEQ ID NO: 136); AMAGSDap(Oct)FLSPE (SEQ ID NO: 137); AMAGSDap(Oct)FLSPEH (SEQ ID NO: 138); AMAGSDap(Oct)FLSPEHQ (SEQ ID NO: 139); AMAGSDap(Oct)FLSPEHQR (SEQ ID NO: 140); AMAGSDap(Oct)FLSPEHQRV (SEQ ID NO: 141); AMAGSDap(Oct)FLSPEHQRVQ (SEQ ID NO: 142); AMAGSDap(Oct)FLSPEHQRVQQ (SEQ ID NO: 143); AMAGSDap(Oct)FLSPEHQRVQQR (SEQ ID NO: 144); AMAGSDap(Oct)FLSPEHQRVQQRK (SEQ ID NO: 145); AMAGSDap(Oct)FLSPEHQRVQQRKE (SEQ ID NO: 146); AMAGSDap(Oct)FLSPEHQRVQQRKES (SEQ ID NO: 147); AMAGSDap(Oct)FLSPEHQRVQQRKESK (SEQ ID NO: 148); AMAGSDap(Oct)FLSPEHQRVQQRKESKK (SEQ ID NO: 149); AMAGSDap(Oct)FLSPEHQRVQQRKESKKP (SEQ ID NO: 150); AMAGSDap(Oct)FLSPEHQRVQQRKESKKPP (SEQ ID NO: 151); AMAGSDap(Oct)FLSPEHQRVQQRKESKKPPA (SEQ ID NO: 152); AMAGSDap(Oct)FLSPEHQRVQQRKESKKPPAK (SEQ ID NO: 153); AMAGSDap(Oct)FLSPEHQRVQQRKESKKPPAKL (SEQ ID NO: 154); AMAGSDap(Oct)FLSPEHQRVQQRKESKKPPAKLQ (SEQ ID NO: 155); AMAGSDap(Oct)FLSPEHQRVQQRKESKKPPAKLQP (SEQ ID NO: 156); AMAGSDap(Oct)FLSPEHQRVQQRKESKKPPAKLQPR (SEQ ID NO: 157); AMAGSDap(Oct)FLSPEHQRVQQRKESKKPPAKLQPRW (SEQ ID NO: 158); GMAGSS(Oct)FL-NH$_2$ (SEQ ID NO: 159); GMAGSS(Oct)FLS-NH$_2$ (SEQ ID NO: 160); GMAGSS(Oct)FLSP-NH$_2$ (SEQ ID NO: 161); GMAGSS(Oct)FLSPE-NH$_2$ (SEQ ID NO: 162); GMAGSS(Oct)FLSPEH-NH$_2$ (SEQ ID NO: 163); GMAGSS(Oct)FLSPEHQ-NH$_2$ (SEQ ID NO: 164); GMAGSS(Oct)FLSPEHQR-NH$_2$ (SEQ ID NO: 165); GMAGSS(Oct)FLSPEHQRV-NH$_2$ (SEQ ID NO: 166); GMAGSS(Oct)FLSPEHQRVQ-NH$_2$ (SEQ ID NO: 167); GMAGSS(Oct)FLSPEHQRVQQ-NH$_2$ (SEQ ID NO: 168); GMAGSS(Oct)FLSPEHQRVQQR-NH$_2$ (SEQ ID NO: 169); GMAGSS(Oct)FLSPEHQRVQQRK-NH$_2$ (SEQ ID NO: 170); GMAGSS(Oct)FLSPEHQRVQQRKE-NH$_2$ (SEQ ID NO: 171); GMAGSS(Oct)FLSPEHQRVQQRKES-NH$_2$ (SEQ ID NO: 172); GMAGSS(Oct)FLSPEHQRVQQRKESK-NH$_2$ (SEQ ID NO: 173); GMAGSS(Oct)FLSPEHQRVQQRKESKK-NH$_2$ (SEQ ID NO: 174); GMAGSS(Oct)FLSPEHQRVQQRKESKKP-NH$_2$ (SEQ ID NO: 175); GMAGSS(Oct)FLSPEHQRVQQRKESKKPP-NH$_2$ (SEQ ID NO: 176); GMAGSS(Oct)FLSPEHQRVQQRKESKKPPA-NH$_2$ (SEQ ID NO: 177); GMAGSS(Oct)FLSPEHQRVQQRKESKKPPAK-NH$_2$ (SEQ ID NO: 178); GMAGSS(Oct)FLSPEHQRVQQRKESKKPPAKL-NH$_2$ (SEQ ID NO: 179); GMAGSS(Oct)FLSPEHQRVQQRKESKKPPAKLQ-NH$_2$ (SEQ ID NO: 180); GMAGSS(Oct)FLSPEHQRVQQRKESKKPPAKLQP-NH$_2$ (SEQ ID NO: 181); GMAGSS(Oct)FLSPEHQRVQQRKESKKPPAKLQPR-NH$_2$ (SEQ ID NO: 182); GMAGSS(Oct)FLSPEHQRVQQRKESKKPPAKLQPRW-NH$_2$ (SEQ ID NO: 183); GMAGSDap(Oct)FL-NH$_2$ (SEQ ID NO: 184); GMAGSDap(Oct)FLS-NH$_2$ (SEQ ID NO: 185); GMAGSDap(Oct)FLSP-NH$_2$ (SEQ ID NO: 186); GMAGSDap(Oct)FLSPE-NH$_2$ (SEQ ID NO: 187); GMAGSDap(Oct)FLSPEH-NH$_2$ (SEQ ID NO: 188); GMAGSDap(Oct)FLSPEHQ-NH$_2$ (SEQ ID NO: 189); GMAGSDap(Oct)FLSPEHQR-NH$_2$ (SEQ ID NO: 190); GMAGSDap(Oct)FLSPEHQRV-NH$_2$ (SEQ ID NO: 191); GMAGSDap(Oct)FLSPEHQRVQ-NH$_2$ (SEQ ID NO: 192); GMAGSDap(Oct)FLSPEHQRVQQ-NH$_2$ (SEQ ID NO: 193); GMAGSDap(Oct)FLSPEHQRVQQR-NH$_2$ (SEQ ID NO: 194); GMAGSDap(Oct)FLSPEHQRVQQRK-NH$_2$ (SEQ ID NO: 195); GMAGSDap(Oct)FLSPEHQRVQQRKE-NH$_2$ (SEQ ID NO: 196); GMAGSDap(Oct)FLSPEHQRVQQRKES-NH$_2$ (SEQ ID NO: 197); GMAGSDap(Oct)FLSPEHQRVQQRKESK-NH$_2$ (SEQ ID NO: 198); GMAGSDap(Oct)FLSPEHQRVQQRKESKK-NH$_2$ (SEQ ID NO: 199); GMAGSDap(Oct)FLSPEHQRVQQRKESKKP-NH$_2$ (SEQ ID NO: 200); GMAGSDap(Oct)FLSPEHQRVQQRKESKKPP-NH$_2$ (SEQ ID NO: 201); GMAGSDap(Oct)FLSPEHQRVQQRKESKKPPA-NH$_2$ (SEQ ID NO: 202); GMAGSDap(Oct)FLSPEHQRVQQRKESKKPPAK-NH$_2$ (SEQ ID NO: 203); GMAGSDap(Oct)FLSPEHQRVQQRKESKKPPAKL-NH$_2$ (SEQ ID NO: 204); GMAGSDap(Oct)FLSPEHQRVQQRKESKKPPAKLQ-NH$_2$ (SEQ ID NO: 205); GMAGSDap(Oct)FLSPEHQRVQQRKESKKPPAKLQP-NH$_2$ (SEQ ID NO: 206); GMAGSDap(Oct)FLSPEHQRVQQRKESKKPPAKLQPR-NH$_2$ (SEQ ID NO: 207); GMAGSDap(Oct)FLSPEHQRVQQRKESKKPPAKLQPRW-NH$_2$ (SEQ ID NO: 208); AMAGSS(Oct)FL-NH$_2$ (SEQ ID NO: 209); AMAGSS(Oct)FLS-NH$_2$ (SEQ ID NO: 210); AMAGSS(Oct)FLSP-NH$_2$ (SEQ ID NO: 211); AMAGSS(Oct)FLSPE-NH$_2$ (SEQ ID NO: 212); AMAGSS(Oct)FLSPEH-NH$_2$ (SEQ ID NO: 213); AMAGSS(Oct)FLSPEHQ-NH$_2$ (SEQ ID NO: 214); AMAGSS(Oct)FLSPEHQR-NH$_2$ (SEQ ID NO: 215); AMAGSS(Oct)FLSPEHQRV-NH$_2$ (SEQ ID NO: 216); AMAGSS(Oct)FLSPEHQRVQ-NH₂ (SEQ ID NO: 217); AMAGSS(Oct)FLSPEHQRVQQ-NH₂ (SEQ ID NO: 218); AMAGSS(Oct)FLSPEHQRVQQR-NH₂ (SEQ ID NO: 219); AMAGSS(Oct)FLSPEHQRVQQRK-NH₂ (SEQ ID NO: 220); AMAGSS(Oct)FLSPEHQRVQQRKE-NH₂ (SEQ ID NO: 221); AMAGSS(Oct)FLSPEHQRVQQRKES-NH₂ (SEQ ID NO: 222); AMAGSS(Oct)FLSPEHQRVQQRKESK-NH₂ (SEQ ID NO: 223); AMAGSS(Oct)FLSPEHQRVQQRKESKK-NH₂ (SEQ ID NO: 224); AMAGSS(Oct)FLSPEHQRVQQRKESKKP-NH₂ (SEQ ID NO: 225); AMAGSS(Oct)FLSPEHQRVQQRKESKKPP-NH₂ (SEQ ID NO: 226); AMAGSS(Oct)FLSPEHQRVQQRKESKKPPA-NH₂ (SEQ ID NO: 227); AMAGSS(Oct)FLSPEHQRVQQRKESKKPPAK-NH₂ (SEQ ID NO: 228); AMAGSS(Oct)FLSPEHQRVQQRKESKKPPAKL-NH₂ (SEQ ID NO: 229); AMAGSS(Oct)FLSPEHQRVQQRKESKKPPAKLQ-NH₂ (SEQ ID NO: 230); AMAGSS(Oct)FLSPEHQRVQQRKESKKPPAKLQP-NH₂ (SEQ ID NO: 231); AMAGSS(Oct)FLSPEHQRVQQRKESKKPPAKLQPR-NH₂ (SEQ ID NO: 232); AMAGSS(Oct)FLSPEHQRVQQRKESKKPPAKLQPRW-NH₂ (SEQ ID NO: 233); AMAGSDap(Oct)FL-NH₂ (SEQ ID NO: 234); AMAGSDap(Oct)FLS-NH₂ (SEQ ID NO: 235); AMAGSDap(Oct)FLSP-NH₂ (SEQ ID NO: 236); AMAGSDap(Oct)FLSPE-NH₂ (SEQ ID NO: 237); AMAGSDap(Oct)FLSPEH-NH₂ (SEQ ID NO: 238); AMAGSDap(Oct)FLSPEHQ-NH₂ (SEQ ID NO: 239); AMAGSDap(Oct)FLSPEHQR-NH₂ (SEQ ID NO: 240); AMAGSDap(Oct)FLSPEHQRV-NH₂ (SEQ ID NO: 241); AMAGSDap(Oct)FLSPEHQRVQ-NH₂ (SEQ ID NO: 242); AMAGSDap(Oct)FLSPEHQRVQQ-NH₂ (SEQ ID NO: 243); AMAGSDap(Oct)FLSPEHQRVQQR-NH₂ (SEQ ID NO: 244); AMAGSDap(Oct)FLSPEHQRVQQRK-NH₂ (SEQ ID NO: 245); AMAGSDap(Oct)FLSPEHQRVQQRKE-NH₂ (SEQ ID NO: 246); AMAGSDap(Oct)FLSPEHQRVQQRKES-NH₂ (SEQ ID NO: 247); AMAGSDap(Oct)FLSPEHQRVQQRKESK-NH₂ (SEQ ID NO: 248); AMAGSDap(Oct)FLSPEHQRVQQRKESKK-NH₂ (SEQ ID NO: 249); AMAGSDap(Oct)FLSPEHQRVQQRKESKKP-NH₂ (SEQ ID NO: 250); AMAGSDap(Oct)FLSPEHQRVQQRKESKKPP-NH₂ (SEQ ID NO: 251); AMAGSDap(Oct)FLSPEHQRVQQRKESKKPPA-NH₂ (SEQ ID NO: 252); AMAGSDap(Oct)FLSPEHQRVQQRKESKKPPAK-NH₂ (SEQ ID NO: 253); AMAGSDap(Oct)FLSPEHQRVQQRKESKKPPAKL-NH₂ (SEQ ID NO: 254); AMAGSDap(Oct)FLSPEHQRVQQRKESKKPPAKLQ-NH₂ (SEQ ID NO: 255); AMAGSDap(Oct)FLSPEHQRVQQRKESKKPPAKLQP-NH₂ (SEQ ID NO: 256); AMAGSDap(Oct)FLSPEHQRVQQRKESKKPPAKLQPR-NH₂ (SEQ ID NO: 257); AMAGSDap(Oct)FLSPEHQRVQQRKESKKPPAKLQPRW-NH₂ (SEQ ID NO: 258); GMAGSYFL (SEQ ID NO: 259); GMAGSYFLS (SEQ ID NO: 260); GMAGSYFLSP (SEQ ID NO: 261); GMAGSYFLSPE (SEQ ID NO: 262); GMAGSYFLSPEH (SEQ ID NO: 263); GMAGSYFLSPEHQ (SEQ ID NO: 264); GMAGSYFLSPEHQR (SEQ ID NO: 265); GMAGSYFLSPEHQRV (SEQ ID NO: 266); GMAGSYFLSPEHQRVQ (SEQ ID NO: 267); GMAGSYFLSPEHQRVQQ (SEQ ID NO: 268); GMAGSYFLSPEHQRVQQR (SEQ ID NO: 269); GMAGSYFLSPEHQRVQQRK (SEQ ID NO: 270); GMAGSYFLSPEHQRVQQRKE (SEQ ID NO: 271); GMAGSYFLSPEHQRVQQRKES (SEQ ID NO: 272); GMAGSYFLSPEHQRVQQRKESK (SEQ ID NO: 273); GMAGSYFLSPEHQRVQQRKESKK (SEQ ID NO: 274); GMAGSYFLSPEHQRVQQRKESKKP (SEQ ID NO: 275); GMAGSYFLSPEHQRVQQRKESKKPP (SEQ ID NO: 276); GMAGSYFLSPEHQRVQQRKESKKPPA (SEQ ID NO: 277); GMAGSYFLSPEHQRVQQRKESKKPPAK (SEQ ID NO: 278); GMAGSYFLSPEHQRVQQRKESKKPPAKL (SEQ ID NO: 279); GMAGSYFLSPEHQRVQQRKESKKPPAKLQ (SEQ ID NO: 280); GMAGSYFLSPEHQRVQQRKESKKPPAKLQP (SEQ ID NO: 281); GMAGSYFLSPEHQRVQQRKESKKPPAKLQPR (SEQ ID NO: 282); GMAGSYFLSPEHQRVQQRKESKKPPAKLQPRW (SEQ ID NO: 283); AMAGSYFL (SEQ ID NO: 284); AMAGSYFLS (SEQ ID NO: 285); AMAGSYFLSP (SEQ ID NO: 286); AMAGSYFLSPE (SEQ ID NO: 287); AMAGSYFLSPEH (SEQ ID NO: 288); AMAGSYFLSPEHQ (SEQ ID NO: 289); AMAGSYFLSPEHQR (SEQ ID NO: 290); AMAGSYFLSPEHQRV (SEQ ID NO: 291); AMAGSYFLSPEHQRVQ (SEQ ID NO: 292); AMAGSYFLSPEHQRVQQ (SEQ ID NO: 293); AMAGSYFLSPEHQRVQQR (SEQ ID NO: 294); AMAGSYFLSPEHQRVQQRK (SEQ ID NO: 295); AMAGSYFLSPEHQRVQQRKE (SEQ ID NO: 296); AMAGSYFLSPEHQRVQQRKES (SEQ ID NO: 297); AMAGSYFLSPEHQRVQQRKESK (SEQ ID NO: 298); AMAGSYFLSPEHQRVQQRKESKK (SEQ ID NO: 299); AMAGSYFLSPEHQRVQQRKESKKP (SEQ ID NO: 300); AMAGSYFLSPEHQRVQQRKESKKPP (SEQ ID NO: 301); AMAGSYFLSPEHQRVQQRKESKKPPA (SEQ ID NO: 302); AMAGSYFLSPEHQRVQQRKESKKPPAK (SEQ ID NO: 303); AMAGSYFLSPEHQRVQQRKESKKPPAKL (SEQ ID NO: 304); AMAGSYFLSPEHQRVQQRKESKKPPAKLQ (SEQ ID NO: 305); AMAGSYFLSPEHQRVQQRKESKKPPAKLQP (SEQ ID NO: 306); AMAGSYFLSPEHQRVQQRKESKKPPAKLQPR (SEQ ID NO: 307); AMAGSYFLSPEHQRVQQRKESKKPPAKLQPRW (SEQ ID NO: 308); GMAGSYFL-NH₂ (SEQ ID NO: 309); GMAGSYFLS-NH₂ (SEQ ID NO: 310); GMAGSYFLSP-NH₂ (SEQ ID NO: 311); GMAGSYFLSPE-NH₂ (SEQ ID NO: 312); GMAGSYFLSPEH-NH₂ (SEQ ID NO: 313); GMAGSYFLSPEHQ-NH₂ (SEQ ID NO: 314); GMAGSYFLSPEHQR-NH₂ (SEQ ID NO: 315); GMAGSYFLSPEHQRV-NH₂ (SEQ ID NO: 316); GMAGSYFLSPEHQRVQ-NH₂ (SEQ ID NO: 317); GMAGSYFLSPEHQRVQQ-NH₂ (SEQ ID NO: 318); GMAGSYFLSPEHQRVQQR-NH₂ (SEQ ID NO: 319); GMAGSYFLSPEHQRVQQRK-NH₂ (SEQ ID NO: 320); GMAGSYFLSPEHQRVQQRKE-NH₂ (SEQ ID NO: 321); GMAGSYFLSPEHQRVQQRKES-NH₂ (SEQ ID NO: 322); GMAGSYFLSPEHQRVQQRKESK-NH₂ (SEQ ID NO: 323); GMAGSYFLSPEHQRVQQRKESKK-NH₂ (SEQ ID NO: 324); GMAGSYFLSPEHQRVQQRKESKKP-NH₂ (SEQ ID NO: 325); GMAGSYFLSPEHQRVQQRKESKKPP-NH₂ (SEQ ID NO: 326); GMAGSYFLSPEHQRVQQRKESKKPPA-NH₂ (SEQ ID NO: 327); GMAGSYFLSPEHQRVQQRKESKKPPAK-NH₂ (SEQ ID NO: 328); GMAGSYFLSPEHQRVQQRKESKKPPAKL-NH₂ (SEQ ID NO: 329); GMAGSYFLSPEHQRVQQRKESKKPPAKLQ-NH₂ (SEQ ID NO: 330); GMAGSYFLSPEHQRVQQRKESKKPPAKLQP-NH₂ (SEQ ID NO: 331); GMAGSYFLSPEHQRVQQRKESKKPPAKLQPR-NH₂ (SEQ ID NO: 332); GMAGSYFLSPEHQRVQQRKESKKPPAKLQPRW-NH₂ (SEQ ID NO: 333); AMAGSYFL-NH₂ (SEQ ID NO: 334); AMAGSYFLS-NH₂ (SEQ ID NO: 335); AMAGSYFLSP-NH₂ (SEQ ID NO: 336); AMAGSYFLSPE-NH₂ (SEQ ID NO: 337); AMAGSYFLSPEH-NH₂ (SEQ ID NO: 338); AMAGSYFLSPEHQ-NH₂ (SEQ ID NO: 339); AMAGSYFLSPEHQR-NH₂ (SEQ ID NO: 340); AMAGSYFLSPEHQRV-NH₂ (SEQ ID NO: 341); AMAGSYFLSPEHQRVQ-NH₂ (SEQ ID NO: 342); AMAGSYFLSPEHQRVQQ-NH₂ (SEQ ID NO: 343); AMAGSYFLSPEHQRVQQR-NH₂ (SEQ ID NO: 344); AMAGSYFLSPEHQRVQQRK-NH₂ (SEQ ID NO: 345); AMAGSYFLSPEHQRVQQRKE-NH₂ (SEQ ID NO: 346); AMAGSYFLSPEHQRVQQRKES-NH₂ (SEQ ID NO: 347); AMAGSYFLSPEHQRVQQRKESK-NH₂ (SEQ ID NO: 348); AMAGSYFLSPEHQRVQQRKESKK-NH₂ (SEQ ID NO: 349); AMAGSYFLSPEHQRVQQRKESKKP-NH₂ (SEQ ID NO: 350); AMAGSYFLSPEHQRVQQRKESKKPP-NH₂ (SEQ ID NO: 351); AMAGSYFLSPEHQRVQQRKESKKPPA-NH₂ (SEQ ID NO: 352); AMAGSYFLSPEHQRVQQRKESKKPPAK-NH₂ (SEQ ID NO: 353); AMAGSYFLSPEHQRVQQRKESKKPPAKL-NH₂ (SEQ ID NO: 354); AMAGSYFLSPEHQRVQQRKESKKPPAKLQ-NH₂ (SEQ ID NO: 355); AMAGSYFLSPEHQRVQQRKESKKPPAKLQP-NH₂ (SEQ ID NO: 356); AMAGSYFLSPEHQRVQQRKESKKPPAKLQPR-NH₂ (SEQ ID NO: 357); AMAGSYFLSPEHQRVQQRKESKKPPAKLQPRW-NH₂ (SEQ ID NO: 358); Gly-Met-Ala-Gly-Ser-Dap(Oct)-Phe-Leu-Ser-Pro-Glu-His (SEQ ID NO: 359); Gly-Met-Ala-Gly-Ser-Dap(palmityl)-Phe-Leu-Ser-Pro-Glu-His (SEQ ID NO: 360); Gly-Met-Ala-Gly-Ser-Ser(Des-Octanoyl)-Phe-Leu (SEQ ID NO: 361); Gly-Met-Ala-Gly-Ser-Dap(Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO: 362); Gly-Met-Ala-Gly-Ser-Dap(Octanoyl)-Phe-Leu (SEQ ID NO: 363); Gly-Met-Ala-Gly-Ser-Ser(Des-Octanoyl)-Phe (SEQ ID NO: 364); Gly-Met-Ala-Gly-Ser-Ser(Des-Octanoyl)-Phe-Leu-Ser-Pro-Glu-His-Gln-Arg-Val-Gln-Gln-Arg-Lys-Glu-Ser (SEQ ID NO: 365); Gly-Met-Ala-Gly-Ser-Ser(Des-Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-Tyr (SEQ ID NO: 366); Gly-Met-Ala-Tyr-DTrp-DLys-Trp-DPhe-NH₂; Gly-Met-Ala-Tyr-DTrp-Lys-Trp-DPhe-NH₂; Gly-Met-Ala-His-DTrp-DLys-Trp-DPhe-NH₂; Gly-Met-Ala-His-DTrp-DLys-Phe-DTrp-NH₂; Gly-Met-Ala-His-DTrp-DArg-DPhe-NH₂; Gly-Met-Ala-His-DTrp-DLys-Trp-DPhe-Lys-NH₂; Gly-Met-Ala-DesaminoTyr-DTrp-Ala-Trp-DPhe-NH₂; Gly-Met-Ala-DesaminoTyr-DTrp-DLys-Trp-DPhe-NH₂; Gly-Met-Ala-DeaminoTyr-DTrp-Ser-Trp-DPhe-Lys-NH₂; Gly-Met-Ala-DesaminoTyr-DTrp-Ser-Trp-DPhe-NH₂; Gly-Met-Ala-His-DTrp-DTrp-Phe-Met-NH₂; Gly-Met-Ala-Tyr-DTrp-DTrp-Phe-Phe-NH₂; Gly-Met-Ala-Glyψ[CH₂NH]-DβNal-Ala-Trp-DPhe-Lys-NH₂; Gly-Met-Ala-Glyψ[CH2NH]-DβNal-DLys-Trp-DPhe-Lys-NH₂; Gly-Met-Ala-DAla-DβNal-DLys-DTrp-Phe-Lys-NH₂; Gly-Met-Ala-His-DβNal-DLys-Trp-DPhe-Lys-NH₂; Gly-Met-Ala-Ala-His-DTrp-DLys-Trp-DPhe-Lys-NH₂; Gly-Met-Ala-Alaψ[CH₂NH]-DβNal-Ala-Trp-DPhe-Lys-NH₂; Gly-Met-Alaψ[CH₂NH]-Ala-DβNal-Ala-Trp-DPhe-Lys-NH₂; Gly-Met-Ala-DβNal-Ala-Trp-DPhe-Ala-NH₂; Gly-Met-Ala-DAla-DcyclohexylAla-Ala-Phe-DPhe-Nle-NH₂; Gly-Met-Ala-DcyclohexylAla-Ala-Phe-DTrp-Lys-NH₂; Gly-Met-Ala-DAla-DβNal-Thr-DThr-Lys-NH₂; Gly-Met-Ala-DcyclohexylAla-Ala-Trp-DPhe-NH₂; Gly-Met-Ala-DAla-DβNal-Ala-Ala-DAla-Lys-NH₂; Gly-Met-Ala-DβNal-Ala-Trp-DPhe-Leu-NH₂; Gly-Met-Ala-His-DTrp-Phe-Trp-DPhe-Lys-NH₂; Gly-Met-Ala-DAla-DβNal-DAla-DTrp-Phe-Lys-NH₂; Gly-Met-Ala-βAla-Trp-DAla-DTrp-Phe-NH₂; Gly-Met-Ala-His-Trp-DAla-DTrp-Phe-LysNH₂; Gly-Met-Ala-DLys-DβNal-Ala-Trp-DPhe-Lys-NH₂; Gly-Met-Ala-DAla-DβNal-DLys-DTrp-Phe-Lys-NH₂; Gly-Met-Ala-Tyr-DAla-Phe-Aib-NH₂; Gly-Met-Ala-Tyr-DAla-Sar-NMePhe-NH₂; Gly-Met-Ala-αγAbu-DTrp-DTrp-Ser-NH₂; Gly-Met-Ala-αγAbu-DTrp-DTrp-Lys-NH₂; Gly-Met-Ala-αγAbu-DTrp-DTrp-Orn-NH₂; Gly-Met-Ala-αAbu-DTrp-DTrp-Orn-NH₂; Gly-Met-Ala-DThr-DαNal-DTrp-DPro-Arg-NH₂; Gly-Met-Ala-DAla-Ala-DAla-DTrp-Phe-Lys-NH₂; Gly-Met-Ala-Alaψ[CH₂NH]His-DTrp-Ala-Trp-DPhe-Lys-NH₂; Gly-Met-Ala-Lys-DHis-DTrp-Phe-NH₂; Gly-Met-Ala-γAbu-DTrp-DTrp-Orn-NH₂; Gly-Met-Ala-inip-Trp-Trp-Phe-NH₂ (SEQ ID NO: 375); Gly-Met-Ala-DTrp-Phe-DTrp-Leu-NH₂; Gly-Met-Ala-DTrp-Phe-DTrp-Lys-NH₂; Gly-Met-Ala-DTrp-DTrp-Lys-NH₂; Gly-Met-Ala-DLys-Tyr-DTrp-DTrp-Phe-Lys-NH₂; Gly-Met-Ala-DβNal-Leu-Pro-NH₂; Gly-Met-Ala-βAla-Trp-DTrp-DTrp-Orn-NH₂; Gly-Met-Ala-DVal-DαNal-DTrp-Phe-Arg-NH₂; Gly-Met-Ala-DLeu-DαNal-DTrp-Phe-Arg-NH₂; Gly-Met-Ala-CyclohexylAla-DαNal-DTrp-Phe-Arg-NH₂; Gly-Met-Ala-DTrp-DαNal-DTrp-Phe-Arg-NH₂; Gly-Met-Ala-DAla-DβNal-DPro-Phe-Arg-NH₂; Gly-Met-Ala-DαNal-DTrp-Phe-Arg-NH₂; Gly-Met-Ala-DαNal-DTrp-Phe-Arg-NH₂; Gly-Met-Ala-His-DTrp-DTrp-Lys-NH₂; Gly-Met-Ala-DβNal-DTrp-NH₂; Gly-Met-Ala-αAib-DTrp-DcyclohexylAla-NH₂; Gly-Met-Ala-αAib-DTrp-DAla-cyclohexylAla-NH₂; Gly-Met-Ala-DAla-DcyclohexylAla-Ala-Ala-Phe-DPhe-Nle-NH₂; Gly-Met-Ala-DPhe-Ala-Phe-DPal-NH₂; Gly-Met-Ala-DPhe-Ala-Phe-DPhe-Lys-NH₂; Gly-Met-Ala-DLys-Tyr-DTrp-DTrp-Phe-NH₂; Gly-Met-Ala-DLys-Tyr-DTrp-DTrp-Phe-NH₂; Gly-Met-Ala-Arg-DTrp-Leu-Tyr-Trp-Pro(cyclicArg-Pro); Gly-Met-Ala-DβNal-PicLys-ILys-DPhe-NH₂; Gly-Met-Ala-DPal-Phe-DTrp-Phe-Met-NH₂; Gly-Met-Ala-DPhe-Trp-DPhe-Phe-Met-NH₂; Gly-Met-Ala-DPal-Trp-DPhe-Phe-Met-NH₂; Gly-Met-Ala-βAla-Pal-DTrp-DTrp-Orn-NH₂; Gly-Met-Ala-αγAbu-Trp-DTrp-DTrp-Orn-NH₂; Gly-Met-Ala-βAla-Trp-DTrp-DTrp-Lys-NH₂; Gly-Met-Ala-γAbu-Trp-DTrp-DTrp-Orn-NH₂; Gly-Met-Ala-Ava-Trp-DTrp-DTrp-Orn-NH₂; Gly-Met-Ala-DLys-Tyr-DTrp-Ala-Trp-DPhe-NH₂; Gly-Met-Ala-His-DTrp-DArg-Trp-DPhe-NH₂; Gly-Met-Ala-<Glu-His-Trp-DSer-DArg-NH₂; Gly-Met-Ala-DPhe-DPhe-DTrp-Met-DLys-NH₂; Gly-Met-Ala-DHis-DTrp-DPro-DIleNH₂; Gly-Met-Ala-DHis-DTrp-DPro-DArgNH₂; Gly-Met-Ala-DβNal-DTrp-DPro-DArgNH₂; Gly-Met-Ala-Tyr-DTrp-DLys-Trp-DPhe; Gly-Met-Ala-Tyr-DTrp-Lys-Trp-DPhe; Gly-Met-Ala-His-DTrp-DLys-Trp-DPhe; Gly-Met-Ala-His-DTrp-DLys-Phe-DTrp; Gly-Met-Ala-His-DTrp-DArg-Trp-DPhe; Gly-Met-Ala-His-DTrp-DLys-Trp-DPhe-Lys; Gly-Met-Ala-DesaminoTyr-DTrp-Ala-Trp-DPhe; Gly-Met-Ala-DesaminoTyr-DTrp-DLys-Trp-DPhe; Gly-Met-Ala-DeaminoTyr-DTrp-Ser-Trp-DPhe-Lys; Gly-Met-Ala-DesaminoTyr-DTrp-Ser-Trp-DPhe; Gly-Met-Ala-His-DTrp-DTrp-Phe-Met; Gly-Met-Ala-Tyr-DTrp-DTrp-Phe-Phe; Gly-Met-Ala-Glyψ[CH₂NH]-DβNal-Ala-Trp-DPhe-Lys; Gly-Met-Ala-Glyψ[CH2NH]-DβNal-DLys-Trp-DPhe-Lys; Gly-Met-Ala-DAla-DβNal-DLys-DTrp-Phe-Lys; Gly-Met-Ala-His-DβNal-DLys-Trp-DPhe-Lys; Gly-Met-Ala-Ala-His-DTrp-DLys-Trp-DPhe-Lys; Gly-Met-Ala-Alaψ[CH₂NH]-DβNal-Ala-Trp-DPhe-Lys; Gly-Met-Ala-DβNal-Ala-Trp-DPhe-Ala; Gly-Met-Ala-DAla-DcyclohexylAla-Ala-Phe-DPhe-Nle; Gly-Met-Ala-DcyclohexylAla-Ala-Phe-DTrp-Lys; Gly-Met-Ala-DAla- DβNal-Ala-Thr-DThr-Lys; Gly-Met-Ala-DcyclohexylAla-Ala-Trp-DPhe; Gly-Met-Ala-DAla-DβNal-Ala-Ala-DAla-Lys; Gly-Met-Ala-DβNal-Trp-DPhe-Leu; Gly-Met-Ala-His-DTrp-Phe-Trp-DPhe-Lys; Gly-Met-Ala-DAla-DβNal-DAla-DTrp-Phe-Lys; Gly-Met-Ala-βAla-Trp-DAla-DTrp-Phe; Gly-Met-Ala-His-Trp-DAla-DTrp-Phe-LysNH₂; Gly-Met-Ala-DLys-DβNal-Ala-Trp-DPhe-Lys; Gly-Met-Ala-DAla-DβNal-DLys-DTrp-Phe-Lys; Gly-Met-Ala-Tyr-DAla-Phe-Aib; Gly-Met-Ala-Tyr-DAla-Sar-NMePhe; Gly-Met-Ala-αγAbu-DTrp-DTrp-Ser; Gly-Met-Ala-αγAbu-DTrp-DTrp-Lys; Gly-Met-Ala-αγAbu-DTrp-DTrp-Orn; Gly-Met-Ala-αAbu-DTrp-DTrp-Orn; Gly-Met-Ala-DThr-DαNal-DTrp-DPro-Arg; Gly-Met-Ala-DAla-Ala-DAla-DTrp-Phe-Lys; Gly-Met-Ala-Alaψ[CH₂NH]His-DTrp-Ala-Trp-DPhe-Lys; Gly-Met-Ala-Lys-DHis-DTrp-Phe; Gly-Met-Ala-γAbu-DTrp-DTrp-Orn; Gly-Met-Ala-inip-Trp-Trp-Phe (SEQ ID NO: 376); Gly-Met-Ala-DTrp-Phe-DTrp-Leu; Gly-Met-Ala-DTrp-Phe-DTrp-Lys; Gly-Met-Ala-DTrp-DTrp-Lys; Gly-Met-Ala-DLys-Tyr-DTrp-DTrp-Phe-Lys; Gly-Met-Ala-DβNal-Leu-Pro; Gly-Met-Ala-βAla-Trp-DTrp-DTrp-Orn; Gly-Met-Ala-DVal-DαNal-DTrp-Phe-Arg; Gly-Met-Ala-DLeu-DαNal-DTrp-Phe-Arg; Gly-Met-Ala-CyclohexylAla-DαNal-DTrp-Phe-Arg; Gly-Met-Ala-DTrp-DαNal-DTrp-Phe-Arg; Gly-Met-Ala-DAla-DβNal-DPro-Phe-Arg; Gly-Met-Ala-DαNal-DTrp-Phe-Arg; Gly-Met-Ala-DαNal-DTrp-Phe-Arg; Gly-Met-Ala-His-DTrp-DTrp-Lys; Gly-Met-Ala-DβNal-DTrp; Gly-Met-Ala-αAib-DTrp-DcyclohexylAla; Gly-Met-Ala-αAib-DTrp-DAla-cyclohexylAla; Gly-Met-Ala-DAla-DcyclohexylAla-Ala-Ala-Phe-DPhe-Nle; Gly-Met-Ala-DPhe-Ala-Phe-DPal; Gly-Met-Ala-DPhe-Ala-Phe-DPhe-Lys; Gly-Met-Ala-DLys-Tyr-DTrp-DTrp-Phe; Gly-Met-Ala-DLys-Tyr-DTrp-DTrp-Phe; Gly-Met-Ala-Arg-DTrp-Leu-Tyr-Trp-Pro(cyclicArg-Pro); Gly-Met-Ala-DβNal-PicLys-ILys-DPhe; Gly-Met-Ala-DPal-Phe-DTrp-Phe-Met; Gly-Met-Ala-DPhe-Trp-DPhe-Phe-Met; Gly-Met-Ala-DPal-Trp-DPhe-Phe-Met; Gly-Met-Ala-βAla-Pal-DTrp-DTrp-Orn; Gly-Met-Ala-αγAbu-Trp-DTrp-DTrp-Orn; Gly-Met-Ala-βAla-Trp-DTrp-DTrp-Lys; Gly-Met-Ala-γAbu-Trp-DTrp-DTrp-Orn; Gly-Met-Ala-Ava-Trp-DTrp-DTrp-Orn; Gly-Met-Ala-DLys-Tyr-DTrp-Ala-Trp-DPhe; Gly-Met-Ala-His-DTrp-DArg-Trp-DPhe; Gly-Met-Ala-<Glu-His-Trp-DSer-DArg; Gly-Met-Ala-DPhe-DPhe-DTrp-Met-DLys; Gly-Met-Ala-DHis-DTrp-DPro-DIle; Gly-Met-Ala-DHis-DTrp-DPro-DArg; Gly-Met-Ala-DβNal-DTrp-DPro-DArg; Gly-Met-Ala-DbetaNalAlaTrpDPheLysGlnGly; Gly-Met-Ala-alphaAibDTrpDPro; Gly-Met-Ala-alphaAibDTrpDProDIle; Gly-Met-Ala-alphaAibDTrpDProDVal; Gly-Met-Ala-alphaAibDTrpDProDIleArg; Gly-Met-Ala-alphaAibDTrpDProDValArg; Gly-Met-Ala-DAlaDBNalDLysTrpDPheLys; Gly-Met-Ala-HisDBNalDLysTrpDPheLys; Gly-Met-Ala-DBNalAlaTrpDPheLysGlnGlyNH2; Gly-Met-Ala-alphaAibDTrpDProNH2; Gly-Met-Ala-alphaAibDTrpDProDIleNH2; Gly-Met-Ala-alphaAibDTrpDProDValNH2; Gly-Met-Ala-alphaAibDTrpDProDIleArgNH2; Gly-Met-Ala-alphaAibDTrpDProDValArgNH2; Gly-Met-Ala-DAlaDBNalDLysTrpDPheLysNH2; Gly-Met-Ala-HisDBNalDLysTrpDPheLysNH2; Gly-Met-Ala-DBNalAlaTrpDPheLysGlnGlyNH2; Gly-Met-Ala-DBNalDLysTrpDPheLysNH2; Gly-Met-Ala-DAlaDBNalDLysTrpDPheLysNH2; Gly-Met-Ala-DTrpDProDIleNH2; Gly-Met-Ala-alphaAibDTrpDProDIleArgNH2; Gly-Met-Ala-DTrpDProDIleArgNH2; Gly-Met-Ala-DTrpDProDValNH2; Gly-Met-Ala-DTrpDProDValArgNH2; Gly-Met-Ala-alphaAibDTrpDProDValArgNH2; Gly-Met-Ala-HisDBNalDLysTrpDPheLysNH2; Gly-Met-Ala-alphaAibDTrpDProNH2; Gly-Met-Ala-DTrpDProNH2; Ala-Met-Ala-DBNalAlaTrpDPheLysGlnGlyNH2; Ala-Met-Ala-alphaAibDTrpDProNH2; Ala-Met-Ala-alphaAibDTrpDProDIleNH2; Ala-Met-Ala-alphaAibDTrpDProDValNH2; Ala-Met-Ala-alphaAibDTrpDProDIleArgNH2; Ala-Met-Ala-alphaAibDTrpDProDValArgNH2; Ala-Met-Ala-DAlaDBNa1DLysTrpDPheLysNH2; Ala-Met-Ala-HisDBNalDLysTrpDPheLysNH2; Ala-Met-Ala-DBNalAlaTrpDPheLysGlnGlyNH2; Ala-Met-Ala-DBNa1DLysTrpDPheLysNH2; Ala-Met-Ala-DAlaDBNalDLysTrpDPheLysNH2; Ala-Met-Ala-DTrpDProDIleNH2; Ala-Met-Ala-alphaAibDTrpDProDIleArgNH2; Ala-Met-Ala-DTrpDProDIleArgNH2; Ala-Met-Ala-DTrpDProDValNH2; Ala-Met-Ala-DTrpDProDValArgNH2; Ala-Met-Ala-alphaAibDTrpDProDValArgNH2; Ala-Met-Ala-HisDBNalDLysTrpDPheLysNH2; Ala-Met-Ala-alphaAibDTrpDProNH2; Ala-Met-Ala-DTrpDProNH2; Gly-Met-Ala-DAlaDIleNalAlaTrpDPheLys; Ala-Met-Ala-DAlaDβNalAlaTrpDPheLys; Ala-Met-Ala-DAlaDβ-NalDLysTrpDPheLys; Gly-Met-Ala-DAlaDβNalDLysTrpDPheLys; GlyMetAlaSer(Bzl)LysDTrp; GlyMetAlaαAibDTrp; GlyMetAlaγAbuDTrp; GlyMetAlaαAibDSer(Bzl); GlyMetAlaαγAbuDSer(Nap); Gly-MetAlaDSerDLysTrp; GlyMetAlaSer(Bzl)Lys(Ac)DTrp; GlyMetAlaαγAbuDTrpDTrpLys; GlyMetAlaαγAbuDTrpDTrpOrn; GlyMetAlaαγAbuDTrpDTrpSer; GlyMetAlaTyrDAlaPheAib; GlyMetAlaTyrDAlaSarNMePhe; GlyMetAlaLysDHisDTrpPhe; GlyMetAlaγAbuDTrpDTrpOrn; GlyMetAlainipTrpTrpPhe (SEQ ID NO: 376); GlyMetAlaTrpPheDTrpLeu; GlyMetAlaDTrpPheDTrpLys; GlyMetAlaDβNalLeuPro; GlyMetAlaαAibSer(Bzl)-X⁴, wherein X⁴ is optionally substituted 4-phenylpiperazin-1-yl, 3a-benzyl-4,5,6,7-tetrahydro-2-methyl-2H-pyrazolo[4,3-c]pyridin-3(3 aH)-on-5-yl or 1-(methylsulfonyl)spiro[indoline-3,4'-piperdine]-1'-yl (SEQ ID NO: 377); GlyMetAlaψ[CH₂NH]αAibSer(Bzl)-X⁴, wherein X⁴ is optionally substituted 4-phenylpiperazin-1-yl, 3a-benzyl-4,5,6,7-tetrahydro-2-methyl-2H-pyrazolo[4,3-c]pyridin-3(3 aH)-on-5-yl or 1-(methylsulfonyl)spiro[indoline-3,4'-piperdine]-1'-yl (SEQ ID NO: 378); GlyMetAla[C(O)N(Me)]αAibSer(Bzl)-X⁴, wherein X⁴ is optionally substituted 4-phenylpiperazin-1-yl, 3a-benzyl-4,5,6,7-tetrahydro-2-methyl-2H-pyrazolo[4,3-c]pyridin-3(3 aH)-on-5-yl or 1-(methylsulfonyl)spiro[indoline-3,4'-piperdine]-1'-yl (SEQ ID NO: 379); and any combinations thereof.

19. A pharmaceutical composition comprising a peptide of any of paragraphs 1-18 and a pharmaceutically acceptable carrier or excipient.

20. A method for treatment, prevention or management of obesity, obesity related disease or disorder, diabetes mellitus, metabolic syndrome, or cancer in a subject in need thereof, said method comprising administering an effective amount of a peptide of any of paragraphs 1-19 to the subject.

21. The method of paragraph 20, further comprising an anti-obesity treatment.

22. The method of paragraph 21, wherein the anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, PYY(1-36), PYY(3-36), an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a lipase drug inhibitor, an inhibitor of food intake, an incretin, an incretin agonist, an incretin analog or an incretin mimic administered simultaneously, concurrently or sequentially.

23. The method of paragraph 22, wherein the inhibitor of food intake is glucagon-like-peptide (Glip-1/Glip-2) or oxyntomodulin or their analogs, derivatives, or mimics.

24. The method of paragraph 23, wherein the anti-obesity treatment is bariatric surgery.

25. The method of any of paragraphs 20-24, wherein the diabetes mellitus is type I or II.

26. The method of any of paragraphs 20-25, wherein the subject is obese or at risk of obesity.

27. The method of any of paragraphs 20-26, wherein the subject has a body mass index (BMI) of over 25.

28. The method of any of paragraphs 20-27, wherein the subject has a body mass index (BMI) of between 25 and 30.

29. The method of any of paragraphs 20-28, wherein the subject has a body mass index (BMI) of over 30.

30. The method of any of paragraphs 20-29, wherein said administration is prior to taking a meal.

31. The method of any of paragraphs 20-30, wherein the effective amount is 1 µg/kg to 150 mg/kg.

32. Use of a peptide of any of paragraphs 1-19 for the preparation of a pharmaceutical composition for the treatment, prevention or management of obesity, obesity related disease or disorder, diabetes mellitus, metabolic syndrome, or cancer.

33. Use of a peptide of any of paragraphs 1-19 for treatment, prevention or management of obesity, obesity related disease or disorder, diabetes mellitus, metabolic syndrome, or cancer in a subject in need thereof.

34. The use of paragraph 33, further comprising an anti-obesity treatment.

35. The use of paragraph 34, wherein the anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, PYY(1-36), PYY(3-36), an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a lipase drug inhibitor, an inhibitor of food intake, an incretin, an incretin agonist, an incretin analog or an incretin mimic administered simultaneously, concurrently or sequentially.

36. The use of paragraph 35, wherein the inhibitor of food intake is glucagon-like-peptide (Glip-1/Glip-2) or oxyntomodulin or their analogs, derivatives, or mimics.

37. The use of paragraph 36, wherein the anti-obesity treatment is bariatric surgery.

38. The use of any of paragraphs 33-37, wherein the diabetes mellitus is type I or II.

39. The use of any of paragraphs 33-38, wherein the subject is obese or at risk of obesity.

40. The use of any of paragraphs 33-39, wherein the subject has a body mass index (BMI) of over 25.

41. The use of any of paragraphs 33-40, wherein the subject has a body mass index (BMI) of between 25 and 30.

42. The use of any of paragraphs 33-41, wherein the subject has a body mass index (BMI) of over 30.

43. The peptide of any of paragraphs 1-19, wherein $X^1$ is a GlyMetAla tripeptide.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Animals and Experimental Procedures

Adult male Sprague Dawley rats (225-260 g) were purchased from Charles River Canada (St. Constant, Canada) and individually housed on a 12-h light, 12-h dark cycle (lights on, 0600-1800 h) in a temperature (22±1° C.)—and humidity-controlled room. Purina rat chow (Ralston Purina Co., St. Louis, Mo.) and tap water were available ad libitum.

Chronic intracerebroventricular (i.c.v.) and intracardiac venous cannulas were implanted under sodium pentobarbital (50 mg/kg, i.p.) anesthesia using previously described techniques in (2) and (11). The placement of the icy cannulae was verified by both a positive drinking response to i.c.v. carbachol (100 ng/10 µl) injection on the day after surgery and methylene blue dye at the time of death. After surgery, the rats were placed directly in isolation test chambers with food and H$_2$O freely available until body weight returned to preoperative levels (usually within 5-7 d). During this time the rats were handled daily to minimize any stress associated with handling on the day of the experiment. On the test day, food was removed 1.5 h before the start of sampling and was returned at the end.

The efficacy of GHS-A to antagonize ghrelin's stimulatory action on GH at both central and peripheral sites was examined. For the central experiments, free-moving rats were i.c.v. injected with either normal saline or GHS-A (5 µg) at 1045 h and, 15 min later (at 1100 h), were subsequently administered ghrelin i.c.v. (500 ng). Both the human ghrelin peptide (provided by Dr. K. Chang, Phoenix Pharmaceuticals, Inc., Belmont, Calif.) and the GHS-A were diluted in normal saline just before use. Blood samples (0.35 ml) were withdrawn every 15 min over a 6-h sampling period (1000-1600 h) from all animals. To document the rapidity of the GH response to ghrelin, an additional blood sample was obtained 5 min after injection of ghrelin. All blood samples were immediately centrifuged, and plasma was separated and stored at −20° C. for subsequent assay of GH. To avoid hemodynamic disturbance, the red blood cells were resuspended in normal saline and returned to the animal after removal of the next blood sample.

For the peripheral experiments, free-moving rats were iv injected with either normal saline or GHS-A (250 µg) at 1045 h and subsequently with ghrelin i.v. (5 µg) at 1100 h. Blood samples were withdrawn from 1000-1600 h, as described above.

For the study designed to assess the involvement of endogenous ghrelin in the genesis of pulsatile GH secretion, free-moving animals were i.c.v.-injected with either normal saline or GHS-A (5 μg) at two different times in the 6-h sampling period: 1045 h and 1345 h. These time points were chosen because they correspond closely to the time of onset of the spontaneous GH secretory episodes, as previously documented in our laboratory (2, 4). Blood samples were withdrawn from 1000-1600 h, as described above; however, no blood sample was withdrawn 5 min after the injections.

The effects of the GHS-A on both spontaneous and ghrelin-induced food intake and body weight gain were investigated. For the spontaneous experiments, the rats were fasted overnight (1600-1100 h next morning) and were i.c.v.-injected with either normal saline or GHS-A (5 μg) at 1100 h. Food intake was monitored on an hourly basis for 5 h after the initial injection (until 1600 h) and subsequently overnight (1600-0900 h next morning). A measured amount of rat chow pellets was placed in the cage every hour. Spillage was collected by placement of a diaper under the rat cages, and total food consumed for each period was calculated by subtracting uneaten food plus spillage from total given. Body weights were recorded daily at 0900 h. The latency to the onset of the first meal after the injection and the duration of that meal were also monitored.

To examine the effect of GHS-A on ghrelin-stimulated food intake, animals were icy injected with either normal saline or GHS-A (5 μg) at 1045 h and subsequently with ghrelin (500 ng) at 1100 h. Food intake was monitored on an hourly basis as described above. In this experiment, food was removed 1.5 h before the start of the test.

All animal-based procedures were approved by the McGill University Animal Care Committee.

Receptor Binding and Calcium Mobilization Studies

The human ghrelin receptor type 1a (GHS-R1a) was expressed in HEK-293 cells, whose cell membranes were subsequently harvested and used in the binding assay. The receptor concentration (Bmax) used in the assay was 2.3 pmol/mg of protein, resulting in a Kd for ghrelin binding of 0.016 nM. The ability of the antagonist to displace 0.009 nM radiolabelled ghrelin was then tested, at a concentration range of 0.1 nM to 10 μM. The binding affinities (Ki) for ghrelin, GHRP-6 and hexarelin in this system were 0.016 nM, 0.58 nM and 0.59 nM respectively.

The ability of the antagonist to mobilize calcium or to inhibit ghrelin-stimulated calcium mobilization was examined using Euroscreen's AequoScreen platform. This method is based on the co-expression in recombinant cell lines of the GHS-R1a and aequorin, a photoprotein capable of detecting calcium concentrations in the lower micromolar range. The agonistic properties of GHS-A were tested at a concentration range of 1 nM to 3 μM, and its capacity to inhibit the calcium mobilized by 22.15 nM ghrelin was tested at a concentration range of 1 nM to 1.5 μM. In this system, ghrelin was found to have an EC50 of 9.33 nM, EC80 of 22.15 nM, and induced maximal activation at a cncentration of 100 nM.

The peptides were synthesized by the solid phase method and purified by HPLC. GH was determined by Radioimmunoassay (RIA).

The In Vitro Cell Culture Method

In vitro GH Release-Female rats of the CD-1 strain were housed in a constant temperature room at 24° C. with 14 h light and 10 h darkness. The rats were fed Purina Rat chow and water at libitum. All studies were started between 0800-1000 hours. Pituitaries of mature female Sprague Dawley rats were rapidly removed after decapitation, neurointermediate lobe discarded and then placed in a pH 7.4 buffer. The pituitaries were cut into ~3-mm pieces and then transferred to a flask containing HEPS buffer with trypsin and incubated at 37° C. Cells were triturated several times during this period. After dispersion, the cells were collected by centrifugation, wash with DMEM and placed into culture well. Cell cultures were maintained for 4 days at 37° with 8% $CO_2$ added to the incubator atmosphere. After 4 days in culture, cells were washed with lactated Ringer's solution adjusted to pH 7.2-7.4 and then vehicle, peptide alone or peptide plus stimulator was added to media. Incubation time was 60-120 minutes after which media was removed from each well for GH determination. The GH RIA reagents were distributed by the NIH. Control data was collected from cell cultures treated with only the corresponding vehicle in the absence of peptide or stimulator. Control stimulated data was collected from cell cultures treated with stimulator alone in the absence of any peptide.

The In Vitro Pituitary Incubation Method

Hormonal activities were obtained from in vitro studies using pituitaries of 20 day old CD-1 strain Sprague Dawley female rats. Two pituitaries were incubated for a total of 4-6 hours. Medium was removed each hour for RIA of GH level and fresh medium was added again. After two one hour pre-incubation periods (P1-P2), the vehicle/peptides were added to two one hour incubations (I3-I4). Peptide activity was calculated as the change in the hormonal level (delta) between I3+I4 and P2. For antagonist activity, the incubation was continued for 2 additional hours (I5-I6) where both the peptide and a stimulator of GH secretion was added and the antagonist activity was calculated as the change in the hormonal level (delta) between I5+I6 and P2. The peptides were assayed in triplicate and the hormone was assayed in duplicate. Each value recorded represents the mean of 6. The GH RIA reagents were distributed by the NIH. Control data was collected from isolated pituitary glands treated with only the corresponding vehicle in the absence of peptide or stimulator. Control stimulated data was collected from isolated pituitary glands treated with stimulator alone in the absence of any peptide.

The In Vivo Assay

For the in vivo assay of GH Release in rat, immature female Sprague Dawley rats were obtained from Charles River from Wilmington, Mass. After arrival they were housed at 25° C. with a 14:10 h light:dark cycle. Water and Purina rat chow were available ad libitum. Pups were weaned at 21 days of age.

Immature twenty six day old female Sprague Dawley rats, 3-6 rats per treatment dose, were pretreated with pentobarbital 20 minutes before iv injection of vehicle/peptide or peptide plus stimulator. Injection was made as a 0.1 ml solution. For the non-pentobarbital treated rat assay, peptides were administered iv into the tail vein of conscious rats. All animals were sacrificed by guillotine after iv peptide or vehicle. Trunk blood was collected at +10-15 minutes after decapitation, allowed to clot, centrifuged and serum stored until assayed for GH levels by RIA. The GH RIA reagents were distributed by the NIH. Control data was collected from rats treated with only the corresponding vehicle in the absence of peptide or stimulator. Control stimulated data was collected from rats treated with stimulator alone in the absence of any peptide.

Results

Figure 1A:
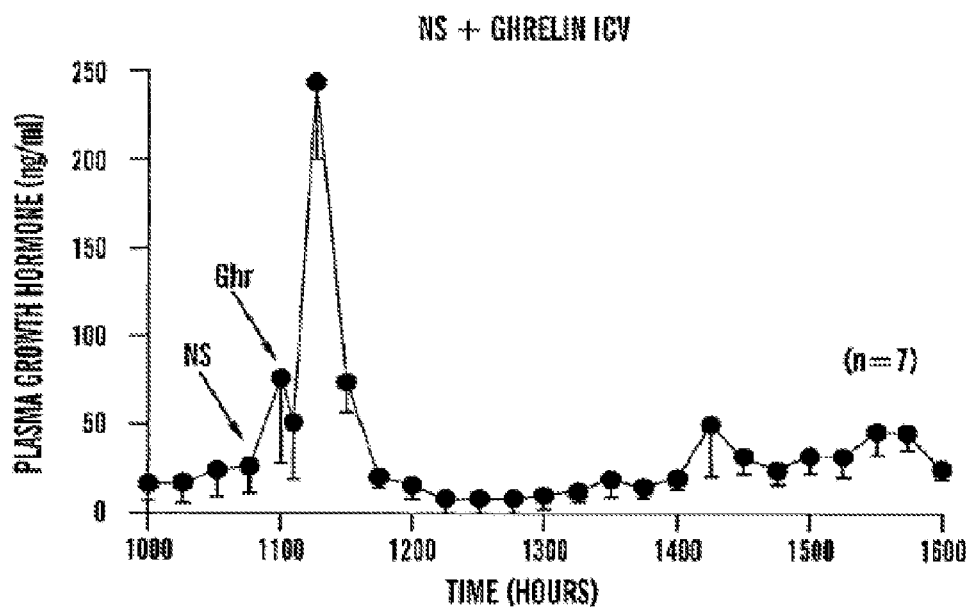
FIGS. 1A and 1B show mean plasma GH responses to 500 ng ghrelin administered icy 15 min after the icy injection of 5 μg GHS-A (FIG. 1B) or normal saline (FIG. 1A). Central pretreatment with GHS-A abolished the stimulatory action of ghrelin on GH release compared with normal saline i.c.v. pretreated controls. Values are the mean±SE. The number of animals in each group is shown in parentheses. Arrows indicate the times of i.c.v. injections.
Figure 1B:
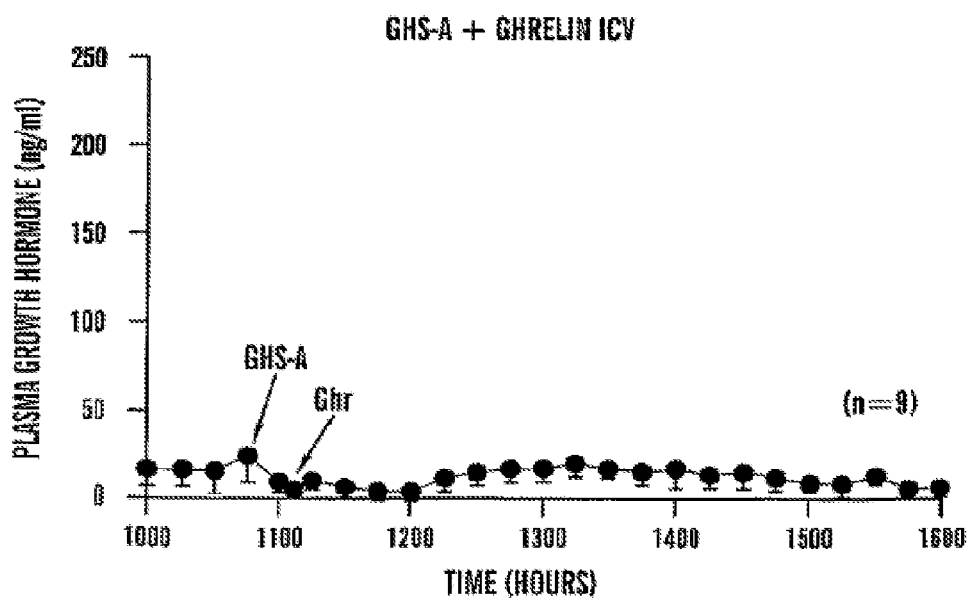
Figure 2A:
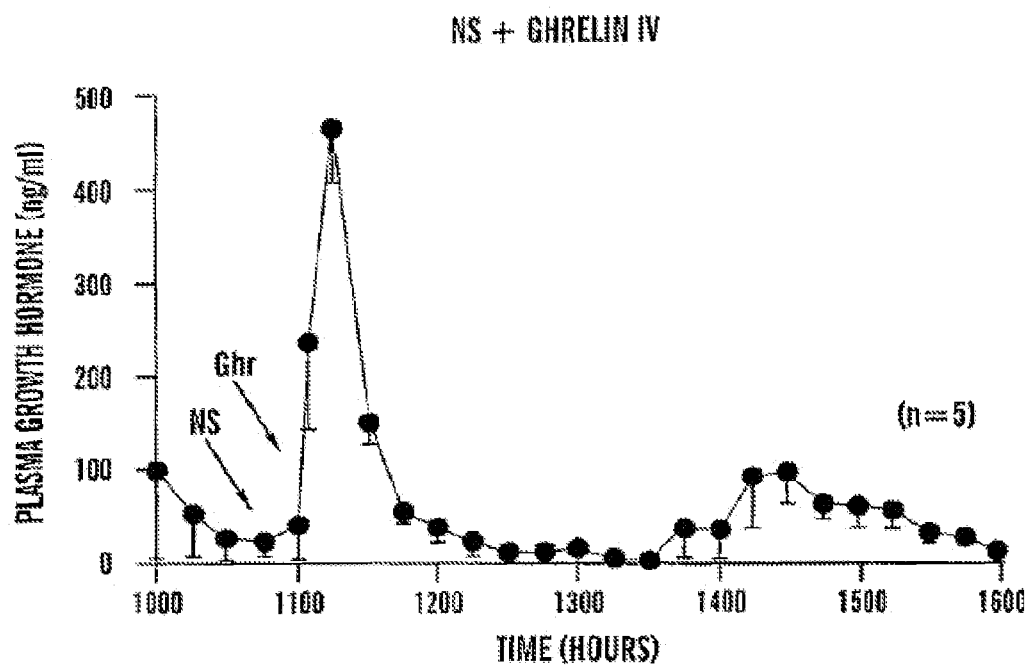
FIGS. 2A and 2B show mean plasma GH responses to 5 μg ghrelin administered iv 15 min after the iv injection of 250 μg GHS-A (FIG. 2B) or normal saline (FIG. 2A). Peripheral administration of GHS-A strongly blocked ghrelin's ability to release GH compared with normal saline-pretreated controls. Values are the mean±SE. The number of animals in each group is shown in parentheses. Arrows indicate the times of i.v. injections.
Figure 2B:
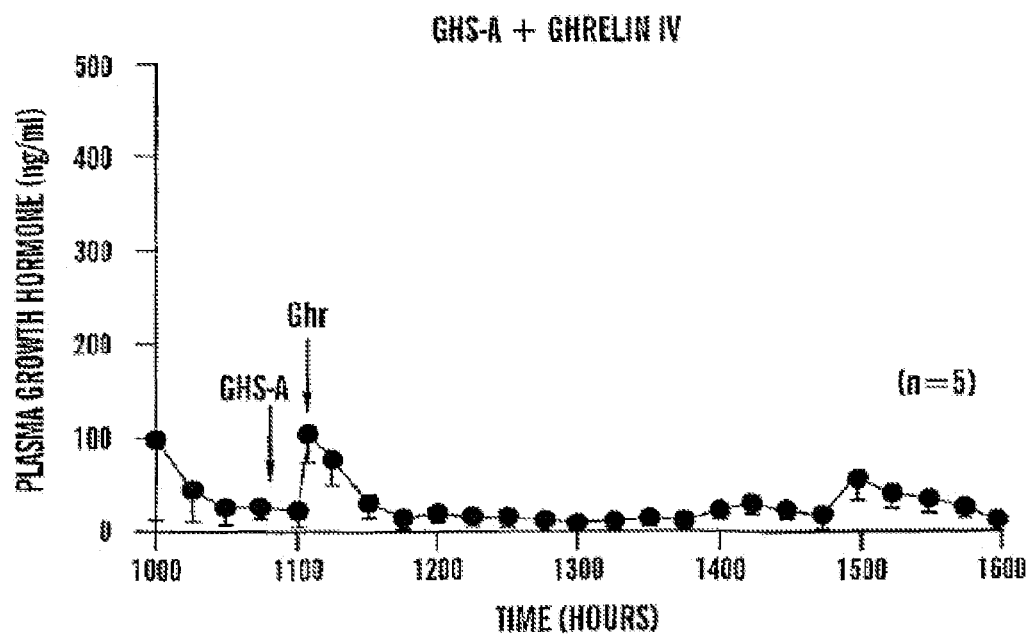
Figure 3:
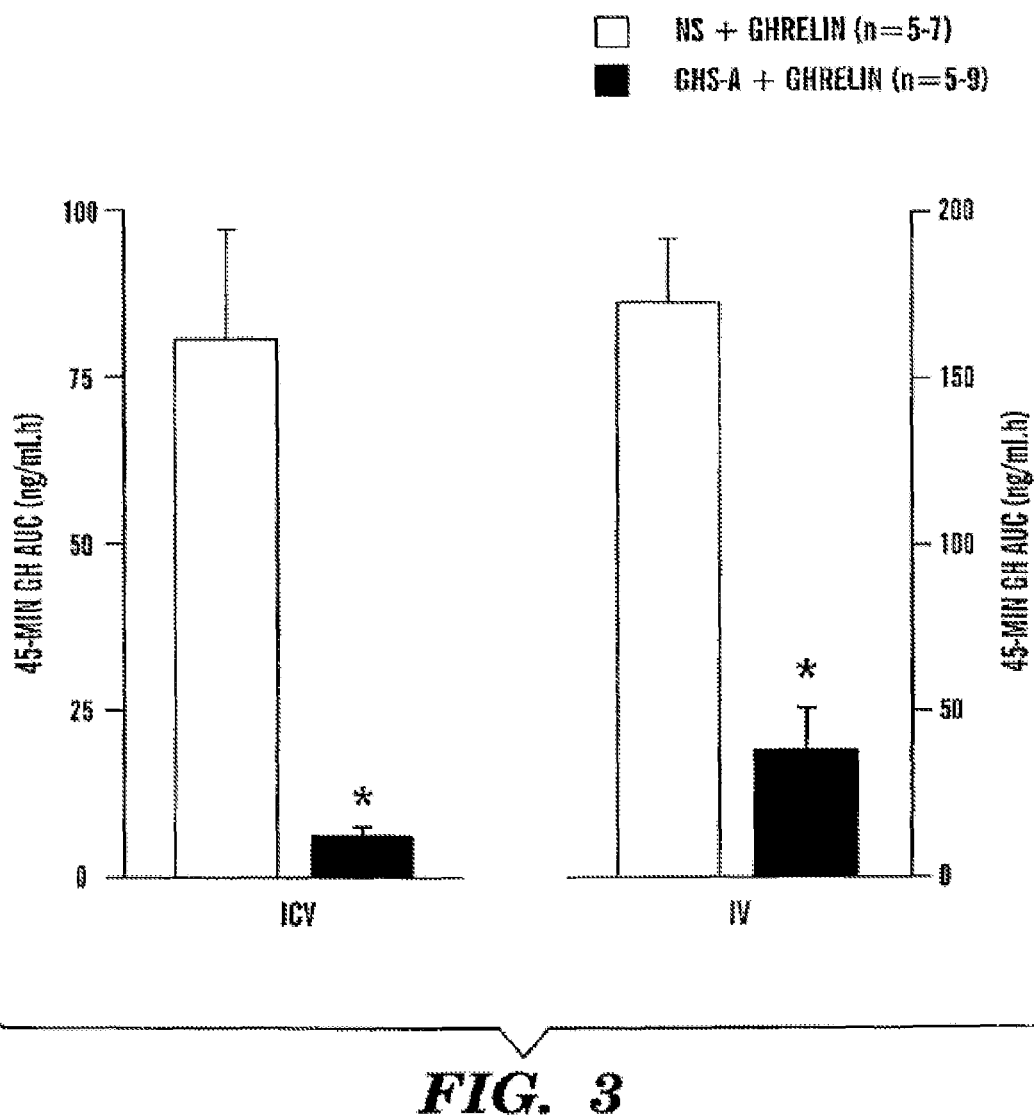
FIG. 3 shows a summary of the effects of GHS-A, given centrally (icy) or peripherally (iv), on ghrelin-induced GH release. The GH AUC following i.c.v. (500 ng) and i.v. (5 μg) ghrelin injection was reduced by 15- and 5-fold, respectively, in the GHS-A pretreated groups compared with their respective normal saline-treated controls. Each bar represents the mean±SE. *, P<0.0003 or less compared with normal saline-pretreated animals.
Figure 4A:
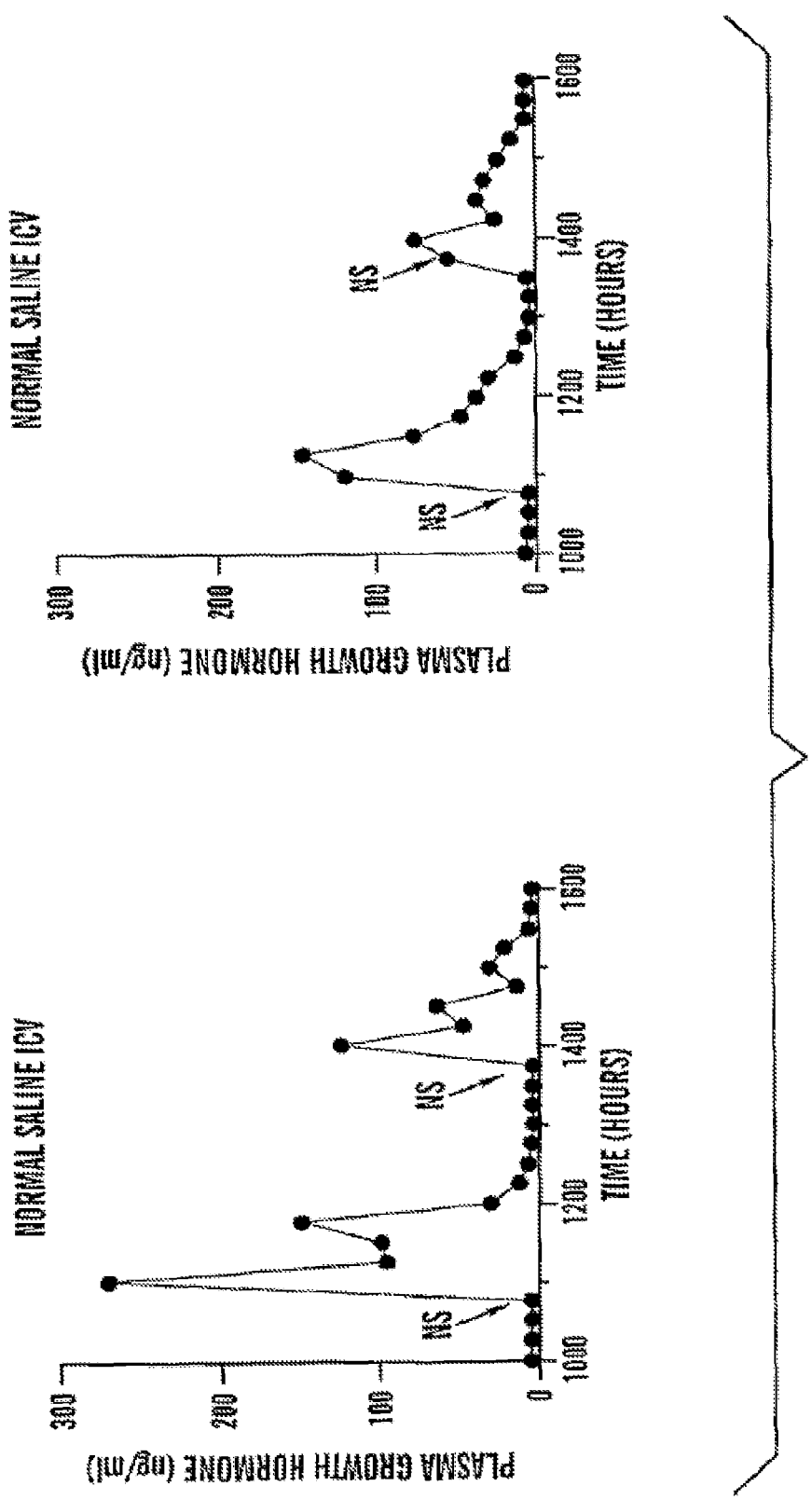
FIGS. 4A and 4B show that Individual representative plasma GH profiles in rats i.c.v. administered either 5 μg GHS-A (FIG. 4B) or normal saline (FIG. 4A) 15 min prior to the expected onset of the spontaneous GH secretory bursts typical of the male rat. GHS-A administration severely attenuated the amplitude of the spontaneous GH pulses compared with normal saline icy-injected controls. Arrows indicate the times of i.c.v. injections.
Figure 4B:
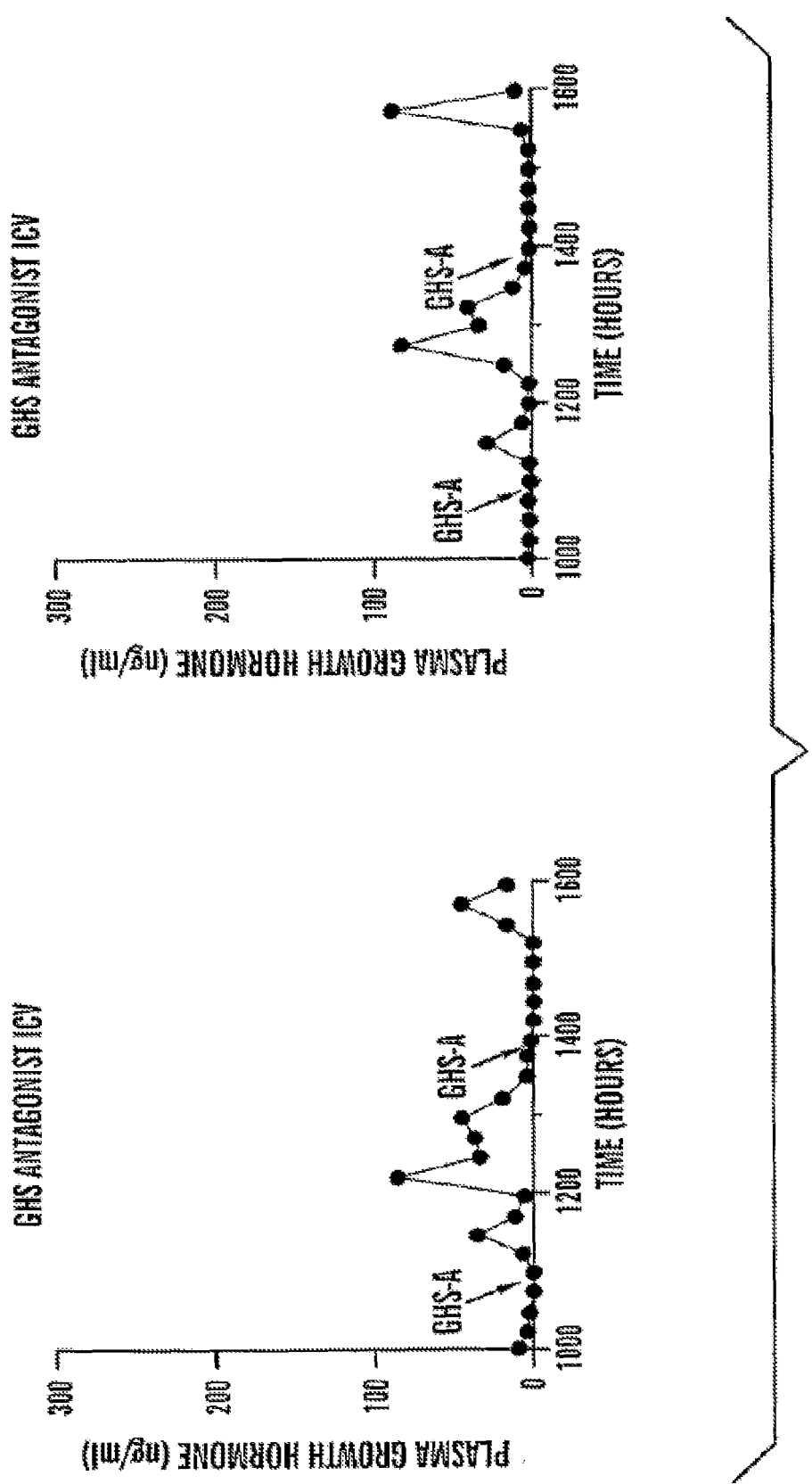
Figure 5:
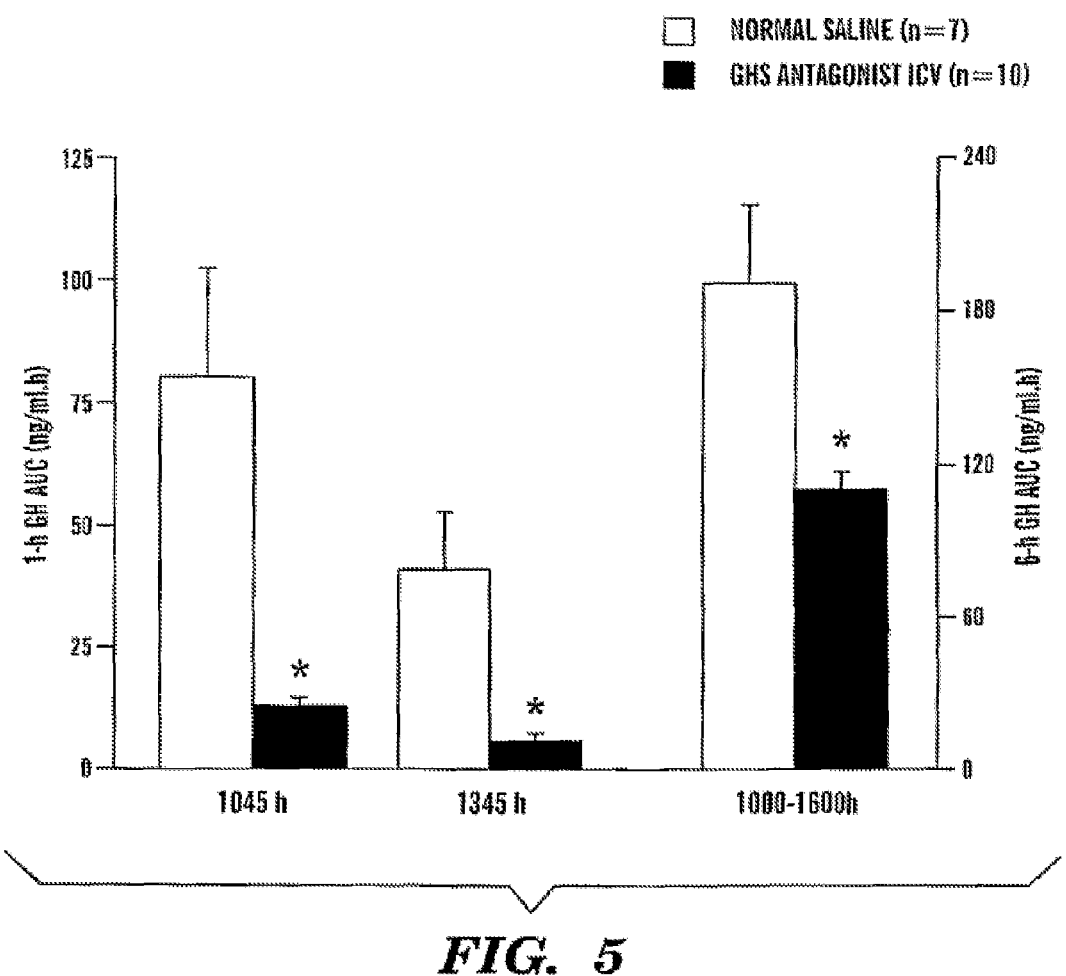
FIG. 5 shows that the 1-h GH AUC's of the spontaneous GH secretory episodes at 1100 h and 1400 h, and the overall 6-h GH AUC, were significantly reduced in animals treated i.c.v. with 5 μg GHS-A compared with normal saline i.c.v.- treated controls. Values are the mean±SE. *, P<0.01 or less compared with normal saline i.c.v.-treated group.

The data obtained show that ghrelin receptor antagonists of the present invention such as HisDβNalDLysTrpD-PheLysNH$_2$, can be used as a tool to disrupt the activity of ghrelin at the level of the CNS. This peptide is a GHRP derivative antagonist. ICV administration of 5 μg of this antagonist prior to i.c.v. injection of ghrelin (500 ng) in free moving, adult rats virtually obliterated the GH response to ghrelin, FIG. 1. A similar block of ghrelin (5 μg iv) induced GH release was observed when rats were pretreated peripherally with the GHS-R antagonist (250 μg i.v.), FIG. 2. In contrast, this GHS-R antagonist did not significantly reduce the GH response to GHRH (5 μg i.v.). With respect to feeding, i.c.v. administered GHS antagonist (5 μg) significantly inhibited ghrelin's (500 ng i.c.v.) stimulatory effects on food intake in the first hr after injections, FIGS. 7A and 8A. These results show the modulatory role for endogenous ghrelin in maintaining the high amplitude of spontaneous GH pulses under physiological conditions, likely acting through the GHS-R 1a on GHRH containing neurons in the arcuate nucleus (16, 17). Without wishing to be bound by theory, while ghrelin may be necessary for the full response of GHRH (the major driving regulator) on pulsatile GH release, it is not an active player in generating the ultradian rhythm of GH secretion. The lack of a dissociated effect on GH and food intake by the GHS antagonist shows that the GHS-R 1a mediates the effects of ghrelin on feeding (via NPY-containing neurons) as well as on GH.

The administration of the peptide Gly-Met-Ala-Gly-Ser-(Dap-Oct)-Phe-Leu-Ser-Pro-Glu-His-NH$_2$ (SEQ ID NO: 2) reduced both cumulative food intake and inhibited plasma growth hormone levels, FIGS. 10 and 11. Without wishing to be bound by theory, this peptide acts on the hypothalamic ghrelin-R (GHS-R 1a) and inhibits the action of endogenous ghrelin on its hypothalamic receptor. In this peptide, the N-terminal, which is necessary for ghrelin's activity, of the ghrelin pentapeptide core is blocked by the tripeptide Gly-Met-Ala.

A similar peptide, Gly-Met-Ala-Gly-Ser-(Dap-Palmityl)-Phe-Leu-Ser-Pro-Glu-His-NH$_2$ (SEQ ID NO: 3), which has a Dap-palmityl residue instead of the Dap-octyl did not inhibit GH secretion or decreased food intake on administration, FIGS. 10 and 11. Without wishing to be bound by theory, the presence of the larger palmityl group may lower or inhibit the interaction of this peptide with the ghrelin receptor.

Inhibition of Food Intake, Body Weight Gain and Growth Hormone Release by GMA[Dap$^3$Oct]Ghrelin Peptides Six newly designed ghrelin analogs were synthesiszed with the following changes: peptides of 8-12 amino acids; GMA (Gly-Met-Ala) tripeptide N terminus (NT) addition; substitution of a α,β-diaminopropionic carboxylic acid (Dap$^3$) for Ser$^3$; octonaoate or palmitate linked to Dap$^3$-via an amide rather than an ester; and amidated rather than a carboxylic C terminus (CT).

Freely-moving adult male rats bearing intracerebroventicular (icv) and intracardiac (iv) cannulae were injected icv with ghrelin analogs (10 μg) or the DMSO vehicle. In vivo effects were measured on spontaneous and ghrelin-stimulated GH secrtion over a 6-h sampling period, and food intake monitored hourly over a 5-h period and body weight change over 24 h. Results are shown in FIGS. 10-13.

Only one of the six new structurally interrelated ghrelin analogs, i.e., a duodecapeptide was effective in inhibitinh cumulative food intake and body weight gain supporting its specificity of action. When palmitate was substituted of octanoate it ineffective as expected.

The GMA duodecapeptide ghrelin analog was ineffective in inhibiting the Acyl Transferase Activity of GOAT in vitro (FIG. 14). Moreover, the six ghrelin analogs did not inhibit the acyl (octanoyl) transferase activity of ERAT (Ozawa A, Speaker RB III, Lindber I, 2009, PLoS One, 4:e5426) (data not shown)

Pretreatment with GMA[Dap$^3$Oct]ghrNH$_2$ 1-9 blocked the stimulatory action of ghrelin on GH release (FIG. 15). This suggests that GMA[Dap$^3$Oct]ghrNH$_2$ 1-9 may be acting via a direct inhibition of the hypothalamic ghrelin receptor.

Without wishing to be bound by theory, the in vitro/in vivo dissociated results indicate overlapping binding sites of GOAT and ghrelin receptors. Thus certain analogs may have dual inhibitory actions on GOAT and GHS-R. Accordingly, understanding the mechanisms involved provides novel strategies/useful drugs to regulate food intake and GH secretion in the treatment of metabolic disorders such as obesity and its complications.

TABLE 1

In Vitro Ghrelin/GHRP/GHS Receptor Antagonist Activity on Stimulated GH (ng/ml) release from isolated pituitary glands by the pituitary incubation method. Stimulator is His-DTrp-Ala-Trp-DPhe-Lys-NH$_2$ at 10 ng/ml

| Peptide Antagonist | Control | Stimulated Control | Peptide Antagonist Dosage μg/ml | | |
|---|---|---|---|---|---|
| | | | 0.1 | 0.3 | 1 |
| 1-Tyr-DTrp-DLys-Trp-DPhe-NH$_2$ | 47 ± 22 | 1528 ± 214 | | | |
| 2-Tyr-DTrp-DLys-Trp-DPhe-NH$_2$ | −461 ± 163 | 1053 ± 182 | | | |
| 3-His-DTrp-DLys-Trp-DPhe-NH$_2$ | 57 ± 77 | 2120 ± 311 | | 1765 ± 460 | |
| 4-His-DTrp-DLys-Phe-DTrp-NH$_2$ | N/A | | | | |
| 5-His-DTrp-DArg-Trp-DPhe-NH$_2$ | −161 ± 163 | 1953 ± 182 | | | |
| 6-His-DTrp-DLys-Trp-DPhe-Lys-NH$_2$ | −129 ± 52 | 1267 ± 64 | | 952 ± 200 | 324 ± 181 |
| 7-DesaminoTyr-DTrp-Ala-Trp-DPhe-NH$_2$ | 58 ± 77 | 2120 ± 311 | | | |
| 8-DesaminoTyr-DTrp-DLys-Trp-DPhe-NH$_2$ | 223 ± 203 | 5189 ± 1513 | 4297 ± 1061 | 2404 ± 802 | 688 ± 327 |
| 9-DeaminoTyr-DTrp-Ser-Trp-DPhe-Lys-NH$_2$ | 8 ± 305 | 4436 ± 1006 | | | |
| 10-DesaminoTyr-DTrp-Ser-Trp-DPhe-NH$_2$ | 8 ± 305 | 4436 ± 1006 | | | |
| 11-His-DTrp-DTrp-Phe-Met-NH$_2$ | −129 ± 52 | 1267 ± 164 | | 1542 ± 523 | 323 ± 69 |
| 12-Tyr-DTrp-DTrp-Phe-Phe-NH$_2$ | 47 ± 22 | 1528 ± 214 | | 1274 ± 329 | |

| Peptide Antagonist | Peptide Antagonist Dosage μg/ml | | | |
|---|---|---|---|---|
| | 3 | 10 | 30 | 100 |
| 1-Tyr-DTrp-DLys-Trp-DPhe-NH$_2$ | −480 ± 95 | | −363 ± 66 | |
| 2-Tyr-DTrp-DLys-Trp-DPhe-NH$_2$ | | | | −555 ± 121 |
| 3-His-DTrp-DLys-Trp-DPhe-NH$_2$ | 949 ± 178 | | 91 ± 103 | |
| 4-His-DTrp-DLys-Phe-DTrp-NH$_2$ | | | | |
| 5-His-DTrp-DArg-Trp-DPhe-NH$_2$ | 341 ± 222 | −125 ± 101 | −122 ± 44 | |
| 6-His-DTrp-DLys-Trp-DPhe-Lys-NH$_2$ | 134 ± 91 | −83 ± 132 | −175 ± 59 | |
| 7-DesaminoTyr-DTrp-Ala-Trp-DPhe-NH$_2$ | 1302 ± 269 | | −959 ± 75 | |

TABLE 1-continued

In Vitro Ghrelin/GHRP/GHS Receptor Antagonist Activity on Stimulated GH (ng/ml) release from isolated pituitary glands by the pituitary incubation method. Stimulator is His-DTrp-Ala-Trp-DPhe-Lys-NH$_2$ at 10 ng/ml

| | | | |
|---|---|---|---|
| 8-DesaminoTyr-DTrp-DLys-Trp-DPhe-NH$_2$ | −466 ± 432 | −1068 ± 318 | −576 ± 110 |
| 9-DeaminoTyr-DTrp-Ser-Trp-DPhe-Lys-NH$_2$ | | 3325 ± 391 | 3810 ± 621 |
| 10-DesaminoTyr-DTrp-Ser-Trp-DPhe-NH$_2$ | | 3119 ± 488 | 3258 ± 682 |
| 11-His-DTrp-DTrp-Phe-Met-NH$_2$ | 445 ± 188 | 287 ± 68 | −319 ± 95 |
| 12-Tyr-DTrp-DTrp-Phe-Phe-NH$_2$ | | 1034 ± 182 | −167 ± 157 |

TABLE 2

In Vivo Ghrelin/GHRP/GHS Receptor Antagonist Activity on Stimulated GH (ng/ml) release from rat. Sitmulator is DAla-DβNal-Ala-Trp-DPhe-Lys-NH2 at 0.3 μg or 1 μg

| Peptide Antagonist | Control | Stimulated Control 0.3 μg | Stimulated Control 1 μg | Peptide Antagonist Dosage μg/i.v. 1 |
|---|---|---|---|---|
| 1-Glyψ[CH$_2$NH]-DβNal-Ala-Trp-DPhe-Lys-NH$_2$ | 138 ± 11 | 1412 ± 400 | | |
| | 138 ± 11 | | 3214 ± 276 | |
| | 164 ± 14 | | 3105 ± 429 | |
| 2-Glyψ[CH$_2$NH]-DβNal-DLys-Trp-DPhe-Lys-NH$_2$ | 143 ± 19 | | 2406 ± 288 | 2305 ± 320 |
| 3-DAla-DβNal-DLys-DTrp-Phe-Lys-NH$_2$ | 327 ± 39 | | 4950 ± 98 | |
| 4-His-DβNal-DLys-Trp-DPhe-Lys-NH$_2$ | 91 ± 46 | 2253 ± 252 | | |
| | 91 ± 46 | | 2825 ± 134 | |
| 5-Ala-His-DTrp-DLys-Trp-DPhe-Lys-NH$_2$ | 91 ± 46 | 2253 ± 252 | | |
| 6-Alaψ[CH$_2$NH]-DβNal-Ala-Trp-DPhe-Lys-NH$_2$ | 164 ± 14 | | 3104 ± 429 | |

| Peptide Antagonist | Peptide Antagonist Dosage μg/i.v. | | | |
|---|---|---|---|---|
| | 3 | 10 | 30 | 100 |
| 1-Glyψ[CH$_2$NH]-DβNal-Ala-Trp-DPhe-Lys-NH$_2$ | | 1112 ± 200 | 578 ± 82 | |
| | | 2307 ± 176 | 890 ± 236 | |
| | | 1842 ± 454 | 1135 ± 140 | |
| 2-Glyψ[CH$_2$NH]-DβNal-DLys-Trp-DPhe-Lys-NH$_2$ | 1990 ± 196 | 1550 ± 284 | 946 ± 133 | 462 ± 122 |
| 3-DAla-DβNal-DLys-DTrp-Phe-Lys-NH$_2$ | | | 2884 ± 828 | 1198 ± 114 |
| 4-His-DβNal-DLys-Trp-DPhe-Lys-NH$_2$ | | | 733 ± 85 | |
| | | | | 818 ± 269 |
| 5-Ala-His-DTrp-DLys-Trp-DPhe-Lys-NH$_2$ | | | 1487 ± 397 | |
| 6-Alaψ[CH$_2$NH]-DβNal-Ala-Trp-DPhe-Lys-NH$_2$ | 2771 ± 157 | 2341 ± 416 | 1948 ± 450 | 1639 ± 221 |

TABLE 3

In Vivo Ghrelin/GHRP/GHS Receptor Antagonist Activity on Unstimulated Basal GH (ng/ml) Release from rat.

| Partial Agonist/Antagonist Peptide | Control | Stimulated Control 0.3 μg | Stimulated Control 1 μg | Peptide Dosage μg/i.v. | | | | |
|---|---|---|---|---|---|---|---|---|
| | | | | 1 | 3 | 10 | 30 | 100 |
| 1-DβNal-Ala-Trp-DPhe-Ala-NH$_2$ | 253 ± 34 | 1991 ± 214 | | 623 ± 60 | 694 ± 70 | 654 ± 58 | 713 ± 71 | |
| 2-DAla-DcyclohexylAla-Ala-Phe-DPhe-Nle-NH$_2$ | 204 ± 46 | 1850 ± 324 | | 435 ± 152 | 195 ± 34 | 250 ± 41 | 393 ± 51 | 697 ± 75 |
| 3-DcyclohexylAla-Ala-Phe-DTrp-Lys-NH$_2$ | 204 ± 46 | 1765 ± 330 | | 199 ± 63 | 266 ± 68 | 199 ± 23 | 346 ± 82 | 350 ± 61 |
| 4-Ala-DβNal-Ala-Thr-DThr-Lys-NH$_2$ | 244 ± 56 | 1538 ± 215 | | | 255 ± 38 | | 288 ± 31 | 386 ± 57 |
| 5-DcyclohexylAla-Ala-Trp-DPhe-NH$_2$ | 176 ± 44 | 2282 ± 258 | | | 181 ± 28 | 237 ± 18 | 354 ± 81 | 771 ± 76 |
| 6-DAla-DβNal-Ala-Ala-DAla-Lys-NH$_2$ | 135 ± 19 | 1485 ± 200 | | | 235 ± 43 | 178 ± 33 | 172 ± 15 | 185 ± 39 |
| 7-DβNal-Ala-Trp-DPhe-Leu-NH$_2$ | 145 ± 48 | 1470 ± 338 | | | 253 ± 79 | 277 ± 43 | 347 ± 66 | 645 ± 117 |
| 8-His-DTrp-Phe-Trp-DPhe-Lys-NH$_2$ | 240 ± 55 | | 2766 ± 726 | 67 ± 14 | 141 ± 53 | 197 ± 70 | 509 ± 48 | |
| 9-DAla-DβNal-DAla-DTrp-Phe-Lys-NH$_2$ | 100 ± 22 | | 4785 ± 798 | 184 ± 55 | 467 ± 201 | 244 ± 107 | | |
| 10-βAla-Trp-DAla-DTrp-Phe-NH$_2$ | 195 ± 33 | | 4130 ± 349 | | | | 341 ± 46 | 636 ± 171 |
| 11-His-Trp-DAla-DTrp-Phe-LysNH$_2$ | 150 ± 26 | 1847 ± 362 | | 204 ± 44 | 127 ± 44 | 83 ± 5 | | |

TABLE 4

In Vivo Ghrelin/GHRP/GHS Receptor Antagonist Activity on Unstimulated and Stimulated (S) GH (ng/ml) release from rats. The Stimulator is DAla-DβNal-Ala-Trp-DPhe-Lys-NH2 at 0.3 μg, 1 μg, or 10 μg.

| Peptide Antagonist (P) | | Control | Stimulated Control 0.3 | Stimulated Control 1 | Peptide Antagonist Dosage μg/i.v. | | | | |
|---|---|---|---|---|---|---|---|---|---|
| | | | | | 1 | 3 | 10 | 30 | 100 |
| Pentobarbital Rats | | | | | | | | | |
| 1-DLys-DβNal-Ala-Trp-DPhe-Lys-NH₂ | −S | 197 ± 81 | | | | 616 ± 169 | 847 ± 17 | 629 ± 146 | 228 ± 45 |
| 1-DLys-DβNal-Ala-Trp-DPhe-Lys-NH₂ | P + S | | 5052 ± 511 | | | 5232 ± 346 | 3404 ± 396 | 704 ± 169 | |
| 2-DAla-DβNal-DLys-DTrp-Phe-Lys-NH₂ | −S | 327 ± 39 | | | | | | 323 ± 50 | 812 ± 6 |
| 2-DAla-DβNal-DLys-DTrp-Phe-Lys-NH₂ | P + S | | | 4950 ± 98 | | | | 2864 ± 828 | 1198 ± 114 |
| Non-Pentobarbital Rats | | | | 10 μg | | | | | |
| 1-Tyr-DAla-Phe-Aib-NH₂ | −S | 12 ± 1 | | | | | | 18 ± 1 | |
| 1-Tyr-DAla-Phe-Aib-NH₂ | P + S | | | 72 ± 9 | | | | 23 ± 5 | |
| 2-Tyr-DAla-Sar-NMePhe-NH₂ | −S | 12 ± 1 | | | | | | 18 ± 4 | |
| 2-Tyr-DAla-Sar-NMePhe-NH₂ | P + S | | | 72 ± 9 | | | | 24 ± 6 | |

TABLE 5

In Vivo Ghrelin/GHRP/GHS Receptor Antagonist Activity on Unstimulated Basal GH (ng/ml) release from rats.

| Peptide Antagonist | Control | Stimulated Control 0.3 μg | Stimulated Control 1 μg | Peptide Antagonist Dosage μg/i.v. | | | | |
|---|---|---|---|---|---|---|---|---|
| | | | | 1 | 3 | 10 | 30 | 100 |
| 1-αγAbu-DTrp-DTrp-Ser-NH₂ | 106 ± 9 | | 2742 ± 206 | 80 ± 35 | | 62 ± 15 | 67 ± 8 | |
| 2-αγAbu-DTrp-DTrp-Lys-NH₂ | 136 ± 31 | | 1968 ± 294 | 57 ± 7 | 84 ± 18 | 62 ± 15 | | |
| 3-αγAbu-DTrp-DTrp-Orn-NH₂ | 167 ± 13 | | 2819 ± 530 | 118 ± 16 | | 126 ± 27 | 79 ± 31 | |
| 4-αAbu-DTrp-DTrp-Orn-NH₂ | 167 ± 13 | | 2819 ± 530 | 85 ± 25 | | 88 ± 18 | 50 ± 6 | |
| 5-DThr-DαNal-DTrp-DPro-Arg-NH₂ | 164 ± 23 | | 2691 ± 281 | 60 ± 5 | 130 ± 24 | 134 ± 31 | | |
| 6-DAla-Ala-DAla-DTrp-Phe-Lys-NH₂ | 180 ± 20 | | 4785 ± 798 | | | 228 ± 76 | 172 ± 14 | 153 ± 45 |
| 7-Alaψ[CH₂NH]His-DTrp-Ala-Trp-DPhe-Lys-NH₂ | 211 ± 30 | | 2335 ± 323 | 127 ± 32 | 147 ± 37 | | | |
| 8-Lys-DHis-DTrp-Phe-NH₂ | 211 ± 30 | | 2335 ± 323 | | | 121 ± 24 | | |
| 9-γAbu-DTrp-DTrp-Orn-NH₂ | 167 ± 13 | | 2819 ± 530 | 82 ± 28 | | 90 ± 5 | 113 ± 32 | |
| 10-inip-Trp-Trp-Phe-NH₂ | 155 ± 31 | | 2503 ± 240 | | | 69 ± 3 | 81 ± 10 | | inip = isonipecotic carboxylic acid
αγAbu = alpha gamma diaminobutyric acid

TABLE 6

In Vitro Ghrelin/GHRP/GHS Receptor Antagonist Activity on Unstimulated and Stimulated(S) GH (ng/ml) release from cell culture of pituitary cells. The Sitmulator is DAla-DβNal-Ala-Trp-DPhe-Lys-NH₂ at at 10 ng/ml.

| Peptide Antagonist (P) | | Control | Stimulated Control 10 ng/ml | Peptide Antagonist Dosage μg/m/l | | | | | |
|---|---|---|---|---|---|---|---|---|---|
| | | | | 0.1 | 0.3 | 1 | 3 | 10 | 30 |
| 1-Ac-DTrp-Phe-DTrp-Leu-NH₂ | −S | 1640 ± 100 | | | | | | | 400 ± 20 |
| 1-Ac-DTrp-Phe-DTrp-Leu-NH₂ | P + S | | 2420 ± 0 | | | | 2100 ± 0 | 1200 ± 20 | 600 ± 20 |
| 2-Ac-DTrp-Phe-DTrp-Lys-NH₂ | −S | 1640 ± 100 | | | | | | | 350 ± 80 |
| 2-Ac-DTrp-Phe-DTrp-Lys-NH₂ | P + S | | 2420 ± 0 | | | | 1750 ± 10 | 800 ± 0 | 470 ± 30 |
| 3-Ac-DTrp-DTrp-Lys-NH₂ | −S | 1640 ± 100 | | | | | | 610 ± 30 | 420 ± 20 |
| 3-Ac-DTrp-DTrp-Lys-NH₂ | P + S | | 2420 ± 0 | | | | 1970 ± 70 | 1130 ± 30 | 900 ± 0 |
| 4-DLys-Tyr-DTrp-DTrp-Phe-Lys-NH₂ | −S | 1640 ± 100 | | | | | | 1340 ± 60 | 1060 ± 0 |
| 4-DLys-Tyr-DTrp-DTrp-Phe-Lys-NH₂ | P + S | | 2420 ± 0 | | | | 2100 ± 40 | 1710 ± 10 | 1270 ± 10 |
| 5-Ac-DβNal-Leu-Pro-NH₂ | −S | 1233 ± 49 | | | | | | | |
| 5-Ac-DβNal-Leu-Pro-NH₂ | P + S | | 2811 ± 229 | | | | 1998 ± 36 | 1206 ± 53 | 860 ± 33 |
| 6-βAla-Trp-DTrp-DTrp-Orn-NH₂ | −S | 1722 ± 205 | | | | | | | |
| 6-βAla-Trp-DTrp-DTrp-Orn-NH₂ | P + S | | 2385 ± 8 | | | 3103 ± 471 | | 1633 ± 34 | 1166 ± 13 |

TABLE 7

In Vitro Ghrelin/GHRP/GHS Receptor Antagonist Activity on Unstimulated and Stimulated (S) GH (ng/ml) release from cell culture of pituitary cells. The Stimulator is DAla-DβNal-Ala-Trp-DPhe-Lys-$NH_2$ at 1 ng/ml.

| Partial Agonist/Antagonist Peptide (P) | | Control | Stimulated Control 1 ng/ml | Peptide Dosage μg/ml | | | | |
|---|---|---|---|---|---|---|---|---|
| | | | | 1 | 3 | 10 | 30 | 100 |
| 1-DVal-DαNal-DTrp-Phe-Arg-$NH_2$ | −S | 480 ± 16 | | | 934 ± 34 | 850 ± 19 | 598 ± 7 | |
| 1-DVal-DαNal-DTrp-Phe-Arg-$NH_2$ | P + S | | 1399 ± 27 | | 949 ± 52 | 672 ± 64 | 520 ± 5 | |
| 2-DLeu-DαNal-DTrp-Phe-Arg-$NH_2$ | −S | 460 ± 16 | | | 1156 ± 10 | 971 ± 5 | 520 ± 5 | |
| 2-DLeu-DαNal-DTrp-Phe-Arg-$NH_2$ | P + S | | 1399 ± 27 | | 1136 ± 7 | 957 ± 44 | 777 ± 71 | |
| 3-CyclohexylAla-DαNal-DTrp-Phe-Arg-$NH_2$ | P + S | 734 ± 6 | 1841 ± 41 | | 1362 ± 59 | 1021 ± 22 | | |
| 4-DTrp-DαNal-DTrp-Phe-Arg-$NH_2$ | P + S | 734 ± 6 | 1851 ± 41 | | 1239 ± 17 | 878 ± 28 | | |
| 5-DAla-DβNal-DPro-Phe-Arg-$NH_2$ | P + S | 734 ± 6 | 1851 ± 41 | | 1779 ± 27 | 1328 ± 59 | | |
| 6-Ac-DαNal-DTrp-Phe-Arg-$NH_2$ | −S | 480 ± 16 | | | 1106 ± 7 | 996 ± 16 | 704 ± 76 | |
| 6-Ac-DαNal-DTrp-Phe-Arg-$NH_2$ | P + S | | 1399 ± 27 | | 1128 ± 12 | 970 ± 25 | 704 ± 76 | |
| 7-DαNal-DTrp-Phe-Arg-$NH_2$ | −S | 480 ± 16 | | | 1170 ± 43 | 987 ± 52 | 727 ± 44 | |
| 7-DαNal-DTrp-Phe-Arg-$NH_2$ | P + S | | 1399 ± 27 | | 1288 ± 40 | 1079 ± 17 | 824 ± 29 | |
| 8-inip-Trp-Trp-Phe-$NH_2$ | −S | 625 ± 12 | | | | 553 ± 111 | 247 ± 9 | 132 ± 7 |
| 8-inip-Trp-Trp-Phe-$NH_2$ | P + S | | 749 ± 28 | | | 393 ± 6 | 278 ± 35 | 154 ± 4 | inip = isonipecotic carboxylic acid

TABLE 8

In Vitro Ghrelin/GHRP/GHS Receptor Antagonist Activity on Unstimulated Basal GH (ng/ml) release from cell cultures of pituitary cells.

| Peptide Antagonist (P) | Control | Stimulated control 1 ng/ml | Peptide Antagonist Dosage μg/ml | | | | |
|---|---|---|---|---|---|---|---|
| | | | 1 | 3 | 10 | 30 | 100 |
| 1-His-DTrp-DTrp-Lys-$NH_2$ | 1089 ± 47 | 1551 ± 2 | | 1124 ± 37 | 749 ± 10 | 615 ± 41 | |
| 2-Ac-DβNal-DTrp-$NH_2$ | 1089 ± 47 | 1551 ± 2 | | 1264 ± 2 | 980 ± 72 | 699 ± 7 | |
| 3-αAib-DTrp-DcyclohexylAla-$NH_2$ | 478 ± 8 | 1014 ± 8 | 980 ± 44 | 826 ± 32 | 602 ± 53 | 492 ± 11 | |
| 4-αAib-DTrp-DAla-cyclohexylAla-$NH_2$ | 478 ± 8 | 1014 ± 8 | 1086 ± 52 | 1103 ± 18 | 994 ± 22 | 704 ± 115 | |
| 5-DAla-DcyclohexylAla-Ala-Ala-Phe-DPhe-Nle-$NH_2$ | 500 ± 116 | 1991 ± 214 | 286 ± 75 | 177 ± 44 | 271 ± 38 | 376 ± 28 | |
| 6-DPhe-Ala-Phe-DPal-$NH_2$ | 176 ± 44 | | | 170 ± 19 | 181 ± 31 | 161 ± 20 | 146 ± 21 |
| 7-DPhe-Ala-Phe-DPhe-Lys-$NH_2$ | 368 ± 32 | | | | 267 ± 27 | 276 ± 65 | 360 ± 84 |
| 8-DLys-Tyr-DTrp-DTrp-Phe-$NH_2$ | 1403 ± 13 | | 1451 ± 19 | 1175 ± 77 | 1129 ± 6 | 744 ± 44 | |
| 9-Ac-DLys-Tyr-DTrp-DTrp-Phe-$NH_2$ | 1403 ± 13 | | | 105 ± 8 | 950 ± 91 | 782 ± 56 | 756 ± 1 |
| 10-Arg-DTrp-Leu-Tyr-Trp-Pro(cyclic Arg-Pro) | 1403 ± 13 | | | 1480 ± 19 | 802 ± 26 | 601 ± 16 | 509 ± 49 |
| 11-Ac-DβNal-PlcLys-ILys-DPhe-$NH_2$ | 1333 ± 41 | | | 1013 ± 207 | 976 ± 13 | 928 ± 16 | |
| 12-DPal-DTrp-DTrp-Phe-Met-$NH_2$ | 1333 ± 41 | | | 1081 ± 50 | 997 ± 30 | 425 ± 25 | |
| 13-DPhe-Trp-DPhe-Phe-Met-$NH_2$ | 1333 ± 41 | | | 1146 ± 34 | 1086 ± 32 | 871 ± 89 | |
| 14-DPal-Trp-DPhe-Phe-Met-$NH_2$ | 1333 ± 41 | | | 1105 ± 18 | 891 ± 4 | 567 ± 24 | |

ILys = Lys(IPr)

TABLE 9

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-$NH_2$ at 1 ng/ml.

| Peptide Antagonist (P) | | Control | Stimulated control 1 ng/ml | Peptide Antagonist Dosage μg/ml | | | | |
|---|---|---|---|---|---|---|---|---|
| | | | | 1 | 3 | 10 | 30 | 100 |
| 1-βAla-Pal-DTrp-DTrp-Orn-$NH_2$ | −S | 894 ± 18 | | | | 759 ± 11 | 861 ± 25 | |
| | P + S | | 1232 ± 34 | | | 855 ± 11 | 828 ± 11 | |
| 2-αγAbu-Trp-DTrp-DTrp-Orn-$NH_2$ | −S | 894 ± 18 | | | | 609 ± 3 | 503 ± 5 | |
| | P + S | | 1232 ± 34 | | | 666 ± 2 | 578 ± 31 | |
| 3-βAla-Trp-DTrp-DTrp-Lys-$NH_2$ | −S | 894 ± 18 | | | | 733 ± 25 | 616 ± 21 | |
| | P + S | | 1232 ± 34 | | | 806 ± 45 | 596 ± 18 | |
| 4-γAbu-Trp-DTrp-DTrp-Orn-$NH_2$ | −S | 894 ± 18 | | | | 840 ± 30 | 634 ± 1 | |
| | P + S | | 1232 ± 34 | | | 835 ± 5 | 655 ± 40 | |
| 5-Ava-Trp-DTrp-DTrp-Orn-$NH_2$ | −S | 894 ± 18 | | | | 481 ± 3 | 406 ± 21 | |
| | P + S | | 1232 ± 34 | | | 505 ± 19 | 420 ± 34 | |

αγAbu = alpha gamma diaminobutyric acid
Ava = aminovaleric acid

TABLE 10

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | | Control | Stimulated Control 1 ng/ml | Partial Peptide/Non-peptide Dosage μg/ml | | | |
|---|---|---|---|---|---|---|---|
| | | | | 1 | 3 | 10 | 30 |
| 1-DTrp-4-phenylpiperdinamide | | 385 ± 49 | | 815 ± 26 | 390 ± 35 | 520 ± 61 | 577 ± 24 |
| | P + S | | 1060 ± 24 | 1085 ± 1 | 917 ± 4 | 344 ± 6 | 486 ± 29 |
| 2-2,3-di[N-(2-methoxylphenyl) piperazyl-naphthalene carboxylamide | | 361 ± 30 | | 338 ± 3 | 204 ± 10 | 262 ± 4 | |
| | P + S | | 905 ± 6 | 654 ± 18 | 442 ± 4 | 537 ± 28 | |
| | | 385 ± 17 | | | | 136 ± 11 | 118 ± 8 |
| | P + S | | 1153 ± 36 | | | 648 ± 16 | 309 ± 46 |
| 3-Benzamide-DSerDLysTrp-p-phenylpiperidinamide | | 370 ± 24 | | | 393 ± 54 | 369 ± 30 | |
| | P + S | | 1216 ± 26 | | 432 ± 25 | 353 ± 10 | |
| 4-Ser(Bzl)Lys(Ac)DTrp-p-phenylpiperidinamide | | 385 ± 17 | | | | 388 ± 41 | 273 ± 39 |
| | P + S | | 1153 ± 36 | | | 571 ± 32 | 399 ± 24 |
| 5-O-(2-methylallyl) benzophonone oxime | | 969 ± 33 | | | | 929 ± 28 | 616 ± 23 |
| | P + S | | 1461 ± 58 | | | 1281 ± 58 | 699 ± 53 |
| 6-D Ser(BZL)-N'-phenyl-N-piperazinamide | | 626 ± 4 | | | | 585 ± 10 | 368 ± 2 |
| | P + S | | 1016 ± 18 | | | 719 ± 26 | 435 ± 0 |
| 7-αAibDSer(BZL)-N'-phenyl-N-piperazinamide | | 626 ± 4 | | | | 777 ± 34 | 499 ± 18 |
| | P + S | | 1016 ± 18 | | | 878 ± 30 | 510 ± 15 |
| 8-2-[acetylester]-3-(p-m-methoxyl phenyl) piperidinamide]-naphthalene carboxamide | | 421 ± 16 | | | | 373 ± 2 | 176 ± 11 |
| | P + S | | 859 ± 4 | | | 480 ± 9 | 223 ± 22 |

TABLE 11

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | | Control | Stimulated Control 1 ng/ml | Partial Peptide/Non-peptide Dosage μg/ml | | | |
|---|---|---|---|---|---|---|---|
| | | | | 1 | 3 | 10 | 30 |
| 1-2-[methylester]-3-[p-methylphenylamide naphthalene carboxylamide | | 626 ± 4 | | | | 754 ± 32 | 498 ± 26 |
| | P + S | | 1016 ± 18 | | | 1149 ± 33 | 886 ± 29 |
| 2-p-phenyl(piperidinamide-DTrpLysSer(BZL)-acetylamide | P + S | 408 ± 40 | 905 ± 6 | 680 ± 13 | 489 ± 41 | 245 ± 16 | |
| 3-γAbuDTrp-p-[m-methoxyphenyl] piperidinamide | | 364 ± 31 | | | | 557 ± 19 | 378 ± 18 |
| | P + S | | 947 ± 11 | | | 526 ± 27 | 428 ± 22 |
| 4-αAibDTrp-p-(α-methoxylphenyl) piperidinamide | | 377 ± 24 | | | | 365 ± 2 | 375 ± 30 |
| | P + S | | 947 ± 33 | | | 441 ± 21 | 384 ± 16 |
| 5-2-[ethylester-3-m-methoxylphenylamide] naphthalene carboxylamide | | 364 ± 31 | | | | 698 ± 18 | 552 ± 20 |
| | P + S | | 947 ± 11 | | | 670 ± 32 | 458 ± 15 |
| 6-1,3-diaminobutyricamide-DβNal-4-phenylpiperidinamide | | 626 ± 4 | | | | 794 ± 34 | 504 ± 20 |
| | P + S | | 1016 ± 18 | | | 644 ± 33 | 529 ± 20 |

TABLE 12

In Vitro Ghrelin/GHRP/GHS Receptor Antagonist Activity on Unstimulated and Stimulated(S) GH (ng/ml) release from isolated pituitary glands by the pituitary incubation method. The Stimulator S = His-DTrp-Ala-Trp-DPhe-Lys-NH$_2$ (10 ng/ml) and Stimulator *S = Tyr-DTrp-Ala-Trp-DPhe-NH$_2$ (0.3 μg/ml)

| Peptide(P) | | Control | Stimulated Control | Peptide Dosage μg/ml | | | | |
|---|---|---|---|---|---|---|---|---|
| | | | | 1 | 3 | 10 | 30 | 100 |
| 1-His-DTrp-DLys-Trp-DPhe-NH$_2$ | P + S | 854 ± 255 | 8769 ± 583 | 8121 ± 687 | 5929 ± 857 | 3017 ± 413 | 269 ± 140 | |
| 2-Ala-His-DTrp-DLys-Trp-DPhe-Lys-NH$_2$ | | 1674 ± 1171 | | | | | 3977 ± 1360 | |
| | P + S | | 5218 ± 507 | 4850 ± 539 | 947 ± 551 | −2384 ± 868 | | |
| 3-DLys-Tyr-DTrp-Ala-Trp-DPhe-NH$_2$* | P + S | 148 ± 137 | 2218 ± 194 | | 1233 ± 268 | 688 ± 3233 | 916 ± 80 | |
| 4-His-DTrp-DArg-Trp-DPhe-NH$_2$ | P + S | −14 ± 62 | | | −109 ± 124 | | −500 ± 104 | |
| | | | 776 ± 142 | | 136 ± 108 | 290 ± 124 | −454 ± 95 | |
| 5-<Glu-His-Trp-DSer-DArg-NH$_2$ | | 246 ± 67 | | | | −4 ± 25 | 6 ± 34 | |
| 6-DPhe-DPhe-DTrp-Met-DLys-NH$_2$* | P + S | 148 ± 137 | | | | | | |
| | | | 2218 ± 194 | | 1584 ± 136 | 1398 ± 98 | 1388 ± 300 | |

TABLE 13

(SEQ ID NOS 383-385, respectively, in order of appearance)
Ghrelin/GHS Antagonist Receptor Activity

| Antagonist | No. | % INH | IC$_{50}$ nM | K$_i$ nM |
|---|---|---|---|---|
| GlyMetAlaGlySer(OctDap$^6$)Phe LeuSerPro GluHisNH$_2$ | #3 | 54 | 7,960 | 4,450 |
| GlyMetAlaGlySer(OctDap$^6$)PheLeuSer ProGluHisGlnArgValGlnGlnArgLysGlu SerLysLysProProAlaLysLeuGlnProArg NH$_2$ | #4 | 98 | 22.2 | 12.4 |
| GlyMetAlaDAlaDβNalAlaTrpDPheLys NH$_2$ | #5 | 94 | 296 | 166 |
| GlyMetAlaDAlaDβNalDLysTrpDPhe LysNH$_2$ | #6a | 89 | 707 | 395 |
| GlyMetAlaGlySerTrpPheLeuSerProGlu HisGlnArgValGlnGlnArgLysGluSerLys LysProProAlaLysLeuGlnProArg | #7 | 86 | 284 | 159 |

All patents and other publications identified throughout the specification and examples and in the references section are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Kojima M, Hosada H, Date Y, Nakazato M, Matsuo H, Kangawa K. Ghrelin is a growth-hormone-releasing acylated peptide from stomach. Nature 1999; 402:656-60.
2. Bowers C Y. Growth Hormone Releasing Peptides (GH-RPs). In: Handbook of Physiology, Eds. J Kostyo, H Goodman 1999; Oxford University Press, New York, pg 267-297.
3. Bowers C Y. Unnatural growth hormone-releasing peptide begets natural ghrelin. J Clin Endocrinol Metab 2001; 86:1464-1469.
4. Wren A M, Seal L J, Cohen M A, Brynes A E, Frost G S, Murphy K G et al. Ghrelin enhances appetite and increases food intake in humans. J Clin Endocrinol Metab 2001; 86:5992-5995.
5. Laferrere B, Abraham C, Russell C D, Bowers C Y. Growth hormone releasing peptide-2 (GHRP-2), like ghrelin, increases food intake in healthy men. J Clin Endocrinol Metab 2005; 90:611-614.
6. Laferrere B, Hart A B, Bowers C Y. Obese subjects respond to the stimulatory effect of the ghrelin agonist Growth Hormone Releasing Peptide-2 (GHRP-2) on food intake. Obesity 14(6):1056-63, 2006.
7. Bowers C Y. Octanoyl ghrelin is hypothalamic rooted. Endocrinology 146:2508-9, 2005.
8. Sethumadhaven K, Veeraragavan K, Bowers C Y. Demonstration and characterization of the specific binding of growth hormone-releasing peptide (GHRP) to rat anterior pituitary and hypothalamic membranes. Biochem Biophy Res Comm 178(1):31-37, 1991.
9. Bitar K G, Bowers C Y, Coy D H. Effects of Substance P/Bombesin antagonists on the release of growth hormone by GHRP and GHRH. Biochem Biophy Res Comm 180 (1):156-161, 1991.
10. Veeraragavan K, Sethumadhavan K, Bowers C Y. Growth hormone releasing peptide (GHRP) binding to porcine anterior pituitary and hypothalamic membranes. Life Sciences 50:1149-1155, 1992
11. Camina J P. Cell biology of the ghrelin receptor. J Neuroendocrinol 2006; 18:65-76.
12. Bodart V, Febbraio M, Demers A, McNicoll N, Pohankova P, Perreault A et al. CD36 mediates cardiovascular action of growth hormone-releasing peptides in the heart. Circ Res 2002; 90:844-49.
13. Holst B, Cygankiewicz A, Jensen T H, Ankersen M, Schwartz T W. High constitutive signaling of the ghrelin receptor-identification of a potent inverse agonist. Mol. Endocrinol 2003; 17 (11):2201-10.
14. Holst B, Holliday N D, Bach A, Elling C E, Cox H M, Schwartz T W. Common structural basis for constitutive activity of the ghrelin receptor family. J Biol Chem 2004; 279:53805-53817.
15. Petersen P S, Wolsbye D, Lang M, Beck-Sickinger A, Schwartz T W, Holst B. Effect of icv infusion of the ghrelin receptor selective inverse agonist [DArg$^1$, DPhe$^5$, DTrp$^{7,9}$Leu$^{11}$]-Sub P on body weight gain in rats. Keystone Symposium Gut Hormone and Other Regulators of Appetite, Satiety and Energy Expenditure Mar. 2-7, 2006, p. 53.
16. Holst B, Mokrosinski J, Lang M, Brandt E, Nygaard R, Frimurer T M, Beck-Sickinger A G, Schwartz T W. Identification of an efficacy switch region in the ghrelin receptor responsible for interchange between agonism and inverse agonism. Journal Biol Chem doi/10.1074, 2007.
17. Zigman J M, Jones J E, Lee C E, Saper C B, Elmquist J K. Expression of ghrelin receptor mRNA in the rat and the mouse brain. J Comparative Neurology 2006; 494:528-548.
18. Zigman K M, Nakano Y, Coppari R, Balthasar N, Marcus J N, Lee C E et al. Mice lacking ghrelin receptors resist the development of diet induced obesity. J Clin Invest 2005; 115:3564-3572.
19. Wortley K E, del Rincon J P, Murray J D, Garcia J, Iida K, Thorner M O, Sleeman M W. Absence of ghrelin protects against early-onset obesity. J Clin Invest 2005; 115:3573-3578.
20. Gelling R W, Overduin J, Morrison C D, Morton G J, Frayo R S, Cummings D E, Schwartz M W. Effect of uncontrolled diabetes on plasma ghrelin concentrations and ghrelin-induced feeding. Endocrinology 2004; 145: 4575-4582.
21. Tannenbaum G S, Epelbaum J, Bowers C Y. Interrelationship between the novel peptide ghrelin and somatostatin/GHRH in regulation of pulsatile growth hormone secretion. Endocrinology 2003; 144:967-974.
22. Tannenbaum G S, Epelbaum J, Bowers C Y. Ghrelin and growth hormone neuroendocrine axis. In: Brain Somatic Cross-Talk and the Central Control of Metabolism. Eds. C Kordon et al. 2003; Springer-Verlag, Berlin/Heidelberg pg 65-80.
23. Bowers C Y, Chang, J-K, Wu S, Linse K D, Hurley D L, Veldhuis J D. Biochemistry of growth hormone secretagogue molecules, In: Fat Loss, Wasting and Cachexia in Medicine, (Ed) Schuster M and Mantovani G, Springer Verlag, Chapter 5.7, p 219-234, 2006.
24. Bowers C Y, Laferrere B, Hurley D L, Veldhuis J D. The role of GHS/Ghrelin in Feeding and Body Composition.

Obesity and Energy Metabolism: research and Clinical Applications (Eds) Conn P M and Donohoue P. The Humans Press, 2007.
25. Inui A, Asakawa A, Bowers C Y, Montovani G, Laviano A, Meguid M, Fujimiya M. Ghrelin, appetite and growth— The emerging role of the stomach as an endocrine organ. FASEB Journal 2004; 18:439-456.
26. Van der Lely A J, Tschop M, Heiman M L, Ghigo E. Biological, physiological, pathophysiological and pharmacological aspects of ghrelin. Endocrine Reviews 2004; 25:426-457.
27. Korbonits M, Goldstone A P, Gueorguiev M, Grossman A B. Ghrelin-a hormone with multiple functions. Neuroendocrinology 2004; 25:27-68.
28. Yang J, Brown M S, Liang G, Grishin N V, Goldstein J L. Identification of the acyltransferase that octanoylates ghrelin, an appetite-stimulating peptide hormone. Cell. 2008 Feb. 8; 132(3):387-96.
29. Yang J, Zhao T J, Goldstein J L, Brown M S. Inhibition of ghrelin O-acyltransferase (GOAT) by octanoylated pentapeptides. Proc Natl Acad Sci USA. 2008 Aug. 5; 105(31): 10750-5. Epub 2008 Jul. 31.

What is claimed:

1. A synthetic peptide, wherein the peptide
(i) comprises an amino acid sequence of formula (I):

$X^1$-Gly-Ser-$X^2$-Phe-Leu-$(X^3)_n$-$X^4$   (I) (SEQ ID NO: 4), wherein:

$X^1$ is Gly-Met-Ala-, Gly-DMet-Ala-, Ala-DMet-Ala-, Gly-Met-Alaψ[CH$_2$NH]—, Ala-Met-Alaψ[CH$_2$NH]—, Gly-DMet-Alaψ[CH$_2$NH]—, Ala-DMet-Alaψ[CH$_2$NH]—, Gly-Met-Ala[C(O)N(Me)]-, Ala-

Met-Ala[C(O)N(Me)]-, Gly-DMet-Ala[C(O)N(Me)]-, Ala-DMet-Ala[C(O)N(Me)]-, Leu-Asp-Leu-Gly-Met-Ala-(SEQ ID NO: 6), Leu-Asp-Leu-Gly-DMet-Ala-, Leu-Asp-Leu-Ala-DMet-Ala-, Leu-Asp-Leu-Gly-Met-Alaψ[CH$_2$NH]-(SEQ ID NO: 7), Leu-Asp-Leu-Ala-Met-Alaψ[CH$_2$NH]-(SEQ ID NO: 8), Leu-Asp-Leu-Gly-DMet-Alaψ[CH$_2$NH]—, Leu-Asp-Leu-Ala-DMet-Alaψ[CH$_2$NH]—, Leu-Asp-Leu-Gly-Met-Ala[C(O)N(Me)]-(SEQ ID NO: 381), Leu-Asp-Leu-Ala-Met-Ala[C(O)N(Me)]-(SEQ ID NO: 382), Leu-Asp-Leu-Gly-DMet-Ala[C(O)N(Me)]-, or Leu-Asp-Leu-Ala-DMet-Ala[C(O)N(Me)]-;

$X^2$ is not a serine conjugated with a —C(O)C$_1$-C$_{20}$ alkyl group on the side chain OH of said serine, or $X^2$ is a diaminopropionic acid conjugated with a —C(O)C$_1$-C$_{20}$ alkyl group on one of the amino groups of the diaminopropionic acid, or $X^2$ is D- or L-tryptophan;

each $X^3$ is independently an amino acid;

$X^4$ is absent, NH$_2$, or a carboxyl protecting group;

amino acid residues of the dipeptide, tripeptide, tetrapeptide, pentapeptide, and hexapepetide are same or different and are selected from D amino acid, L amino acid, α-amino acid, β-amino acid, γ-amino acid, and γ-amino acid;

n is an integer from 0 to 24; and pharmaceutically acceptable salts thereof;

or (ii) consists of an amino acid sequence of formula (I):

$X^1$-Gly-Ser-$X^2$-Phe-Leu-$(X^3)_n$—$X^4$     (I) (SEQ ID NO: 4), wherein:

$X^1$ is Gly-Met-Ala-, Gly-DMet-Ala-, Ala-DMet-Ala-, Gly-Met-Alaψ[CH$_2$NH]—, Ala-Met-Alaψ[CH$_2$NH]—, Gly-DMet-Alaψ[CH$_2$NH]—, Ala-DMet-Alaψ[CH$_2$NH]—, Gly-Met-Ala[C(O)N(Me)]-, Ala-Met-Ala[C(O)N(Me)]-, Gly-DMet-Ala[C(O)N(Me)]-, Ala-DMet-Ala[C(O)N(Me)]-, Leu-Asp-Leu-Gly-Met-Ala-(SEQ ID NO: 6), Leu-Asp-Leu-Gly-DMet-Ala-, Leu-Asp-Leu-Ala-DMet-Ala-, Leu-Asp-Leu-Gly-Met-Alaψ[CH$_2$NH]— (SEQ ID NO: 7), Leu-Asp-Leu-Ala-Met-Alaψ[CH$_2$NH]— (SEQ ID NO: 8), Leu-Asp-Leu-Gly-DMet-Alaψ[CH$_2$NH]—, Leu-Asp-Leu-Ala-DMet-Alaψ[CH$_7$NH]—, Leu-Asp-Leu-Gly-Met-Ala[C(O)N(Me)]- (SEQ ID NO: 381), Leu-Asp-Leu-Ala-Met-Ala[C(O)N(Me)]- (SEQ ID NO: 382), Leu-Asp-Leu-Gly-DMet-Ala[C(O)N(Me)]-, or Leu-Asp-Leu-Ala-DMet-Ala[C(O)N(Me)]-;

$X^2$ is a serine conjugated with a —C(O)C$_1$-C$_{20}$ alkyl group on the side chain OH of said serine;

each $X^3$ is independently an amino acid;

$X^4$ is absent, NH$_2$, or a carboxyl protecting group;

n is an integer from 0 to 24; and pharmaceutically acceptable salts thereof.

2. The peptide of claim 1, wherein the peptide is of formula (I'):

$X^1$-Gly-Ser-$X^2$-Phe-Leu-Ser-Pro-Glu-His-$(X^3)_m$—$X^4$     (I') (SEQ ID NO: 1), wherein:

m is an integer from 1 to 20; and pharmaceutically acceptable salts thereof.

3. The peptide of claim 1, wherein $X^2$ is a serine conjugated with an octanoyl group on the side chain OH of the serine, a diaminopropionic acid conjugated with an octanoyl group on one of the amino groups of the diaminopropionic acid, or L-tryptophan.

4. The peptide of claim 2, wherein the peptide is of formula (I'): GMA-GS-$X^2$-FLSPEH-$(X^3)_m$—$X^4$ (SEQ ID NO: 380).

5. The peptide of claim 2, wherein $(X^3)_m$ is Q, QR, QRV, QRVQ (SEQ ID NO: 10), QRVQQ (SEQ ID NO: 11), QRVQQR (SEQ ID NO: 12), QRVQQRK (SEQ ID NO: 13), QRVQQRKE (SEQ ID NO: 14), QRVQQRKES (SEQ ID NO: 15), QRVQQRKESK (SEQ ID NO: 16), QRVQQRKESKK (SEQ ID NO: 17), QRVQQRKESKKP (SEQ ID NO: 18), QRVQQRKESKKPP (SEQ ID NO: 19), QRVQQRKESKKPPA (SEQ ID NO: 20), QRVQQRKESKKPPAK (SEQ ID NO: 21), QRVQQRKESKKPPAKL (SEQ ID NO: 22), QRVQQRKESKKPPAKLQ (SEQ ID NO: 23), QRVQQRKESKKPPAKLQP (SEQ ID NO: 24), QRVQQRKESKKPPAKLQPR (SEQ ID NO: 25), or QRVQQRKESKKPPAKLQPRW (SEQ ID NO: 26).

6. The peptide of claim 1, wherein $X^4$ is absent, NH$_2$, optionally substituted 4-phenylpiperazine, optionally substituted 4-phenylpiperidine, or 1-(methylsulfonyl)spiro[indoline-3,4'-piperdine].

7. The peptide of claim 1, wherein the peptide comprises at least one D amino acid.

8. The peptide of claim 1, wherein the peptide comprises at least one beta amino acid.

9. The peptide of claim 1, wherein the peptide comprises at least one peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group.

10. The peptide of claim 1, wherein $X^1$ is GlyMetAla.

11. The peptide of claim 1, wherein $(X^3)$n consists of an amino acid sequence represented by amino acid residue 6 to amino acid residue p, wherein p is 7-28, of the amino acid sequence selected from the group consisting of GSS(Oct)FLSPEHQRVQQRKESKKPPAKLQPR (human ghrelin) (SEQ ID NO: 27), GSS(Oct)FLSPEHQKAQQRKESKKP-PAKLQPR (rat ghrelin) (SEQ ID NO: 28), GSS(Oct)FLSPE-HQKAQQRKESKKPPAKLQPR (mouse ghrelin) (SEQ ID NO: 29), GSS(Oct)FLSPEHQKVQQRKESKKPAAKLKPR (porcine ghrelin) (SEQ ID NO: 30), GSS(Oct)FLSPE-HQKLQRKEAKKPSGRLKPRT (bovine ghrelin) (SEQ ID NO: 31), and GSS(Oct)FLSPEHQKLQQRKESKKPPAK-LQPR (canine ghrelin) (SEQ ID NO: 32).

12. The peptide of claim 11, wherein when n is 4, $X^3$ is SPEH (SEQ ID NO: 386).

13. The peptide of claim 6, wherein $X^4$ is NH$_2$.

14. The peptide of claim 1, wherein the peptide is selected from the group consisting of GMAGSS(Oct)FL (SEQ ID NO: 59); GMAGSS(Oct)FLS (SEQ ID NO: 60); GMAGSS(Oct)FLSP (SEQ ID NO: 61); GMAGSS(Oct)FLSPE (SEQ ID NO: 62); GMAGSS(Oct)FLSPEH (SEQ ID NO: 63); GMAGSS(Oct)FLSPEHQ (SEQ ID NO: 64); GMAGSS(Oct)FLSPEHQR (SEQ ID NO: 65); GMAGSS(Oct)FLSPE-HQRV (SEQ ID NO: 66); GMAGSS(Oct)FLSPEHQRVQ (SEQ ID NO: 67); GMAGSS(Oct)FLSPEHQRVQQ (SEQ ID NO: 68); GMAGSS(Oct)FLSPEHQRVQQR (SEQ ID NO: 69); GMAGSS(Oct)FLSPEHQRVQQRK (SEQ ID NO: 70); GMAGSS(Oct)FLSPEHQRVQQRKE (SEQ ID NO: 71); GMAGSS(Oct)FLSPEHQRVQQRKES (SEQ ID NO: 72); GMAGSS(Oct)FLSPEHQRVQQRKESK (SEQ ID NO: 73); GMAGSS(Oct)FLSPEHQRVQQRKESKK (SEQ ID NO: 74); GMAGSS(Oct)FLSPEHQRVQQRKESKKP (SEQ ID NO: 75); GMAGSS(Oct)FLSPEHQRVQQRKESKKPP (SEQ ID NO: 76); GMAGSS(Oct)FLSPE-HQRVQQRKESKKPPA (SEQ ID NO: 77); GMAGSS(Oct)FLSPEHQRVQQRKESKKPPAK (SEQ ID NO: 78); GMAGSS(Oct)FLSPEHQRVQQRKESKKPPAKL (SEQ ID NO: 79); GMAGSS(Oct)FLSPEHQRVQQRKESKKPPAKLQ (SEQ ID NO: 80); GMAGSS(Oct)FLSPEHQRVQQRKESKKPPAKLQP (SEQ ID NO: 81); GMAGSS(Oct)FLSPEHQRVQQRKESKKPPAKLQPR (SEQ ID NO: 82); GMAGSS(Oct)FLSPEHQRVQQRKESKKPPAKLQPRW (SEQ ID NO: 83); GMAGSDap(Oct)FL (SEQ ID NO: 84); GMAGSDap(Oct)FLS (SEQ ID NO: 85); GMAGSDap(Oct)FLSP (SEQ ID NO: 86); GMAGSDap(Oct)FLSPE (SEQ ID NO: 87); GMAGSDap(Oct)FLSPEH (SEQ ID NO: 88); GMAGSDap(Oct)FLSPEHQ (SEQ ID NO: 89); GMAGSDap(Oct)FLSPEHQR (SEQ ID NO: 90); GMAGSDap(Oct)FLSPEHQRV (SEQ ID NO: 91); GMAGSDap(Oct)FLSPEHQRVQ (SEQ ID NO: 92); GMAGSDap(Oct)FLSPEHQRVQQ (SEQ ID NO: 93); GMAGSDap(Oct)FLSPEHQRVQQR (SEQ ID NO: 94); GMAGSDap(Oct)FLSPEHQRVQQRK (SEQ ID NO: 95); GMAGSDap(Oct)FLSPEHQRVQQRKE (SEQ ID NO: 96); GMAGSDap(Oct)FLSPEHQRVQQRKES (SEQ ID NO: 97); GMAGSDap(Oct)FLSPEHQRVQQRKESK (SEQ ID NO: 98); GMAGSDap(Oct)FLSPEHQRVQQRKESKK (SEQ ID NO: 99); GMAGSDap(Oct)FLSPEHQRVQQRKESKKP (SEQ ID NO: 100); GMAGSDap(Oct)FLSPEHQRVQQRKESKKPP (SEQ ID NO: 101); GMAGSDap(Oct)FLSPEHQRVQQRKESKKPPA (SEQ ID NO: 102); GMAGSDap(Oct)FLSPEHQRVQQRKESKKPPAK (SEQ ID NO: 103); GMAGSDap(Oct)FLSPEHQRVQQRKESKKPPAKL (SEQ ID NO: 104); GMAGSDap(Oct)FLSPEHQRVQQRKESKKPPAKLQ (SEQ ID NO: 105); GMAGSDap(Oct)FLSPEHQRVQQRKESKKPPAKLQP (SEQ ID NO: 106); GMAGSDap(Oct)FLSPEHQRVQQRKESKKPPAKLQPR (SEQ ID NO: 107); GMAGSDap(Oct)FLSPEHQRVQQRKESKKPPAKLQPRW (SEQ ID NO: 108); GMAGSS(Oct)FL-NH$_2$ (SEQ ID NO: 159); GMAGSS(Oct)FLS-NH$_2$ (SEQ ID NO: 160); GMAGSS(Oct)FLSP-NH$_2$ (SEQ ID NO: 161); GMAGSS(Oct)FLSPE-NH$_2$ (SEQ ID NO: 162); GMAGSS(Oct)FLSPEH-NH$_2$ (SEQ ID NO: 163); GMAGSS(Oct)FLSPEHQ-NH$_2$ (SEQ ID NO: 164); GMAGSS(Oct)FLSPEHQR-NH$_2$ (SEQ ID NO: 165); GMAGSS(Oct)FLSPEHQRV-NH$_2$ (SEQ ID NO: 166); GMAGSS(Oct)FLSPEHQRVQ-NH$_2$ (SEQ ID NO: 167); GMAGSS(Oct)FLSPEHQRVQQ-NH$_2$ (SEQ ID NO: 168); GMAGSS(Oct)FLSPEHQRVQQR-NH$_2$ (SEQ ID NO: 169); GMAGSS(Oct)FLSPEHQRVQQRK-NH$_2$ (SEQ ID NO: 170); GMAGSS(Oct)FLSPEHQRVQQRKE-NH$_2$ (SEQ ID NO: 171); GMAGSS(Oct)FLSPEHQRVQQRKES-NH$_2$ (SEQ ID NO: 172); GMAGSS(Oct)FLSPEHQRVQQRKESK-NH$_2$ (SEQ ID NO: 173); GMAGSS(Oct)FLSPEHQRVQQRKESKK-NH$_2$ (SEQ ID NO: 174); GMAGSS(Oct)FLSPEHQRVQQRKESKKP-NH$_2$ (SEQ ID NO: 175); GMAGSS(Oct)FLSPEHQRVQQRKESKKPP-NH$_2$ (SEQ ID NO: 176); GMAGSS(Oct)FLSPEHQRVQQRKESKKPPA-NH$_2$ (SEQ ID NO: 177); GMAGSS(Oct)FLSPEHQRVQQRKESKKPPAK-NH$_2$ (SEQ ID NO: 178); GMAGSS(Oct)FLSPEHQRVQQRKESKKPPAKL-NH$_2$ (SEQ ID NO: 179); GMAGSS(Oct)FLSPEHQRVQQRKESKKPPAKLQ-NH$_2$ (SEQ ID NO: 180); GMAGSS(Oct)FLSPEHQRVQQRKESKKPPAKLQP-NH$_2$ (SEQ ID NO: 181); GMAGSS(Oct)FLSPEHQRVQQRKESKKPPAKLQPR-NH$_2$ (SEQ ID NO: 182); GMAGSS(Oct)FLSPEHQRVQQRKESKKPPAKLQPRW-NH$_2$ (SEQ ID NO: 183); GMAGSDap(Oct)FL-NH$_2$ (SEQ ID NO: 184); GMAGSDap(Oct)FLS-NH$_2$ (SEQ ID NO: 185); GMAGSDap(Oct)FLSP-NH$_2$ (SEQ ID NO: 186); GMAGSDap(Oct)FLSPE-NH$_2$ (SEQ ID NO: 187); GMAGSDap(Oct)FLSPEH-NH$_2$ (SEQ ID NO: 188); GMAGSDap(Oct)FLSPEHQ-NH$_2$ (SEQ ID NO: 189); GMAGSDap(Oct)FLSPEHQR-NH$_2$ (SEQ ID NO: 190); GMAGSDap(Oct)FLSPEHQRV-NH$_2$ (SEQ ID NO: 191); GMAGSDap(Oct)FLSPEHQRVQ-NH$_2$ (SEQ ID NO: 192); GMAGSDap(Oct)FLSPEHQRVQQ-NH$_2$ (SEQ ID NO: 193); GMAGSDap(Oct)FLSPEHQRVQQR-NH$_2$ (SEQ ID NO: 194); GMAGSDap(Oct)FLSPEHQRVQQRK-NH$_2$ (SEQ ID NO: 195); GMAGSDap(Oct)FLSPEHQRVQQRKE-NH$_2$ (SEQ ID NO: 196); GMAGSDap(Oct)FLSPEHQRVQQRKES-NH$_2$ (SEQ ID NO: 197); GMAGSDap(Oct)FLSPEHQRVQQRKESK-NH$_2$ (SEQ ID NO: 198); GMAGSDap(Oct)FLSPEHQRVQQRKESKK-NH$_2$ (SEQ ID NO: 199); GMAGSDap(Oct)FLSPEHQRVQQRKESKKP-NH$_2$ (SEQ ID NO: 200); GMAGSDap(Oct)FLSPEHQRVQQRKESKKPP-NH$_2$ (SEQ ID NO: 201); GMAGSDap(Oct)FLSPEHQRVQQRKESKKPPA-NH$_2$ (SEQ ID NO: 202); GMAGSDap(Oct)FLSPEHQRVQQRKESKKPPAK-NH$_2$ (SEQ ID NO: 203); GMAGSDap(Oct)FLSPEHQRVQQRKESKKPPAKL-NH$_2$ (SEQ ID NO: 204); GMAGSDap(Oct)FLSPEHQRVQQRKESKKPPAKLQ-NH$_2$ (SEQ ID NO: 205); GMAGSDap(Oct)FLSPEHQRVQQRKESKKPPAKLQP-NH$_2$ (SEQ ID NO: 206); GMAGSDap(Oct)FLSPEHQRVQQRKESKKPPAKLQPR-NH$_2$ (SEQ ID NO: 207); GMAGSDap(Oct)FLSPEHQRVQQRKESKKPPAKLQPRW-NH$_2$ (SEQ ID NO: 208); GMAGSDap(Oct)FLSPEH (SEQ ID NO: 359); GMAGSDap(palmityl)FLSPEH (SEQ ID NO: 360); GMAGS(Des-Octanoyl)FL (SEQ ID NO: 361); GMAGSDap(Octanoyl)FLSPEHQRVQQRKESKKPPAKLQPR (SEQ ID NO: 362); GMAGSDap(Octanoyl)FL (SEQ ID NO: 363); GMAGSS(Des-Octanoyl)F (SEQ ID NO: 364); GMAGSS(Des-Octanoyl)FLSPEHQRVQQRKES (SEQ ID NO: 365); and GMAGSS(Des-Octanoyl)FLSPEHQRVQQRKESKKPPAKLQPRW (SEQ ID NO: 366).

15. The peptide of claim 14, wherein the peptide consists of amino acid sequence GMAGS(Dap$^3$Oct)FLSPEH-NH$_2$ (SEQ ID NO: 188).

16. The peptide of claim 1, wherein when n is 1, $X^3$ is serine.

17. A pharmaceutical composition comprising a peptide of claim 1 and a pharmaceutically acceptable carrier or excipient.

* * * * *